US012127829B2

(12) United States Patent
Crowley

(10) Patent No.: US 12,127,829 B2
(45) Date of Patent: Oct. 29, 2024

(54) RESEARCH STUDY USER INTERFACES

(71) Applicant: Apple Inc., Cupertino, CA (US)

(72) Inventor: Matthew Crowley, Sunnyvale, CA (US)

(73) Assignee: Apple Inc., Cupertino, CA (US)

(*) Notice: Subject to any disclaimer, the term of this patent is extended or adjusted under 35 U.S.C. 154(b) by 0 days.

(21) Appl. No.: 17/584,190

(22) Filed: Jan. 25, 2022

(65) Prior Publication Data

US 2022/0142515 A1 May 12, 2022

Related U.S. Application Data

(63) Continuation of application No. 16/990,846, filed on Aug. 11, 2020, now Pat. No. 11,266,330.

(60) Provisional application No. 62/897,693, filed on Sep. 9, 2019.

(51) Int. Cl.
*G06F 3/16* (2006.01)
*A61B 5/12* (2006.01)
*G06F 3/04812* (2022.01)

(52) U.S. Cl.
CPC .......... *A61B 5/123* (2013.01); *G06F 3/04812* (2013.01); *G06F 3/167* (2013.01)

(58) Field of Classification Search
CPC ..... A61B 5/123; G06F 3/04812; G06F 3/167; G06F 3/0481; G06F 3/04847; G06F 3/0488; G06F 3/162; G06F 9/451; G16H 40/57; G16H 10/20; G16H 10/60
See application file for complete search history.

(56) References Cited

U.S. PATENT DOCUMENTS

| | | | |
|---|---|---|---|
| 5,515,344 A | 5/1996 | Ng | |
| 5,642,731 A | 7/1997 | Kehr | |
| 6,416,471 B1 | 7/2002 | Kumar et al. | |
| 6,600,696 B1 | 7/2003 | Lynn | |
| 6,705,972 B1 | 3/2004 | Takano et al. | |
| 6,873,709 B2 | 3/2005 | Hou | |

(Continued)

FOREIGN PATENT DOCUMENTS

| | | |
|---|---|---|
| CA | 2815518 A1 | 5/2012 |
| CN | 1752973 A | 3/2006 |

(Continued)

OTHER PUBLICATIONS

International Preliminary Report on Patentability received for PCT Patent Application No. PCT/US2021/035227, mailed on Dec. 15, 2022, 10 pages.

(Continued)

*Primary Examiner* — Andrey Belousov
(74) *Attorney, Agent, or Firm* — DLA Piper LLP (US)

(57) ABSTRACT

The present disclosure generally relates to techniques and user interfaces for interacting with research studies. In some embodiments, an electronic device displays a user interface that includes a task view with active tasks from multiple research studies. In some embodiments, an electronic device, while displaying a research study user interface, displays an indication of a problem that prevents enrollment in the research study when enrollment problem criteria are met. In some embodiments, an electronic device, while performing a hearing test, suspends the test and displays a restart affordance when the ambient noise level exceeds a threshold.

51 Claims, 70 Drawing Sheets

(56) References Cited

U.S. PATENT DOCUMENTS

| | | |
|---|---|---|
| 6,950,839 B1 | 9/2005 | Green et al. |
| 7,111,157 B1 | 9/2006 | Hooper |
| 7,128,693 B2 | 10/2006 | Brown et al. |
| 7,166,078 B2 | 1/2007 | Saini et al. |
| 7,313,435 B2 | 12/2007 | Nakada et al. |
| 7,739,148 B2 | 6/2010 | Suzuki et al. |
| 7,771,320 B2 | 8/2010 | Riley et al. |
| 8,045,739 B2 | 10/2011 | Paludan-Mueller et al. |
| 8,152,694 B2 | 4/2012 | Srinivasan et al. |
| 8,200,323 B2 | 6/2012 | Dibenedetto et al. |
| 8,321,006 B1 | 11/2012 | Snyder et al. |
| 8,475,339 B2 | 7/2013 | Hwang et al. |
| 8,676,170 B2 | 3/2014 | Porrati et al. |
| 8,725,527 B1 | 5/2014 | Kahn et al. |
| 8,758,262 B2 | 6/2014 | Rhee et al. |
| 8,784,115 B1 | 7/2014 | Chuang |
| 8,888,707 B2 | 11/2014 | Shirasaki et al. |
| 9,011,292 B2 | 4/2015 | Weast et al. |
| 9,026,927 B2 | 5/2015 | Brumback et al. |
| 9,224,291 B2 | 12/2015 | Moll-Carrillo et al. |
| 9,490,763 B2 | 11/2016 | Taniguchi et al. |
| 9,579,060 B1 | 2/2017 | Lisy et al. |
| 9,589,445 B2 | 3/2017 | White et al. |
| 9,606,695 B2 | 3/2017 | Matas |
| 9,672,715 B2 | 6/2017 | Roberts et al. |
| 9,712,629 B2 | 7/2017 | Molettiere et al. |
| 9,721,066 B1 | 8/2017 | Funaro et al. |
| 9,730,621 B2 | 8/2017 | Cohen et al. |
| 9,740,825 B2 | 8/2017 | Sansale et al. |
| 9,801,562 B1 | 10/2017 | Host-Madsen |
| 9,808,206 B1 | 11/2017 | Zhao et al. |
| 9,813,642 B1 | 11/2017 | Chen et al. |
| 9,940,682 B2 | 4/2018 | Hoffman et al. |
| 10,004,451 B1 | 6/2018 | Proud |
| 10,150,002 B2 | 12/2018 | Kass et al. |
| 10,175,781 B2 | 1/2019 | Karagozler et al. |
| 10,226,195 B2 | 3/2019 | Briante et al. |
| 10,254,911 B2 | 4/2019 | Yang |
| 10,275,262 B1 | 4/2019 | Bull et al. |
| 10,339,830 B2 | 7/2019 | Han et al. |
| 10,365,811 B2 | 7/2019 | Robinson et al. |
| 10,437,962 B2 | 10/2019 | Soni et al. |
| 10,445,702 B1 * | 10/2019 | Hunt .................. G06Q 10/1097 |
| 10,568,533 B2 | 2/2020 | Soli et al. |
| 10,576,327 B2 | 3/2020 | Kim et al. |
| 10,592,088 B2 | 3/2020 | Robinson et al. |
| 10,602,964 B2 | 3/2020 | Kerber |
| 10,635,267 B2 | 4/2020 | Williams |
| 10,674,942 B2 | 6/2020 | Williams et al. |
| 10,685,090 B2 | 6/2020 | Petterson et al. |
| 10,692,593 B1 | 6/2020 | Young et al. |
| 10,762,990 B1 | 9/2020 | Schilling et al. |
| 10,764,700 B1 | 9/2020 | Felton |
| 10,796,549 B2 | 10/2020 | Roberts et al. |
| 11,073,942 B2 | 7/2021 | Lee et al. |
| 11,103,161 B2 | 8/2021 | Williams et al. |
| 11,107,580 B1 | 8/2021 | Felton et al. |
| 11,209,957 B2 | 12/2021 | Dryer et al. |
| 2001/0039503 A1 | 11/2001 | Chan et al. |
| 2002/0095292 A1 | 7/2002 | Mittal et al. |
| 2003/0126114 A1 | 7/2003 | Tedesco |
| 2003/0130867 A1 | 7/2003 | Coelho et al. |
| 2003/0140044 A1 | 7/2003 | Mok et al. |
| 2003/0181291 A1 | 9/2003 | Ogawa |
| 2003/0191609 A1 | 10/2003 | Bernardi et al. |
| 2003/0200483 A1 | 10/2003 | Sutton |
| 2003/0216971 A1 | 11/2003 | Sick et al. |
| 2003/0226695 A1 | 12/2003 | Mault |
| 2004/0017300 A1 | 1/2004 | Kotzin et al. |
| 2004/0034288 A1 | 2/2004 | Hennessy et al. |
| 2004/0077958 A1 | 4/2004 | Kato et al. |
| 2004/0081024 A1 | 4/2004 | Weng |
| 2004/0190729 A1 | 9/2004 | Yonovitz et al. |
| 2004/0193069 A1 | 9/2004 | Takehara |
| 2004/0210117 A1 | 10/2004 | Ueno et al. |
| 2004/0236189 A1 | 11/2004 | Hawthorne et al. |
| 2005/0010117 A1 | 1/2005 | Agutter et al. |
| 2005/0027208 A1 | 2/2005 | Shiraishi et al. |
| 2005/0075214 A1 | 4/2005 | Brown et al. |
| 2005/0079905 A1 | 4/2005 | Martens |
| 2005/0149362 A1 | 7/2005 | Peterson et al. |
| 2005/0165627 A1 | 7/2005 | Fotsch et al. |
| 2005/0187794 A1 | 8/2005 | Kimak |
| 2005/0228735 A1 | 10/2005 | Duquette |
| 2005/0244013 A1 | 11/2005 | Battenberg et al. |
| 2005/0272564 A1 | 12/2005 | Pyles et al. |
| 2006/0074863 A1 | 4/2006 | Kishore et al. |
| 2006/0094969 A1 | 5/2006 | Nissila |
| 2006/0098109 A1 | 5/2006 | Ooki |
| 2006/0106741 A1 | 5/2006 | Janarthanan |
| 2006/0136173 A1 | 6/2006 | Case, Jr. et al. |
| 2006/0149144 A1 | 7/2006 | Lynn et al. |
| 2006/0152372 A1 | 7/2006 | Stout |
| 2006/0182287 A1 | 8/2006 | Schulein et al. |
| 2006/0205564 A1 | 9/2006 | Peterson |
| 2006/0210096 A1 | 9/2006 | Stokes et al. |
| 2006/0235319 A1 | 10/2006 | Belohlavek et al. |
| 2006/0274908 A1 | 12/2006 | Choi |
| 2007/0016440 A1 * | 1/2007 | Stroup .................. G16H 15/00 705/2 |
| 2007/0033066 A1 | 2/2007 | Ammer et al. |
| 2007/0056727 A1 | 3/2007 | Newman |
| 2007/0179434 A1 | 8/2007 | Weinert et al. |
| 2007/0250505 A1 | 10/2007 | Yang et al. |
| 2007/0250613 A1 | 10/2007 | Gulledge |
| 2007/0274531 A1 | 11/2007 | Camp |
| 2008/0005106 A1 | 1/2008 | Schumacher et al. |
| 2008/0012701 A1 | 1/2008 | Kass et al. |
| 2008/0021884 A1 | 1/2008 | Jones et al. |
| 2008/0058626 A1 | 3/2008 | Miyata et al. |
| 2008/0133742 A1 | 6/2008 | Southiere et al. |
| 2008/0146892 A1 | 6/2008 | Leboeuf et al. |
| 2008/0159547 A1 | 7/2008 | Schuler et al. |
| 2008/0172361 A1 | 7/2008 | Wong et al. |
| 2008/0200312 A1 | 8/2008 | Tagliabue |
| 2008/0205660 A1 | 8/2008 | Goldstein |
| 2008/0228045 A1 | 9/2008 | Gao et al. |
| 2008/0240519 A1 | 10/2008 | Nagamitsu |
| 2008/0243885 A1 | 10/2008 | Harger et al. |
| 2008/0300110 A1 | 12/2008 | Smith et al. |
| 2009/0007596 A1 | 1/2009 | Goldstein et al. |
| 2009/0052677 A1 | 2/2009 | Smith |
| 2009/0065578 A1 | 3/2009 | Peterson et al. |
| 2009/0105552 A1 | 4/2009 | Nishiyama et al. |
| 2009/0118100 A1 | 5/2009 | Oliver et al. |
| 2009/0172773 A1 | 7/2009 | Moore |
| 2009/0180631 A1 | 7/2009 | Michael et al. |
| 2009/0210078 A1 | 8/2009 | Crowley |
| 2009/0216556 A1 | 8/2009 | Martin et al. |
| 2009/0235253 A1 * | 9/2009 | Hope .................. G06Q 10/10 718/100 |
| 2009/0240521 A1 | 9/2009 | Simons et al. |
| 2009/0245537 A1 | 10/2009 | Morin |
| 2009/0259134 A1 | 10/2009 | Levine |
| 2009/0262088 A1 | 10/2009 | Moll-carrillo et al. |
| 2009/0267776 A1 | 10/2009 | Glenn et al. |
| 2009/0287103 A1 | 11/2009 | Pillai |
| 2009/0287327 A1 | 11/2009 | Hsu et al. |
| 2009/0290721 A1 | 11/2009 | Goldstein et al. |
| 2009/0307105 A1 | 12/2009 | Lemay et al. |
| 2010/0003951 A1 | 1/2010 | Ray et al. |
| 2010/0010832 A1 | 1/2010 | Boute et al. |
| 2010/0017489 A1 | 1/2010 | Birnbaum et al. |
| 2010/0027807 A1 | 2/2010 | Jeon |
| 2010/0046767 A1 | 2/2010 | Bayley et al. |
| 2010/0062905 A1 | 3/2010 | Rottler et al. |
| 2010/0073162 A1 | 3/2010 | Johnson et al. |
| 2010/0076331 A1 | 3/2010 | Chan et al. |
| 2010/0094658 A1 | 4/2010 | Mok et al. |
| 2010/0099539 A1 | 4/2010 | Haataja |
| 2010/0119093 A1 | 5/2010 | Uzuanis et al. |
| 2010/0121700 A1 | 5/2010 | Wigder et al. |
| 2010/0132044 A1 | 5/2010 | Kogan et al. |
| 2010/0145220 A1 | 6/2010 | Van |

(56) References Cited

U.S. PATENT DOCUMENTS

| | | |
|---|---|---|
| 2010/0150378 A1 | 6/2010 | Lee et al. |
| 2010/0161353 A1 | 6/2010 | Mayaud |
| 2010/0222645 A1 | 9/2010 | Nadler et al. |
| 2010/0292600 A1 | 11/2010 | Dibenedetto et al. |
| 2010/0312138 A1 | 12/2010 | Regas |
| 2011/0010195 A1 | 1/2011 | Cohn |
| 2011/0057799 A1 | 3/2011 | Taneff |
| 2011/0066051 A1 | 3/2011 | Moon et al. |
| 2011/0071765 A1 | 3/2011 | Yodfat et al. |
| 2011/0093481 A1* | 4/2011 | Hussam ............... G16H 10/20 |
| | | 707/756 |
| 2011/0098928 A1 | 4/2011 | Hoffman et al. |
| 2011/0119088 A1 | 5/2011 | Gunn |
| 2011/0152656 A1 | 6/2011 | Weinert et al. |
| 2011/0166631 A1 | 7/2011 | Breining |
| 2011/0195383 A1 | 8/2011 | Weiss |
| 2011/0214162 A1 | 9/2011 | Brakensiek et al. |
| 2011/0218407 A1 | 9/2011 | Haberman et al. |
| 2011/0245623 A1 | 10/2011 | Chutani et al. |
| 2011/0307821 A1 | 12/2011 | Martens |
| 2012/0002510 A1 | 1/2012 | Berman, Jr. |
| 2012/0023586 A1 | 1/2012 | Flickner et al. |
| 2012/0029303 A1 | 2/2012 | Shaya |
| 2012/0038651 A1 | 2/2012 | Case et al. |
| 2012/0041767 A1 | 2/2012 | Hoffman et al. |
| 2012/0059664 A1 | 3/2012 | Georgiev et al. |
| 2012/0065480 A1 | 3/2012 | Badilini et al. |
| 2012/0071770 A1 | 3/2012 | Grey et al. |
| 2012/0112908 A1 | 5/2012 | Prykari et al. |
| 2012/0116550 A1 | 5/2012 | Hoffman et al. |
| 2012/0185267 A1 | 7/2012 | Kamen et al. |
| 2012/0203124 A1 | 8/2012 | Lim |
| 2012/0215115 A1 | 8/2012 | Takahashi |
| 2012/0232929 A1 | 9/2012 | Experton |
| 2012/0245447 A1 | 9/2012 | Karan et al. |
| 2012/0283524 A1 | 11/2012 | Kiani et al. |
| 2012/0283587 A1 | 11/2012 | Gosh et al. |
| 2012/0283855 A1 | 11/2012 | Hoffman et al. |
| 2012/0311585 A1* | 12/2012 | Gruber ............... G06Q 10/109 |
| | | 718/100 |
| 2012/0316455 A1 | 12/2012 | Rahman et al. |
| 2012/0317167 A1 | 12/2012 | Rahman et al. |
| 2012/0321094 A1 | 12/2012 | Schiller et al. |
| 2013/0002425 A1 | 1/2013 | Hatch et al. |
| 2013/0011819 A1 | 1/2013 | Horseman |
| 2013/0012788 A1 | 1/2013 | Horseman |
| 2013/0013331 A1 | 1/2013 | Horseman |
| 2013/0033376 A1 | 2/2013 | Seyed Momen et al. |
| 2013/0065569 A1 | 3/2013 | Leipzig et al. |
| 2013/0072765 A1 | 3/2013 | Kahn et al. |
| 2013/0073933 A1 | 3/2013 | Eppolito |
| 2013/0073960 A1 | 3/2013 | Eppolito et al. |
| 2013/0095459 A1 | 4/2013 | Tran |
| 2013/0110264 A1 | 5/2013 | Weast et al. |
| 2013/0114100 A1 | 5/2013 | Torii et al. |
| 2013/0115583 A1 | 5/2013 | Gordon et al. |
| 2013/0144653 A1 | 6/2013 | Poe et al. |
| 2013/0151285 A1 | 6/2013 | Mclaren et al. |
| 2013/0158416 A1 | 6/2013 | Hatlestad et al. |
| 2013/0191647 A1 | 7/2013 | Ferrara et al. |
| 2013/0197679 A1 | 8/2013 | Balakrishnan et al. |
| 2013/0202121 A1 | 8/2013 | Georgiou et al. |
| 2013/0215042 A1 | 8/2013 | Messerschmidt et al. |
| 2013/0231575 A1 | 9/2013 | Erkkila et al. |
| 2013/0231947 A1 | 9/2013 | Shusterman |
| 2013/0262155 A1 | 10/2013 | Hinkamp |
| 2013/0268398 A1 | 10/2013 | Agami et al. |
| 2013/0274628 A1 | 10/2013 | Fausti et al. |
| 2013/0299769 A1 | 11/2013 | Maxwell |
| 2013/0304510 A1 | 11/2013 | Chen et al. |
| 2013/0304616 A1 | 11/2013 | Raleigh et al. |
| 2013/0317380 A1 | 11/2013 | Liley et al. |
| 2013/0325396 A1 | 12/2013 | Yuen et al. |
| 2013/0325493 A1 | 12/2013 | Wong et al. |
| 2013/0325511 A1 | 12/2013 | Neagle, Iii |
| 2013/0332286 A1 | 12/2013 | Medelius et al. |
| 2014/0005947 A1 | 1/2014 | Jeon et al. |
| 2014/0019162 A1 | 1/2014 | Skowronski et al. |
| 2014/0037107 A1 | 2/2014 | Marino et al. |
| 2014/0038781 A1 | 2/2014 | Foley et al. |
| 2014/0046926 A1 | 2/2014 | Walton |
| 2014/0073486 A1 | 3/2014 | Ahmed et al. |
| 2014/0081118 A1 | 3/2014 | Reinhold, Jr. et al. |
| 2014/0088995 A1 | 3/2014 | Damani |
| 2014/0100885 A1 | 4/2014 | Stern |
| 2014/0127996 A1 | 5/2014 | Park et al. |
| 2014/0129007 A1 | 5/2014 | Utter, II |
| 2014/0129243 A1 | 5/2014 | Utter, II |
| 2014/0135592 A1 | 5/2014 | Ohnemus et al. |
| 2014/0142403 A1 | 5/2014 | Brumback et al. |
| 2014/0143678 A1 | 5/2014 | Mistry et al. |
| 2014/0164611 A1 | 6/2014 | Molettiere et al. |
| 2014/0173521 A1 | 6/2014 | Mayor |
| 2014/0176335 A1 | 6/2014 | Brumback et al. |
| 2014/0176475 A1 | 6/2014 | Myers et al. |
| 2014/0180595 A1 | 6/2014 | Brumback et al. |
| 2014/0184422 A1 | 7/2014 | Mensinger et al. |
| 2014/0189510 A1 | 7/2014 | Ozcan |
| 2014/0197946 A1 | 7/2014 | Park et al. |
| 2014/0200426 A1 | 7/2014 | Taub et al. |
| 2014/0240122 A1 | 8/2014 | Roberts et al. |
| 2014/0240349 A1 | 8/2014 | Tuukkanen |
| 2014/0266776 A1 | 9/2014 | Miller et al. |
| 2014/0275852 A1 | 9/2014 | Hong et al. |
| 2014/0275856 A1 | 9/2014 | Kohlrausch et al. |
| 2014/0278220 A1 | 9/2014 | Yuen |
| 2014/0288390 A1 | 9/2014 | Hong et al. |
| 2014/0297217 A1 | 10/2014 | Yuen |
| 2014/0327527 A1 | 11/2014 | Goldstein et al. |
| 2014/0336796 A1 | 11/2014 | Agnew |
| 2014/0344687 A1 | 11/2014 | Durham et al. |
| 2014/0354494 A1 | 12/2014 | Katz |
| 2014/0358012 A1 | 12/2014 | Richards et al. |
| 2014/0371887 A1 | 12/2014 | Hoffman et al. |
| 2015/0057942 A1 | 2/2015 | Self et al. |
| 2015/0073285 A1 | 3/2015 | Albert et al. |
| 2015/0081210 A1 | 3/2015 | Yeh et al. |
| 2015/0089536 A1 | 3/2015 | Byerley |
| 2015/0099991 A1 | 4/2015 | Yamaguchi et al. |
| 2015/0100348 A1 | 4/2015 | Connery et al. |
| 2015/0106025 A1 | 4/2015 | Keller et al. |
| 2015/0110277 A1 | 4/2015 | Pidgeon et al. |
| 2015/0110279 A1 | 4/2015 | Tejerina |
| 2015/0120633 A1 | 4/2015 | Norlander et al. |
| 2015/0124067 A1 | 5/2015 | Bala et al. |
| 2015/0125832 A1 | 5/2015 | Tran |
| 2015/0127365 A1 | 5/2015 | Rizvi et al. |
| 2015/0142689 A1 | 5/2015 | Squires |
| 2015/0164349 A1 | 6/2015 | Gopalakrishnan et al. |
| 2015/0173686 A1 | 6/2015 | Furuta et al. |
| 2015/0179186 A1 | 6/2015 | Swierk et al. |
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0193217 A1 | 7/2015 | Xiang et al. |
| 2015/0196804 A1 | 7/2015 | Koduri et al. |
| 2015/0205947 A1 | 7/2015 | Berman et al. |
| 2015/0216448 A1 | 8/2015 | Lotan et al. |
| 2015/0217163 A1 | 8/2015 | Amis et al. |
| 2015/0220883 A1 | 8/2015 | Bfar et al. |
| 2015/0230717 A1 | 8/2015 | Wan |
| 2015/0261918 A1 | 9/2015 | Thornbury, Jr. |
| 2015/0262499 A1 | 9/2015 | Wicka et al. |
| 2015/0286800 A1 | 10/2015 | Kanagala et al. |
| 2015/0287421 A1 | 10/2015 | Benway et al. |
| 2015/0288797 A1 | 10/2015 | Vincent |
| 2015/0288944 A1 | 10/2015 | Nistico et al. |
| 2015/0289823 A1 | 10/2015 | Rack-gomer et al. |
| 2015/0297134 A1 | 10/2015 | Albert et al. |
| 2015/0324751 A1 | 11/2015 | Orenstein et al. |
| 2015/0347690 A1 | 12/2015 | Keen et al. |
| 2015/0347711 A1 | 12/2015 | Soli et al. |
| 2015/0350799 A1 | 12/2015 | Schnaare et al. |
| 2015/0350861 A1 | 12/2015 | Soli et al. |

(56) References Cited

U.S. PATENT DOCUMENTS

| | | |
|---|---|---|
| 2016/0000379 A1 | 1/2016 | Pougatchev et al. |
| 2016/0019360 A1 | 1/2016 | Pahwa et al. |
| 2016/0055420 A1 | 2/2016 | Karanam et al. |
| 2016/0058313 A1 | 3/2016 | Sato |
| 2016/0058336 A1 | 3/2016 | Blahnik et al. |
| 2016/0058337 A1 | 3/2016 | Blahnik et al. |
| 2016/0062540 A1 | 3/2016 | Yang et al. |
| 2016/0062582 A1 | 3/2016 | Wilson et al. |
| 2016/0063215 A1 | 3/2016 | Zamer |
| 2016/0066842 A1 | 3/2016 | Kokkoneva et al. |
| 2016/0085937 A1 | 3/2016 | Dettinger et al. |
| 2016/0086500 A1 | 3/2016 | Kaleal, III |
| 2016/0089569 A1 | 3/2016 | Blahnik |
| 2016/0098522 A1 | 4/2016 | Weinstein |
| 2016/0103985 A1 | 4/2016 | Shim et al. |
| 2016/0106398 A1 | 4/2016 | Kuppuswami |
| 2016/0109961 A1 | 4/2016 | Parshionikar |
| 2016/0110523 A1 | 4/2016 | Francois |
| 2016/0132046 A1 | 5/2016 | Beoughter et al. |
| 2016/0132645 A1 | 5/2016 | Charpentier et al. |
| 2016/0135719 A1 | 5/2016 | Von Kraus et al. |
| 2016/0135731 A1 | 5/2016 | Drennan |
| 2016/0150978 A1 | 6/2016 | Yuen et al. |
| 2016/0166181 A1 | 6/2016 | Shennib |
| 2016/0166195 A1 | 6/2016 | Radecka et al. |
| 2016/0174857 A1 | 6/2016 | Eggers et al. |
| 2016/0180026 A1 | 6/2016 | Kim et al. |
| 2016/0189051 A1 | 6/2016 | Mahmood |
| 2016/0196635 A1 | 7/2016 | Cho et al. |
| 2016/0210099 A1 | 7/2016 | Hampapuram et al. |
| 2016/0210434 A1 | 7/2016 | Al-sharif |
| 2016/0235325 A1 | 8/2016 | Chou |
| 2016/0235374 A1 | 8/2016 | Miller et al. |
| 2016/0249857 A1 | 9/2016 | Choi et al. |
| 2016/0250517 A1 | 9/2016 | Tilvis et al. |
| 2016/0256082 A1 | 9/2016 | Ely et al. |
| 2016/0263435 A1 | 9/2016 | Venkatraman et al. |
| 2016/0270717 A1 | 9/2016 | Luna et al. |
| 2016/0270740 A1 | 9/2016 | Raisoni et al. |
| 2016/0275310 A1 | 9/2016 | Tribble et al. |
| 2016/0275990 A1 | 9/2016 | Vassort |
| 2016/0285985 A1 | 9/2016 | Molettiere et al. |
| 2016/0287177 A1 | 10/2016 | Huppert et al. |
| 2016/0292373 A1 | 10/2016 | Spors et al. |
| 2016/0296210 A1 | 10/2016 | Matsushima |
| 2016/0301761 A1 | 10/2016 | Sanchez-sandoval et al. |
| 2016/0301794 A1 | 10/2016 | Schlakman et al. |
| 2016/0302666 A1 | 10/2016 | Shaya |
| 2016/0313869 A1 | 10/2016 | Jang et al. |
| 2016/0314670 A1 | 10/2016 | Roberts et al. |
| 2016/0314683 A1 | 10/2016 | Felch et al. |
| 2016/0317341 A1 | 11/2016 | Galvan |
| 2016/0324457 A1 | 11/2016 | Dagum |
| 2016/0324488 A1 | 11/2016 | Olsen |
| 2016/0328991 A1 | 11/2016 | Simpson et al. |
| 2016/0332025 A1 | 11/2016 | Repka |
| 2016/0346607 A1 | 12/2016 | Rapfogel |
| 2016/0357403 A1 | 12/2016 | Chang et al. |
| 2016/0357616 A1 | 12/2016 | Yu et al. |
| 2016/0360100 A1 | 12/2016 | Kim et al. |
| 2016/0360972 A1 | 12/2016 | Kusakabe et al. |
| 2016/0367138 A1 | 12/2016 | Kim et al. |
| 2017/0000348 A1 | 1/2017 | Karsten et al. |
| 2017/0000359 A1 | 1/2017 | Kohli et al. |
| 2017/0007159 A1 | 1/2017 | Dieffenderfer et al. |
| 2017/0007167 A1 | 1/2017 | Kostic et al. |
| 2017/0032168 A1 | 2/2017 | Kim |
| 2017/0039327 A1 | 2/2017 | Bitran et al. |
| 2017/0042485 A1 | 2/2017 | Chung et al. |
| 2017/0043214 A1 | 2/2017 | Higashi |
| 2017/0046024 A1 | 2/2017 | Dascola et al. |
| 2017/0046052 A1 | 2/2017 | Lee et al. |
| 2017/0053542 A1 | 2/2017 | Wilson et al. |
| 2017/0070833 A1 | 3/2017 | Shennib |
| 2017/0071551 A1 | 3/2017 | Jain et al. |
| 2017/0075551 A1 | 3/2017 | Robinson et al. |
| 2017/0084196 A1 | 3/2017 | Nusbaum et al. |
| 2017/0086693 A1 | 3/2017 | Peterson et al. |
| 2017/0091567 A1 | 3/2017 | Wang et al. |
| 2017/0127997 A1 | 5/2017 | Hyde et al. |
| 2017/0132395 A1 | 5/2017 | Futch |
| 2017/0136297 A1 | 5/2017 | Penie |
| 2017/0147197 A1 | 5/2017 | Yang et al. |
| 2017/0150917 A1 | 6/2017 | Brief et al. |
| 2017/0156593 A1 | 6/2017 | Ferber et al. |
| 2017/0161014 A1 | 6/2017 | Kikugawa et al. |
| 2017/0172522 A1 | 6/2017 | Insler et al. |
| 2017/0177797 A1 | 6/2017 | Kurniawan et al. |
| 2017/0181645 A1 | 6/2017 | Mahalingam et al. |
| 2017/0181678 A1 | 6/2017 | Newberry |
| 2017/0188841 A1 | 7/2017 | Ma et al. |
| 2017/0188893 A1 | 7/2017 | Venkatraman et al. |
| 2017/0188979 A1 | 7/2017 | Volpe |
| 2017/0202496 A1 | 7/2017 | Ramanathan |
| 2017/0215811 A1 | 8/2017 | Newberry |
| 2017/0225034 A1 | 8/2017 | Kass et al. |
| 2017/0235443 A1 | 8/2017 | Suzuki |
| 2017/0237694 A1 | 8/2017 | Choudhary et al. |
| 2017/0243508 A1 | 8/2017 | Cheng et al. |
| 2017/0258455 A1 | 9/2017 | Qi |
| 2017/0274149 A1 | 9/2017 | Aeschlimann |
| 2017/0274267 A1 | 9/2017 | Blahnik |
| 2017/0287313 A1 | 10/2017 | Park et al. |
| 2017/0293727 A1 | 10/2017 | Klaassen et al. |
| 2017/0294174 A1 | 10/2017 | Albadawi et al. |
| 2017/0300186 A1 | 10/2017 | Kuhar et al. |
| 2017/0300643 A1 | 10/2017 | Bezark et al. |
| 2017/0303844 A1 | 10/2017 | Baker et al. |
| 2017/0319184 A1 | 11/2017 | Sano |
| 2017/0329933 A1 | 11/2017 | Brust et al. |
| 2017/0330297 A1 | 11/2017 | Cronin et al. |
| 2017/0332980 A1 | 11/2017 | Fifield et al. |
| 2017/0348562 A1 | 12/2017 | Jung et al. |
| 2017/0354845 A1 | 12/2017 | Williams et al. |
| 2017/0357329 A1 | 12/2017 | Park et al. |
| 2017/0357520 A1 | 12/2017 | De Vries et al. |
| 2017/0364637 A1 | 12/2017 | Kshepakaran et al. |
| 2018/0000426 A1 | 1/2018 | Li |
| 2018/0001184 A1 | 1/2018 | Tran et al. |
| 2018/0011686 A1 | 1/2018 | Zhao et al. |
| 2018/0014121 A1 | 1/2018 | Lawrence et al. |
| 2018/0032234 A1 | 2/2018 | Michalske |
| 2018/0039410 A1 | 2/2018 | Kim et al. |
| 2018/0042559 A1 | 2/2018 | Cabrera et al. |
| 2018/0047277 A1 | 2/2018 | Thyroff |
| 2018/0049689 A1 | 2/2018 | Chung et al. |
| 2018/0049696 A1 | 2/2018 | Eom et al. |
| 2018/0055490 A1 | 3/2018 | Lee et al. |
| 2018/0056130 A1 | 3/2018 | Bitran et al. |
| 2018/0060522 A1 | 3/2018 | Petterson et al. |
| 2018/0064356 A1 | 3/2018 | Mendenhall et al. |
| 2018/0064388 A1 | 3/2018 | Heneghan et al. |
| 2018/0065025 A1 | 3/2018 | Toda et al. |
| 2018/0070861 A1 | 3/2018 | Eastman et al. |
| 2018/0074462 A1 | 3/2018 | Helder et al. |
| 2018/0074464 A1 | 3/2018 | Essery et al. |
| 2018/0081918 A1 | 3/2018 | Gravenites et al. |
| 2018/0096739 A1 | 4/2018 | Sano |
| 2018/0107962 A1 | 4/2018 | Lundin et al. |
| 2018/0110465 A1 | 4/2018 | Naima |
| 2018/0117414 A1 | 5/2018 | Miyasaka et al. |
| 2018/0120985 A1 | 5/2018 | Wallace et al. |
| 2018/0122214 A1 | 5/2018 | Freedman et al. |
| 2018/0129994 A1* | 5/2018 | Fowler et al. .. G06Q 10/063116 |
| 2018/0132768 A1 | 5/2018 | Sasahara et al. |
| 2018/0137937 A1 | 5/2018 | Gass et al. |
| 2018/0140211 A1 | 5/2018 | Nakazawa et al. |
| 2018/0140927 A1 | 5/2018 | Kito et al. |
| 2018/0154212 A1 | 6/2018 | Park et al. |
| 2018/0157864 A1 | 6/2018 | Tribble et al. |
| 2018/0189077 A1 | 7/2018 | Gupta et al. |
| 2018/0189343 A1 | 7/2018 | Embiricos et al. |
| 2018/0211020 A1 | 7/2018 | Fukuda |
| 2018/0226150 A1 | 8/2018 | Hayter et al. |

(56) References Cited

U.S. PATENT DOCUMENTS

| | | |
|---|---|---|
| 2018/0239869 A1 | 8/2018 | Laing et al. |
| 2018/0255159 A1 | 9/2018 | Cohen et al. |
| 2018/0256036 A1 | 9/2018 | Kogure et al. |
| 2018/0256078 A1 | 9/2018 | Vaterlaus |
| 2018/0256095 A1 | 9/2018 | Arnold et al. |
| 2018/0263510 A1 | 9/2018 | Cronin et al. |
| 2018/0263517 A1 | 9/2018 | Kubo |
| 2018/0279885 A1 | 10/2018 | Bulut |
| 2018/0329584 A1 | 11/2018 | Williams et al. |
| 2018/0336530 A1 | 11/2018 | Johnson et al. |
| 2018/0350451 A1 | 12/2018 | Ohnemus et al. |
| 2018/0368814 A1 | 12/2018 | R. Kudtarkar |
| 2018/0376107 A1 | 12/2018 | Shibaev et al. |
| 2019/0012898 A1 | 1/2019 | Wittrup |
| 2019/0014205 A1 | 1/2019 | Miloseski et al. |
| 2019/0018588 A1 | 1/2019 | Debates et al. |
| 2019/0034050 A1 | 1/2019 | Williams et al. |
| 2019/0034494 A1 | 1/2019 | Bradley et al. |
| 2019/0043337 A1 | 2/2019 | Liu et al. |
| 2019/0073618 A1 | 3/2019 | Kanukurthy et al. |
| 2019/0090800 A1 | 3/2019 | Bosworth et al. |
| 2019/0090816 A1 | 3/2019 | Horseman |
| 2019/0104951 A1 | 4/2019 | Valys et al. |
| 2019/0108908 A1 | 4/2019 | Faulks et al. |
| 2019/0122523 A1 | 4/2019 | Roberts et al. |
| 2019/0138696 A1 | 5/2019 | Carpenter et al. |
| 2019/0150854 A1 | 5/2019 | Chung et al. |
| 2019/0192086 A1 | 6/2019 | Menon et al. |
| 2019/0206538 A1 | 7/2019 | Xing et al. |
| 2019/0223843 A1 | 7/2019 | Vitti |
| 2019/0228179 A1 | 7/2019 | Rakshit et al. |
| 2019/0228640 A1 | 7/2019 | Freedman et al. |
| 2019/0228847 A1 | 7/2019 | Soli |
| 2019/0240534 A1 | 8/2019 | Black |
| 2019/0252054 A1 | 8/2019 | Dirani et al. |
| 2019/0274562 A1 | 9/2019 | Soli et al. |
| 2019/0274563 A1 | 9/2019 | Soli et al. |
| 2019/0274564 A1 | 9/2019 | Soli et al. |
| 2019/0274565 A1 | 9/2019 | Soli et al. |
| 2019/0278556 A1 | 9/2019 | Usher et al. |
| 2019/0298230 A1 | 10/2019 | Nicholson et al. |
| 2019/0302995 A1 | 10/2019 | Robinson et al. |
| 2019/0313180 A1 | 10/2019 | Kadiwala et al. |
| 2019/0333614 A1 | 10/2019 | Burger et al. |
| 2019/0336044 A1 | 11/2019 | Williams et al. |
| 2019/0336045 A1 | 11/2019 | Williams et al. |
| 2019/0339849 A1 | 11/2019 | Williams et al. |
| 2019/0341027 A1 | 11/2019 | Vescovi et al. |
| 2019/0365332 A1 | 12/2019 | Fedichev et al. |
| 2019/0380624 A1 | 12/2019 | Ota et al. |
| 2019/0385708 A1 | 12/2019 | Hong et al. |
| 2020/0000441 A1 | 1/2020 | Lafon et al. |
| 2020/0054931 A1 | 2/2020 | Martin et al. |
| 2020/0069258 A1 | 3/2020 | Grinberg |
| 2020/0100693 A1 | 4/2020 | Velo |
| 2020/0126673 A1 | 4/2020 | Tanabe et al. |
| 2020/0203012 A1 | 6/2020 | Kamath et al. |
| 2020/0214650 A1 | 7/2020 | Lee et al. |
| 2020/0245928 A1 | 8/2020 | Kang et al. |
| 2020/0261011 A1 | 8/2020 | Seppänen et al. |
| 2020/0273566 A1 | 8/2020 | Bhowmik et al. |
| 2020/0297249 A1 | 9/2020 | Williams et al. |
| 2020/0315544 A1 | 10/2020 | Levine |
| 2020/0323441 A1 | 10/2020 | Deno et al. |
| 2020/0350052 A1 | 11/2020 | Saint et al. |
| 2020/0356687 A1 | 11/2020 | Salzman et al. |
| 2020/0374682 A1 | 11/2020 | Newman et al. |
| 2020/0379611 A1 | 12/2020 | Dryer et al. |
| 2020/0381099 A1 | 12/2020 | Crowley et al. |
| 2020/0381123 A1 | 12/2020 | Dryer et al. |
| 2020/0382866 A1 | 12/2020 | Felton |
| 2020/0382867 A1 | 12/2020 | Felton |
| 2020/0384314 A1 | 12/2020 | Lee et al. |
| 2021/0019713 A1* | 1/2021 | Vangala et al. .... G06Q 10/1093 |
| 2021/0068714 A1 | 3/2021 | Crowley et al. |
| 2021/0113137 A1 | 4/2021 | Soli et al. |
| 2021/0204815 A1 | 7/2021 | Koskela et al. |
| 2021/0225482 A1 | 7/2021 | Crowley et al. |
| 2021/0257091 A1 | 8/2021 | Spang et al. |
| 2021/0287520 A1 | 9/2021 | Maeda et al. |
| 2021/0369130 A1 | 12/2021 | Felton et al. |
| 2021/0373746 A1 | 12/2021 | Felton et al. |
| 2021/0373747 A1 | 12/2021 | Felton et al. |
| 2021/0373748 A1 | 12/2021 | Felton et al. |
| 2021/0375157 A1 | 12/2021 | Sundstrom et al. |
| 2021/0375450 A1 | 12/2021 | Felton et al. |
| 2021/0401378 A1 | 12/2021 | Pho et al. |
| 2022/0047250 A1 | 2/2022 | Clements et al. |
| 2022/0066902 A1 | 3/2022 | Narra et al. |
| 2022/0109932 A1 | 4/2022 | Felton et al. |
| 2022/0157143 A1 | 5/2022 | Panneer Selvam et al. |
| 2022/0160258 A1 | 5/2022 | Williams et al. |
| 2022/0273204 A1 | 9/2022 | Kamath et al. |
| 2023/0016144 A1 | 1/2023 | Dryer et al. |
| 2023/0020517 A1 | 1/2023 | Narra et al. |
| 2023/0101625 A1 | 3/2023 | Soli et al. |
| 2023/0114054 A1 | 4/2023 | Crowley et al. |
| 2024/0013889 A1 | 1/2024 | Crowley et al. |
| 2024/0050016 A1 | 2/2024 | Soli et al. |
| 2024/0053862 A1 | 2/2024 | Narra et al. |

FOREIGN PATENT DOCUMENTS

| | | |
|---|---|---|
| CN | 101107619 A | 1/2008 |
| CN | 102448555 A | 5/2012 |
| CN | 102790761 A | 11/2012 |
| CN | 103474080 A | 12/2012 |
| CN | 103191557 A | 7/2013 |
| CN | 103250158 A | 8/2013 |
| CN | 103403627 A | 11/2013 |
| CN | 103561640 A | 2/2014 |
| CN | 103927175 A | 7/2014 |
| CN | 103986813 A | 8/2014 |
| CN | 104584020 A | 4/2015 |
| CN | 104680459 A | 6/2015 |
| CN | 104720765 A | 6/2015 |
| CN | 105260078 A | 1/2016 |
| CN | 105283840 A | 1/2016 |
| CN | 105388998 A | 3/2016 |
| CN | 105632508 A | 6/2016 |
| CN | 105721667 A | 6/2016 |
| CN | 105980008 A | 9/2016 |
| CN | 106164808 A | 11/2016 |
| CN | 106371816 A | 2/2017 |
| CN | 106415559 A | 2/2017 |
| CN | 106537397 A | 3/2017 |
| CN | 106709235 A | 5/2017 |
| CN | 106725384 A | 5/2017 |
| CN | 106901720 A | 6/2017 |
| CN | 107278138 A | 10/2017 |
| CN | 107361755 A | 11/2017 |
| CN | 107454831 A | 12/2017 |
| CN | 107508995 A | 12/2017 |
| CN | 107545930 A | 1/2018 |
| CN | 107591211 A | 1/2018 |
| CN | 107713981 A | 2/2018 |
| CN | 108604327 A | 9/2018 |
| CN | 109287140 A | 1/2019 |
| CN | 109670007 A | 4/2019 |
| CN | 111344796 A | 6/2020 |
| DE | 202017002874 U1 | 9/2017 |
| EP | 1077046 A1 | 2/2001 |
| EP | 2391004 A1 | 11/2011 |
| EP | 2568409 A1 | 3/2013 |
| EP | 2921899 A2 | 9/2015 |
| EP | 3042606 A1 | 7/2016 |
| EP | 3096235 A1 | 11/2016 |
| EP | 3101882 A2 | 12/2016 |
| EP | 3557590 A1 | 10/2019 |
| JP | 2004-80496 A | 3/2004 |
| JP | 2004318503 A | 11/2004 |
| JP | 2005-79814 A | 3/2005 |
| JP | 2006-107136 A | 4/2006 |
| JP | 2008-11865 A | 1/2008 |

(56) References Cited

FOREIGN PATENT DOCUMENTS

| | | |
|---|---|---|
| JP | 2009-232301 A | 10/2009 |
| JP | 2009-238571 A | 11/2009 |
| JP | 2010-517725 A | 5/2010 |
| JP | 2010-122901 A | 6/2010 |
| JP | 2010-162297 A | 7/2010 |
| JP | 2010-181280 A | 8/2010 |
| JP | 2011-197992 A | 10/2011 |
| JP | 2011-200575 A | 10/2011 |
| JP | 2012-502343 A | 1/2012 |
| JP | 2012-45373 A | 3/2012 |
| JP | 2012-59264 A | 3/2012 |
| JP | 2012-524640 A | 10/2012 |
| JP | 2012-239808 A | 12/2012 |
| JP | 2013-17631 A | 1/2013 |
| JP | 2013-192608 A | 9/2013 |
| JP | 2013-207323 A | 10/2013 |
| JP | 2013-544140 A | 12/2013 |
| JP | 2015-28686 A | 2/2015 |
| JP | 2015-73590 A | 4/2015 |
| JP | 2015-213686 A | 12/2015 |
| JP | 2016-502875 A | 2/2016 |
| JP | 2016-528016 A | 9/2016 |
| JP | 2016-177151 A | 10/2016 |
| JP | 2016-202751 A | 12/2016 |
| JP | 2016-538926 A | 12/2016 |
| JP | 2017-40981 A | 2/2017 |
| JP | 2017-117265 A | 6/2017 |
| JP | 2017-515520 A | 6/2017 |
| JP | 2017-134689 A | 8/2017 |
| JP | 2017-526073 A | 9/2017 |
| JP | 2017-182393 A | 10/2017 |
| JP | 2017-529880 A | 10/2017 |
| JP | 2017-211994 A | 11/2017 |
| JP | 2017-532069 A | 11/2017 |
| JP | 2018-504660 A | 2/2018 |
| JP | 2018-523554 A | 8/2018 |
| JP | 6382433 B1 | 8/2018 |
| JP | 2018-191122 A | 11/2018 |
| JP | 2019-28806 A | 2/2019 |
| JP | 2019-32461 A | 2/2019 |
| JP | 2019-505035 A | 2/2019 |
| JP | 2019-36226 A | 3/2019 |
| JP | 2019-55076 A | 4/2019 |
| JP | 2019-207536 A | 12/2019 |
| JP | 2020-651 A | 1/2020 |
| JP | 2021-512429 A | 5/2021 |
| KR | 10-2002-0060421 A | 7/2002 |
| KR | 10-2008-0051460 A | 6/2008 |
| KR | 10-2012-0023657 A | 3/2012 |
| KR | 10-2013-0093837 A | 8/2013 |
| KR | 10-2013-0111569 A | 10/2013 |
| KR | 10-2013-0111570 A | 10/2013 |
| KR | 10-2015-0115385 A | 10/2015 |
| KR | 10-1594486 B1 | 2/2016 |
| KR | 10-2016-0028351 A | 3/2016 |
| KR | 10-2016-0076264 A | 6/2016 |
| KR | 10-2016-0077199 A | 7/2016 |
| KR | 10-2017-0003608 A | 1/2017 |
| KR | 10-2017-0019040 A | 2/2017 |
| KR | 10-2017-0019745 A | 2/2017 |
| KR | 10-2017-0029014 A | 3/2017 |
| KR | 10-2018-0129188 A | 12/2018 |
| KR | 10-2019-0094795 A | 8/2019 |
| WO | 2001/096986 A2 | 12/2001 |
| WO | 02/41134 A2 | 5/2002 |
| WO | 2003/067202 A2 | 8/2003 |
| WO | 2006/046648 A1 | 5/2006 |
| WO | 2008/073359 A2 | 6/2008 |
| WO | 2009/095908 A2 | 8/2009 |
| WO | 2010/028320 A1 | 3/2010 |
| WO | 2010/126825 A1 | 11/2010 |
| WO | 2012/048832 A1 | 4/2012 |
| WO | 2012/060588 A2 | 5/2012 |
| WO | 2012/061440 A2 | 5/2012 |
| WO | 2012061438 A2 | 5/2012 |
| WO | 2013/103570 A1 | 7/2013 |
| WO | 2013/109916 A1 | 7/2013 |
| WO | 2014/006862 A1 | 1/2014 |
| WO | 2014/015378 A1 | 1/2014 |
| WO | 2014/033673 A1 | 3/2014 |
| WO | 2014/197339 A1 | 12/2014 |
| WO | 2014/207875 A1 | 12/2014 |
| WO | 2015/027133 A1 | 2/2015 |
| WO | 2015/084353 A1 | 6/2015 |
| WO | 2015/153803 A1 | 10/2015 |
| WO | 2015/164845 A1 | 10/2015 |
| WO | 2015/183828 A1 | 12/2015 |
| WO | 2015/187799 A1 | 12/2015 |
| WO | 2015/198488 A1 | 12/2015 |
| WO | 2016/036472 A1 | 3/2016 |
| WO | 2016/036582 A2 | 3/2016 |
| WO | 2016/151479 A1 | 9/2016 |
| WO | 2016/161152 A1 | 10/2016 |
| WO | 2016/164475 A1 | 10/2016 |
| WO | 2016/179559 A2 | 11/2016 |
| WO | 2016/207745 A1 | 12/2016 |
| WO | 2017/003045 A1 | 1/2017 |
| WO | 2017/037242 A1 | 3/2017 |
| WO | 2017/054277 A1 | 4/2017 |
| WO | 2017/062621 A1 | 4/2017 |
| WO | 2017/087642 A1 | 5/2017 |
| WO | 2017/090810 A1 | 6/2017 |
| WO | 2017/172046 A1 | 10/2017 |
| WO | 2017/215203 A1 | 12/2017 |
| WO | 2018/132507 A1 | 7/2018 |
| WO | 2018/148356 A1 | 8/2018 |
| WO | 2018/213401 A1 | 11/2018 |
| WO | 2019/020977 A1 | 1/2019 |
| WO | 2019/099553 A1 | 5/2019 |
| WO | 2019/168956 A1 | 9/2019 |
| WO | 2019/177769 A1 | 9/2019 |
| WO | 2019/240513 A1 | 12/2019 |
| WO | 2021/212112 A1 | 10/2021 |
| WO | 2022/010573 A1 | 1/2022 |

OTHER PUBLICATIONS

International Preliminary Report on Patentability received for PCT Patent Application No. PCT/US2021/035504, mailed on Dec. 15, 2022, 8 pages.
Office Action received for Australian Patent Application No. 2020313970, mailed on Dec. 22, 2022, 3 pages.
Office Action received for Japanese Patent Application No. 2021-192437, mailed on Dec. 16, 2022, 4 pages (2 pages of English Translation and 2 pages of Official Copy).
Notice of Allowance received for Japanese Patent Application No. 2022-078280, mailed on Sep. 4, 2023, 4 pages (1 page of English Translation and 3 pages of Official Copy).
Notice of Allowance received for U.S. Appl. No. 18/078,444, mailed on Aug. 31, 2023, 6 pages.
Office Action received for Australian Patent Application No. 2023212604, mailed on Sep. 4, 2023, 3 pages.
Applicant-Initiated Interview Summary received for U.S. Appl. No. 16/249,627, mailed on Mar. 23, 2022, 3 pages.
Applicant-Initiated Interview Summary received for U.S. Appl. No. 17/031,723, mailed on Mar. 21, 2021, 5 pages.
Applicant-Initiated Interview Summary received for U.S. Appl. No. 17/031,779, mailed on Mar. 10, 2022, 2 pages.
Brief Communication Regarding Oral Proceedings received for European Patent Application No. 20182116.2, mailed on Apr. 13, 2022, 3 pages.
Corrected Notice of Allowance received for U.S. Appl. No. 17/031,717, mailed on Apr. 15, 2022, 3 pages.
Decision to Refuse received for European Patent Application No. 20180581.9, mailed on Apr. 13, 2022, 16 pages.
Intention to Grant received for European Patent Application No. 20180592.6, mailed on Apr. 20, 2022, 21 pages.
International Preliminary Report on Patentability received for PCT Patent Application No. PCT/US2020/070280, mailed on Mar. 17, 2022, 15 pages.

(56) References Cited

OTHER PUBLICATIONS

International Search Report and Written Opinion received for PCT Patent Application No. PCT/US2021/048568, mailed on Jan. 7, 2022, 14 pages.
Minutes of the Oral Proceedings received for European Patent Application No. 20180581.9, mailed on Apr. 13, 2022, 10 pages.
Minutes of the Oral Proceedings received for European Patent Application No. 20180592.6, mailed on Apr. 7, 2022, 10 pages.
Non-Final Office Action received for U.S. Appl. No. 16/888,780, mailed on Apr. 20, 2022, 22 pages.
Non-Final Office Action received for U.S. Appl. No. 17/041,415, mailed on Mar. 29, 2022, 11 pages.
Notice of Acceptance received for Australian Patent Application No. 2020239692, mailed on Apr. 6, 2022, 3 pages.
Notice of Acceptance received for Australian Patent Application No. 2020239740, mailed on Feb. 22, 2022., 3 pages.
Notice of Acceptance received for Japanese Patent Application No. 2020-160023, mailed on Apr. 11, 2022, 4 pages (1 page of English Translation and 3 pages of Official Copy).
Notice of Acceptance received for Japanese Patent Application No. 2021-571467, mailed on Apr. 11, 2022, 4 pages (1 page of English Translation and 3 pages of Official Copy).
Notice of Allowance received for U.S. Appl. No. 17/031,717, mailed on Mar. 16, 2022, 12 pages.
Supplemental Notice of Allowance received for U.S. Appl. No. 16/894,309, mailed on Apr. 8, 2022, 3 pages.
Advisory Action received for U.S. Appl. No. 16/144,864, mailed on Jul. 29, 2019, 6 pages.
Advisory Action received for U.S. Appl. No. 16/143,909, mailed on Nov. 7, 2019, 5 pages.
Advisory Action received for U.S. Appl. No. 16/143,997, mailed on Dec. 26, 2019, 7 pages.
Advisory Action received for U.S. Appl. No. 16/144,849, mailed on Aug. 12, 2019, 5 pages.
Advisory Action received for U.S. Appl. No. 16/144,864, mailed on Jul. 6, 2020, 6 pages.
Applicant-Initiated Interview Summary received for U.S. Appl. No. 16/138,809, mailed on Dec. 16, 2020, 7 pages.
Applicant-Initiated Interview Summary received for U.S. Appl. No. 16/138,809, mailed on Jun. 9, 2020, 4 pages.
Applicant-Initiated Interview Summary received for U.S. Appl. No. 16/143,997, mailed on Aug. 13, 2020, 3 pages.
Applicant-Initiated Interview Summary received for U.S. Appl. No. 16/143,997, mailed on May 3, 2021, 4 pages.
Applicant-Initiated Interview Summary received for U.S. Appl. No. 16/144,849, mailed on Jan. 21, 2020, 6 pages.
Applicant-Initiated Interview Summary received for U.S. Appl. No. 16/144,864, mailed on Apr. 29, 2020, 4 pages.
Applicant-Initiated Interview Summary received for U.S. Appl. No. 16/144,864, mailed on Jun. 22, 2020, 3 pages.
Applicant-Initiated Interview Summary received for U.S. Appl. No. 16/249,627, mailed on Jun. 2, 2021, 5 pages.
Applicant-Initiated Interview Summary received for U.S. Appl. No. 16/249,627, mailed on Oct. 6, 2021, 4 pages.
Applicant-Initiated Interview Summary received for U.S. Appl. No. 16/584,186, mailed on Feb. 3, 2020, 4 pages.
Applicant-Initiated Interview Summary received for U.S. Appl. No. 16/584,154, mailed on Apr. 14, 2021, 4 pages.
Applicant-Initiated Interview Summary received for U.S. Appl. No. 16/584,154, mailed on Dec. 11, 2020, 5 pages.
Applicant-Initiated Interview Summary received for U.S. Appl. No. 16/584,154, mailed on Mar. 11, 2020, 4 pages.
Applicant-Initiated Interview Summary received for U.S. Appl. No. 16/584,154, mailed on Sep. 3, 2021, 4 pages.
Applicant-Initiated Interview Summary received for U.S. Appl. No. 16/880,552, mailed on Apr. 21, 2021, 3 pages.
Applicant-Initiated Interview Summary received for U.S. Appl. No. 16/880,552, mailed on Dec. 16, 2020, 6 pages.
Applicant-Initiated Interview Summary received for U.S. Appl. No. 16/880,552, mailed on Oct. 20, 2020, 6 pages.
Applicant-Initiated Interview Summary received for U.S. Appl. No. 16/880,714, mailed on Feb. 26, 2021, 5 pages.
Applicant-Initiated Interview Summary received for U.S. Appl. No. 16/894,309, mailed on Jan. 26, 2021, 3 pages.
Applicant-Initiated Interview Summary received for U.S. Appl. No. 16/894,309, mailed on Jun. 25, 2021, 4 pages.
Applicant-Initiated Interview Summary received for U.S. Appl. No. 16/907,261, mailed on Dec. 16, 2020, 6 pages.
Applicant-Initiated Interview Summary received for U.S. Appl. No. 16/907,261, mailed on Jul. 16, 2021, 10 pages.
Applicant-Initiated Interview Summary received for U.S. Appl. No. 16/907,261, mailed on Mar. 25, 2021, 2 pages.
Applicant-Initiated Interview Summary received for U.S. Appl. No. 17/031,704, mailed on Feb. 9, 2021, 3 pages.
Applicant-Initiated Interview Summary received for U.S. Appl. No. 17/031,704, mailed on Jun. 25, 2021, 3 pages.
Applicant-Initiated Interview Summary received for U.S. Appl. No. 17/031,717, mailed on Jan. 29, 2021, 5 pages.
Applicant-Initiated Interview Summary received for U.S. Appl. No. 17/031,717, mailed on May 17, 2021, 5 pages.
Applicant-Initiated Interview Summary received for U.S. Appl. No. 17/031,717, mailed on Nov. 4, 2021, 5 pages.
Brief Communication Regarding Oral Proceedings received for European Patent Application No. 13812320.3, mailed on Sep. 16, 2021, 2 pages.
Brief Communication Regarding Oral Proceedings received for European Patent Application No. 20180581.9, mailed on Nov. 30, 2021, 1 page.
Brief Communication Regarding Oral Proceedings received for European Patent Application No. 20180592.6, mailed on Dec. 21, 2021, 1 page.
Casella Cel Casella, "The Casella dBadge2—World's First Truly Wireless Noise Dosimeter and Airwave App!", Retrieved from URL: https://www.youtube.com/watch?v=Xvy2fl3cgYo, Mat 27, 2015, 3 pages.
Certificate of Examination received for Australian Patent Application No. 2019100222, mailed on Aug. 29, 2019, 2 pages.
Chatrzarrin Hanieh, "Feature Extraction for the Differentiation of Dry and Wet Cough Sounds", Carleton University, Sep. 2011, 144 pages.
CNET, "Google Fit's automatic activity tracking is getting smarter on Android Wear", Available online at: https://www.youtube.com/watch?v=lttzlCid_d8, May 18, 2016, 1 page.
Cook James, "German Period Tracking App Clue Has Over 2.5 Million Active Users—But It's Still Not Sure How It's Going to Make Money", Available online at: https://www.businessinsider.in/tech/german-period-tracking-app-clue-has-over-2-5-million-active-users-but-its-still-not-sure-how-its-going-to-make-money/articleshow/50511307.cms, Jan. 9, 2016, 9 pages.
Corrected Notice of Allowance received for U.S. Appl. No. 16/143,909, mailed on Feb. 20, 2020, 3 pages.
Corrected Notice of Allowance received for U.S. Appl. No. 16/143,909, mailed on Mar. 18, 2020, 3 pages.
Corrected Notice of Allowance received for U.S. Appl. No. 16/143,959, mailed on Dec. 13, 2019, 2 pages.
Corrected Notice of Allowance received for U.S. Appl. No. 16/143,997, mailed on Jul. 2, 2021, 2 pages.
Corrected Notice of Allowance received for U.S. Appl. No. 16/143,997, mailed on Jun. 4, 2021, 2 pages.
Corrected Notice of Allowance received for U.S. Appl. No. 16/143,997, mailed on Nov. 16, 2021, 2 pages.
Corrected Notice of Allowance received for U.S. Appl. No. 16/143,997, mailed on Oct. 21, 2021, 2 pages.
Corrected Notice of Allowance received for U.S. Appl. No. 16/584,186, mailed on Jul. 31, 2020, 2 pages.
Corrected Notice of Allowance received for U.S. Appl. No. 16/586,154, mailed on Oct. 27, 2021, 2 pages.
Corrected Notice of Allowance received for U.S. Appl. No. 16/880,552, mailed on Dec. 22, 2021, 2 pages.
Corrected Notice of Allowance received for U.S. Appl. No. 16/880,552, mailed on Dec. 23, 2020, 2 pages.
Corrected Notice of Allowance received for U.S. Appl. No. 16/880,552, mailed on Jul. 7, 2021, 2 pages.

(56) References Cited

OTHER PUBLICATIONS

Corrected Notice of Allowance received for U.S. Appl. No. 16/921,312, mailed on Dec. 7, 2021, 2 pages.
Corrected Notice of Allowance received for U.S. Appl. No. 16/921,312, mailed on Sep. 24, 2021, 2 pages.
Corrected Notice of Allowance received for U.S. Appl. No. 16/990,846, mailed on Feb. 9, 2022, 3 pages.
Corrected Notice of Allowance received for U.S. Appl. No. 17/031,704, mailed on Nov. 2, 2021, 7 pages.
DC Rainmaker, "Garmin Fenix3 New Auto Climb Functionality", Available online at: https://www.youtube.com/watch?v=iuavOSNpVRc, Feb. 19, 2015, 1 page.
Decision on Appeal received for Korean Patent Application No. 10-2019-7025538, mailed on Feb. 24, 2021, 20 pages.
Decision to Grant received for Danish Patent Application No. PA201870379, mailed on Jul. 5, 2019, 2 pages.
Decision to Grant received for Danish Patent Application No. PA201870600, mailed on Oct. 17, 2019, 2 pages.
Decision to Grant received for Danish Patent Application No. PA201870601, mailed on Aug. 17, 2020, 2 pages.
Decision to Grant received for Danish Patent Application No. PA201870602, mailed on Aug. 18, 2020, 2 pages.
Decision to Refuse received for European Patent Application No. 13812320.3, mailed on Oct. 14, 2021, 4 pages.
Epstein et al., "Examining Menstrual Tracking to Inform the Design of Personal Informatics Tools", Proceedings of the 2017 CHI Conference on Human Factors in Computing Systems, CHI '17, ACM Press, Denver, CO, USA, May 6-11, 2017, pp. 6876-6888.
European Search Report received for European Patent Application No. 20182116.2, mailed on Oct. 21, 2020, 4 pages.
Evergreen et al., "Bar Chart", Better Evaluation, Available Online at: https://www.betterevaluation.org/en/evaluation-options/BarChart, Oct. 31, 2014, 8 pages.
Extended European Search Report received for European Patent Application No. 20180581.9, mailed on Aug. 12, 2020, 9 pages.
Extended European Search Report received for European Patent Application No. 20180592.6, mailed on Aug. 11, 2020, 10 pages.
Extended European Search Report received for European Patent Application No. 20203526.7, mailed on Jan. 29, 2021, 13 pages.
Final Office Action received for U.S. Appl. No. 15/167,699, mailed on Jun. 30, 2017, 8 pages.
Final Office Action received for U.S. Appl. No. 16/138,809, mailed on Aug. 27, 2020, 24 pages.
Final Office Action received for U.S. Appl. No. 16/143,909, mailed on Aug. 28, 2019, 20 pages.
Final Office Action received for U.S. Appl. No. 16/143,997, mailed on Feb. 9, 2021, 16 pages.
Final Office Action received for U.S. Appl. No. 16/143,997, mailed on Sep. 30, 2019, 16 pages.
Final Office Action received for U.S. Appl. No. 16/144,030, mailed on Feb. 13, 2020, 11 pages.
Final Office Action received for U.S. Appl. No. 16/144,030, mailed on Oct. 1, 2019, 13 pages.
Final Office Action received for U.S. Appl. No. 16/144,849, mailed on Jun. 7, 2019, 29 pages.
Final Office Action received for U.S. Appl. No. 16/144,864, mailed on May 17, 2019, 24 pages.
Final Office Action received for U.S. Appl. No. 16/144,864, mailed on May 28, 2020, 29 pages.
Final Office Action received for U.S. Appl. No. 16/586,154, mailed on Jul. 6, 2020, 27 pages.
Final Office Action received for U.S. Appl. No. 16/586,154, mailed on May 24, 2021, 29 pages.
Final Office Action received for U.S. Appl. No. 16/894,309, mailed on Feb. 24, 2021, 30 pages.
Final Office Action received for U.S. Appl. No. 16/907,261, mailed on Mar. 18, 2021, 20 pages.
Final Office Action received for U.S. Appl. No. 17/031,704, mailed on Apr. 1, 2021, 31 pages.
Final Office Action received for U.S. Appl. No. 17/031,717, mailed on Feb. 24, 2021, 23 pages.
Fitbit App, Available online at: http://web.archive.org/web/20180114083150/https://www.fitbit.com/au/app, Jan. 14, 2018, 8 pages.
Garmin, "Fenix 5x Owner's Manual", Online Available at: https://web.archive.org/web/20180127170640/https://static.garmin.com/pumac/fenix5x_OM_EN.pdf, Jan 27, 2018, 42 pages.
Graphs and Charts, online available at: https://www.teachervision.com/lesson-planning/graph-chart-teacher-resources, retrieved on Dec. 12, 2018, 4 pages.
Gupta Rajat, "Disable High Volume Warning (no root) in Samsung S7, S8 / Android 7.0", Online available at:<https://www.youtube.com/watch?v=9fKwRBtk-x8>, Retrieved on Nov. 26, 2020; esp. 2:04, Aug. 6, 2017, 1 page.
Haslam Oliver, "Stop Coronavirus in its Tracks by Using This Apple Watch App to Time Hand Washes", Available Online at: <https://www.imore.com/stop-coronavirus-its-tracks-using-apple-watch-app-time-hand-washes>, Mar. 12, 2020, 12 pages.
Intention to Grant received for Danish Patent Application No. PA201870379, mailed on May 2, 2019, 2 pages.
Intention to Grant received for Danish Patent Application No. PA201870600, mailed on Jul. 10, 2019, 2 pages.
Intention to Grant received for Danish Patent Application No. PA201870601, mailed on Apr. 24, 2020, 2 pages.
Intention to Grant received for Danish Patent Application No. PA201870602 mailed on Apr. 24, 2020, 2 pages.
International Preliminary Report on Patentability received for PCT Patent Application No. PCT/US2020/035164, mailed on Dec. 16, 2021, 19 pages.
International Preliminary Report on Patentability received for PCT Patent Application No. PCT/US2020/035462, mailed on Dec. 16, 2021, 16 pages.
International Preliminary Report on Patentability received for PCT Patent Application No. PCT/US2013/073188, mailed on Jun. 16, 2016, 6 pages.
International Preliminary Report on Patentability received for PCT Patent Application No. PCT/US2019/014215, mailed on Aug. 6, 2020, 14 pages.
International Preliminary Report on Patentability received for PCT Patent Application No. PCT/US2019/019694, mailed on Sep. 24, 2020, 12 pages.
International Preliminary Report on Patentability received for PCT Patent Application No. PCT/US2019/024570, mailed on Nov. 19, 2020, 10 pages.
International Preliminary Report on Patentability received for PCT Patent Application No. PCT/US2020/025768, mailed on Dec. 16, 2021, 8 pages.
International Preliminary Report on Patentability received for PCT Patent Application No. PCT/US2020/035474, mailed on Dec. 16, 2021, 11 pages.
International Search Report and Written Opinion received for PCT Patent Application No. PCT/US2013/073188 mailed on Feb. 24, 2014, 8 pages.
International Search Report and Written Opinion received for PCT Patent Application No. PCT/US2019/014215, mailed on Jun. 4, 2019, 17 pages.
International Search Report and Written Opinion received for PCT Patent Application No. PCT/US2019/019694, mailed on Sep. 2, 2019, 17 pages.
International Search Report and Written Opinion received for PCT Patent Application No. PCT/US2019/024570, mailed on Aug. 8, 2019, 18 pages.
International Search Report and Written Opinion received for PCT Patent Application No. PCT/US2020/025768, mailed on Aug. 10, 2020, 11 pages.
International Search Report and Written Opinion received for PCT Patent Application No. PCT/US2020/035164, mailed on Feb. 8, 2021, 26 pages.
International Search Report and Written Opinion received for PCT Patent Application No. PCT/US2020/035462, mailed on Sep. 11, 2020, 17 pages.

(56) References Cited

OTHER PUBLICATIONS

International Search Report and Written Opinion received for PCT Patent Application No. PCT/US2020/035474, mailed on Nov. 26, 2020, 16 pages.
International Search Report and Written Opinion received for PCT Patent Application No. PCT/US2020/042439, mailed on Oct. 9, 2020, 14 pages.
International Search Report and Written Opinion received for PCT Patent Application No. PCT/US2020/070280, mailed on Nov. 30, 2020, 20 pages.
International Search Report and Written Opinion received for PCT Patent Application No. PCT/US2021/035227, mailed on Oct. 6, 2021, 17 pages.
International Search Report and Written Opinion received for PCT Patent Application No. PCT/US2021/035504, mailed on Sep. 16, 2021, 12 pages.
Invitation to Pay Addition Fees and Partial International Search Report received for PCT Patent Application No. PCT/US2019/014215, mailed on Apr. 12, 2019, 13 pages.
Invitation to Pay Addition Fees received for PCT Patent Application No. PCT/US2020/035474, mailed on Oct. 2, 2020, 11 pages.
Invitation to Pay Addition Fees and Partial International Search Report received for PCT Patent Application No. PCT/US2020/035164, mailed on Oct. 16, 2020, 14 pages.
Invitation to Pay Addition Fees received for PCT Patent Application No. PCT/US2019/019694, mailed on Jul. 10, 2019, 12 pages.
Invitation to Pay Addition Fees received for PCT Patent Application No. PCT/US2020/070280, mailed on Oct. 7, 2020, 12 pages.
Invitation to Pay Search Fees received for European Patent Application No. 19726205.8, mailed on Feb.14, 2020, 5 pages.
Liaqat et al., "Challenges with Real-World Smartwatch based Audio Monitoring", WearSys'18, Munich, Germany, Available Online at: https://doi.org/10.1145/3211960.3211977, Jun. 10, 2018, 6 pages.
Lovejoy Ben, "Apple Watch blood sugar measurement coming in Series 7, claims report", Available Online at: https://9to5mac.com/2021/01/25/apple-watch-blood-sugar-measurement/, Jan. 25, 2021, 6 pages.
Lyles Taylor, "Wear OS Smartwatches are Now Sending Reminders to Wash Your Hands", Available Online at: https://www.theverge.com/2020/4/14/21221294/google-wear-os-smartwatches-reminders-wash-your-hands, Apr. 14, 2020, 2 pages.
Megadepot, "Casella dBadge2 Noise Dosimeter", Retrieved from URL: https://www.youtube.com/watch?v=pHiHLiYCD08, Jun. 12, 2018, 3 pages.
Moglia et al., "Evaluation of Smartphone Menstrual Cycle Tracking Applications Using an Adapted Applications Scoring System", Obstetrics and Gynecology, vol. 127, No. 6, Jun. 2016, pp. 1153-1160.
Multi-Set Bar Chart, The Data Visualization Catalogue, Available Online at: https://datavizcatalogue.com/methods/multiset_barchart.html, Feb. 8, 2014, 3 pages.
MYFLO App, "Functional Medicine Period Tracker and Hormone Balancing App", Available online at: https://web.archive.org/web/20170127104125/https://myflotracker.com/, Jan. 2017, 14 pages.
MYFLO Tutorial, "How to change the start date of your current period", Available online at <https://www.youtube.com/watch?v=uQQ-odlBJB4>, Jan. 23, 2017, 3 pages.
MYFLO Tutorial, "Setting and changing the end date of your period", Available online at <https://www.youtube.com/watch?v=UvAA4OgqL3E>, Jan. 23, 2017, 3 pages.
Non-Final Office Action received for U.S. Appl. No. 15/167,699, mailed on Oct. 21, 2016, 13 pages.
Non-Final Office Action received for U.S. Appl. No. 15/885,448, mailed on Apr. 16, 2020, 9 pages.
Non-Final Office Action received for U.S. Appl. No. 16/138,809, mailed on Feb. 28, 2020, 22 pages.
Non-Final Office Action received for U.S. Appl. No. 16/143,909, mailed on Apr. 19, 2019, 16 pages.
Non-Final Office Action received for U.S. Appl. No. 16/143,959, mailed on Apr. 17, 2019, 15 pages.
Non-Final Office Action received for U.S. Appl. No. 16/143,997, mailed on Jul. 27, 2020, 15 pages.
Non-Final Office Action received for U.S. Appl. No. 16/143,997, mailed on May 21, 2019, 15 pages.
Non-Final Office Action received for U.S. Appl. No. 16/143,030, mailed on Apr. 12, 2019, 8 pages.
Non-Final Office Action received for U.S. Appl. No. 16/143,030, mailed on Nov. 5, 2020, 5 pages.
Non-Final Office Action received for U.S. Appl. No. 16/144,849, mailed on Dec. 31, 2018, 28 pages.
Non-Final Office Action received for U.S. Appl. No. 16/144,849, mailed on Sep. 17, 2019, 9 pages.
Non-Final Office Action received for U.S. Appl. No. 16/144,864, mailed on Dec. 18, 2018, 19 pages.
Non-Final Office Action received for U.S. Appl. No. 16/144,864, mailed on Jan. 31, 2020, 29 pages.
Non-Final Office Action received for U.S. Appl. No. 16/249,627, mailed on Aug. 31, 2021, 18 pages.
Non-Final Office Action received for U.S. Appl. No. 16/249,627, mailed on Mar. 11, 2021, 21 pages.
Non-Final Office Action received for U.S. Appl. No. 16/584,186, mailed on Dec. 6, 2019, 13 pages.
Non-Final Office Action received for U.S. Appl. No. 16/586,154, mailed on Dec. 9, 2019, 23 pages.
Non-Final Office Action received for U.S. Appl. No. 16/586,154, mailed on Dec. 28, 2020, 26 pages.
Non-Final Office Action received for U.S. Appl. No. 16/880,552, mailed on Feb. 19, 2021, 11 pages.
Non-Final Office Action received for U.S. Appl. No. 16/880,552, mailed on Jul. 23, 2020, 19 pages.
Non-Final Office Action received for U.S. Appl. No. 16/880,714, mailed on Oct. 28, 2020, 11 pages.
Non-Final Office Action received for U.S. Appl. No. 16/894,309, mailed on Oct. 15, 2020, 24 pages.
Non-Final Office Action received for U.S. Appl. No. 16/907,261, mailed on Sep. 30, 2020, 22 pages.
Non-Final Office Action received for U.S. Appl. No. 16/990,846, mailed on May 10, 2021, 16 pages.
Non-Final Office Action received for U.S. Appl. No. 17/031,704, mailed on Dec. 10, 2020, 30 pages.
Non-Final Office Action received for U.S. Appl. No. 17/031,717, mailed on Nov. 19, 2020, 22 pages.
Non-Final Office Action received for U.S. Appl. No. 17/031,717, mailed on Sep. 14, 2021, 35 pages.
Notice from the European Patent Office dated Oct. 1, 2007 Concerning Business Methods, Official Journal EPO, available online at: http://archive.epo.org/epo/pubs/oj007/11_07/11_5927.pdf, Nov. 2007, pp. 592-593.
Notice of Acceptance received for Australian Patent Application No. 2013406817, mailed on Nov. 21, 2017, 3 pages.
Notice of Acceptance received for Australian Patent Application No. 2018201260, mailed on Jan. 15, 2020, 3 pages.
Notice of Acceptance received for Australian Patent Application No. 2019210192, mailed on Dec. 2, 2021, 3 pages.
Notice of Acceptance received for Australian Patent Application No. 2019222943, mailed on May 5, 2020, 3 pages.
Notice of Acceptance received for Australian Patent Application No. 2020204153, mailed on Jul. 6, 2020, 3 pages.
Notice of Acceptance received for Australian Patent Application No. 2020256383, mailed on Aug. 3, 2021, 3 pages.
Notice of Allowance received for Chinese Patent Application No. 201380081315.7, mailed on Jan. 4, 2019, 2 pages.
Notice of Allowance received for Chinese Patent Application No. 201910972529.2, mailed on Sep. 14, 2020, 6 pages.
Notice of Allowance received for Japanese Patent Application No. 2019-162293, mailed on Apr. 9, 2021, 4 pages.
Notice of Allowance received for Japanese Patent Application No. 2020-104679, mailed on Jan. 4, 2021, 4 pages.
Notice of Allowance received for Japanese Patent Application No. 2020-153166, mailed on Sep. 13, 2021, 4 pages.
Notice of Allowance received for Japanese Patent Application No. 2020-547369, mailed on Jul. 16, 2021, 4 pages.

(56) References Cited

OTHER PUBLICATIONS

Notice of Allowance received for Japanese Patent Application No. 2020-560883, mailed on Oct. 29, 2021, 4 pages.
Notice of Allowance received for Korean Patent Application No. 10-2016-7014353, mailed on Aug. 2, 2018, 3 pages.
Notice of Allowance received for Korean Patent Application No. 10-2018-7032096, mailed on Dec. 12, 2018, 4 pages.
Notice of Allowance received for Korean Patent Application No. 10-2019-7025538, mailed on Mar. 10, 2021, 5 pages.
Notice of Allowance received for Korean Patent Application No. 10-2020-7026035, mailed on Aug. 23, 2021, 4 pages.
Notice of Allowance received for Korean Patent Application No. 10-2020-7026391, mailed on May 11, 2021, 3 pages.
Notice of Allowance received for Korean Patent Application No. 10-2020-7026453, mailed on May 11, 2021, 3 pages.
Notice of Allowance received for Korean Patent Application No. 10-2021-7038005, mailed on Dec. 14, 2021, 4 pages.
Notice of Allowance received for U.S. Appl. No. 15/167,699, mailed on Oct. 27, 2017, 8 pages.
Notice of Allowance received for U.S. Appl. No. 15/885,448, mailed on Jun. 16, 2020, 5 pages.
Notice of Allowance received for U.S. Appl. No. 16/138,809, mailed on Apr. 16, 2021, 11 pages.
Notice of Allowance received for U.S. Appl. No. 16/138,809, mailed on Jul. 20, 2021, 6 pages.
Notice of Allowance received for U.S. Appl. No. 16/143,909, mailed on Jan. 21, 2020, 9 pages.
Notice of Allowance received for U.S. Appl. No. 16/143,959, mailed on Oct. 31, 2019, 10 pages.
Notice of Allowance received for U.S. Appl. No. 16/143,997, mailed on May 13, 2021, 10 pages.
Notice of Allowance received for U.S. Appl. No. 16/143,997, mailed on Sep. 30, 2021, 8 pages.
Notice of Allowance received for U.S. Appl. No. 16/143,030, mailed on Apr. 5, 2021, 8 pages.
Notice of Allowance received for U.S. Appl. No. 16/144,849, mailed on Apr. 17, 2020, 2 pages.
Notice of Allowance received for U.S. Appl. No. 16/144,849, mailed on Mar. 6, 2020, 9 pages.
Notice of Allowance received for U.S. Appl. No. 16/144,864, mailed on Feb. 9, 2021, 13 pages.
Notice of Allowance received for U.S. Appl. No. 16/144,864, mailed on Jul. 28, 2020, 27 pages.
Notice of Allowance received for U.S. Appl. No. 16/144,864, mailed on Mar. 12, 2021, 2 pages.
Notice of Allowance received for U.S. Appl. No. 16/144,864, mailed on Mar. 30, 2021, 2 pages.
Notice of Allowance received for U.S. Appl. No. 16/144,864, mailed on Sep. 10, 2020, 3 pages.
Notice of Allowance received for U.S. Appl. No. 16/144,864, mailed on Sep. 16, 2020, 2 pages.
Notice of Allowance received for U.S. Appl. No. 16/144,864, mailed on Sep. 29, 2020, 2 pages.
Notice of Allowance received for U.S. Appl. No. 16/584,186, mailed on Mar. 24, 2020, 10 pages.
Notice of Allowance received for U.S. Appl. No. 16/584,154, mailed on Oct. 15, 2021, 8 pages.
Notice of Allowance received for U.S. Appl. No. 16/880,552, mailed on Dec. 1, 2020, 7 pages.
Notice of Allowance received for U.S. Appl. No. 16/880,552, mailed on Jul. 23, 2021, 5 pages.
Notice of Allowance received for U.S. Appl. No. 16/880,552, mailed on May 12, 2021, 7 pages.
Notice of Allowance received for U.S. Appl. No. 16/880,552, mailed on Nov. 24, 2021, 5 pages.
Notice of Allowance received for U.S. Appl. No. 16/880,714, mailed on Jun. 9, 2021, 6 pages.
Notice of Allowance received for U.S. Appl. No. 16/880,714, mailed on Mar. 19, 2021, 7 pages.
Notice of Allowance received for U.S. Appl. No. 16/894,309, mailed on Nov. 5, 2021, 12 pages.
Notice of Allowance received for U.S. Appl. No. 16/907,261, mailed on Aug. 13, 2021, 8 pages.
Notice of Allowance received for U.S. Appl. No. 16/907,261, mailed on Sep. 28, 2021, 6 pages.
Notice of Allowance received for U.S. Appl. No. 16/921,312, mailed on Nov. 29, 2021, 5 pages.
Notice of Allowance received for U.S. Appl. No. 16/921,312, mailed on Sep. 14, 2021, 9 pages.
Notice of Allowance received for U.S. Appl. No. 16/990,846, mailed on Jan. 20, 2022, 6 pages.
Notice of Allowance received for U.S. Appl. No. 16/990,846, mailed on Sep. 22, 2021, 9 pages.
Notice of Allowance received for U.S. Appl. No. 17/031,704, mailed on Jul. 21, 2021, 10 pages.
Notice of Allowance received for U.S. Appl. No. 17/031,727, mailed on Dec. 24, 2020, 12 pages.
Notice of Allowance received for U.S. Appl. No. 17/031,727, mailed on Jun. 25, 2021, 6 pages.
Notice of Allowance received for U.S. Appl. No. 17/031,727, mailed on Mar. 12, 2021, 7 pages.
Office Action received for Australian Patent Application No. 2013406817, mailed on Aug. 1, 2017, 3 pages.
Office Action received for Australian Patent Application No. 2013406817, mailed on Nov. 14, 2016, 4 pages.
Office Action received for Australian Patent Application No. 2018201260, mailed on Feb. 12, 2019, 6 pages.
Office Action received for Australian Patent Application No. 2018201260, mailed on Jul. 17, 2019, 3 pages.
Office Action received for Australian Patent Application No. 2018201260, mailed on Sep. 5, 2019, 5 pages.
Office Action received for Australian Patent Application No. 2019100222, mailed on May 24, 2019, 6 pages.
Office Action received for Australian Patent Application No. 2019100495, mailed on Mar. 6, 2020, 3 pages.
Office Action received for Australian Patent Application No. 2019100495, mailed on Mar. 16, 2020, 3 pages.
Office Action received for Australian Patent Application No. 2019100495, mailed on Sep. 17, 2019, 7 pages.
Office Action received for Australian Patent Application No. 2019210192, mailed on May 25, 2021, 4 pages.
Office Action received for Australian Patent Application No. 2019210192, mailed on Sep. 9, 2021, 4 pages.
Office Action received for Australian Patent Application No. 2019222943, mailed on Oct. 3, 2019, 3 pages.
Office Action received for Australian Patent Application No. 2019234289, mailed on Jul. 20, 2021, 4 pages.
Office Action received for Australian Patent Application No. 2019234289, mailed on Mar. 16, 2021, 8 pages.
Office Action received for Australian Patent Application No. 2019234289, mailed on Nov. 1, 2021, 4 pages.
Office Action received for Australian Patent Application No. 2019234289, mailed on Nov. 2, 2020, 6 pages.
Office Action received for Australian Patent Application No. 2020230340, mailed on Mar. 2, 2021, 6 pages.
Office Action received for Australian Patent Application No. 2020230340, mailed on May 27, 2021, 5 pages.
Office Action received for Australian Patent Application No. 2020230340, mailed on Nov. 2, 2020, 5 pages.
Office Action received for Australian Patent Application No. 2020230340, mailed on Oct. 11, 2021, 4 pages.
Office Action received for Australian Patent Application No. 2020239692, mailed on Jul. 20, 2021, 5 pages.
Office Action received for Australian Patent Application No. 2020239740, mailed on Jul. 9, 2021, 4 pages.
Office Action received for Australian Patent Application No. 2020239740, mailed on Sep. 28, 2021, 5 pages.
Office Action received for Australian Patent Application No. 2020256383, mailed on Jun. 4, 2021, 3 pages.
Office Action received for Chinese Patent Application No. 201380081315.7, mailed on Aug. 16, 2018, 6 pages.

(56) References Cited

OTHER PUBLICATIONS

Office Action received for Chinese Patent Application No. 201380081315.7, mailed on Mar. 2, 2018, 12 pages.
Office Action received for Chinese Patent Application No. 201910858933.7, mailed on Aug. 18, 2020, 14 pages.
Office Action received for Chinese Patent Application No. 201910858933.7, mailed on Jun. 29, 2021, 8 pages.
Office Action received for Chinese Patent Application No. 201910972529.2, mailed on Jun. 28, 2020, 8 pages.
Office Action received for Chinese Patent Application No. 202010606407.4, mailed on Jan. 27, 2021, 16 pages.
Office Action received for Chinese Patent Application No. 202010606407.4, mailed on Jun. 2, 2021, 12 pages.
Office Action received for Chinese Patent Application No. 202010606407.4, mailed on Nov. 18, 2021, 6 pages.
Office Action received for Chinese Patent Application No. 202010618240.3, mailed on Dec. 3, 2021, 23 pages.
Office Action received for Chinese Patent Application No. 202010618240.3, mailed on Mar. 29, 2021, 21 pages.
Office Action received for Chinese Patent Application No. 202010618569.X, mailed on Mar. 12, 2021, 14 pages.
Office Action received for Chinese Patent Application No. 202010618569.X, mailed on Sep. 7, 2021, 7 pages.
Office Action received for Chinese Patent Application No. 202011220489.5, mailed on Jun. 1, 2021, 12 pages.
Office Action received for Danish Patent Application No. PA201870378, mailed on Feb. 25, 2019, 3 pages.
Office Action received for Danish Patent Application No. PA201870378, mailed on Jan. 6, 2020, 3 pages.
Office Action received for Danish Patent Application No. PA201870378, mailed on Feb. 28, 2019, 3 pages.
Office Action received for Danish Patent Application No. PA201870380, mailed on Mar. 5, 2020, 2 pages.
Office Action received for Danish Patent Application No. PA201870380, mailed on Mar. 27, 2019, 4 pages.
Office Action received for Danish Patent Application No. PA201870380, mailed on Sep. 11, 2018, 9 pages.
Office Action received for Danish Patent Application No. PA201870599, mailed on Dec. 20, 2019, 5 pages.
Office Action received for Danish Patent Application No. PA201870600, mailed on May 8, 2019, 3 pages.
Office Action received for Danish Patent Application No. PA201870601, mailed on Dec. 13, 2018, 8 pages.
Office Action received for Danish Patent Application No. PA201870601, mailed on Jan. 14, 2020, 3 pages.
Office Action received for Danish Patent Application No. PA201870601, mailed on Jun. 25, 2019, 3 pages.
Office Action received for Danish Patent Application No. PA201870602, mailed on Feb. 5, 2020, 3 pages.
Office Action received for Danish Patent Application No. PA201870602, mailed on Jun. 26, 2019, 3 pages.
Office Action received for Danish Patent Application No. PA201970534, mailed on Feb. 16, 2021, 2 pages.
Office Action received for Danish Patent Application No. PA201970534, mailed on Jun. 29, 2020, 2 pages.
Office Action received for Danish Patent Application No. PA202070335, mailed on Jun. 11, 2021, 4 pages.
Office Action received for Danish Patent Application No. PA202070335, mailed on Nov. 17, 2021, 6 pages.
Office Action received for Danish Patent Application No. PA202070395, mailed on Dec. 15, 2021, 5 pages.
Office Action received for Danish Patent Application No. PA202070619, mailed on Aug. 27, 2021, 12 pages.
Office Action received for Danish Patent Application No. PA202070619, mailed on Oct. 14, 2021, 3 pages.
Office Action received for Danish Patent Application No. PA202070620, mailed on May 10, 2021, 5 pages.
Office Action received for Danish Patent Application No. PA202070620, mailed on Nov. 19, 2021, 2 pages.
Office Action received for European Patent Application No. 19721883.7, mailed on Jan. 10, 2020, 4 pages.
Office Action received for European Patent Application No. 19721883.7, mailed on Jun. 15, 2021, 9 pages.
Office Action received for European Patent Application No. 19721883.7, mailed on May 28, 2020, 11 pages.
Office Action received for European Patent Application No. 19726205.8, mailed on Jun. 26, 2020, 9 pages.
Office Action received for European Patent Application No. 20180581.9, mailed on Apr. 1, 2021, 11 pages.
Office Action received for European Patent Application No. 20180592.6, mailed on Apr. 1, 2021, 11 pages.
Office Action received for European Patent Application No. 20182116.2, mailed on May 25, 2021, 9 pages.
Office Action received for European Patent Application No. 20182116.2, mailed on Nov. 6, 2020, 9 pages.
Office Action received for European Patent Application No. 20203526.7, mailed on Nov. 23, 2021, 9 pages.
Office Action received for European Patent Application No. 13812320.3, mailed on Mar. 28, 2018, 7 pages.
Office Action received for Indian Patent Application No. 201617016494, mailed on Apr. 27, 2020, 7 pages.
Office Action received for Indian Patent Application No. 202014041484, mailed on Dec. 8, 2021, 8 pages.
Office Action received for Japanese Patent Application No. 2018-184532, mailed on Mar. 1, 2021, 11 pages.
Office Action received for Japanese Patent Application No. 2019-162293, mailed on Jan. 31, 2020, 8 pages.
Office Action received for Japanese Patent Application No. 2019-162293, mailed on Jul. 27, 2020, 9 pages.
Office Action received for Japanese Patent Application No. 2020-104679, mailed on Sep. 18, 2020, 13 pages.
Office Action received for Japanese Patent Application No. 2020-153166, mailed on May 31, 2021, 6 pages.
Office Action received for Japanese Patent Application No. 2020-547369, mailed on Apr. 9, 2021, 4 pages.
Office Action received for Korean Patent Application No. 10-2016-7014353, mailed on Mar. 21, 2018, 11 pages.
Office Action received for Korean Patent Application No. 10-2019-7025538, mailed on Aug. 15, 2020, 8 pages.
Office Action received for Korean Patent Application No. 10-2019-7025538, mailed on Feb. 17, 2020, 12 pages.
Office Action received for Korean Patent Application No. 10-2020-7026035, mailed on Feb. 19, 2021, 13 pages.
Office Action received for Korean Patent Application No. 10-2020-7026391, mailed on Jan. 27, 2021, 5 pages.
Office Action received for Korean Patent Application No. 10-2020-7026453, mailed on Jan. 27, 2021, 5 pages.
Peters Jay, "Samsung's Smartwatches Get a Hand-Washing Reminder and Timer App", Available Online at: <https://www.theverge.com/2020/4/17/21225205/samsung-smartwatch-galaxy-active-hand-washing-timer-reminder-app>, Apr. 17, 2020, 2 pages.
Result of Consultation received for European Patent Application No. 19721883.7, mailed on Oct. 7, 2020, 3 pages.
Result of Consultation received for European Patent Application No. 19726205.8, mailed on Mar. 15, 2021, 19 pages.
Rizknows, "TomTom Multisport Cardio Review", Online available at: https://www.youtube.com/watch?v=WoVCzLrSN9A, Sep. 4, 2015, 1 page.
Schoon Ben, "Wear OS Now Sends a Reminder to Wash Your Hands Every Few Hours"Available Online at: https://9to5google.com/2020/04/14/wear-os-wash-hands-reminder-coronavirus/, Apr. 14, 2020, 7 pages.
Search Report and Opinion received for Danish Patent Application No. PA201870378, mailed on Sep. 10, 2018, 9 pages.
Search Report and Opinion received for Danish Patent Application No. PA201870379, mailed on Sep. 14, 2018, 9 pages.
Search Report and Opinion received for Danish Patent Application No. PA201870599, mailed on Dec. 21, 2018, 9 pages.
Search Report and Opinion received for Danish Patent Application No. PA201870600, mailed on Jan. 31, 2019, 8 pages.
Search Report and Opinion received for Danish Patent Application No. PA201870602, mailed on Dec. 19, 2018, 8 pages.

(56) References Cited

OTHER PUBLICATIONS

Search Report and Opinion received for Danish Patent Application No. PA201970534, mailed on Sep. 23, 2019, 6 pages.
Search Report and Opinion received for Danish Patent Application No. PA202070335, mailed on Nov. 27, 2020, 10 pages.
Search Report and Opinion received for Danish Patent Application No. PA202070395, mailed on Nov. 24, 2020, 10 pages.
Search Report and Opinion received for Danish Patent Application No. PA202070619, mailed on Dec. 2, 2020, 11 pages.
Search Report and Opinion received for Danish Patent Application No. PA202070620, mailed on Dec. 11, 2020, 9 pages.
Smith, "Garmin Fenix 5 Activity/Smart Watch Review"Online Available at: https://www.youtube.com/watch?v=6PkQxXQxpoU, Sep. 2, 2017, 1 page.
Sportstechguides, "Garmin Fenix 5: How to Add Power Data Fields", Online Available at https://www.youtube.com/watch?v=ZkPptnnXEiQ, Apr. 29, 2017, 2 pages.
Sportstechguides, "Garmin Fenix 5: How to Set Up Run Alerts", Online Available at https://www.youtube.com/watch?v=gSMwv8vlhB4, May 13, 2017, 2 pages.
Studiosixdigital, "Dosimeter", Retrieved from URL: https://studiosixdigital.com/audiotools-modules-2/spl-modules/dosimeter.html, Mar. 3, 2017, 6 pages.
Summons to Attend Oral Proceedings received for European Patent Application No. 13812320.3, mailed on Mar. 12, 2021, 9 pages.
Summons to Attend Oral Proceedings received for European Patent Application No. 19726205.8, mailed on Oct. 29, 2020, 13 pages.
Summons to Attend Oral Proceedings received for European Patent Application No. 20180581.9, mailed on Aug. 18, 2021, 15 pages.
Summons to Attend Oral Proceedings received for European Patent Application No. 20180592.6, mailed on Aug. 11, 2021, 16 pages.
Summons to Attend Oral Proceedings received for European Patent Application No. 20182116.2, mailed on Dec. 21, 2021, 7 pages.
Supplemental Notice of Allowance received for U.S. Appl. No. 16/144,849, mailed on Mar. 31, 2020, 2 pages.
Supplemental Notice of Allowance received for U.S. Appl. No. 16/880,714, mailed on Sep. 16, 2021, 2 pages.
Supplemental Notice of Allowance received for U.S. Appl. No. 16/894,309, mailed on Dec. 24, 2021, 2 pages.
Supplemental Notice of Allowance received for U.S. Appl. No. 17/031,727, mailed on Jan. 15, 2021, 2 pages.
Suunto Spartan Trainer Wrist HR 1.12, Online Available at: https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan—Heart Rate Zones"Online Available at: https://www.youtube.com/watch?v=aixfoCnS0OU, Mar. 19, 2018, 2 page.
Tech, Kalyani, "I See Some problems in Honor Band 5", Retrieved from: https://www.youtube.com/watch?v=5XPnYJFqajl, May 19, 2020, 1 page.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
Ticks, Smartwatch,"Senbono S10 IP67 Waterproof Multi-Function Blood Pressure Sports Smartwatch: One Minute Overview", Retrieved from: https://www.youtube.com/watch?v=rMxLJvKIVBs, Oct. 30, 2019, 1 page.
TomTom, "TomTom Runner & Multi-Sport Reference Guide", Online available at: https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
Visual Pace Alarm app, Available Online at https://apps.garmin.com/en-US/apps/3940f3a2-4847-4078-a911-d77422966c82, Oct. 19, 2016, 1 page.
Weiyu et al., "A Multi-Identities Authentication and Authorization Schema in Cloud Computing", Aug. 20, 2012, pp. 7-10.
Wesley, "Apple Watch Series 1", online available at: http://toolbox.info/blog/archives/1737-unknown.html, May 28, 2015, 5 pages.
Youtube, "Apple Watch Series 3", Online available at: https://www.youtube.com/watch?v=iBPr9gEfkK8, Nov. 21, 2017, 15 pages.
Zlelik, "Garmin Fenix 5 Open Water Swimming Activity Demo", Online Available at: https://www.youtube.com/watch?v=iSVhdvw2dcs, Jun. 9, 2017, 1 page.
Applicant-Initiated Interview Summary received for U.S. Appl. No. 17/031,723, mailed on Jan. 23, 2023, 4 pages.
Brief Communication Regarding Oral Proceedings received for European Patent Application No. 20203526.7, mailed on Jan. 18, 2023, 1 page.
Non-Final Office Action received for U.S. Appl. No. 16/249,627, mailed on Jan. 19, 2023, 19 pages.
Notice of Allowance received for U.S. Appl. No. 17/031,779, mailed on Feb. 1, 2023, 11 pages.
Office Action received for Korean Patent Application No. 10-2022-7036381, mailed on Jan. 6, 2023, 10 pages (5 pages of English Translation and 5 pages of Official Copy).
Supplemental Notice of Allowance received for U.S. Appl. No. 17/317,084, mailed on Jan. 19, 2023, 2 pages.
Applicant-Initiated Interview Summary received for U.S. Appl. No. 16/851,451, mailed on Aug. 5, 2022, 3 pages.
Applicant-Initiated Interview Summary received for U.S. Appl. No. 16/888,780, mailed on Aug. 2, 2022, 4 pages.
Non-Final Office Action received for U.S. Appl. No. 16/953,781, mailed on Jul. 26, 2022, 9 pages.
Notice of Allowance received for Japanese Patent Application No. 2020-551585, mailed on Jul. 22, 2022, 4 pages, (1 page of English Translation and 3 pages of Official Copy).
Notice of Allowance received for Korean Patent Application No. 10-2020-7023277, mailed on Jul. 18, 2022, 5 pages, (2 pages of English Translation and 3 pages of Official Copy).
Office Action received for Korean Patent Application No. 10-2020-0124134, mailed on Jul. 28, 2022, 22 pages, (11 pages of English Translation and 11 pages of Official Copy).
Office Action received for Chinese Patent Application No. 202010618240.3, mailed on May 25, 2022, 20 pages, (11 pages of English Translation and 9 pages of Official Copy).
Office Action received for Chinese Patent Application No. 202111611270.2, mailed on May 10, 2022, 16 pages, (8 pages of English Translation and 8 pages of Official Copy).
Applicant-Initiated Interview Summary received for U.S. Appl. No. 16/249,627, mailed on Mar. 1, 2023, 4 pages.
International Preliminary Report on Patentability received for PCT Patent Application No. PCT/US2021/048568, mailed on Mar. 9, 2023, 11 pages.
Non-Final Office Action received for U.S. Appl. No. 16/851,451, mailed on Feb. 24, 2023, 28 pages.
Non-Final Office Action received for U.S. Appl. No. 17/337,147, mailed on Feb. 21, 2023, 15 pages.
Notice of Allowance received for U.S. Appl. No. 16/953,781, mailed on Feb. 27, 2023, 5 pages.
Office Action received for Australian Patent Application No. 2022201823, mailed on Mar. 9, 2023, 3 pages.
Office Action received for Australian Patent Application No. 2022204568, mailed on Mar. 11, 2023, 4 pages.
Applicant-Initiated Interview Summary received for U.S. Appl. No. 17/031,723, mailed on Aug. 30, 2022, 4 pages.
Applicant-Initiated Interview Summary received for U.S. Appl. No. 17/031,779, mailed on Aug. 29, 2022, 2 pages.
Decisioon to Grant received for European Patent Application No. 20180592.6, mailed on Sep. 1, 2022, 3 pages.
Notice of Allowance received for U.S. Appl. No. 17/041,415, mailed on Aug. 31, 2022, 7 pages.
Notice of Allowance received for U.S. Appl. No. 17/317,084, mailed on Aug. 29, 2022, 10 pages.
Office Action received for Korean Patent Application No. 10-2020-7033395, mailed on Aug. 29, 2022, 11 pages (4 pages of English Translation and 7 pages of Official Copy).
Applicant-Initiated Interview Summary received for U.S. Appl. No. 16/249,627, mailed on Aug. 1, 2023, 3 pages.

(56) References Cited

OTHER PUBLICATIONS

Applicant-Initiated Interview Summary received for U.S. Appl. No. 16/851,451, mailed on Apr. 20, 2023, 4 pages.
Applicant-Initiated Interview Summary received for U.S. Appl. No. 17/031,723, mailed on Jun. 22, 2023, 2 pages.
Applicant-Initiated Interview Summary received for U.S. Appl. No. 17/952,053, mailed on Apr. 5, 2023, 6 pages.
Corrected Notice of Allowance received for U.S. Appl. No. 16/953,781, mailed on Mar. 30, 2023, 2 pages.
Corrected Notice of Allowance received for U.S. Appl. No. 17/031,779, mailed on Jun. 14, 2023, 2 pages.
Corrected Notice of Allowance received for U.S. Appl. No. 17/135,710, mailed on Aug. 18, 2023, 4 pages.
Final Office Action received for U.S. Appl. No. 16/249,627, mailed on Jun. 30, 2023, 19 pages.
Final Office Action received for U.S. Appl. No. 16/851,451, mailed on Jun. 1, 2023, 35 pages.
Non-Final Office Action received for U.S. Appl. No. 16/888,780, mailed on Aug. 17, 2023, 12 pages.
Non-Final Office Action received for U.S. Appl. No. 17/031,723, mailed on Jun. 2, 2023, 23 pages.
Non-Final Office Action received for U.S. Appl. No. 17/952,182, mailed on Mar. 28, 2023, 9 pages.
Notice of Acceptance received for Australian Patent Application No. 2020313970, mailed on Jun. 22, 2023, 3 pages.
Notice of Acceptance received for Australian Patent Application No. 2022202459, mailed on May 11, 2023, 3 pages.
Notice of Acceptance received for Australian Patent Application No. 2022203508, mailed on Jun. 27, 2023, 3 pages.
Notice of Acceptance received for Australian Patent Application No. 2022204568, mailed on Jul. 27, 2023, 3 pages.
Notice of Allowance received for Chinese Patent Application No. 201910204981.4, mailed on Aug. 2, 2023, 4 pages ( 1 page of English Translation and 3 pages of Official Copy).
Notice of Allowance received for Japanese Patent Application No. 2021-192437, mailed on May 19, 2023, 4 pages (1 page of English Translation and 3 pages of Official Copy).
Notice of Allowance received for Japanese Patent Application No. 2022-502594, mailed on Jul. 7, 2023, 4 pages (1 page of English Translation and 3 pages of Official Copy).
Notice of Allowance received for Korean Patent Application No. 10-2022-7036381, mailed on Jul. 12, 2023, 7 pages (2 pages of English Translation and 5 pages of Official Copy).
Notice of Allowance received for U.S. Appl. No. 17/031,779, mailed on May 26, 2023, 9 pages.
Notice of Allowance received for U.S. Appl. No. 17/135,710, mailed on Jul. 27, 2023, 9 pages.
Notice of Allowance received for U.S. Appl. No. 17/952,053, mailed on Apr. 17, 2023, 6 pages.
Notice of Allowance received for U.S. Appl. No. 18/078,444, mailed on May 12, 2023, 9 pages.
Notice of Hearing received for Indian Patent Application No. 201617016494, mailed on Apr. 10, 2023, 2 pages.
Office Action received for Australian Patent Application No. 2020313970, mailed on Mar. 22, 2023, 4 pages.
Office Action received for Australian Patent Application No. 2021261861, mailed on May 3, 2023, 4 pages.
Office Action received for Australian Patent Application No. 2022201823, mailed on Jun. 26, 2023, 6 pages.
Office Action received for Australian Patent Application No. 2022202459, mailed on Mar. 27 2023, 5 pages.
Office Action received for Australian Patent Application No. 2022203508, mailed on May 19, 2023, 2 pages.
Office Action received for Australian Patent Application No. 2022204568, mailed on May 22, 2023, 4 pages.
Office Action received for Chinese Patent Application No. 201910204981.4, mailed on Apr. 29, 2023, 12 pages (4 pages of English Translation and 8 pages of Official Copy).
Office Action received for Chinese Patent Application No. 202210004176.9, mailed on Apr. 28, 2023, 12 pages (6 pages of English Translation and 6 pages of Official Copy).
Office Action received for Chinese Patent Application No. 202210004176.9, mailed on Feb. 19, 2023, 23 pages (14 pages of English Translation and 9 pages of Official Copy).
Office Action received for Danish Patent Application No. PA202070395, mailed on Jul. 5, 2023, 6 pages.
Office Action received for Danish Patent Application No. PA202070395, mailed on Mar. 31, 2023, 3 pages.
Office Action received for European Patent Application No. 20746438.9, mailed on Jul. 4, 2023, 7 pages.
Office Action received for European Patent Application No. 20760607.0, mailed on Aug. 17, 2023, 7 pages.
Office Action received for German Patent Application No. 112020002566.7, mailed on Mar. 24, 2023, 32 pages (14 pages of English Translation and 18 pages of official copy).
Office Action received for Indian Patent Application No. 202215032692, mailed on Jun. 15, 2023, 3 pages.
Office Action received for Japanese Patent Application No. 2022-078277, mailed on Jun. 9, 2023, 11 pages (6 pages of English Translation and 5 pages of Official Copy).
Office Action received for Japanese Patent Application No. 2022-078280, mailed on Jul. 24, 2023, 8 pages (4 pages of English Translation and 4 pages of Official Copy).
Office Action received for Japanese Patent Application No. 2022-502594, mailed on Mar. 20, 2023, 10 pages (5 pages of English Translation and 5 pages of Official Copy).
Office Action received for Korean Patent Application No. 10-2020-0124134, mailed on Jun. 23, 2023, 8 pages (4 pages of English Translation and 4 pages of Official Copy).
Office Action received for Korean Patent Application No. 10-2020-0124134, mailed on Mar. 28, 2023, 9 pages (4 pages of English Translation and 5 pages of Official Copy).
Supplemental Notice of Allowance received for U.S. Appl. No. 18/078,444, mailed on Jun. 15, 2023, 2 pages.
Dabek et al., "A timeline-based framework for aggregating and summarizing electronic health records", IEEE Workshop on Visual Analytics in Healthcare (VAHC), available online at : https://www.researchgate.net/publication/325833364_A_timeline-based_framework_for_aggregating_and_summarizing_electronic_health_records, 2017, 7 pages.
Levy et al., "A good little tool to get to know yourself a bit better", a qualitative study oon users' experiences of app-supported menstrual tracking in Europe., In: BMC Public Health, vol. 19, 2019, pp. 1-11.
Applicant-Initiated Interview Summary received for U.S. Appl. No. 17/041,415, mailed on Jun. 29, 2022, 2 pages.
Final Office Action received for U.S. Appl. No. 17/031,723, mailed on Jul. 12, 2022, 25 pages.
Final Office Action received for U.S. Appl. No. 17/031,779, mailed on Jul. 14, 2022, 19 pages.
Notice of Allowance received for U.S. Appl. No. 17/031,717, mailed on Jul. 7, 2022, 12 pages.
Summons to Attend Oral Proceedings received for European Patent Application No. 20203526.7, mailed on Jun. 23, 2022, 9 pages.
Notice of Allowance received for Japanese Patent Application No. 2021-167557, mailed on Jan. 27, 2023, 4 pages (1 page of English Translation and 3 pages of Official Copy).
Office Action received for European Patent Application No. 20746438.9, mailed on Feb. 1, 2023, 9 pages.
Office Action received for European Patent Application No. 20760607.0, mailed on Feb. 1, 2023, 13 pages.
Corrected Notice of Allowance received for U.S. Appl. No. 17/031,717, mailed on May 19, 2022, 3 pages.
Non-Final Office Action received for U.S. Appl. No. 16/851,451, mailed on May 9, 2022, 26 pages.
Decision to Grant received for Danish Patent Application No. PA202070619, mailed on Aug. 11, 2022, 2 pages.
Non-Final Office Action received for U.S. Appl. No. 16/249,627, mailed on Aug. 22, 2022, 21 pages.

(56) References Cited

OTHER PUBLICATIONS

Office Action received for Japanese Patent Application No. 2021-167557, mailed on Aug. 15, 2022, 5 pages (3 pages of English Translation and 2 pages of Official Copy).
Applicant-Initiated Interview Summary received for U.S. Appl. No. 16/249,627, mailed on Sep. 28, 2022, 4 pages.
Notice of Allowance received for Chinese Patent Application No. 202111611270.2, mailed on Sep. 21, 2022, 4 pages (1 page of English Translation and 3 pages of Official Copy).
Office Action received for Danish Patent Application No. PA202070395, mailed on Oct. 7, 2022, 4 pages.
Supplemental Notice of Allowance received for U.S. Appl. No. 17/041,415, mailed on Oct. 13, 2022, 2 pages.
Intention to Grant received for European Patent Application No. 20182116.2, mailed on Jun. 2, 2022, 8 pages.
Minutes of the Oral Proceedings received for European Patent Application No. 20182116.2, mailed on May 24, 2022, 7 pages.
Notice of Allowance received for Korean Patent Application No. 10-2022-7008569, mailed on May 19, 2022, 5 pages (2 pages of English Translation and 3 pages of Official Copy).
Office Action received for Chinese Patent Application No. 202011220489.5, mailed on Apr. 25, 2022, 15 pages (9 pages of English Translation and 6 pages of Official Copy).
Applicant-Initiated Interview Summary received for U.S. Appl. No. 16/851,451, mailed on Nov. 29, 2022, 4 pages.
Extended European Search Report received for European Patent Application No. 22190169.7, mailed on Nov. 23, 2022, 11 pages.
Final Office Action received for U.S. Appl. No. 16/888,780, mailed on Nov. 25, 2022, 10 pages.
Intention to Grant received for European Patent Application No. 20182116.2, mailed on Nov. 11, 2022, 9 pages.
Invitation to Pay Search Fees received for European Patent Application No. 20746438.9, mailed on Dec. 2, 2022, 4 pages.
Invitation to Pay Search Fees received for European Patent Application No. 20760607.0, mailed on Nov. 21, 2022, 3 pages.
Non-Final Office Action received for U.S. Appl. No. 17/031,723, mailed on Dec. 5, 2022, 27 pages.
Office Action received for Australian Patent Application No. 2021266294, mailed on Nov. 11, 2022, 3 pages.
Advisory Action received for U.S. Appl. No. 17/031,779, mailed on Oct. 20, 2022, 5 pages.
Applicant-Initiated Interview Summary received for U.S. Appl. No. 16/953,781, mailed on Oct. 31, 2022, 12 pages.
Final Office Action received for U.S. Appl. No. 16/851,451, mailed on Oct. 20, 2022, 31 pages.
Office Action received for Australian Patent Application No. 2021261861, mailed on Oct. 14, 2022, 5 pages.
Office Action received for Chinese Patent Application No. 202010618240.3, mailed on Sep. 21, 2022, 16 pages (9 pages of English Translation and 7 pages of Official Copy).
Office Action received for Chinese Patent Application No. 202210004176.9, mailed on Sep. 28, 2022, 12 pages (6 pages of English Translation and 6 pages of Official Copy).
Non-Final Office Action received for U.S. Appl. No. 17/952,053, mailed on Jan. 12, 2023, 12 pages.
Notice of Allowance received for U.S. Appl. No. 17/317,084, mailed on Jan. 6, 2023, 6 pages.
Office Action received for Australian Patent Applicaiton No. 2021261861, mailed on Jan. 12, 2023, 4 pages.
Office Action received for Australian Patent Applicaiton No. 2022202459, mailed on Jan. 6, 2023, 3 pages.
Office Action received for Chinese Patent Applicaiton No. 201910204981.4, mailed on Nov. 29, 2022, 14 pages (5 pages of Engish Translation and 9 pages of Official Copy).
Office Action received for European Patent Applicaiton No. 19703582.7, mailed on Jan. 11, 2023, 11 pages.
Breif Communication Regarding Oral Proceedings received for European Patent Applicaiton No. 20746438.9, mailed on Nov. 7, 2022, 1 page.
Notice of Allowance received for U.S. Appl. No. 16/953,781, mailed on Nov. 9, 2022, 7 pages.
Office Action received for European Patent Application No. 20746438.9, mailed on Oct. 31, 2022, 7 pages.
Invitation to Pay Search Fees received for European Patent Application No. 19703582.7, mailed on Sep. 12, 2022, 3 pages.
Supplemental Notice of Allowance received for U.S. Appl. No. 17/041,415, mailed on Sep. 20, 2022, 2 pages.
Supplemental Notice of Allowance received for U.S. Appl. No. 17/317,084, mailed on Sep. 20, 2022, 2 pages.
Brief Communication Regarding Oral Proceedings received for European Patent Application No. 20180581.9, mailed on Jan. 26, 2022, 1 page.
Brief Communication regarding Oral Proceedings received for European Patent Application No. 20180592.6, mailed on Jan. 26, 2022, 2 pages.
Final Office Action received for U.S. Appl. No. 16/249,627, mailed on Feb. 14, 2022, 19 pages.
Intention to Grant received for Danish Patent Application No. PA202070619, mailed on Jan. 17, 2022, 2 pages.
International Preliminary Report on Patentability received for PCT Patent Application No. PCT/US2020/042439, mailed on Jan. 27, 2022, 10 pages.
Non-Final Office Action received for U.S. Appl. No. 17/031,723, mailed on Jan. 24, 2022, 17 pages.
Non-Final Office Action received for U.S. Appl. No. 17/031,779, mailed on Feb. 16, 2022, 17 pages.
Notice of Acceptance received for Australian Patent Application No. 2020288147, mailed on Dec. 22, 2021, 3 pages.
Notice of Allowance received for Chinese Patent Application No. 202010606407.4, mailed on Jan. 24, 2022, 2 pages (1 page of English Translation and 1 page of Official Copy).
Notice of Allowance received for Chinese Patent Application No. 202010618569.X, mailed on Jan. 7, 2022, 2 pages (1 page of English Translation and 1 page of Official Copy).
Notice of Allowance received for Japanese Patent Application No. 2018-184532, mailed on Jan. 17, 2022, 4 pages (1 page of English Translation and 3 pages of Official Copy).
Notice of Allowance received for Korean Patent Application No. 10-2021-7042504, mailed on Jan. 17, 2022, 6 pages (1 page of English Translation and 5 pages of Official Copy).
Notice of Allowance received for U.S. Appl. No. 16/894,309, mailed on Feb. 25, 2022, 9 pages.
Office Action received for Australian Patent Application No. 2020239692, mailed on Jan. 27, 2022, 3 pages.
Office Action received for Chinese Patent Application No. 201910858933.7, mailed on Dec. 30, 2021, 9 pages (4 pages of English Translation and 5 pages of Official Copy).
Office Action received for Chinese Patent Application No. 202011220489.5, mailed on Dec. 1, 2021, 19 pages (11 pages of English Translation and 8 pages of Official Copy).
Office Action received for Japanese Patent Application No. 2020-160023, mailed on Jan. 27, 2022, 11 pages (6 pages of English Translation and 5 pages of Official Copy).
Office Action received for Japanese Patent Application No. 2020-551585, mailed on Jan. 6, 2022, 11 pages (5 pages of English Translation and 6 pages of Official Copy).
Office Action received for Korean Patent Application No. 10-2020-7023277, mailed on Jan. 26, 2022, 11 pages (5 pages of English Translation and 6 pages of Official Copy).
Result of Consultation received for European Patent Application No. 20180581.9, mailed on Jan. 21, 2022, 14 pages.
Result of Consultation received for European Patent Application No. 20180592.6, mailed on Jan. 26, 2022, 18 pages.
Supplemental Notice of Allowance received for U.S. Appl. No. 16/894,309, mailed on Jan. 25, 2022, 2 pages.
Final Office Action received for U.S. Appl. No. 17/952,182, mailed on Jan. 4, 2024, 9 pages.
Office Action received for European Patent Application No. 20760607.0, mailed on Jan. 3, 2024, 7 pages.
Office Action received for Japanese Patent Application No. 2022-573764, mailed on Dec. 25, 2023, 8 pages (4 pages of English Translation and 4 pages of Official Copy).

(56) References Cited

OTHER PUBLICATIONS

Applicant-Initiated Interview Summary received for U.S. Appl. No. 16/249,627, mailed on Nov. 21, 2023, 5 pages.
Office Action received for Danish Patent Application No. PA202070395, mailed on Nov. 3, 2023, 3 pages.
Office Action received for Korean Patent Application No. 10-2023-7034892, mailed on Nov. 8, 2023, 5 pages (2 pages of English Translation and 3 pages of Official Copy).
Notice of Allowance received for Japanese Patent Application No. 2022-131993, mailed on Dec. 18, 2023, 4 pages (1 page of English Translation and 3 pages of Official Copy).
Office Action received for Korean Patent Application No. 10-2022-7012608, mailed on Dec. 5, 2023, 12 pages (5 pages of English Translation and 7 pages of Official Copy).
Final Office Action received for U.S. Appl. No. 17/031,723, mailed on Oct. 4, 2023, 13 pages.
Notice of Acceptance received for Australian Patent Application No. 2022201823, mailed on Sep. 26, 2023, 3 pages.
Office Action received for Australian Patent Application No. 2021261861, mailed on Sep. 22, 2023, 5 pages.
Office Action received for Japanese Patent Application No. 22022-131993, mailed on Sep. 15, 2023, 6 pages (3 pages of English Translation and 3 pages of Official Copy).
Notice of Acceptance received for Australian Patent Application No. 2023212604, mailed on Oct. 12, 2023, 3 pages.
Office Action received for Australian Patent Application No. 2021283914, mailed on Sep. 25, 2023, 5 pages.
Supplemental Notice of Allowance received for U.S. Appl. No. 18/078,444, mailed on Oct. 16, 2023, 4 pages.
Applicant-Initiated Interview Summary received for U.S. Appl. No. 17/031,723, mailed on Oct. 31, 2023, 4 pages.
Final Office Action received for U.S. Appl. No. 17/337,147, mailed on Oct. 31, 2023, 17 pages.
Non-Final Final Office Action received for U.S. Appl. No. 16/249,627, mailed on Oct. 31, 2023, 23 pages.
Notice of Allowance received for Japanese Patent Appliaction No. 2022-078277, mailed on Oct. 27, 2023, 4 pages (1 page of English Translation and 3 pages of Official Copy).
Notice of Allowance received for U.S. Appl. No. 17/135,710, mailed on Nov. 6, 2023, 7 pages.
Office Action received for Chinese Patent Application No. 202180053264.4, mailed on Sep. 23, 2023, 17 pages (9 pages of English Translation and 8 pages of Official Copy).
Office Action received for European Patent Application No. 20746438.9, mailed on Oct. 31, 2023, 9 pages.
Office Action received for European Patent Application No. 20751022.3, mailed on Oct. 19, 2023, 8 pages.
Office Action received for European Patent Application No. 20753659.0, mailed on Oct. 26, 2023, 9 pages.
Notice of Allowance received for U.S. Appl. No. 17/135,710, mailed on Jan. 23, 2024, 7 pages.
Office Action received for Australian Patent Application No. 2021283914, mailed on Dec. 13, 2023, 5 pages.
Applicant-Initiated Interview Summary received for U.S. Appl. No. 16/888,780, mailed on Dec. 14, 2023, 3 pages.
Decision on Appeal received for Korean Patent Application No. 10-2020-0124134, mailed on Oct. 20, 2023, 24 pages (4 pages of English Translation and 20 pages of Official Copy).
Notice of Allowance received for Korean Patent Application No. 10-2020-0124134, mailed on Nov. 21, 2023, 9 pages (2 pages of English Translation and 6 pages of Official Copy).
Hardwick Tim, "AliveCor 'Kardia Band' Medical Grade EKG Analyzer for Apple Watch Receives FDA Approval", MacRumors, Available online at: https://www.macrumors.com/2017/11/30/alivecor-kardia-ekg-band-medical-fda-apple-watch/, Nov. 30, 2017, 3 pages.
Kardia by Alivecor, "How to Record a Clean EKG With Kardiaband", Available Online at https://www.youtube.com/watch?v=Vlc9VE6VO4&t=2s, Nov. 30, 2017, 2 pages.
Luo et al., "Detection and Prediction of Ovulation from Body Temperature Measured by an In-Ear Wearable Thermometer", IEEE Transactions on Biomedical Engineering, Available online at:10.1109/TBME.2019.2916823, vol. 67, No. 2, May 15, 2019, pp. 512-522.
Prasad et al., "Understanding Sharing Preferences and Behavior for Mhealth Devices", Proceedings of the 2012 ACM workshop on Privacy in the electronic society, Available online at: https://dl.acm.org/doi/10.1145/2381966.2381983, Oct. 15, 2012, pp. 117-128.
Corrected Notice of Allowance received for U.S. Appl. No. 17/952,053, mailed on Jan. 25, 2024, 6 pages.
Non-Final Office Action received for U.S. Appl. No. 17/554,678, mailed on Feb. 1, 2024, 10 pages.
Notice of Allowance received for U.S. Appl. No. 16/851,451, mailed on Jan. 31, 2024, 13 pages.
Office Action received for Korean Patent Application No. 10-2023-7018399, mailed on Jan. 24, 2024, 11 pages (4 pages of English Translation and 7 pages of Offical Copy).
Corrected Notice of Allowance received for U.S. Appl. No. 16/851,451, mailed on Feb. 20, 2024, 3 pages.
Notice of Allowance received for U.S. Appl. No. 17/135,710, mailed on Feb. 14, 2024, 4 pages.
Office Action received for Chinese Patent Application No. 201980018078.7, mailed on Nov. 25, 2023, 20 pages (9 pages of English Translation and 11 pages of Official Copy).
Office Action received for Indian Patent Application No. 202315061713, mailed on Feb. 14, 2024, 8 pages.
Office Action received for Indian Patent Application No. 202315061718, mailed on Feb. 14, 2024, 8 pages.
Office Action received for Chinese Patent Application No. 202210346306.7, mailed on Apr. 10, 2024, 18 pages (10 pages of English Translation and 8 pages of Official Copy).

\* cited by examiner

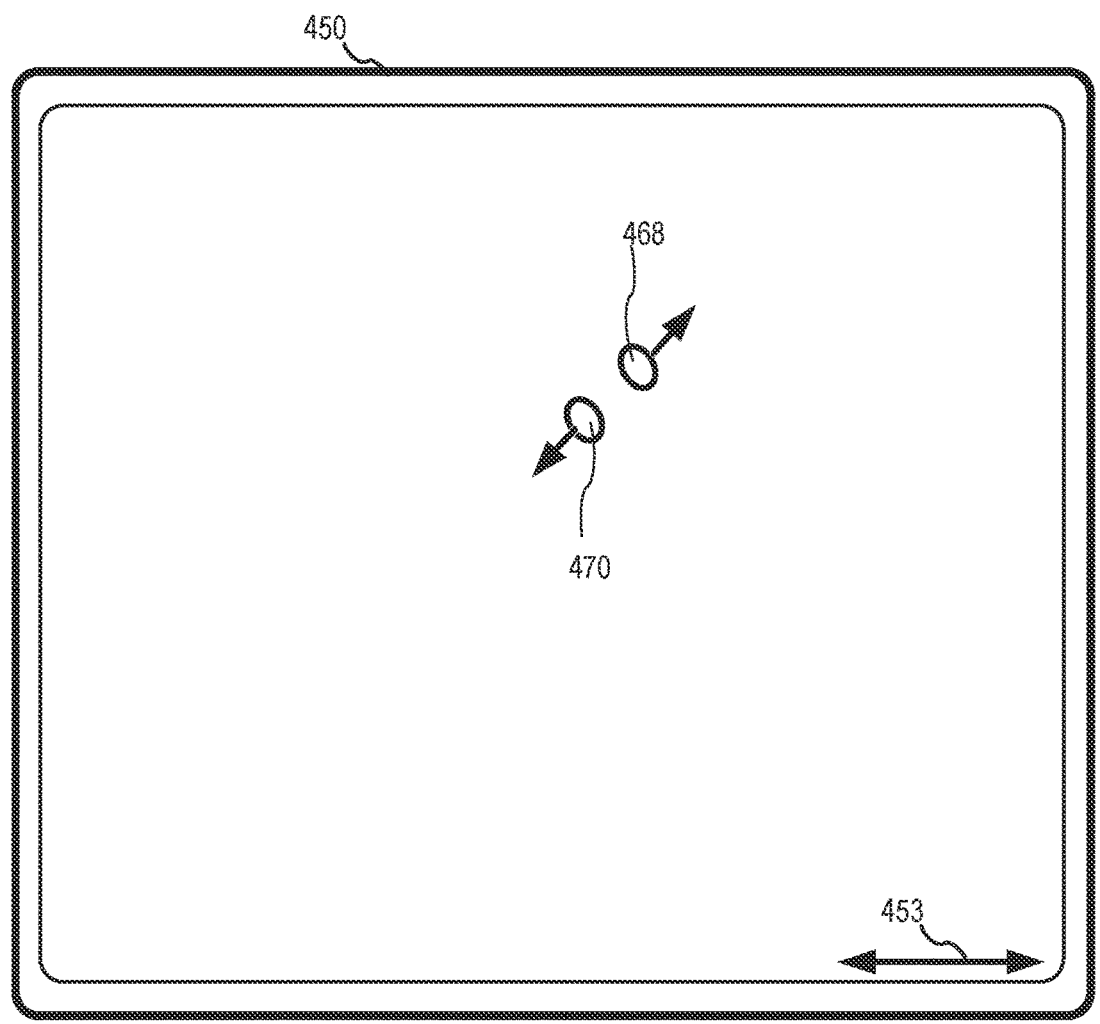
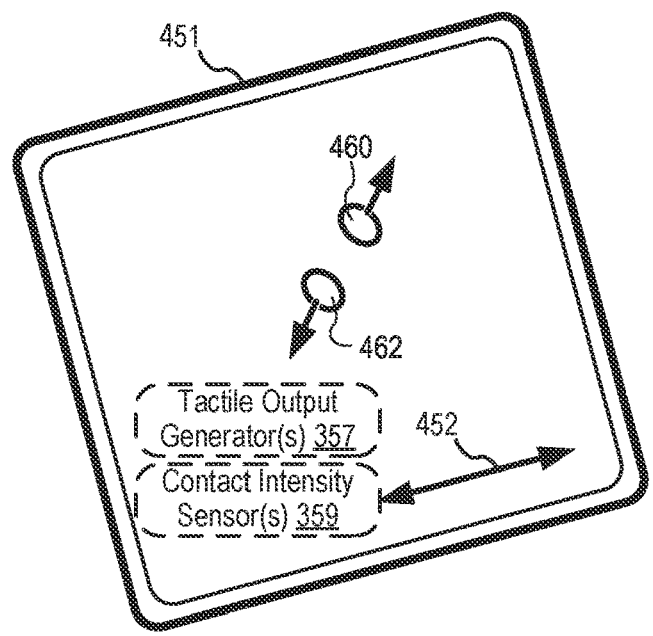
*FIG. 4B*

RESEARCH STUDY USER INTERFACES

CROSS-REFERENCE TO RELATED APPLICATIONS

This application is a continuation of U.S. application Ser. No. 16/990,846, filed Aug. 11, 2020, entitled "RESEARCH STUDY USER INTERFACES," which claims the benefit of U.S. Provisional Application No. 62/897,693, filed Sep. 9, 2019, entitled "RESEARCH STUDY USER INTERFACES," the entire contents of which is hereby incorporated by reference.

FIELD

The present disclosure relates generally to computer user interfaces, and more specifically to techniques and user interfaces for interacting with research studies.

BACKGROUND

Users of electronic devices can provide information to research studies that gather data for use in investigations involving multiple users across multiple electronic devices. Such information can be provided to such studies using user interfaces that include one or more graphical elements adapted for use with research studies.

BRIEF SUMMARY

Some techniques for interacting with research studies using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for interacting with research studies. Such methods and interfaces optionally complement or replace other methods for interacting with research studies. Such methods and interfaces reduce the cognitive burden on a user and produce a more efficient human-machine interface. For battery-operated computing devices, such methods and interfaces conserve power and increase the time between battery charges. For research studies that involve requests for personal and/or sensitive data, such methods and interfaces can improve data-handling security provide users with effective and efficient methods for managing data access permissions.

In accordance with some embodiments, a method is described. In some embodiments, the method is performed at an electronic device having a display device and one or more input devices. In some embodiments, the method comprises: displaying, via the display device, a first user interface that includes a task view affordance associated with a plurality of different studies including a first study in which a user of the electronic device is enrolled and a second study in which the user of the electronic device is enrolled; while displaying the first user interface, detecting, via the one or more input devices, a first input; in response to detecting the first input and in accordance with a determination that the first input corresponds to selection of the task view affordance, displaying, via the display device, a task view that includes concurrently displaying: a first task corresponding to the first study; and a second task corresponding to the second study.

In accordance with some embodiments, a non-transitory computer-readable storage medium storing one or more programs configured to be executed by one or more processors of an electronic device with a display device and one or more input devices is described. In some embodiments, the one or more programs include instructions for: displaying, via the display device, a first user interface that includes a task view affordance associated with a plurality of different studies including a first study in which a user of the electronic device is enrolled and a second study in which the user of the electronic device is enrolled; while displaying the first user interface, detecting, via the one or more input devices, a first input; in response to detecting the first input and in accordance with a determination that the first input corresponds to selection of the task view affordance, displaying, via the display device, a task view that includes concurrently displaying: a first task corresponding to the first study; and a second task corresponding to the second study.

In accordance with some embodiments, a transitory computer-readable storage medium storing one or more programs configured to be executed by one or more processors of an electronic device with a display device and one or more input devices is described. In some embodiments, the one or more programs include instructions for: displaying, via the display device, a first user interface that includes a task view affordance associated with a plurality of different studies including a first study in which a user of the electronic device is enrolled and a second study in which the user of the electronic device is enrolled; while displaying the first user interface, detecting, via the one or more input devices, a first input; in response to detecting the first input and in accordance with a determination that the first input corresponds to selection of the task view affordance, displaying, via the display device, a task view that includes concurrently displaying: a first task corresponding to the first study; and a second task corresponding to the second study.

In accordance with some embodiments, an electronic device is described. In some embodiments, the electronic device comprises: a display device; one or more input devices; one or more processors; and memory storing one or more programs configured to be executed by the one or more processors. In some embodiments, the one or more programs include instructions for: displaying, via the display device, a first user interface that includes a task view affordance associated with a plurality of different studies including a first study in which a user of the electronic device is enrolled and a second study in which the user of the electronic device is enrolled; while displaying the first user interface, detecting, via the one or more input devices, a first input; in response to detecting the first input and in accordance with a determination that the first input corresponds to selection of the task view affordance, displaying, via the display device, a task view that includes concurrently displaying: a first task corresponding to the first study; and a second task corresponding to the second study.

In accordance with some embodiments, an electronic device is described. In some embodiments, the electronic device comprises: a display device; one or more input devices; means for displaying, via the display device, a first user interface that includes a task view affordance associated with a plurality of different studies including a first study in which a user of the electronic device is enrolled and a second study in which the user of the electronic device is enrolled; means for detecting, while displaying the first user interface and via the one or more input devices, a first input; and means for, in response to detecting the first input and in accordance with a determination that the first input corresponds to selection of the task view affordance, displaying, via the display device, a task view that includes concurrently displaying: a first task corresponding to the first study; and a second task corresponding to the second study.

In accordance with some embodiments, a method is described. In some embodiments, the method is performed at an electronic device having a display device and one or more input devices. In some embodiments, the method comprises: displaying, via the display device, a research study user interface that is associated with a first research study; while displaying the research study interface, receiving, via the one or more input devices, a set of one or more inputs that include interaction with the research study user interface that is associated with the first research study; and in response to receiving the set of one or more inputs: in accordance with a determination that a set of enrollment problem criteria are satisfied, displaying an indication of a problem that prevents enrollment in the first research study; and in accordance with a determination that the set of enrollment problem criteria are not met, forgoing display of the indication of the complication that prevents enrollment in the first research study.

In accordance with some embodiments, a non-transitory computer-readable storage medium storing one or more programs configured to be executed by one or more processors of an electronic device with a display device and one or more input devices is described. In some embodiments, the one or more programs include instructions for: displaying, via the display device, a research study user interface that is associated with a first research study; while displaying the research study interface, receiving, via the one or more input devices, a set of one or more inputs that include interaction with the research study user interface that is associated with the first research study; and in response to receiving the set of one or more inputs: in accordance with a determination that a set of enrollment problem criteria are satisfied, displaying an indication of a problem that prevents enrollment in the first research study; and in accordance with a determination that the set of enrollment problem criteria are not met, forgoing display of the indication of the complication that prevents enrollment in the first research study.

In accordance with some embodiments, a transitory computer-readable storage medium storing one or more programs configured to be executed by one or more processors of an electronic device with a display device and one or more input devices is described. In some embodiments, the one or more programs include instructions for: displaying, via the display device, a research study user interface that is associated with a first research study; while displaying the research study interface, receiving, via the one or more input devices, a set of one or more inputs that include interaction with the research study user interface that is associated with the first research study; and in response to receiving the set of one or more inputs: in accordance with a determination that a set of enrollment problem criteria are satisfied, displaying an indication of a problem that prevents enrollment in the first research study; and in accordance with a determination that the set of enrollment problem criteria are not met, forgoing display of the indication of the complication that prevents enrollment in the first research study.

In accordance with some embodiments, an electronic device is described. In some embodiments, the electronic device comprises: a display device; one or more input devices; one or more processors; and memory storing one or more programs configured to be executed by the one or more processors. In some embodiments, the one or more programs include instructions for: displaying, via the display device, a research study user interface that is associated with a first research study; while displaying the research study interface, receiving, via the one or more input devices, a set of one or more inputs that include interaction with the research study user interface that is associated with the first research study; and in response to receiving the set of one or more inputs: in accordance with a determination that a set of enrollment problem criteria are satisfied, displaying an indication of a problem that prevents enrollment in the first research study; and in accordance with a determination that the set of enrollment problem criteria are not met, forgoing display of the indication of the complication that prevents enrollment in the first research study.

In accordance with some embodiments, an electronic device is described. In some embodiments, the electronic device comprises: a display device; one or more input devices; means for displaying, via the display device, a research study user interface that is associated with a first research study; means for, while displaying the research study interface, receiving, via the one or more input devices, a set of one or more inputs that include interaction with the research study user interface that is associated with the first research study; and means for, in response to receiving the set of one or more inputs: in accordance with a determination that a set of enrollment problem criteria are satisfied, displaying an indication of a problem that prevents enrollment in the first research study; and in accordance with a determination that the set of enrollment problem criteria are not met, forgoing display of the indication of the complication that prevents enrollment in the first research study.

In accordance with some embodiments, a method is described. In some embodiments, the method is performed at an electronic device having a display device, one or more input devices, and one or more microphones. In some embodiments, the method comprises: displaying, via the display device, a hearing test user interface that is associated with a hearing test; while displaying the hearing test user interface, receiving, via the one or more input devices, a set of one or more inputs corresponding to a request to initiate the hearing test; in response to receiving the set of one or more inputs, initiating the hearing test; during the hearing test, detecting, via the one or more microphones, an ambient noise level that includes an audio characteristic; in response to detecting the ambient noise level: in accordance with a determination that the audio characteristic of the ambient noise level exceeds a first threshold value, suspending the hearing test and displaying, via the display device, a restart affordance that, when selected, restarts the hearing test; and in accordance with a determination that the audio characteristic of the ambient noise level does not exceed the first threshold value, proceeding with the hearing test and forgoing display of the restart affordance.

In accordance with some embodiments, a non-transitory computer-readable storage medium storing one or more programs configured to be executed by one or more processors of an electronic device with a display device, one or more input devices, and one or more microphones is described. In some embodiments, the one or more programs include instructions for: displaying, via the display device, a hearing test user interface that is associated with a hearing test; while displaying the hearing test user interface, receiving, via the one or more input devices, a set of one or more inputs corresponding to a request to initiate the hearing test; in response to receiving the set of one or more inputs, initiating the hearing test; during the hearing test, detecting, via the one or more microphones, an ambient noise level that includes an audio characteristic; in response to detecting the ambient noise level: in accordance with a determination that the audio characteristic of the ambient noise level exceeds a first threshold value, suspending the hearing test and displaying, via the display device, a restart affordance that, when selected, restarts the hearing test; and in accordance with a determination that the audio characteristic of the ambient noise level does not exceed the first threshold value, proceeding with the hearing test and forgoing display of the restart affordance.

In accordance with some embodiments, a transitory computer-readable storage medium storing one or more programs configured to be executed by one or more processors of an electronic device with a display device, one or more input devices, and one or more microphones is described. In some embodiments, the one or more programs include instructions for: displaying, via the display device, a hearing test user interface that is associated with a hearing test; while displaying the hearing test user interface, receiving, via the one or more input devices, a set of one or more inputs corresponding to a request to initiate the hearing test; in response to receiving the set of one or more inputs, initiating the hearing test; during the hearing test, detecting, via the one or more microphones, an ambient noise level that includes an audio characteristic; in response to detecting the ambient noise level: in accordance with a determination that the audio characteristic of the ambient noise level exceeds a first threshold value, suspending the hearing test and displaying, via the display device, a restart affordance that, when selected, restarts the hearing test; and in accordance with a determination that the audio characteristic of the ambient noise level does not exceed the first threshold value, proceeding with the hearing test and forgoing display of the restart affordance.

In accordance with some embodiments, an electronic device is described. In some embodiments, the electronic device comprises: a display device; one or more input devices; one or more microphones; one or more processors; and memory storing one or more programs configured to be executed by the one or more processors. In some embodiments, the one or more programs include instructions for: displaying, via the display device, a hearing test user interface that is associated with a hearing test; while displaying the hearing test user interface, receiving, via the one or more input devices, a set of one or more inputs corresponding to a request to initiate the hearing test; in response to receiving the set of one or more inputs, initiating the hearing test; during the hearing test, detecting, via the one or more microphones, an ambient noise level that includes an audio characteristic; in response to detecting the ambient noise level: in accordance with a determination that the audio characteristic of the ambient noise level exceeds a first threshold value, suspending the hearing test and displaying, via the display device, a restart affordance that, when selected, restarts the hearing test; and in accordance with a determination that the audio characteristic of the ambient noise level does not exceed the first threshold value, proceeding with the hearing test and forgoing display of the restart affordance.

In accordance with some embodiments, an electronic device is described. In some embodiments, the electronic device comprises: a display device, one or more input devices, one or more microphones; means for displaying, via the display device, a hearing test user interface that is associated with a hearing test; means for, while displaying the hearing test user interface, receiving, via the one or more input devices, a set of one or more inputs corresponding to a request to initiate the hearing test; means for, in response to receiving the set of one or more inputs, initiating the hearing test; means for, during the hearing test, detecting, via the one or more microphones, an ambient noise level that includes an audio characteristic; means for, in response to detecting the ambient noise level: in accordance with a determination that the audio characteristic of the ambient noise level exceeds a first threshold value, suspending the hearing test and displaying, via the display device, a restart affordance that, when selected, restarts the hearing test; and in accordance with a determination that the audio characteristic of the ambient noise level does not exceed the first threshold value, proceeding with the hearing test and forgoing display of the restart affordance.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for interacting with research studies, thereby increasing the effectiveness, efficiency, and user satisfaction with such devices. Such methods and interfaces may complement or replace other methods for interacting with research studies.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for interacting with research studies. Such techniques can reduce the cognitive burden on a user who interact with research studies, thereby enhancing productivity. Further, such techniques can reduce processor and battery power otherwise wasted on redundant user inputs.

Figure 6A:
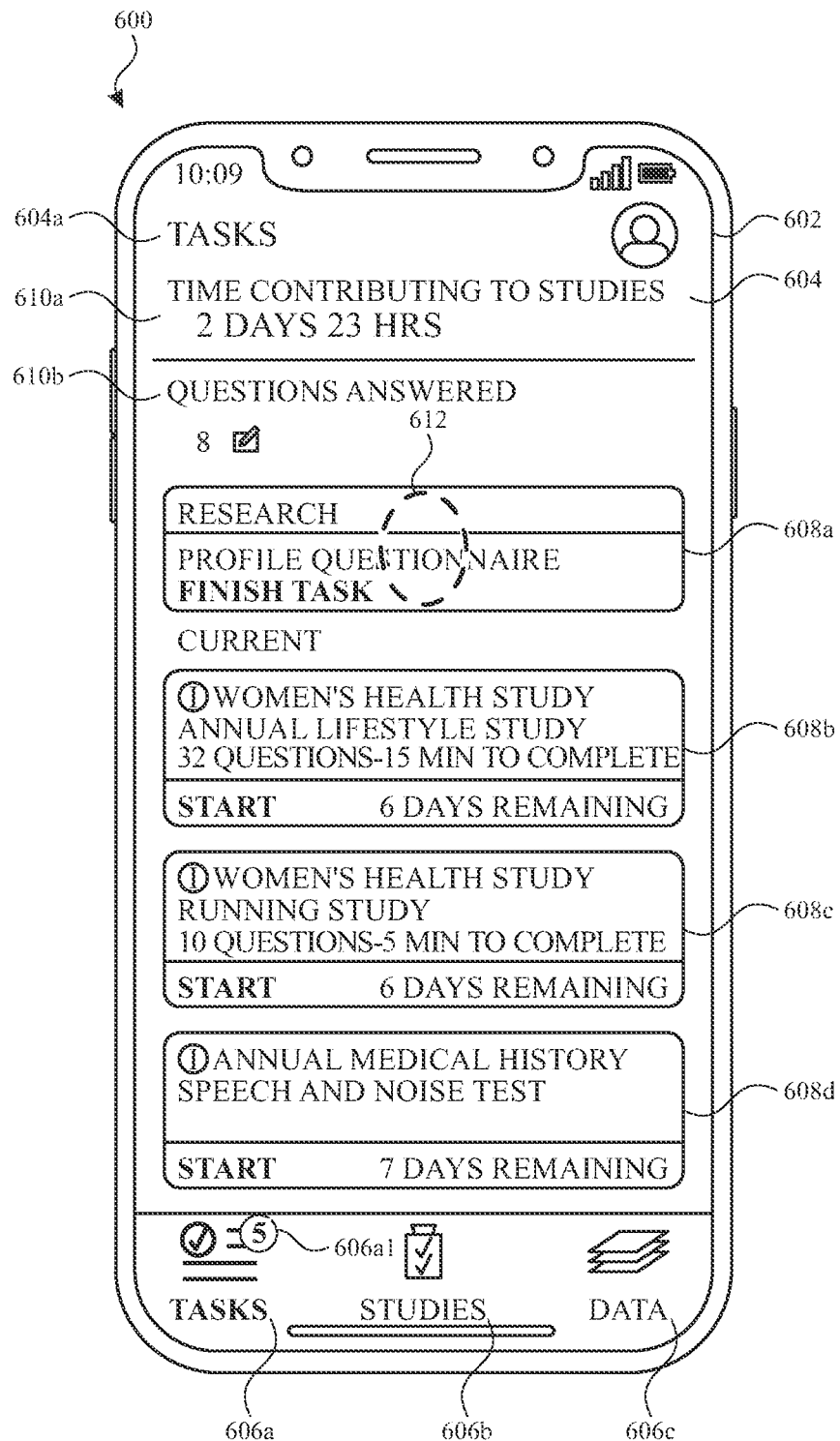
FIGS. 6A-6N illustrate exemplary user interfaces for interacting with and/or managing research studies.
Figure 6N:
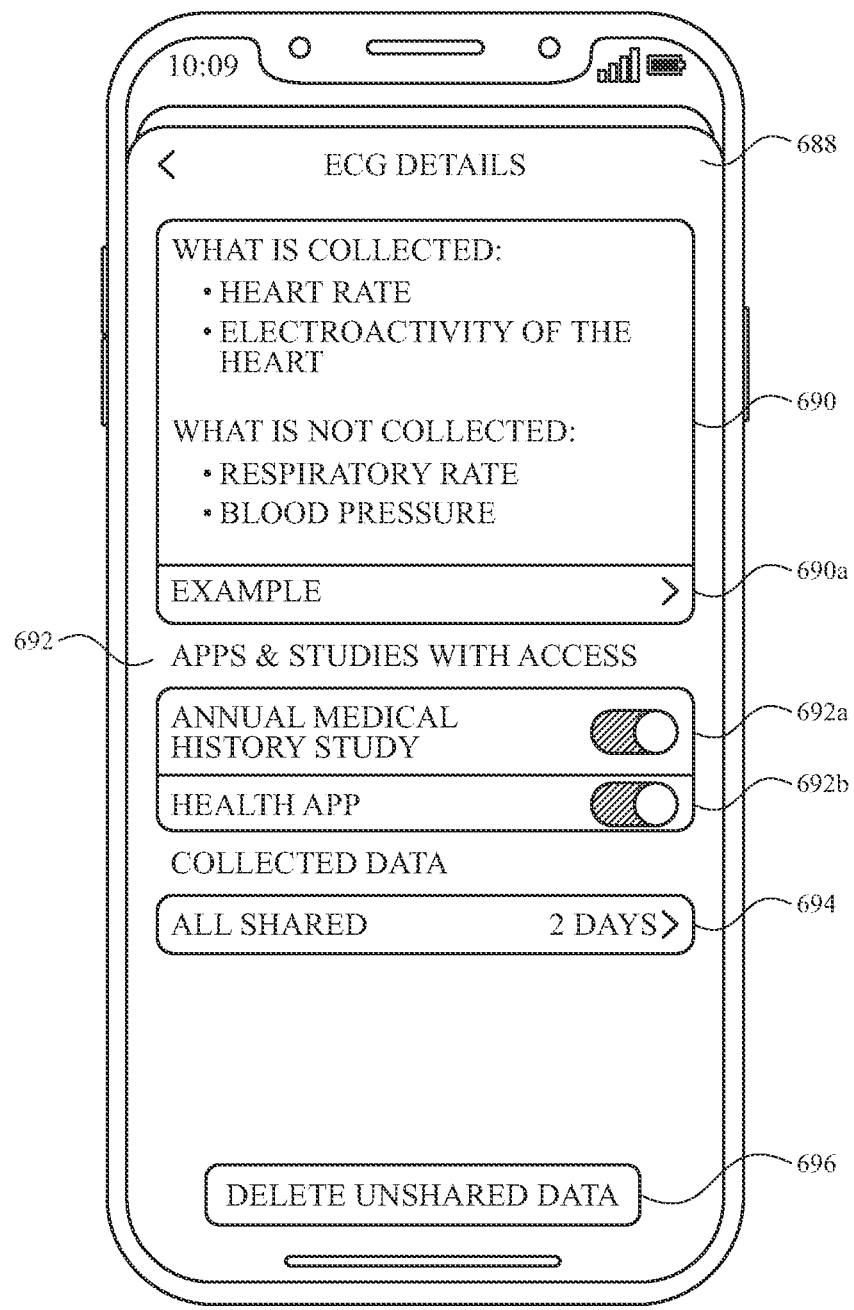
Figure 7:
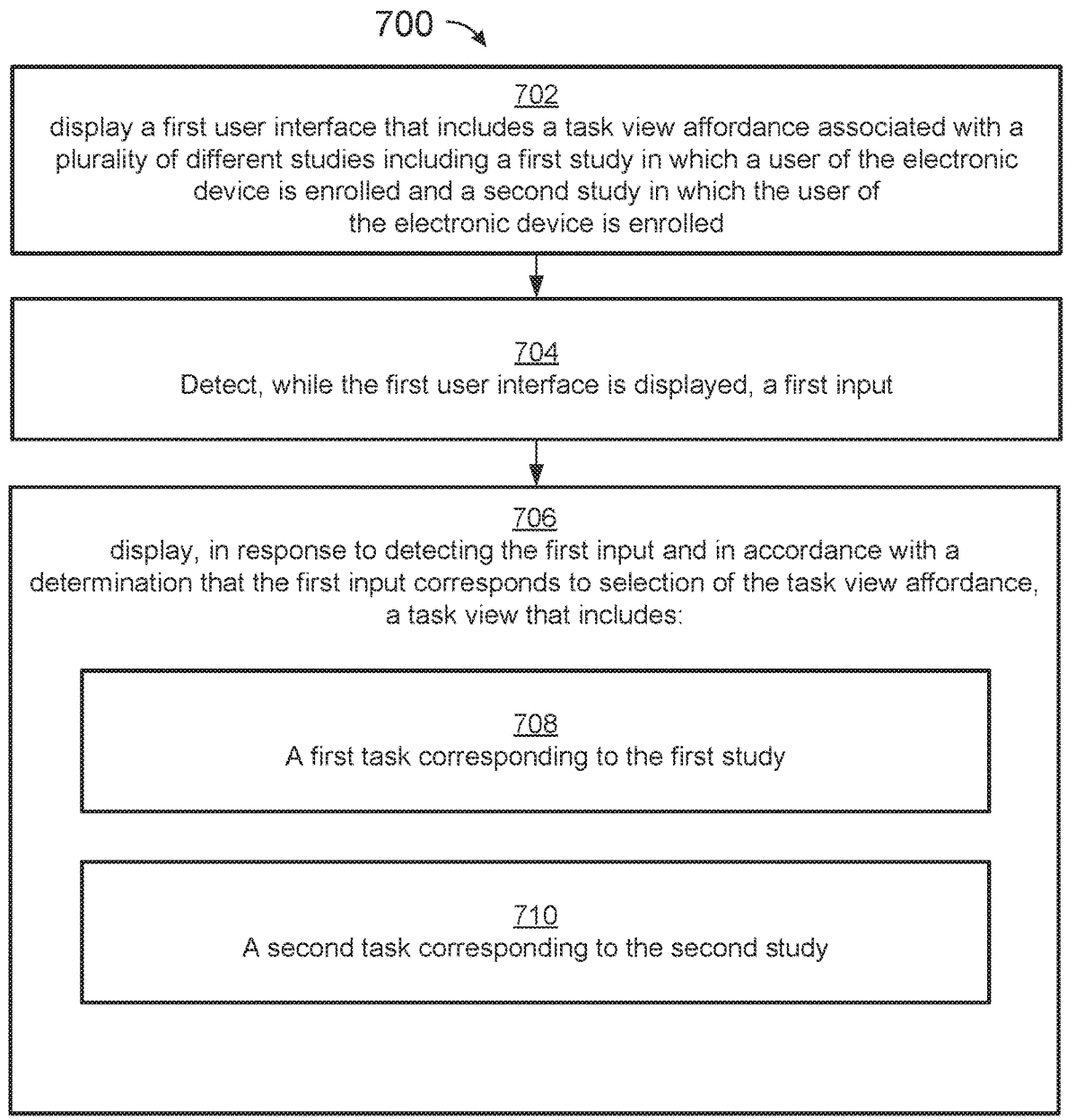
FIG. 7 is a flow diagram illustrating a method for interacting with and/or managing research studies.
Figure 8A:
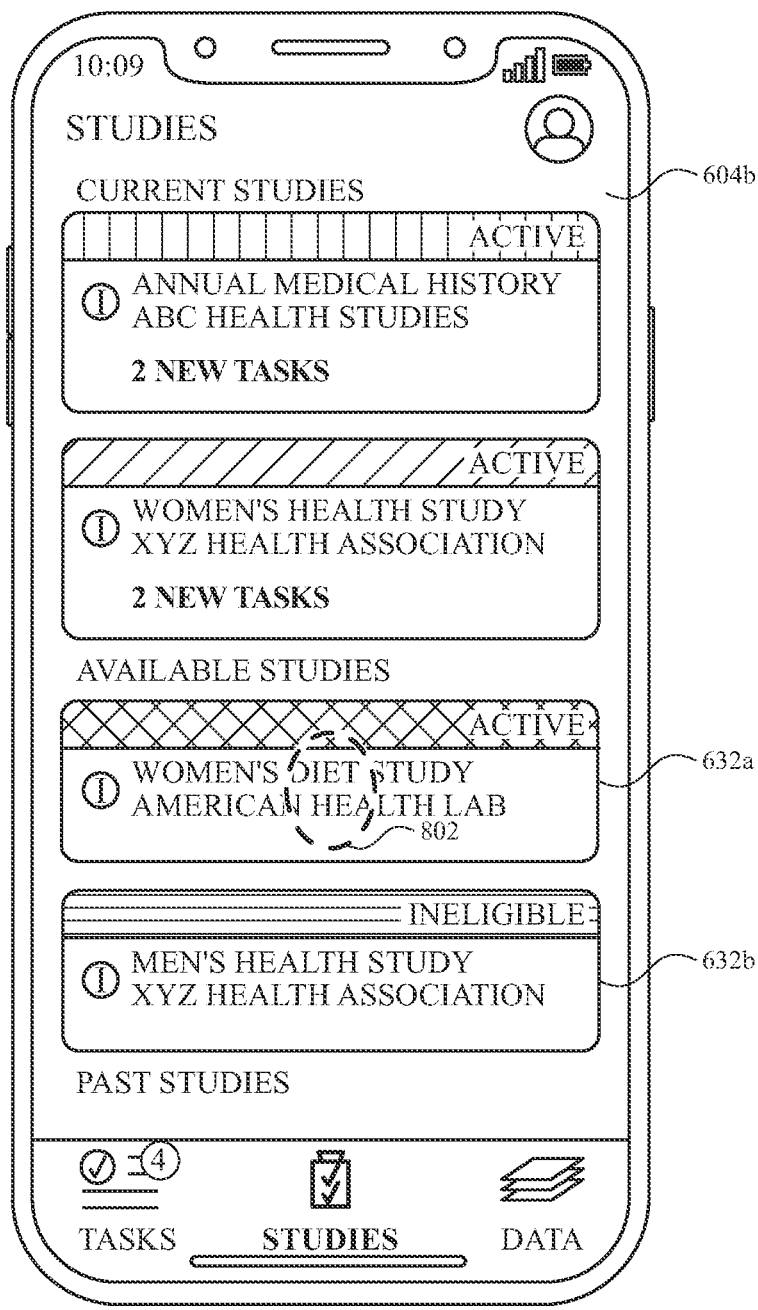
FIGS. 8A-8U illustrate exemplary user interfaces for enrolling in a research study.
Figure 8U:
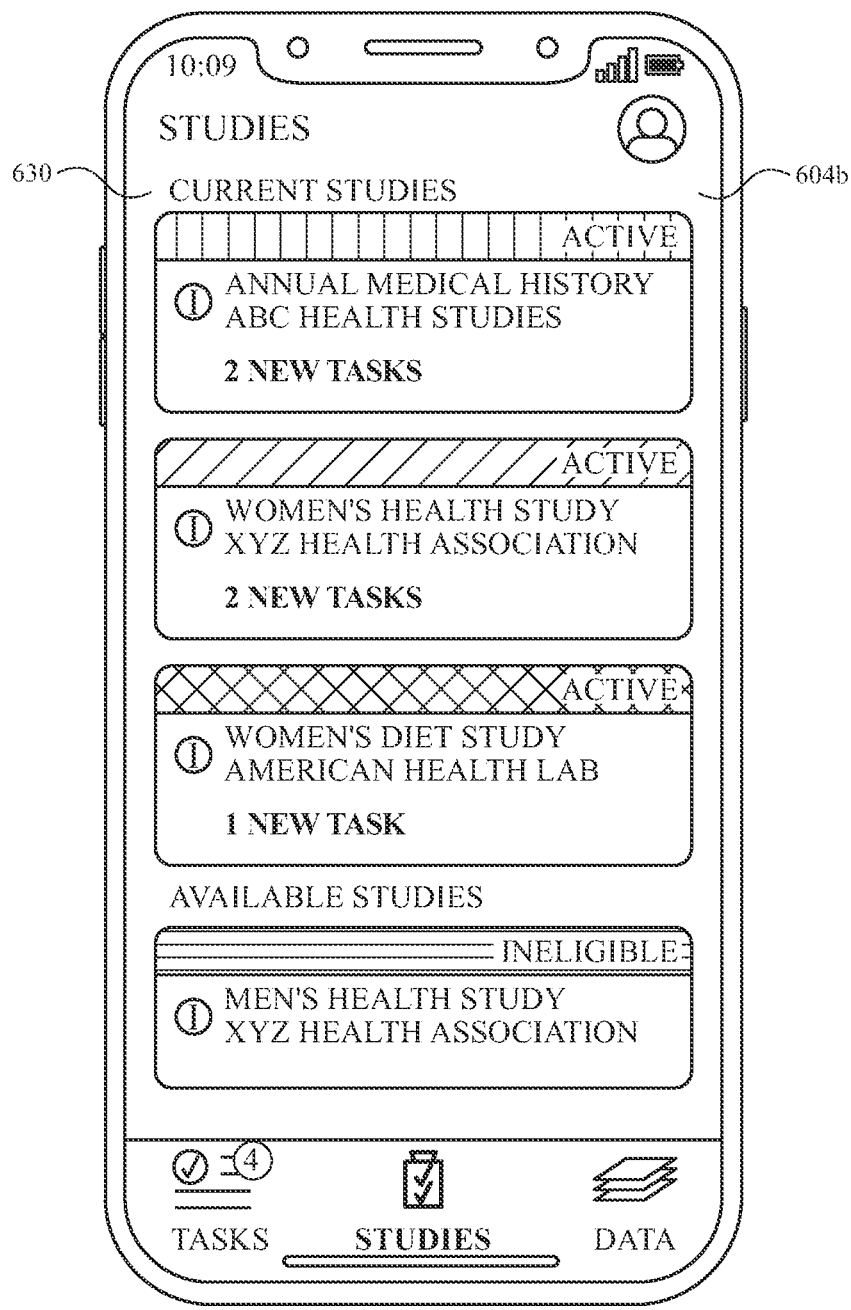
Figure 9:
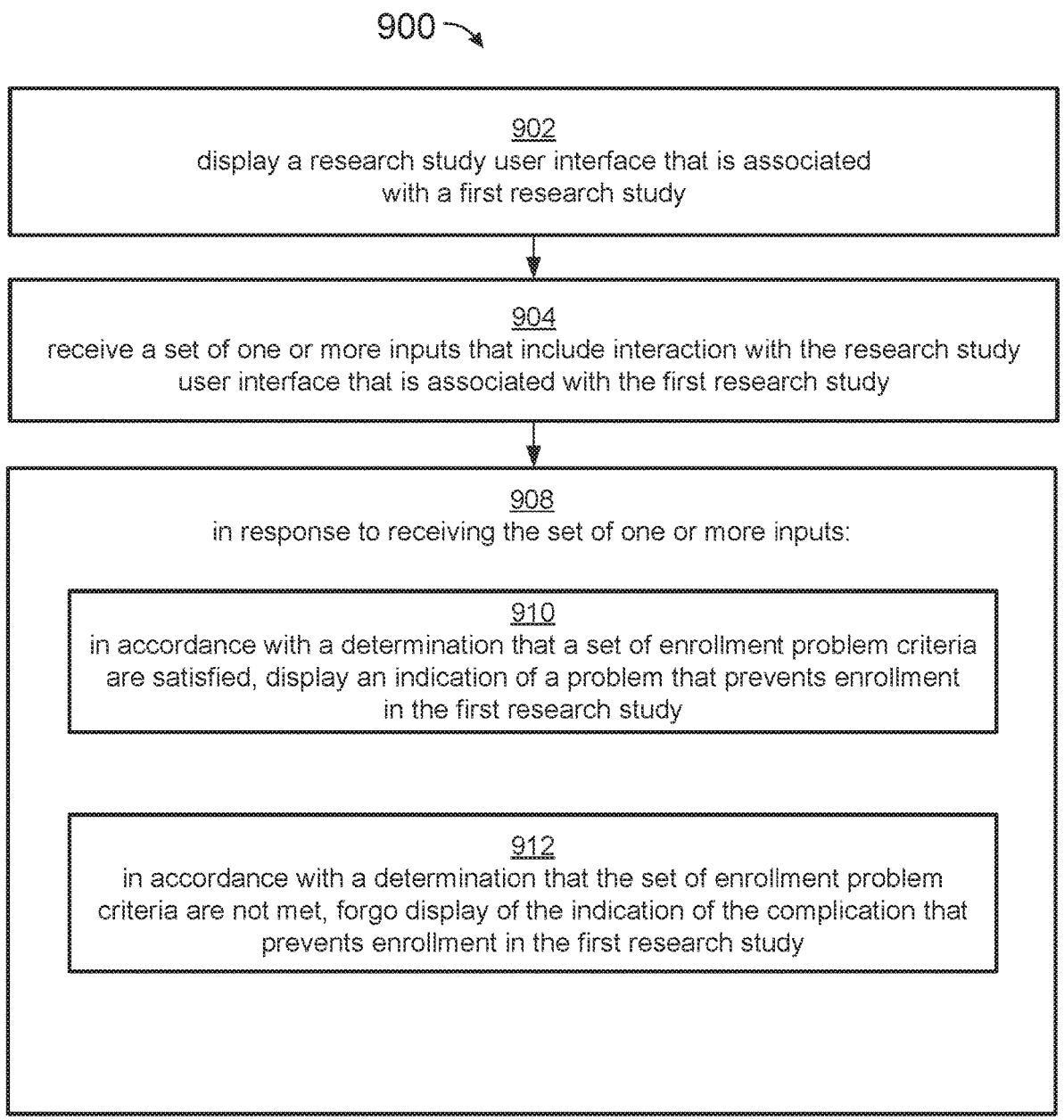
FIG. 9 is a flow diagram illustrating a method for enrolling in a research study.
Figure 10A:
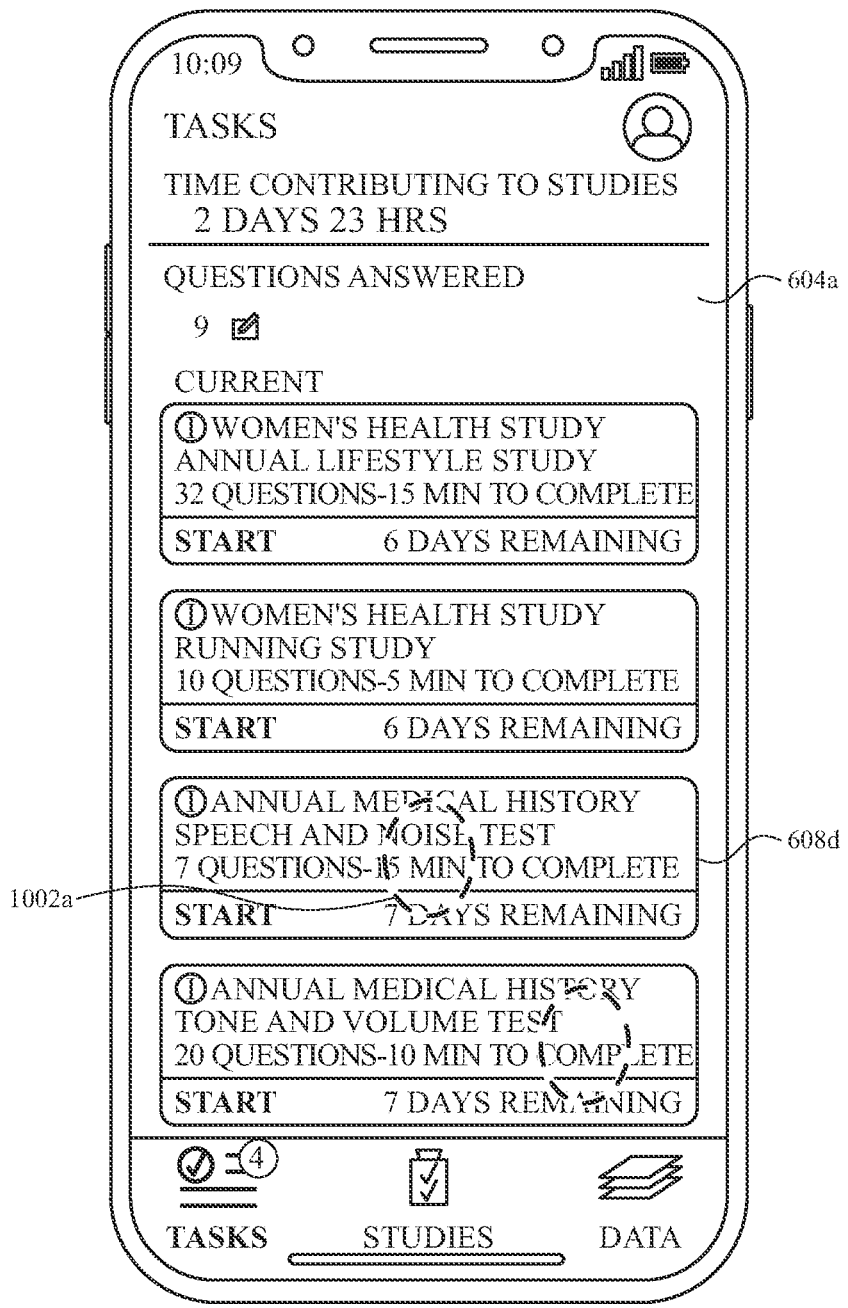
FIGS. 10A-10X illustrate exemplary user interfaces for interacting with a hearing test.
Figure 10X:
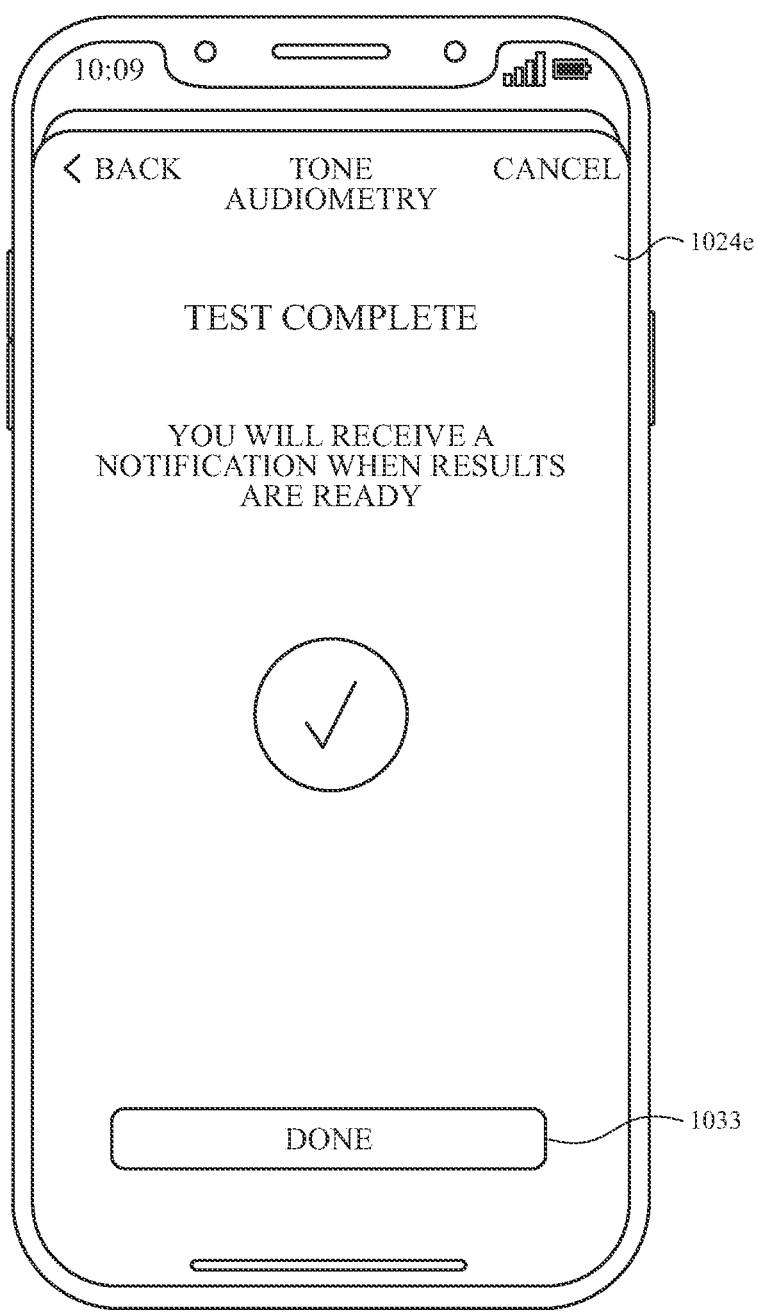
Figure 11:
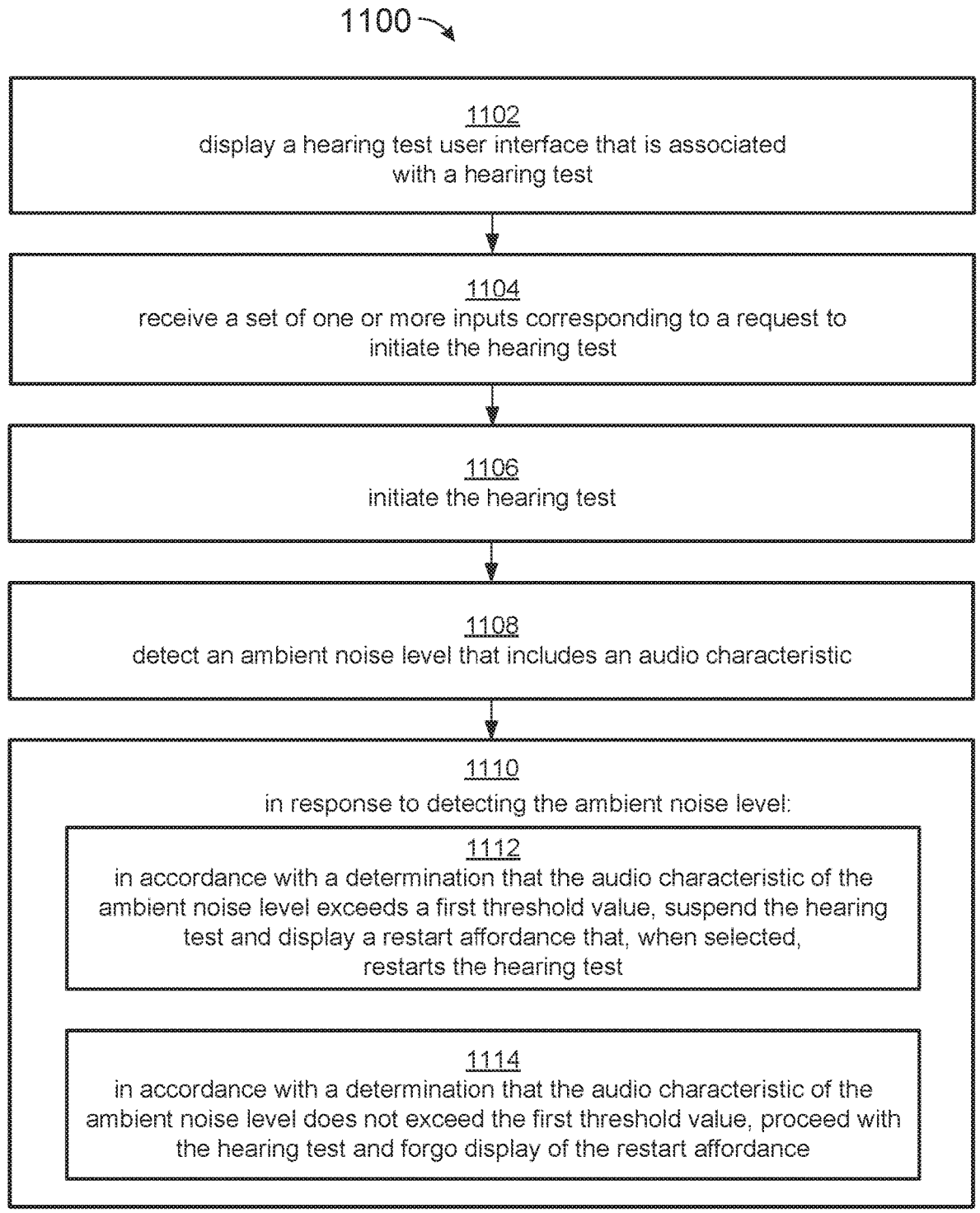
FIG. 11 is a flow diagram illustrating a method for interacting with a hearing test.

Below, FIGS. 1A-1B, 2, 3, 4A-4B, and 5A-5B provide a description of exemplary devices for performing the techniques for interacting with research studies. FIGS. 6A-6N illustrate exemplary user interfaces for interacting with research studies. FIG. 7 is a flow diagram illustrating methods of interacting with research studies in accordance with some embodiments. The user interfaces in FIGS. 6A-6N are used to illustrate the processes described below, including the processes in FIG. 7. FIGS. 8A-8U illustrate exemplary user interfaces for enrolling in a research study. FIG. 9 is a flow diagram illustrating methods of for enrolling in a research study in accordance with some embodiments. The user interfaces in FIGS. 8A-8U are used to illustrate the processes described below, including the processes in FIG. 9. FIGS. 10A-10X illustrate exemplary user interfaces for interacting with a hearing test. FIG. 11 is a flow diagram illustrating methods of for interacting with a hearing test in accordance with some embodiments. The user interfaces in FIGS. 10A-10X are used to illustrate the processes described below, including the processes in FIG. 11.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California Other portable electronic devices, such as laptops or tablet computers with touch-sensitive surfaces (e.g., touch screen displays and/or touchpads), are, optionally, used.

It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
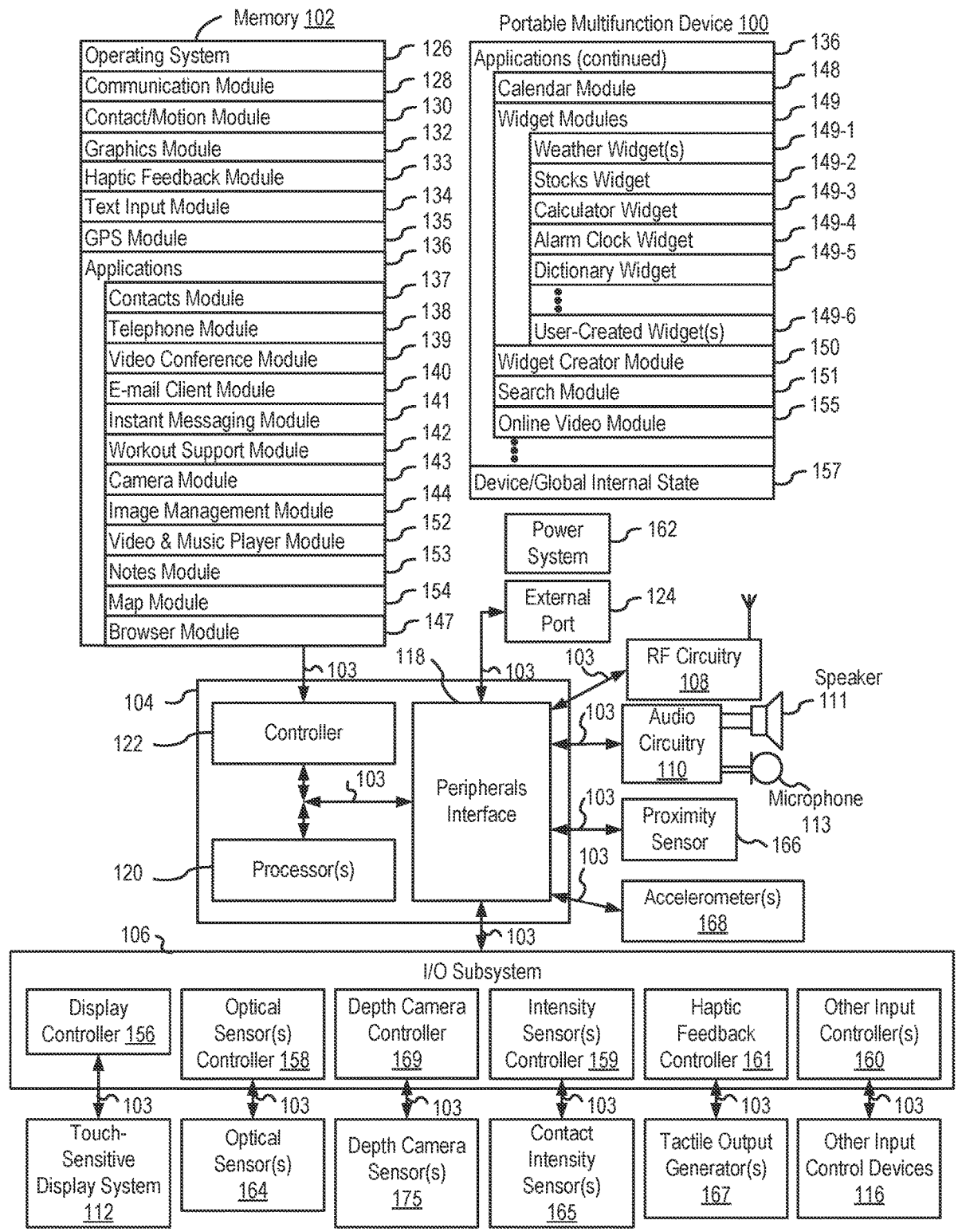
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures) as input. In some embodiments, the one or more input devices are integrated with the computer system. In some embodiments, the one or more input devices are separate from the computer system.

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
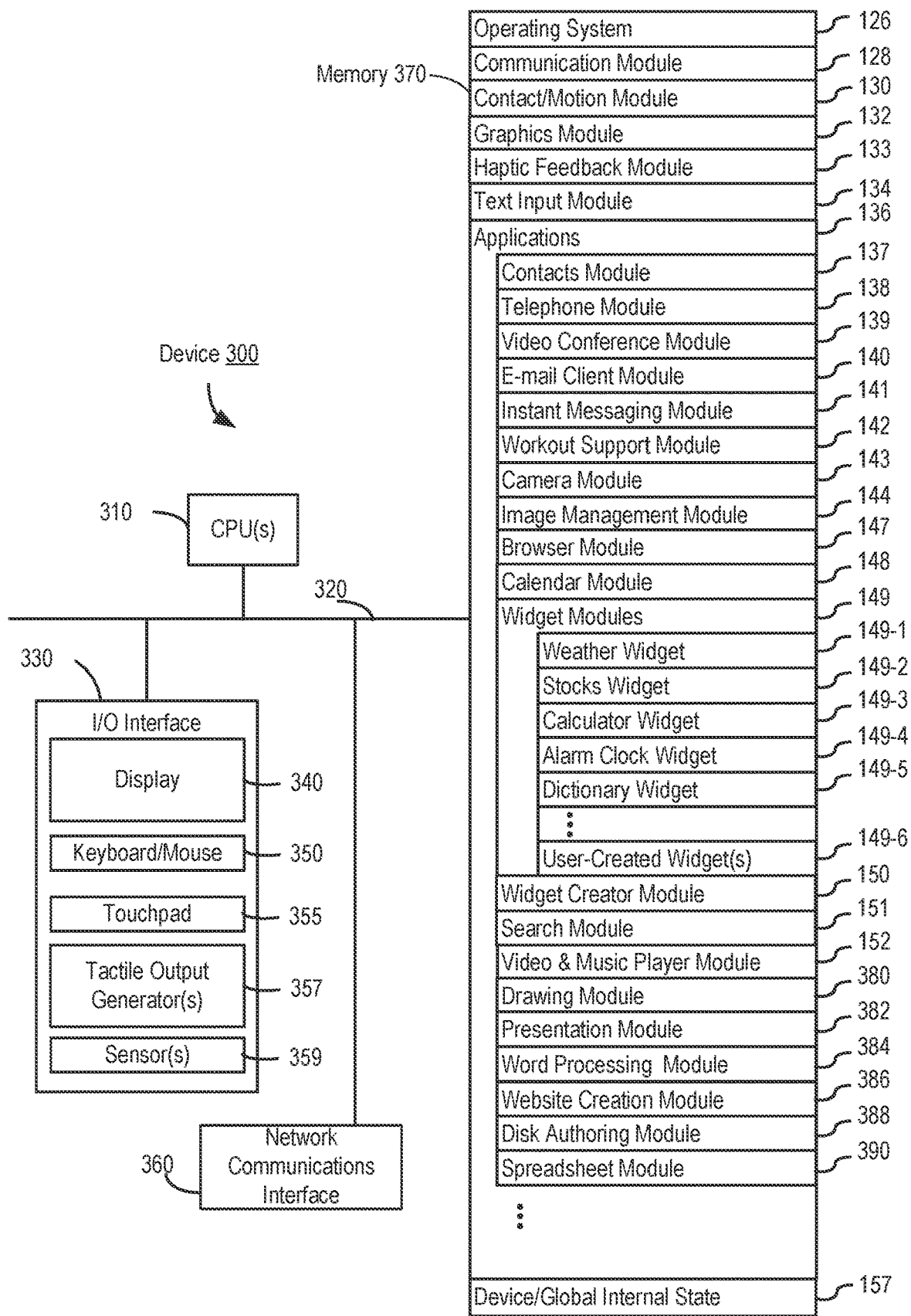
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts).

Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
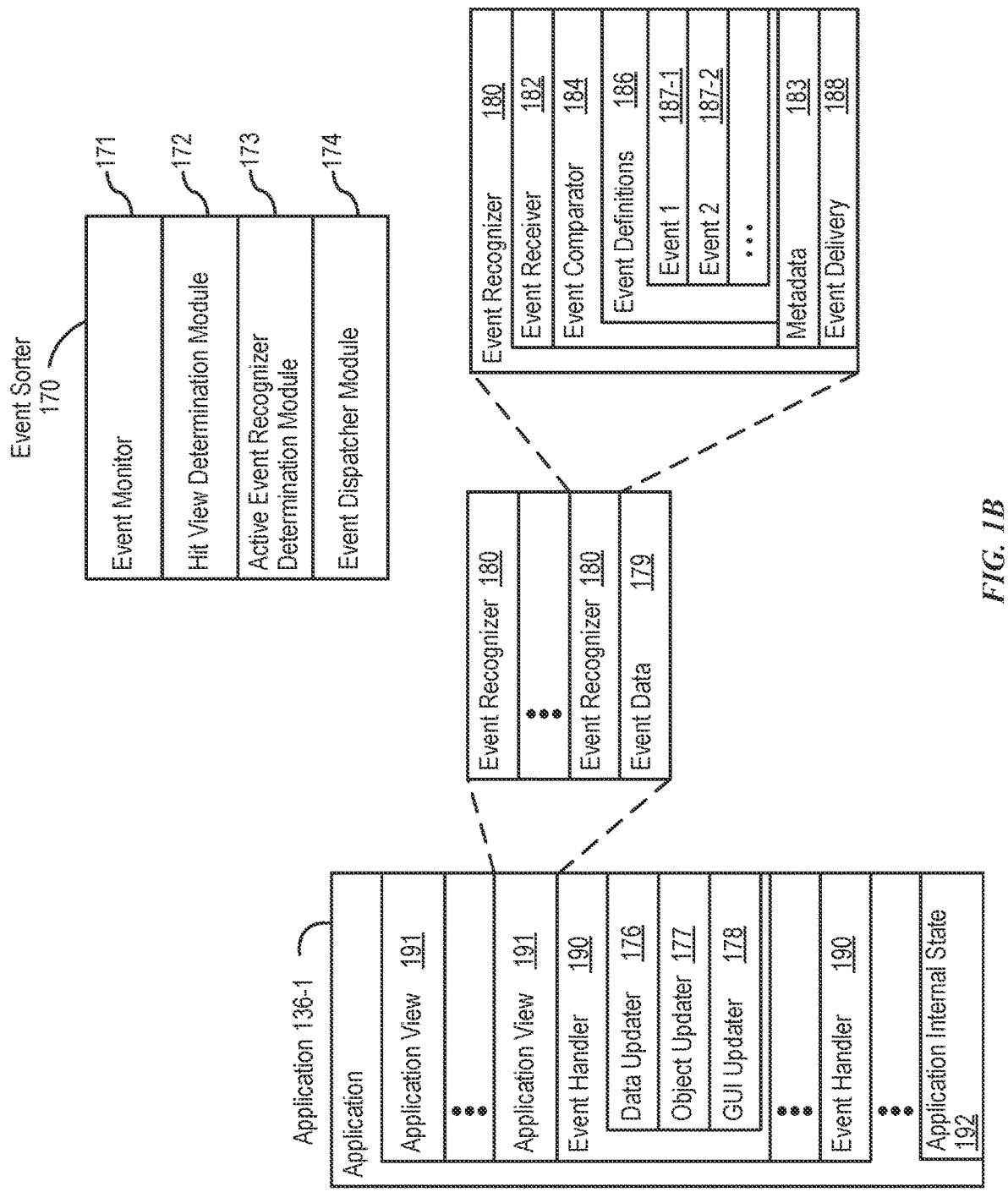
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
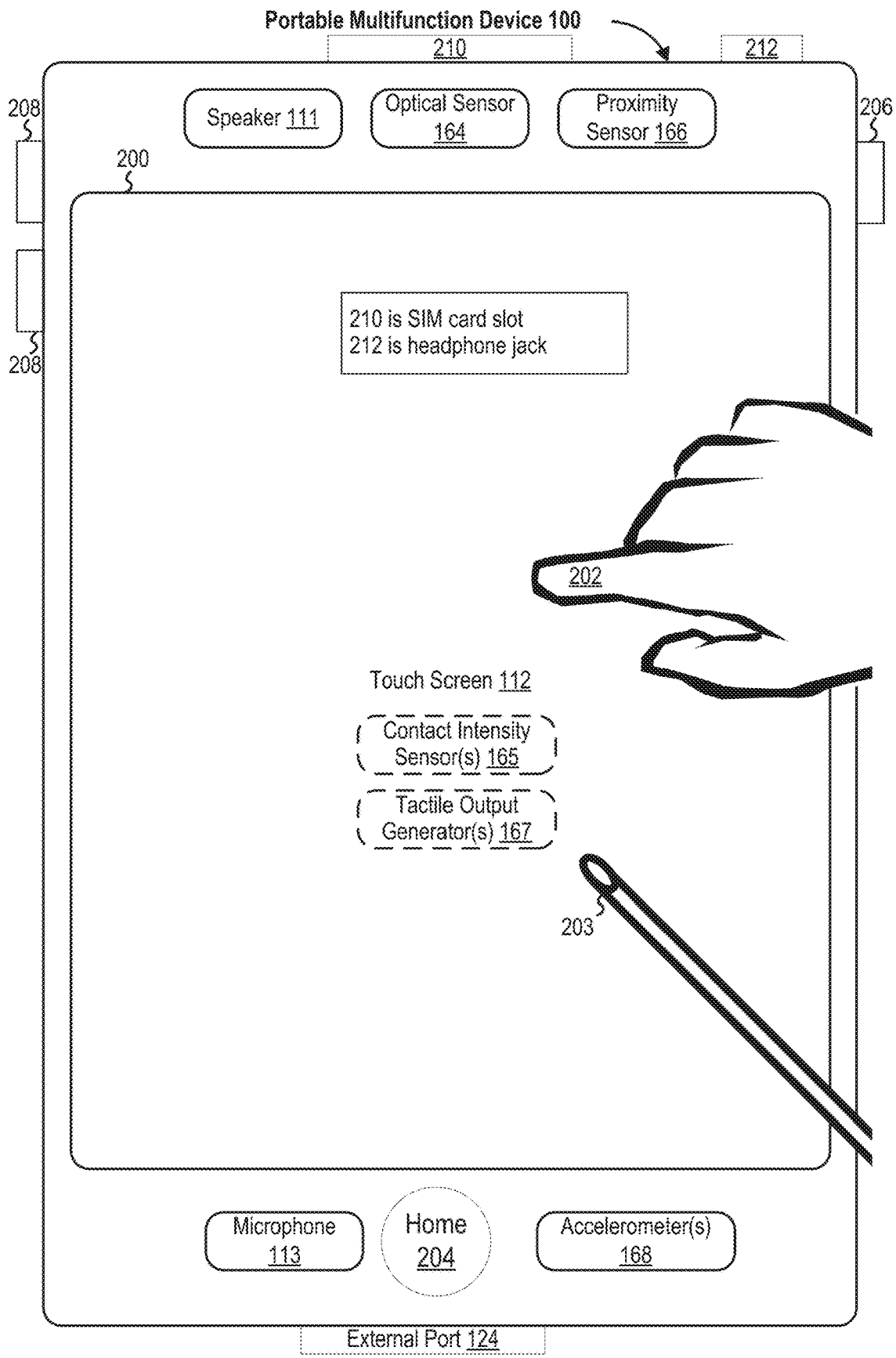
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
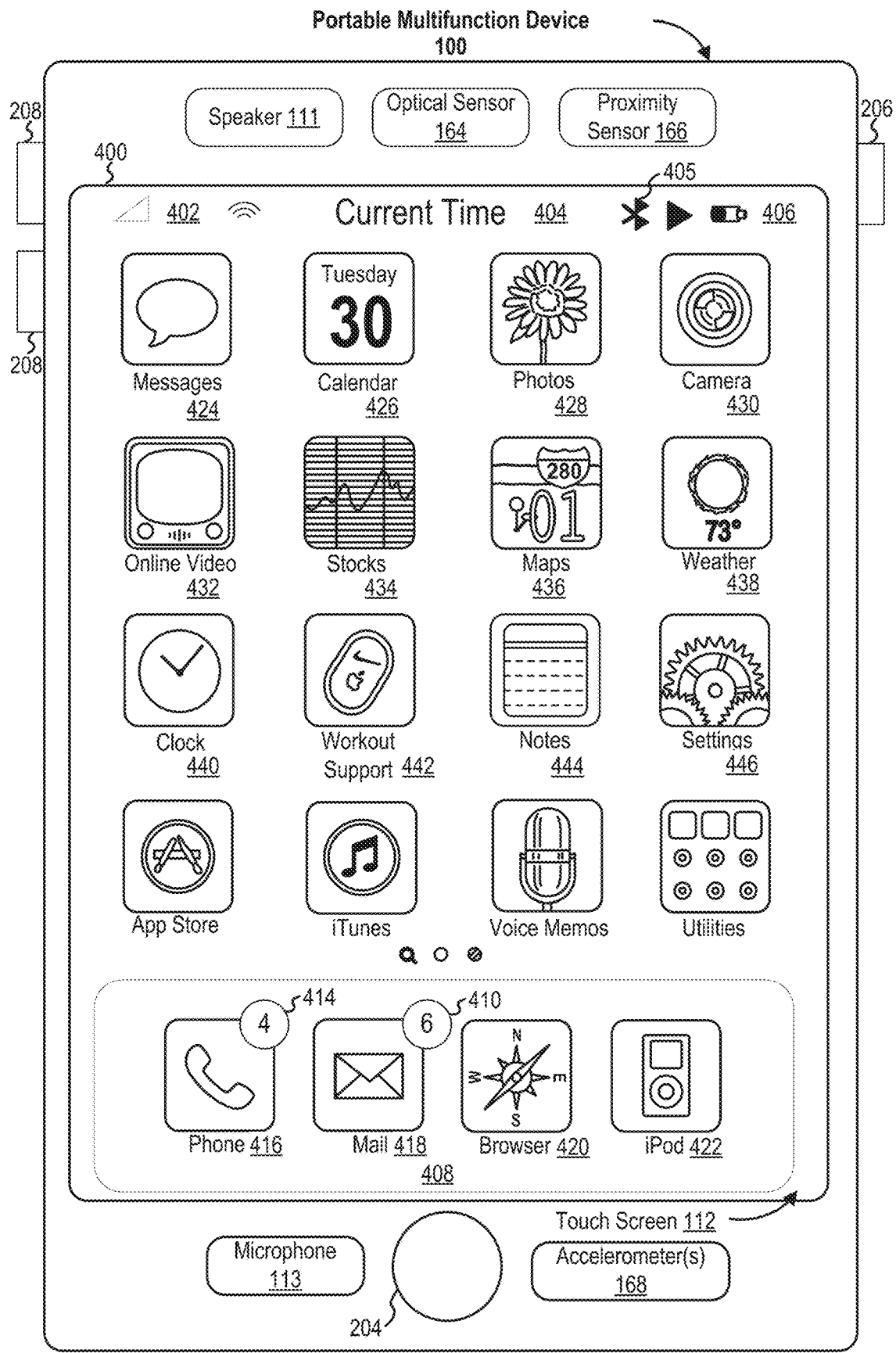
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;

Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
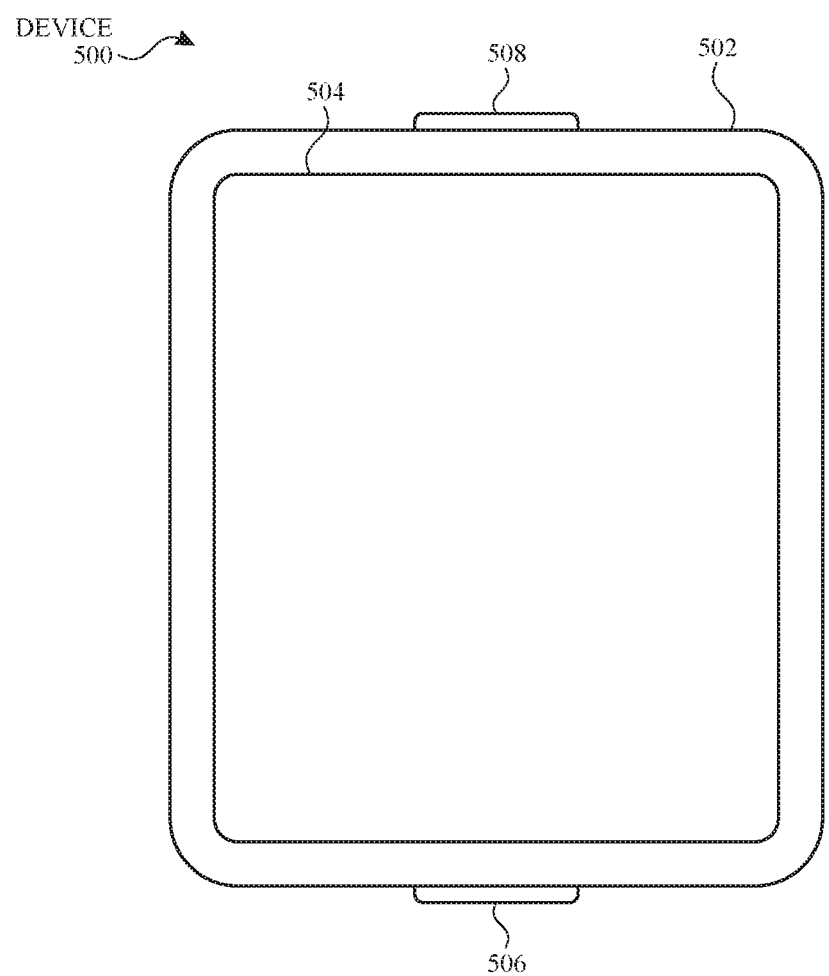
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
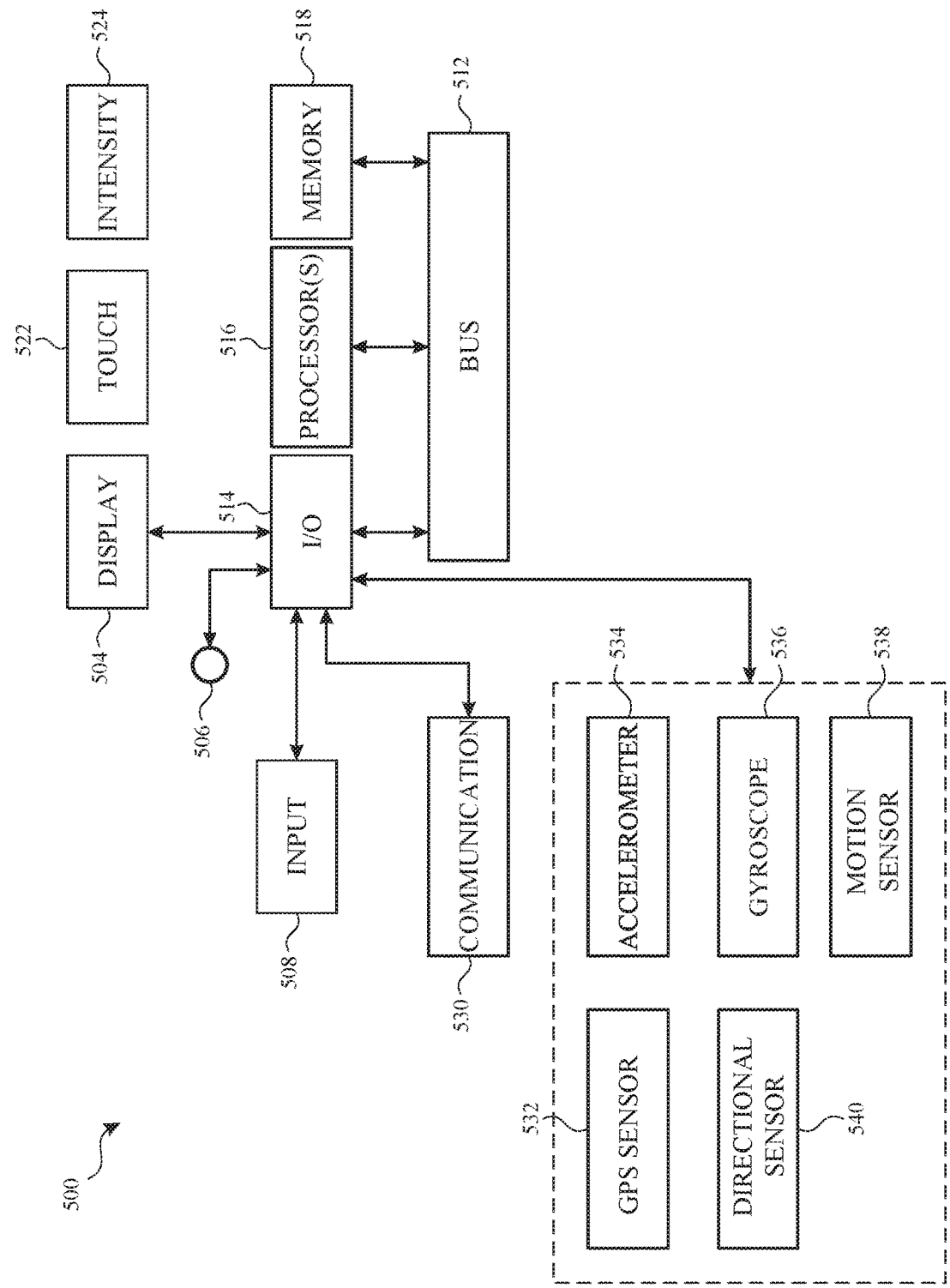
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700, 900, and 1100. A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

- an active application, which is currently displayed on a display screen of the device that the application is being used on;
- a background application (or background processes), which is not currently displayed, but one or more processes for the application are being processed by one or more processors; and
- a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6N illustrate exemplary user interfaces for managing tasks associated with research studies, in accordance with some embodiments. The user interfaces in these figures are used to illustrate the processes described below, including the processes in FIG. 7.

FIG. 6A illustrates an electronic device 600, which is a smart phone. Device 600 includes a touch-sensitive display screen 602 and one or more microphones. In some embodiments, device 600 also includes one or more features of devices 100, 300, and 500.

In FIG. 6A, device 600 is displaying user interface 604 of a research study management application. The research study management application is configured to provide information and functions related to the management of, and interaction with, one or more research studies that a user of device 600 is currently enrolled in (e.g., actively participating in). For example, the research management application facilitates enrollment in new studies, completing tasks for active studies, transmitting data to the organizers of studies, and viewing of information about past/inactive studies. In some embodiments, a research study is an investigation that includes collecting data (e.g., health-related data) from a plurality of users (e.g., the user of the electronic device). In some embodiments, a research study is organized by individuals or institutions (e.g., universities) for the purposes of collecting data for use in multiple research endeavors, including use in published research. In some embodiments, data collected via the methods described herein is periodically forwarded (e.g., exported) to the organizer of a research study that has been granted permissions to access that data (e.g., granted permission during an enrollment process).

Interface 604 of FIG. 6A is configured to display multiple views or tabs, depending on which view is currently selected for display (e.g., selected via view affordances 606 (e.g., task view affordance 606a, studies view affordance 606b, data view affordance 606c)). As seen in FIG. 6A, interface 604 is currently displaying task view 604a, as indicated by the bolding of task view affordance 606a. Task view affordance 606a includes a numeric badge 606a1 that indicates the number of current tasks (e.g., "5" tasks in FIG. 6A), which provides a user with an indication of the number of current tasks, even when interface 604 is currently displaying a view other than the task view.

In FIG. 6A, task view 604a includes multiple current tasks (e.g., to-be-completed tasks) 608, including task 608a that is a research profile questionnaire associated with the research management application (e.g., not associated with any specific study), task 608b that is a lifestyle questionnaire associated with a Women's Health study, task 608c that is a running questionnaire associated with the same Women's Health study, and task 608d that is a speech and noise test that is associated with an Annual Medical History study. Each of tasks 608 is an affordance that, when selected (e.g., selected by providing an input corresponding to the "START" indication of affordance 608b), causes device 600 to initiate a process for completing the respective task. Tasks can have a limited time window for completing the task. For example, task 608b includes an indication "6 Days Remaining," indicating that the task will expire (e.g., become inactive) if not completed within the next 6 days. As seen in FIG. 6A, the current tasks are sorted by the amount of time remaining to complete the tasks, with the tasks expiring sooner presented first (e.g., at the top). In FIG. 6A, task 608c was activated based on device 600 detecting that the user of device 600 had recently completed a running workout (e.g., via a separate physical activity tracking application and/or via one or more sensors (e.g., motion sensors) of device 600). In some embodiments, the set of active tasks is dependent on the permissions (e.g., data access permissions) granted to the research management application, as discussed in more detail below. For example, if permission was not granted to access data from the sensors of device 600 and task 608c was dependent on sensor data, task 608c would not be presented as an active task.

In FIG. 6A, task view 604a also includes research study contribution indications 610a and 610b that provide measures of participation. Indication 610a provides a measure of participation in time (e.g., hours, minutes spent interacting with the research management application or time spent completing tasks) for a user of device 600. Indication 610b provides a total number of questions answered (e.g., answered as part of completing tasks) by a user of device 600. In some embodiments, the measures are made across all research studies.

Figure 6B:
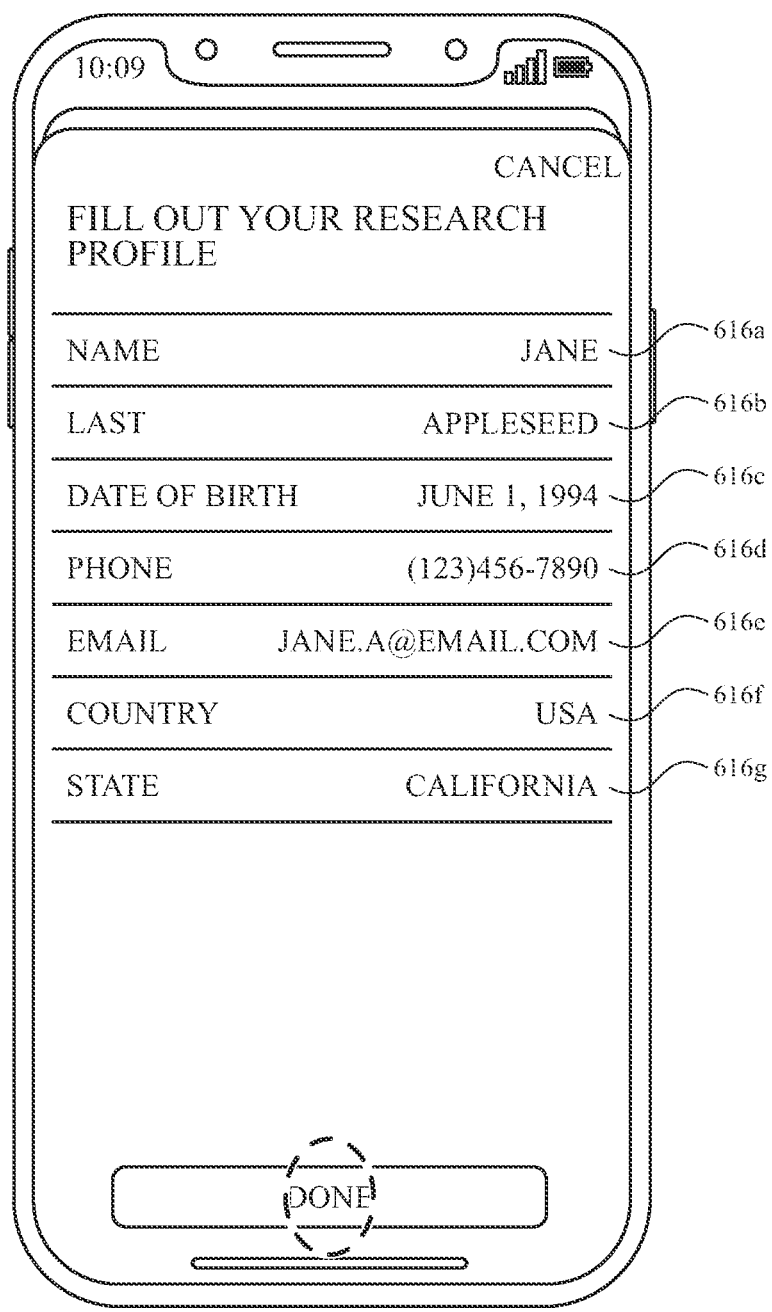

In FIG. 6A, device 600 detects, on touch-sensitive display 602, touch input 612, which is a tap gesture corresponding to task 608a and, in response, displays task completion interface 614, as seen in FIG. 6B.

In FIG. 6B, task completion interface 614 is shown with fields 616a-616g pre-populated using information available to (e.g., stored on) device 600 about the user of device 600. In some embodiments, one or more fields are not pre-populated and are to be completed via further user input (e.g., input provided via a soft keyboard). As shown in FIG. 6B, fields 616a-616g are selectable for entry of new text or editing of existing text. Task completion interface 614 includes a cancel affordance 616 for exiting interface 614 without completing the task associated with task 608*a* (e.g., without submitting the information pre-populated into fields 616*a*-616*g*.

In FIG. 6B, device 600 detects touch input 618, a tap gesture corresponding to done affordance 620. In response to touch input 618, device 620 stores and/or submits the information populated into fields 616*a*-616*g* as a response to the research profile questionnaire task and redisplays task view 604*a* of interface 604, as seen in FIG. 6C.

Figure 6C:
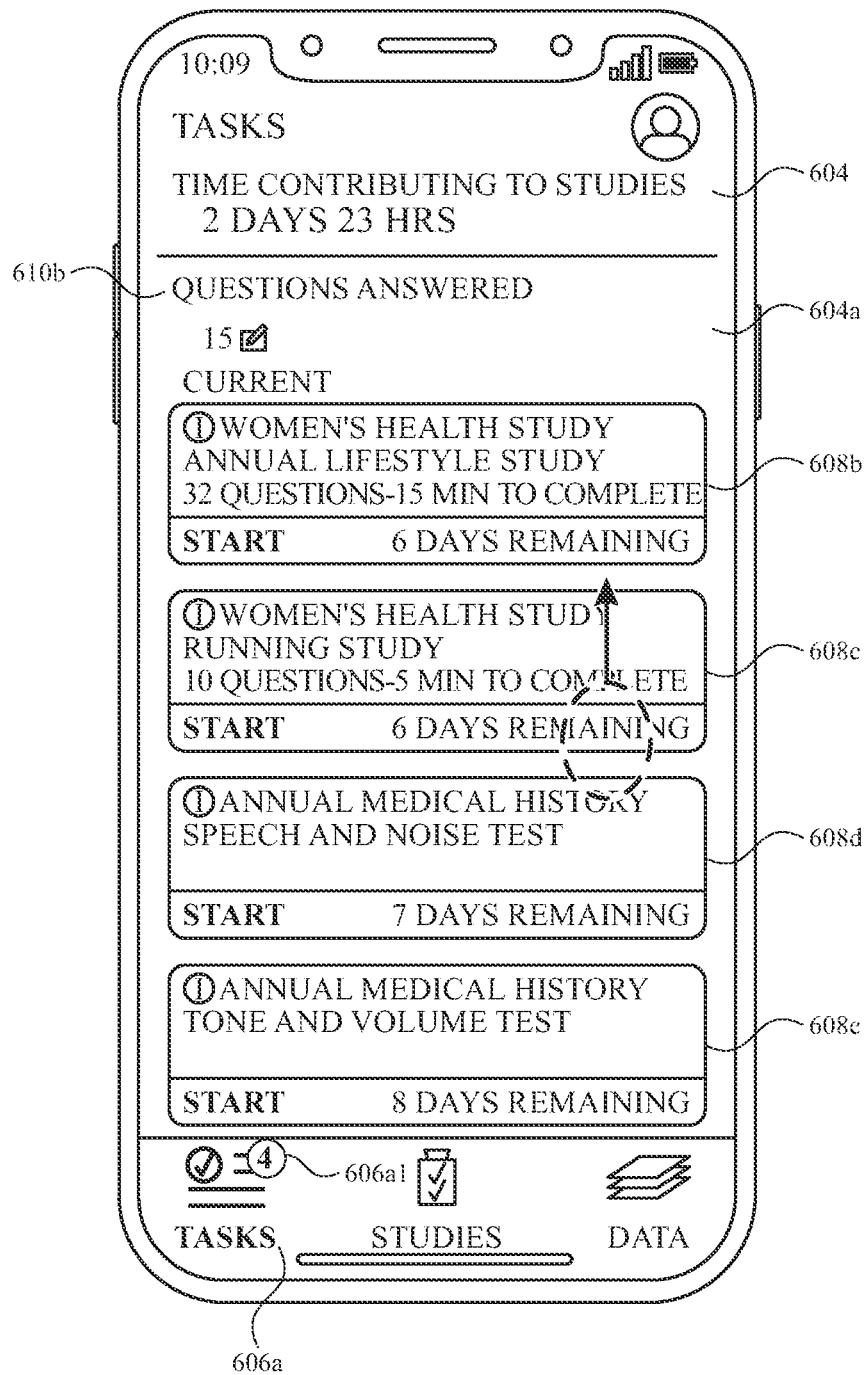

In FIG. 6C, task 608*a*, having been completed, is no longer displayed at the top of task view 604*a*. Indication 610*b* now shows 15 total questions answered (up from 8 questions answered), reflecting the additional 7 questions answered as part of completing task 608*a*. Numeric badge 606*a*1 of task view affordance 606*a* now shows "4" remaining tasks to be completed. Task view 604*a* now includes additional current task 608*e*, which is a tone and volume test associated with the Annual Medical History study (e.g., the same study associated with task 608*d*). Because task 608*e* has 8 days left to complete, it is listed after tasks 608*b-d*, which have less time to complete.

Figure 6D:
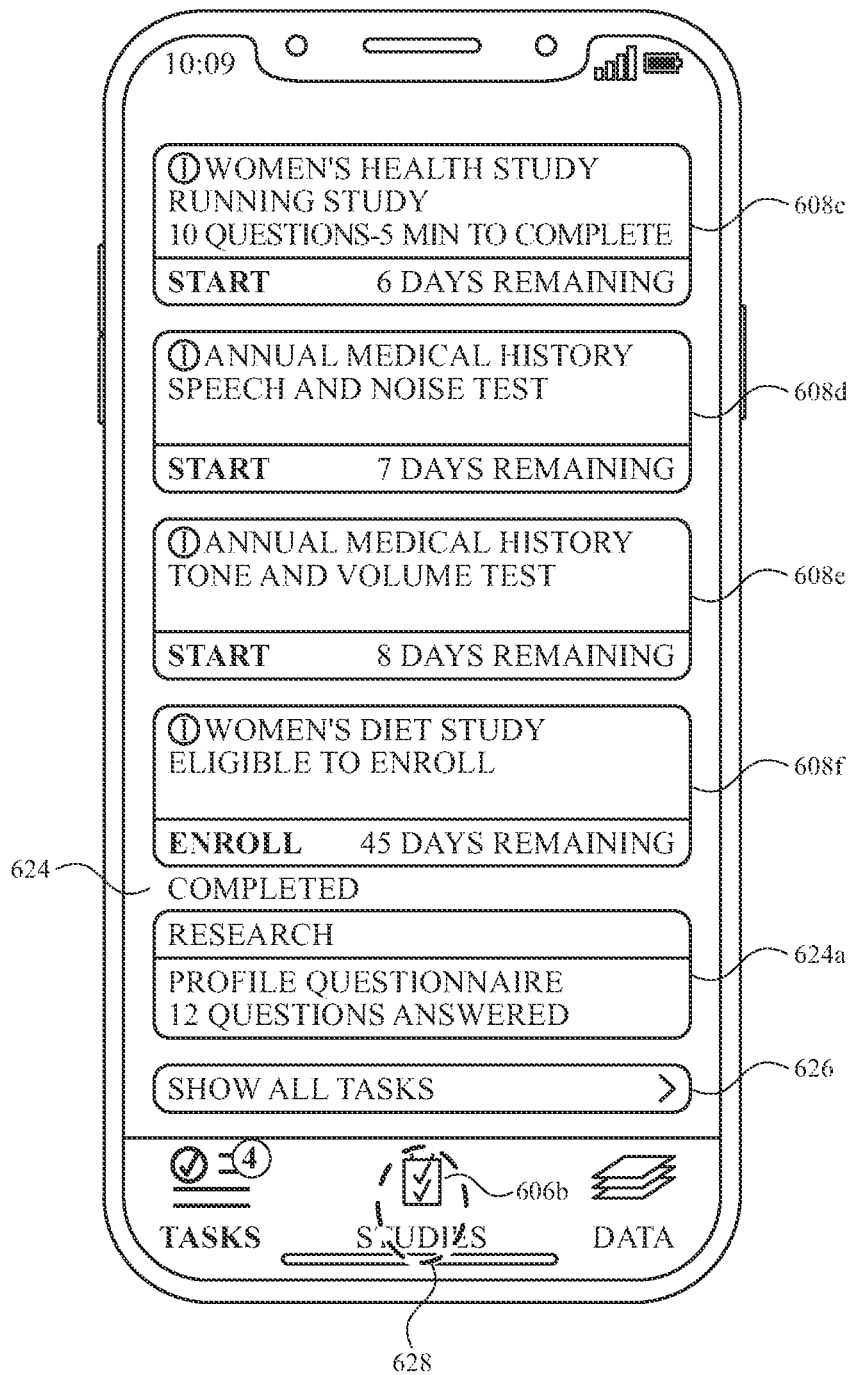

In FIG. 6C, device 600 detects, on touch-sensitive display 602, touch input 622, which is a upwards swipe gesture and, in response, scrolls task view 604*a* of interface 604, as seen in FIG. 6D.

In FIG. 6D, task view 604*a*, after being scrolled up, now includes an additional task 608*f* that corresponds to an available study for enrollment (e.g., an active study that the user is not currently enrolled in but is eligible to enroll in). In some embodiments, task 604*a* is surfaced to the user of device 600 based on the user's enrollment in the related Women's Health study. In FIG. 6D, task view 604*a* also includes a completed tasks section 624 that includes completed task 624*a* that corresponds to previously current task 608*a*. In some embodiments, completed task 624*a* is an affordance that, when selected, displays further information about the task, including the answers submitted to complete the task. In some embodiments, completed tasks section 624 only includes tasks completed within a predefined period (e.g., the last day, week, or month). Task view 604*a*, after being scrolled, also includes show all tasks affordance 626 that, when selected, displays a larger set of completed tasks (e.g., completed tasks for a longer predefined period; all completed tasks).

Figure 6E:
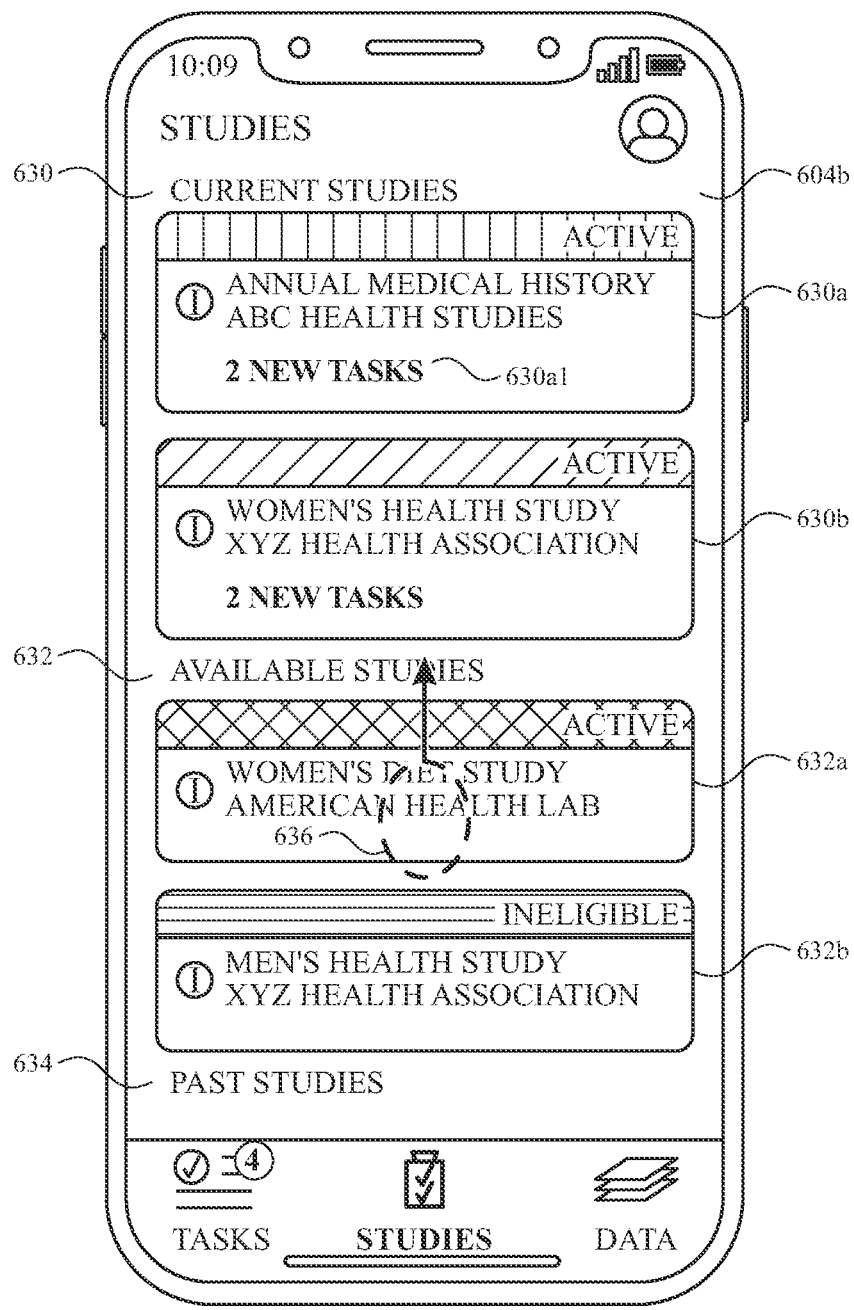

In FIG. 6D, device 600 detects, on touch-sensitive display 602, touch input 628, which is a tap gesture corresponding to study view affordance 606*b* and, in response, transitions user interface 604 to study view 604*b*, as seen in FIG. 6E.

In FIG. 6E, study view affordance 606*b* is bolded, while task view affordance 606*a* is no longer bolded, to indicate that the study view is currently active. Study view 604*b* includes a current studies section 630 that includes multiple current studies that the user of device 600 is currently enrolled in, including current study 630*a* (Annual Medical History study) and current study 630*b* (Women's Health study), each of which includes an indication that the study is active (e.g., not completed; not ended with respect to data collection). Each current study also includes an indication of a number of active tasks, if any. For example, current study 630*a* includes indication 630*a*1 indicating that two tasks, corresponding to tasks 608*d* and 608*e* of task view 604, are currently active and to be completed. Study view 604*b* also includes an available studies section 632 that includes multiple studies that are active and potentially available for enrollment by the user of device 600. As seen in FIG. 6E, available studies section 632 includes a first available study 632*a* that is a Women's Diet study (e.g., associated with task 608*f* of task view 604*a* and a second available study 632*b* that is a Men's Health study. The studies include an indication of the organizer of the study (e.g., the entity that receives data, if the user enrolls). For example, Study 632*a* shows that the organizer is American Health Lab. Study 632*b*, while active, is marked as "Ineligible," based on the requirements of the study and information available to device 600. In FIG. 6E, study 632*b* has a requirement that the user must be male to enroll and current data available to device 600 indicates that the user is female. In some embodiments, if information about the user is updated to indicate that the user is male, the eligibility status of study 632*b* would also be updated to indicate that study 632*b* is no longer an ineligible study. As seen in FIG. 6E, study view 604*b* also includes a past studies section 634 that is described in more detail, below.

Figure 6F:
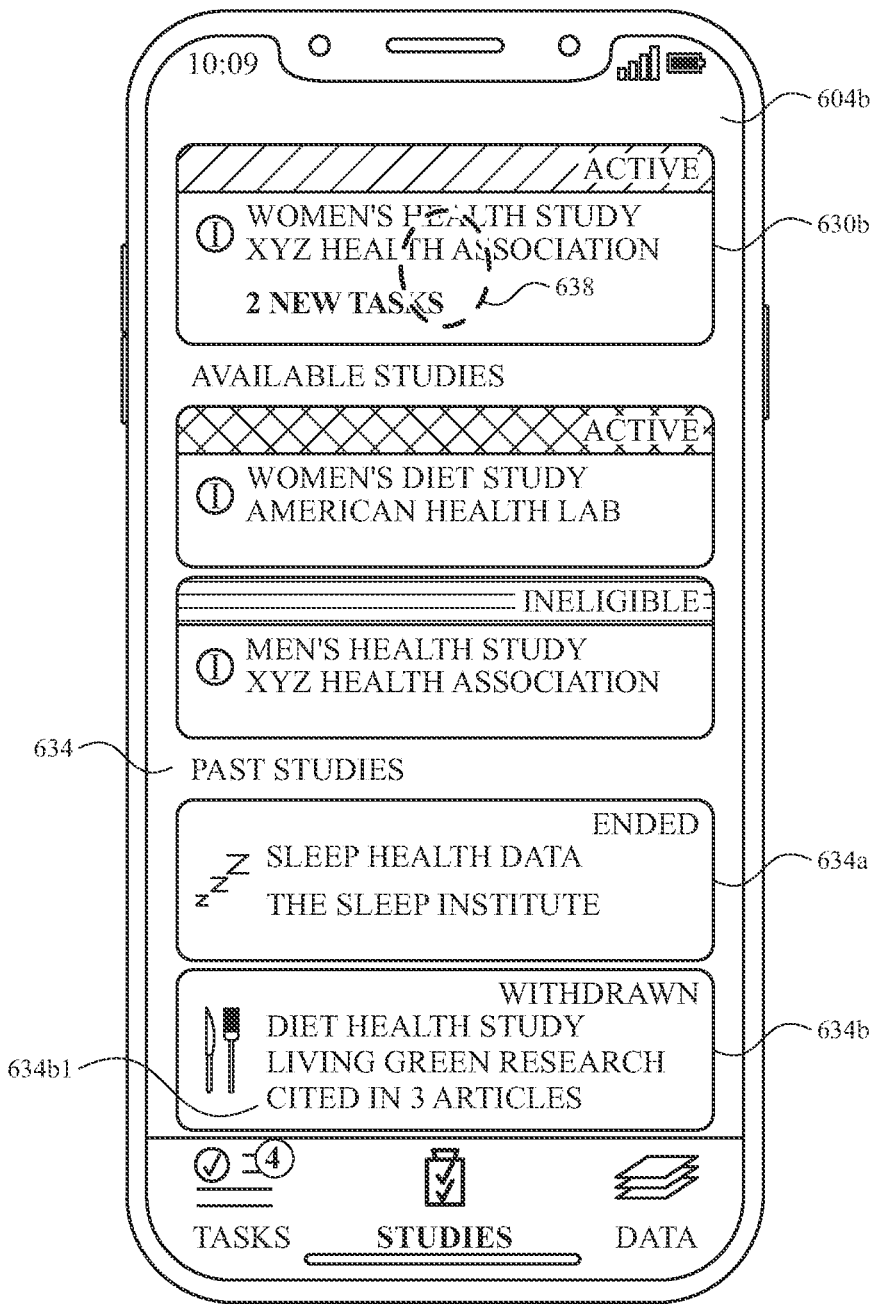

In FIG. 6E, device 600 detects, on touch-sensitive display 602, touch input 636, which is a upwards swipe gesture and, in response, scrolls study view 604*b* of interface 604, as seen in FIG. 6F.

In FIG. 6F, study view 604*b*, after being scrolled up, now includes, in past study section 634, past study 634*a* that is a Sleep Health Data study and past study 634*b* that is a Diet Health Study. Past study 634*a* includes an indication of "Ended" signifying that the study is no longer active. In some embodiments, a past study also includes an indication of the user's enrollment status (e.g., "Enrolled" or "Not Enrolled") for the past study. Past study 634*b* includes an indication "Withdrawn" signifying that the user of device 600 was enrolled in the study while it was active, but that the user withdrew from the study (as described in more detail below) before the study ended. Past study 634*b* also includes an indication 634*b*1 that provides information about how data from the study has been used. In FIG. 6F, 634*b*1 indicates that data from the study has been cited by 3 articles. In some embodiments, indication 634*b*1 is dynamic and updates as further information is received about use of the study data, even after the study has ended and/or after the user has withdrawn from the study.

Figure 6G:
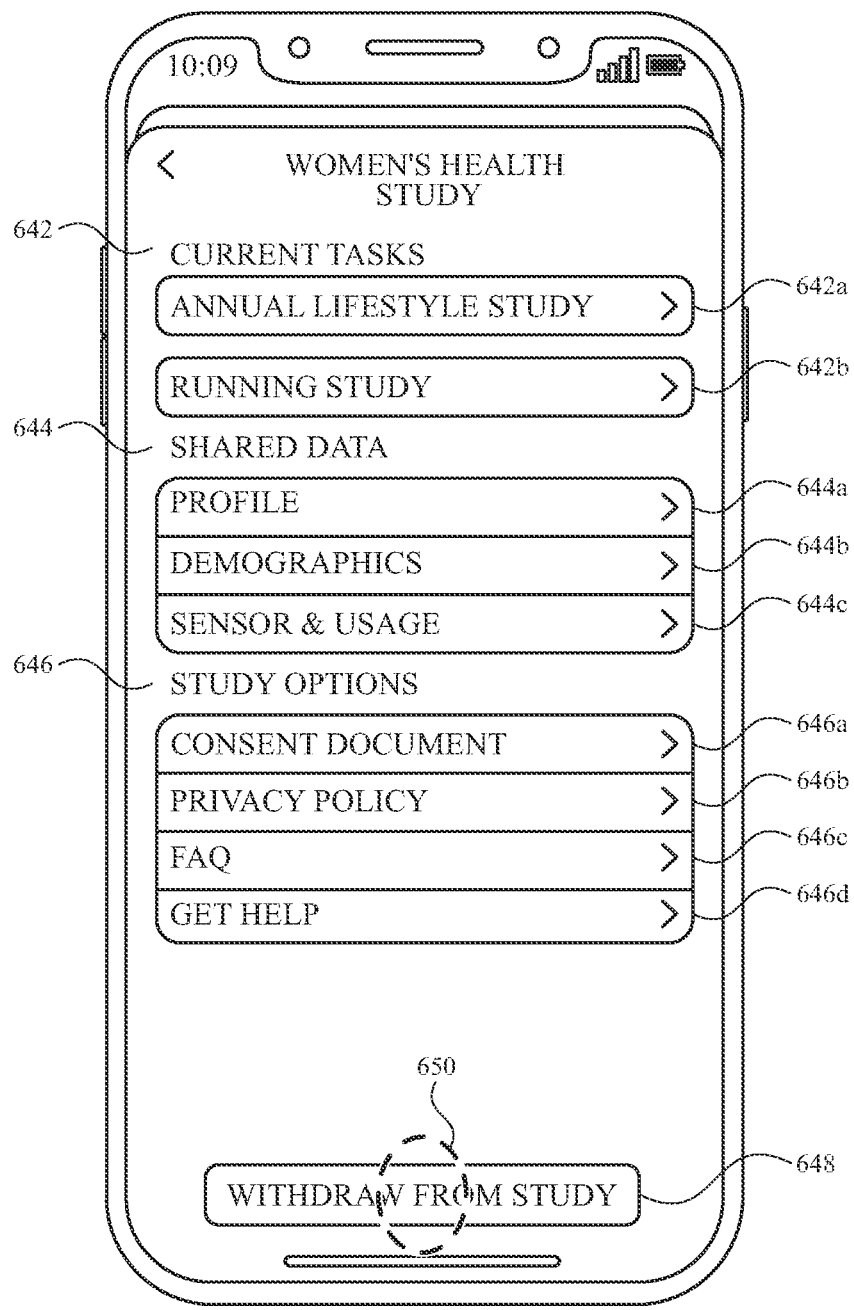

In FIG. 6F, device 600 detects, on touch-sensitive display 602, touch input 638, which is a tap gesture corresponding to current study 630*b* and, in response, displays study detail interface 640 that includes further information and functionality specific to study 630*b*, as seen in FIG. 6G.

In FIG. 6G, study detail interface 640 includes current tasks section 642 that includes current task affordance 642*a* and 642*b* that correspond to active tasks for the Women's Health study corresponding to study 630*b* of study view 604*b*. Task affordance 642*a* and task affordance 642*b* correspond to task 608*b* and task 608*c* of task view 604*a*, respectively, and, when selected, cause device 600 to display user interfaces for completion of the tasks. In some embodiments, task affordance 642*a* and task 608*b* cause device 600 to perform the same function. Study detail interface 640 also includes shared data section 644 that includes affordances 644*a*-644*c* that each correspond to a type of data being shared (e.g., authorized to be shared) with the Women's Health study and that each can be selected to view further information and/or functionality specific to the selected data type. For example, affordance 644*a*, when selected, causes device 600 to display further information about demographic data being shared with the Women's Health study. In some embodiments, the further information is similar to that shown in FIG. 6K. Study detail interface 640 also includes study options section 646 that includes affordances 646*a*-

646d that provided additional functions relating to the Women's Health study. For example, affordance 646a, when selected, causes device 600 to display information about the consents provided while enrolling (e.g., as seen in FIG. 8K). Affordance 646b, when selected, causes device 600 to display information about the study's privacy policy (e.g., data privacy policy, such as would be accessible from FIG. 8O by selecting "View Privacy Policy"). Affordance 646c, when selected, causes device 600 to display frequently asked questions about the current study. Affordance 646d, when selected, causes device 600 initiate a process for contacting a support service that can provide support (e.g., technical support) relating to the current study. Study view 604b also includes initiate withdrawal affordance 648 that, when selected, initiates a process for withdrawing from the current study.

Figure 6H:
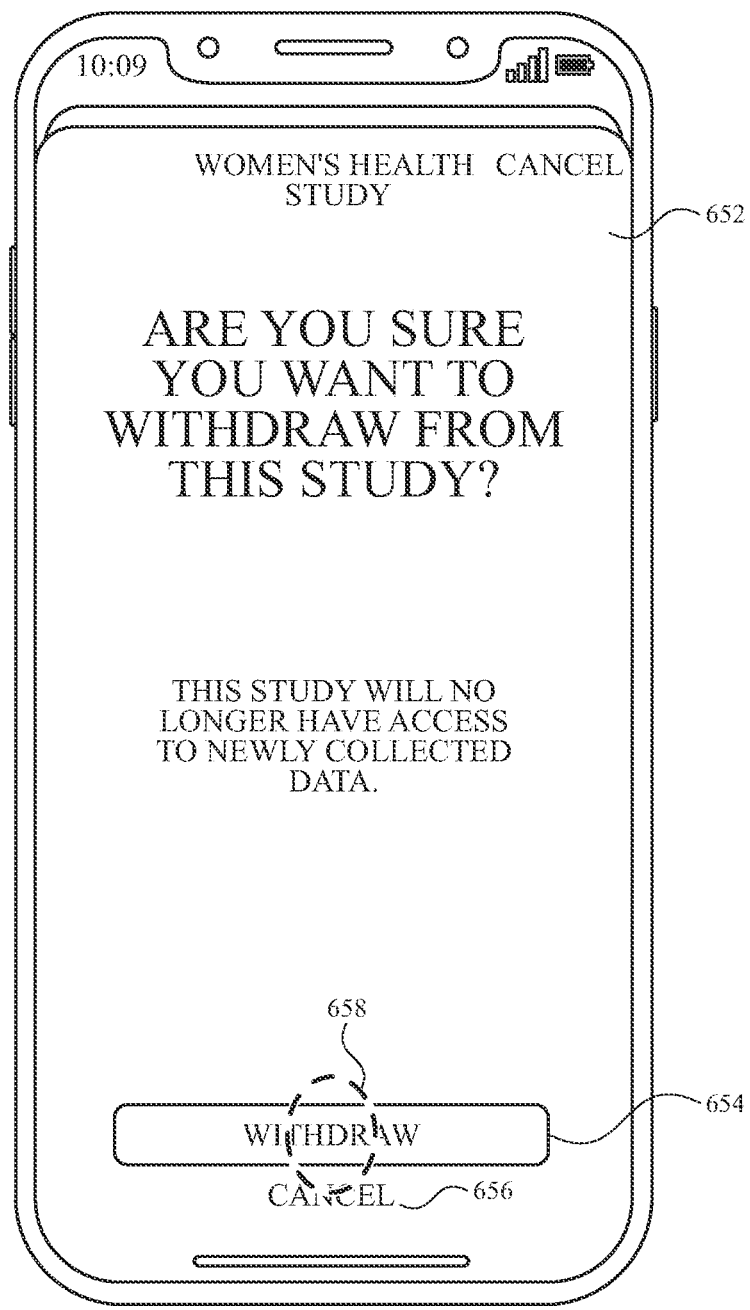

In FIG. 6G, device 600 detects, on touch-sensitive display 602, touch input 650, which is a tap gesture corresponding to initiate withdrawal affordance 648 and, in response, displays withdrawal interface 652 of FIG. 6H.

In FIG. 6H, withdrawal interface 652 provides information about the consequence of withdrawing from the study ("This study will no longer have access to newly collected data"). Interface 652 includes a withdrawal affordance 654 and a cancel affordance 656 that, when selected, cancels the withdrawal process initiated by selection of affordance 648.

In FIG. 6H, device 600 detects, on touch-sensitive display 602, touch input 658, which is a tap gesture corresponding to withdraw affordance 654 and, in response, withdraws the user of device 600 from the Women's Health study and redisplays study view 604b.

Figure 6I:
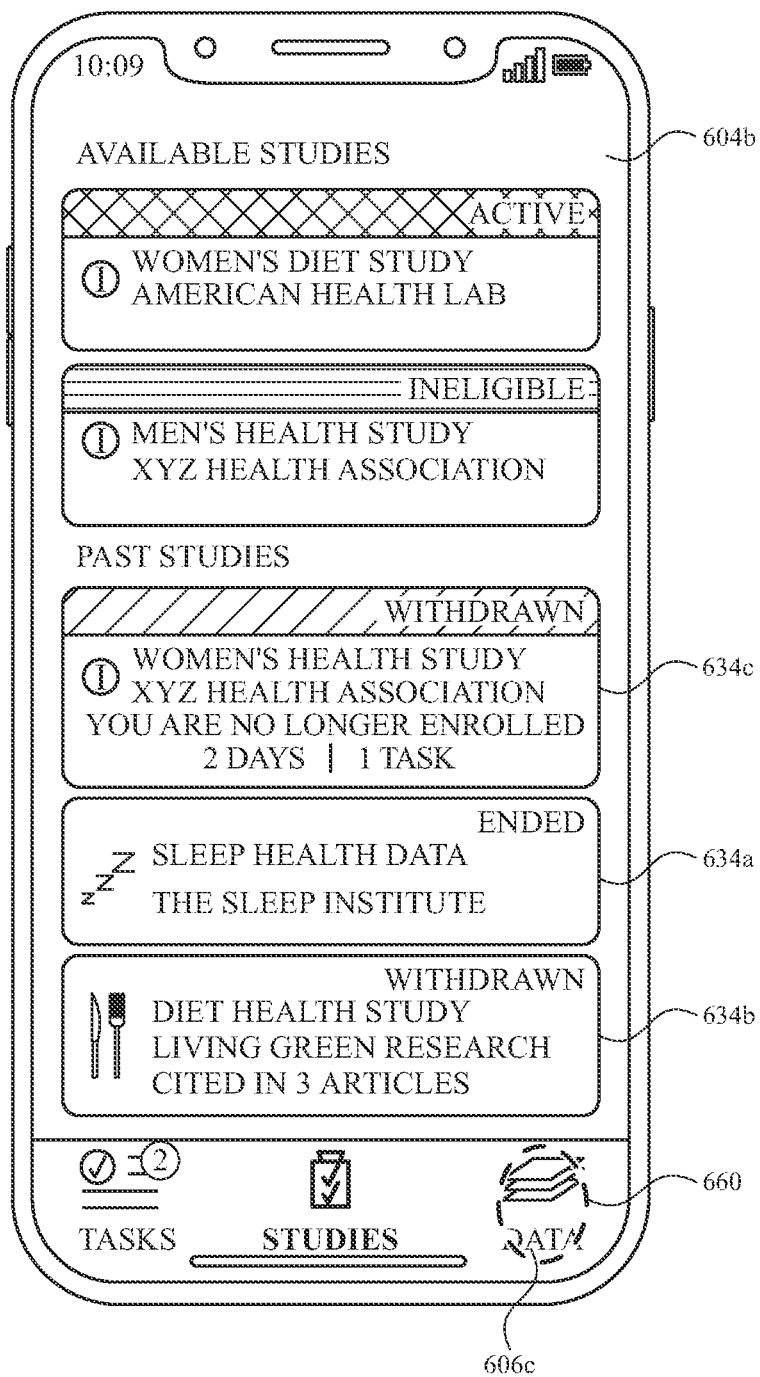

In FIG. 6I, device is displaying study view 604b after withdrawal from the Women's Health study. Past studies section 634 now includes past study 634c corresponding to the withdrawn Women's Health study, which is no longer displayed in current study section 630 as current study 630b. In some embodiments, active tasks associated with the Women's Health study are removed from task view 604a. In some embodiments, withdrawal from a study causes device 600 to cease sharing data (e.g., newly collected data) with the study, including any collected data that has yet to be shared with the study.

Figure 6J:
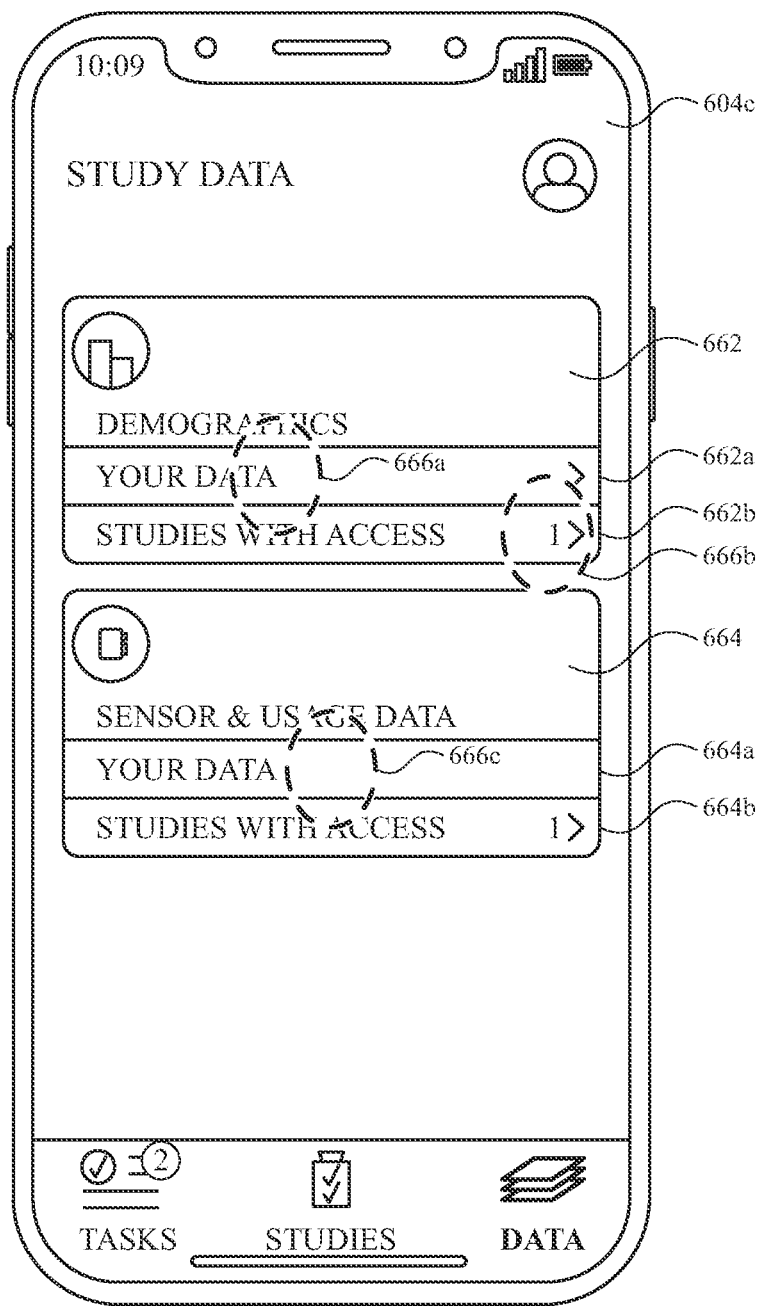

In FIG. 6I, device 600 detects, on touch-sensitive display 602, touch input 660, which is a tap gesture corresponding to data view affordance 606c and, in response, displays data view 604c that provides information and functionality related to the data being shared with studies managed by the research management application, as seen in FIG. 6J.

In FIG. 6J, data view affordance 606c is bolded, while study view affordance 606b is no longer bolded, to indicated that the data view is currently active. Data view 604c includes demographics data section 662 and sensors and usage data section 664, corresponding to different types of data available for sharing with one or more research studies managed via the research management application. Demographics data section 662 includes affordance 662a that, when selected, causes device 600 to display additional information regarding the user's demographic data that is available for sharing. Demographics data section 662 also includes affordance 662b that, when selected, causes device 600 to display additional information regarding which studies currently have access to the user's demographic data. Similarly, sensor and usage data section 664 includes affordance 664a that, when selected, causes device 600 to display additional information regarding the user's sensor and usage data that is available for sharing. Sensor and usage data section 664 also includes affordance 664b that, when selected, causes device 600 to display additional information regarding which studies currently have access to the user's sensor and usage data.

In FIG. 6J, while data view 604c is displayed, device 600 detects, on touch-sensitive display 602, touch inputs 666a-666c and, in response, performs operations as described below.

Figure 6K:
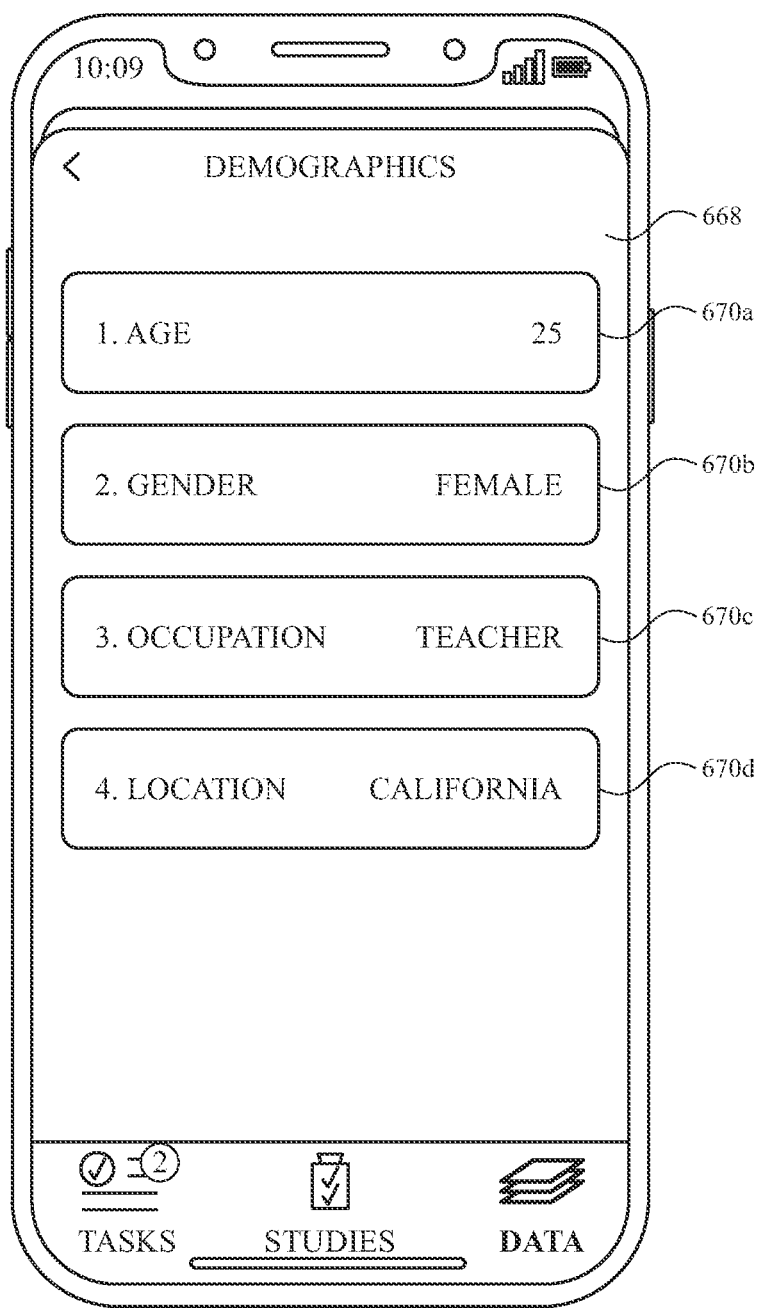

In FIG. 6K, device 600 displays demographic data detail interface 668 in response to input 666a corresponding to affordance 662a of data view 604c. Demographic data detail interface 668 includes data details 670a-670c correspond to demographic data available for sharing with studies that granted access to the user's demographic data. In some embodiments, data detail interface 668 can be used to edit the user's demographic data.

Figure 6L:
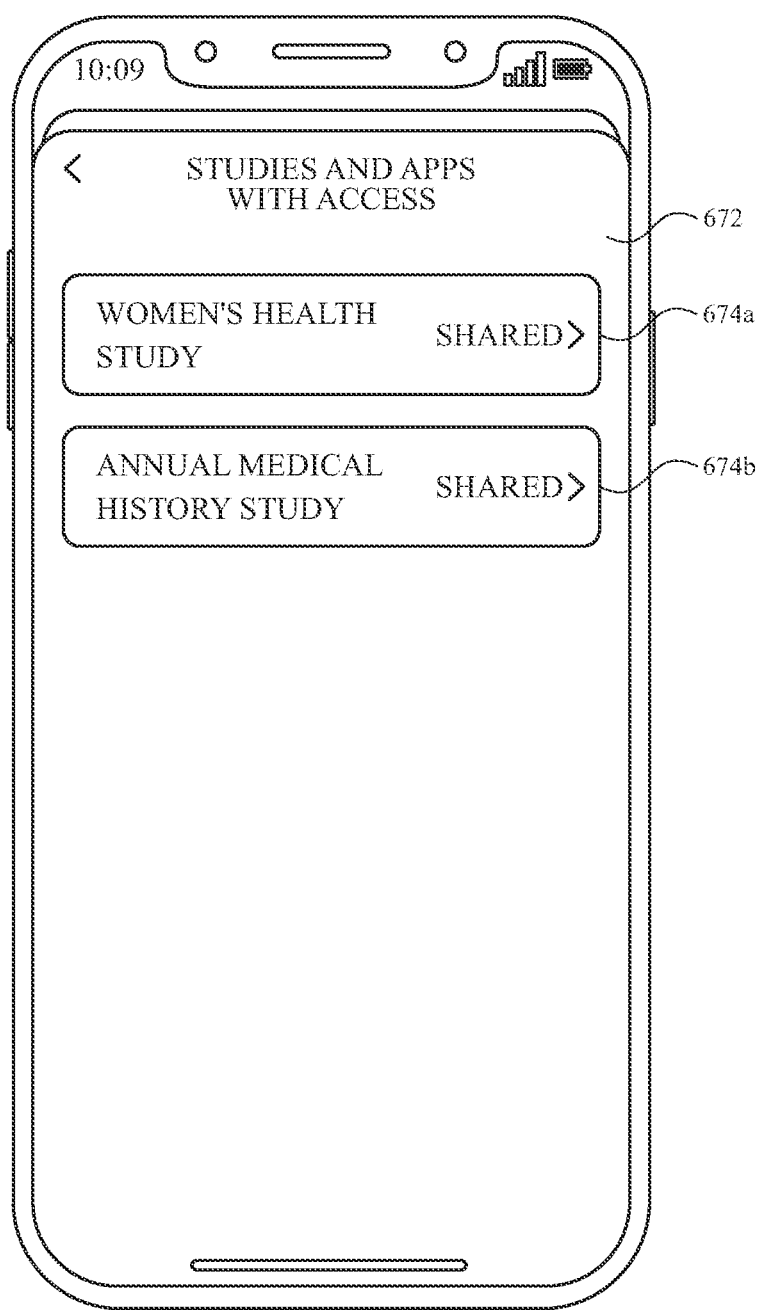

In FIG. 6L, device 600 displays demographic data access interface 672 in response to input 666b corresponding to affordance 662b of data view 604c. Demographic data access interface 672 provides information on what studies have access to the user's demographic data and includes affordances 674a and 674b, corresponding to the Women's Health study and Annual Medical History study, respectively. In some embodiments, demographic data access interface 672 lists all studies that currently have or previously had access to data of the specific type (e.g., demographic data). In some embodiments, only studies that currently have access to data of the specific type are shown (e.g., the Women's Health study would not be shown after the user has withdrawn). In some embodiments, selection of affordance 674a or 674b provides additional details about the respective study (e.g., selection of 674a would cause display of study detail interface 640 of FIG. 6G).

Figure 6M:
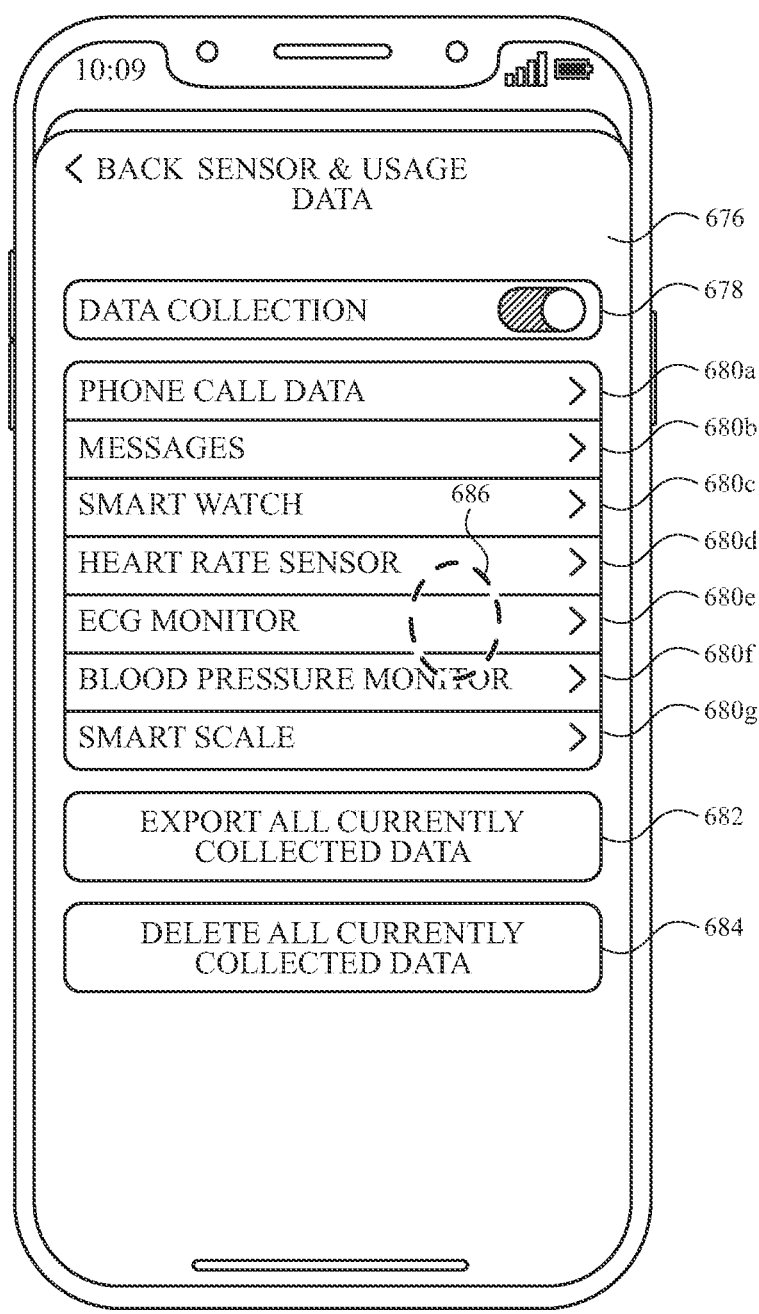

In FIG. 6M, device 600 displays sensor and usage data detail interface 676 in response to input 666c corresponding to affordance 664a of data view 604c. Sensor and usage data detail interface 676 includes details on sensor data (e.g., sensors of device 600 or sensors on devices connected to device 600 to which device 600 has data access) and usage data (e.g., usage of certain functions of device 600 such as phone call usage or messaging usage) that can be made available to studies. Usage data detail interface 676 includes toggle-able affordance 678 that, when selected, changes the state of data collection regarding sensors and usage on device 600. In some embodiments, data collection utilizes additional resources of device 600 and turning off data collection can significantly improve battery life or resource availability on device 600. Usage data detail interface 676 also includes affordances 680a-680g that, when selected, provides additional information and functionality related to the specific type of sensor or usage data. Usage data detail interface 676 also includes data export affordance 682 that, when selected, causes immediate export of collected data that has yet to be exported to studies that have been granted access to sensor and usage data. In some embodiments, device 600 collects data for a period of time (e.g., a day, a week, a month) before exporting the data in a batch at the end of the period. Usage data detail interface 676 also includes data deletion affordance 684 that deletes any collected, but not yet exported, data.

In FIG. 6M, device 600 detects, on touch-sensitive display 602, touch input 686 corresponding to affordance 680e and, in response, displays ECG monitor detail interface 688, as seen in FIG. 6N.

In FIG. 6N, device 600 displays ECG monitor detail interface 688 that provides specific information and functionality related to the ECG monitor sensor that is available to device 600. ECG monitor detail interface 688 includes information section 690 that provides information about what data is collected and shared for the ECG monitor sensor and what information is not selected. Information section 690 includes affordance 690*a* that, when selected, causes device 600 to display examples of ECG monitor data that is collected and available for sharing. ECG monitor detail interface 688 also includes applications and studies with access section 692 that includes affordances 692*a* and 692*b* corresponding to a research study and an application, respectively, that have access to the ECG monitor data. Affordances 692*a* and 692*b* can be used to independently control access to the ECG monitor data (e.g., data can be turned off for one application or study without affecting others). Information section 690 also includes affordance 694 that, when selected, provides what data has been collected from the ECG monitor since the last data export event. Information section 690 also includes affordance 696 that, when selected, deletes all unexported data for the specific sensor or usage (e.g., the ECG monitor) without deleting unexported data for other sensors and/or usage.

FIG. 7 is a flow diagram illustrating a method for interacting with research studies using an electronic device in accordance with some embodiments. Method 700 is performed at a device (e.g., 100, 300, 500, 600) with a display device (e.g., 602) and one or more input devices (e.g., 602). Some operations in method 700 are, optionally, combined, the orders of some operations are, optionally, changed, and some operations are, optionally, omitted.

As described below, method 700 provides an intuitive way for interacting with research studies. The method reduces the cognitive burden on a user for interacting with research studies, thereby creating a more efficient human-machine interface. For battery-operated computing devices, enabling a user to interact with research studies faster and more efficiently conserves power and increases the time between battery charges.

The electronic device (e.g., 600) displays (702), via the display device (e.g., 602), a first user interface (e.g., 604) (e.g., an interface having multiple tabbed views; an interface generated by a research application) that includes a task view affordance (e.g., 606*a*) associated with a plurality of different studies including a first study (e.g., 630*a*) (e.g., an investigation that includes collecting data (e.g., health-related data) from a plurality of users (e.g., the user of the electronic device); an investigation that includes presenting a set of data-collection tasks to a plurality of users (e.g., the user of the electronic device); a heart health study; a reproductive health study; a dietary study) in which a user of the electronic device is enrolled and a second study (e.g., 630*b*) (e.g., a study different from the first study) in which the user of the electronic device is enrolled.

In some embodiments, displaying the task view includes: in accordance with a determination that a first set of permissions (e.g., data access permissions (e.g., sensor data; demographic (e.g., biological data, historical data, medical data) data; call data; messaging data; activity (e.g., physical/exercise activity))) has been granted, the electronic device displaying, via the display device, a third task (e.g., 608*d*) (e.g., a task different from the first task and second task; a task that is associated with one or more of the data types that access permission has been granted for); in accordance with a determination that a second set of permissions (e.g., permissions different than the first set of permissions; a set of permissions that does not include permission to access at least one of the data types included in the first set of permissions; a set of permissions that includes permission to access at least one data type that is not included in the first set of permissions) has been granted (e.g., without the first set of permissions being granted), the electronic device forgoing displaying the third task. In some embodiments, in accordance with a determination the second set of permissions has been granted, displaying, via the display device, a fourth task (e.g., a task different from the first, second, and third tasks). Displaying different sets of tasks based on different sets of permissions having been granted, without requiring further user input, reduces cluttering the user interface with tasks that correspond to permissions that have not been granted and improves security of the device by not surfacing tasks for which the user has not provided the necessary permissions. Reducing clutter of the user interface enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the task view includes an indication (e.g., 610*a*; 610*b*) (e.g., a graphical indication, an alphanumeric indication) of a degree of participation (e.g., a quantification; a measurement (e.g., a total amount of time of participation (e.g., participation by contribution of data), a total number of tasks performed; a total number of questions answered)) by a user associated with the electronic device in a plurality of research studies that includes at least the first study and the second study.

In some embodiments, the task view affordance includes (e.g., as a part of the affordance, displayed adjacent to the affordance) an indication (e.g., a numeric indication, a dynamic number) of available tasks (e.g., 606*a*1) (e.g., tasks that are displayed in the task view; tasks that are active (e.g., that can still be completed) and yet to be completed). Including an indication of available tasks provides the user with visual feedback to the user regarding the task status of multiple studies. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the task view includes a fourth task (e.g., 608*a*) (e.g., a task different from the first, second, and third tasks.) that does not correspond to a specific study (e.g., does not correspond to any specific study; the fourth task is not initiated or generated by a specific study; the fourth task is generated by a research application for managing studies).

In some embodiments, tasks in the task view are displayed in an order (e.g., displayed vertically with tasks earlier in the order displayed at the top; displayed horizontally with tasks earlier in the order displayed at the left) and in accordance with a determination that a remaining time for completion (e.g., "6 days remaining" of 608*b*) (e.g., a time that the task remains active for completion; a time after which the task can no longer be completed and is no longer displayed as active (or displayed at all) in the task view) of the first task is less than a remaining time for completion of the second task (e.g., "7 days remaining" of 608*d*), the first task is displayed before the second task in the order; and in accordance with a determination that the remaining time for completion of the first task is greater than the remaining time for completion of the second task, the first task is displayed after the second task in the order.

In some embodiments, the task view includes a fifth task (e.g., 624a) and in some embodiments, the fifth task is a completed task (e.g., a task that is no longer active; a task that corresponds to a set of steps that have already been completed). In some embodiments, the fifth task (e.g., along with other completed tasks) are displayed, in a displayed order of tasks in the task view, after active tasks (e.g., tasks that are displayed in the task view; tasks that are active (e.g., that can still be completed) and yet to be completed), if any. Displaying completed tasks in the task view provides the user with improved visual feedback as to tasks that have been completed and therefore no longer need to be completed, for multiple studies. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the task view includes a sixth task (e.g., 608f). In some embodiments, the electronic device detects, via the one or more input devices, a third input corresponding to the sixth task; and in response to detecting the third input, initiates a process for enrolling the user of the electronic device in a third study (e.g., 632a) (e.g., a study that is associated with one or more studies the user of the electronic device is currently enrolled in or formerly enrolled in; a study that is a sub-study of a study that the user is currently enrolled in). In some embodiments, initiating the process for enrolling the user of the electronic device in a third study includes displaying a user interface for enrolling the user of the electronic device in the third study (e.g., a user interface that includes one or more questions that can be responded to in order to complete the first task). In some embodiments, initiating the process for enrolling the user of the electronic device in a third study includes completing the enrollment in response to the third input.

The electronic device, while displaying the first user interface, detects (704), via the one or more input devices, a first input (e.g., selection of 606a) (e.g., a tap input; a mouse click).

The electronic device, in response to detecting the first input and in accordance with a determination that the first input corresponds to selection of the task view affordance (e.g., 606a), displays (706), via the display device, a task view (e.g., 604a). Displaying the task view includes displaying (708) a first task (e.g., 608b) (e.g., a data-collection task; a discrete set of steps (e.g., user inputs) to be taken that generates data and/or grants access to data (e.g., health-related data (e.g., exercise data; diet-related data)) corresponding to the first study (e.g., 630b), and (In some embodiments, a task (e.g., a representation of a task), when selected, initiates a process for collecting and/or providing access to data pertinent to an active research study that initiated (e.g., generated) the task.) displaying (710) a second task (e.g., 608d) (e.g., a task different from the first task) corresponding to the second study (e.g., 630a). Concurrently displaying a first task and a second task, from different studies, based on selection of a single affordance reduces the number of inputs required to identify tasks for multiple, different studies and also provides improved feedback as to what tasks are active for multiple studies. Reducing the number of inputs needed to perform an operation enhances the operability of the device and providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first task is a selectable object (e.g., an affordance) and the second task is a selectable object. In some embodiments, the electronic device detects, via the one or more input devices, a second input (e.g., 612). In some embodiments, the electronic device, in response to detecting the second input: in accordance with a determination that the second input corresponds to the first task, initiates a process for completing the first task. In some embodiments, initiating the process for completing the first task includes displaying a user interface for completing the first task (e.g., a user interface that includes one or more questions that can be responded to in order to complete the first task). In some embodiments, initiating the process for completing the first task includes completing the first task in response to the second input (e.g., granting permission to access and/or transmit data required to complete the first task). In some embodiments, the electronic device, in accordance with a determination that the second input corresponds to the second task, initiates a process for completing the second task (e.g., without initiating a process for completing the first task).

In some embodiments, the electronic device includes one or more sensors (e.g., physiological sensors (e.g., a heart rate sensor; a heart rhythm sensor); a motion sensor; a gyroscope). In some embodiments, the electronic device, prior to detecting the first input, detects, via the one or more sensors, a sensor event (e.g., a pattern of sensor data); in response to detecting the sensor event and in accordance with a determination that the sensor event satisfies a set of task generation criteria (e.g., the pattern of sensor data is indicative of an event or activity (e.g., health-related activity such as elevated heart rate, irregular heart rhythm, a fall experienced by the user) that is relevant to the first study), the electronic device generates (e.g., creating the first task and making the first task active) the first task (e.g., task 608c).

In some embodiments, the first user interface includes a study view affordance (e.g., 606b) associated with the plurality of different studies. In some embodiments, the electronic device, in response to detecting the first input and in accordance with a determination that the first input corresponds to selection of the study view affordance, displays, via the display device, a study view (e.g., 604b) that includes concurrently displaying: a graphical representation of the first study (e.g., 630a) (e.g., a graphical and/or textual indication of the first study (e.g., that includes an indication that the study is currently active and/or enrolled); an affordance corresponding to the first study that, when selected, causes the display of further information about the first study); and a graphical representation of the second study (e.g., 630b). In some embodiments, the study view further includes a third study that the user of the electronic device is not enrolled in (e.g., a study that is available for enrollment). Concurrently displaying representations of multiple studies in which the user is enrolled, based on selection of a single affordance reduces the number of inputs required to access representations of different studies and also provides improved feedback as to studies that the user is enrolled in. Reducing the number of inputs needed to perform an operation enhances the operability of the device and providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the study view includes a graphical representation of a third study (e.g., 632b) (e.g., an ongoing study, an active study that is enrollable if ineligibility criteria are not met) in which the user of the electronic device is not enrolled, wherein displaying the graphical representation of the third study includes: in accordance with a determination that a set of one or more ineligibility criteria is met, displaying in the graphical representation of the third study, an indication (e.g., a graphical and/or textual indication) that user of the electronic device is ineligible for enrollment in the third study (e.g., "ineligible" indication of 632b). In some embodiments, a study that includes an ineligible indication cannot be enrolled in by a user of the electronic device. Displaying an indication that the device is ineligible for enrollment in a study, based ineligibility criteria, provides improved feedback on availability status of the study. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, displaying the graphical representation of the third study includes: in accordance with a determination that the set of one or more ineligibility criteria are not met (In some embodiments, no ineligibility criterion are met when a set of eligibility criteria are met), displaying (e.g., in the graphical representation of the third study) an indication that the user of the device is eligible for enrollment in the third study (e.g., and that the third study is currently active). Displaying an indication that the device is eligible for enrollment in a study, based ineligibility criteria, provides improved feedback on availability status of the study. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the study view includes a graphical representation of a fourth study (e.g., includes information about the fourth study; includes an affordance corresponding to the fourth study that, when selected, provides additional information about the fourth study) that is an inactive study (e.g., a completed study, a past study, a study that is no longer enrollable). Displaying a graphical representation of inactive studies provides the user with improved visual feedback as to the inactive status of the inactive study. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, displaying the graphical representation of the fourth study includes: in accordance with a determination that the user of the electronic device was enrolled in the fourth study, displaying (e.g., in the graphical representation of the fourth study) an indication (e.g., a graphical or a textual indication) that the user of the electronic device was enrolled in the fourth study; and in accordance with a determination that the user of the electronic device was not enrolled in the fourth study, displaying (e.g., in the graphical representation of the fourth study) an indication that the user of the electronic device was not enrolled in the fourth study. Displaying an indication of user enrollment, for an inactive study, provides improved feedback on the user's enrollment status for the inactive study. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, displaying the graphical representation of the fourth study includes: in accordance with a determination that data associated with the fourth study has been used in a first data use instance (e.g., used by another study, a research paper, or article), displaying (e.g., in the graphical representation of the fourth study) an indication of the first data use instance (e.g., an indication of the study, research paper, or article that used the data from the fourth study); and in accordance with a determination that data associated with the fourth study has been used in a second data use instance (e.g., a use instance that occurs after the first use instance), displaying (e.g., in the graphical representation of the fourth study) an indication of the second data use instance. In some embodiments, the information relating to a past study continues to be updated over time, even after the study has been completed, to include information pertaining to the ongoing use of data from the past study. Displaying indication of data use instances for past studies provides users with feedback as to how data from the studies have been used and reduces the number of user inputs required to access such use data. Providing improved feedback and reducing the number of inputs required to perform functions enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the graphical representations of studies in the study view are displayed in an order (e.g., order shown in FIGS. 6E and 6F) (e.g., displayed vertically with studies earlier in the order displayed at the top; displayed horizontally with studies earlier in the order displayed at the left). In some embodiments, graphical representations of inactive studies (e.g., a completed study, a past study, a study that is no longer enrollable) are displayed after graphical representations of enrolled studies (e.g., studies that are active and that the user of the electronic device is enrolled in) and after available studies (e.g., an ongoing study, an active study that is enrollable if ineligibility criteria are not met) in the order; and graphical representations of available studies are displayed after graphical representations of enrolled studies in the order.

In some embodiments, the graphical representation of the first study includes a selectable object (e.g., 630b) (e.g., an affordance). In some embodiments, the electronic device detects, via the one or more input devices, a fourth input (e.g., 638) corresponding to the selectable object included in the graphical representation of the first study; in response to detecting the fourth input, the electronic device displays, via the display device, a detailed view for the first study (e.g., 642) (e.g., as a separate user interface or as additional information in the study view), the detailed view including an indication of data (e.g., 644) (e.g., demographic (e.g., biological data, historical data, medical data) data; call data; messaging data; activity (e.g., physical/exercise activity)) being provided (e.g., shared, transmitted to the recipients associated with the first study (e.g., the study's creator/manager)) to the first study. Displaying an indication on data from the device that is being shared with the study (e.g., transmitted to the study) provides feedback to the user as to data-sharing. Providing improved visual feedback on data sharing improves device security and enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the detailed view for the first study includes a withdraw affordance (e.g., 648). In some embodiments, the electronic device detects, via the one or more input devices, a fifth input (e.g., 650) corresponding to selection of the withdraw affordance; in response to the fifth user input, the electronic device ceases to include the first task (e.g., 608*b*) in the task view (e.g., 604*a*) (e.g., deleting all currently active tasks associated with the first study from the task view and ceasing to include any further tasks from the first study in the task view). In some embodiments, in response to the fifth user input, the first study is designated as a completed study and displayed in the order of studies in the study view in a position corresponding to completed studies (and no longer displayed in a position corresponding to active studies. In some embodiments, in response to the fifth user input, the electronic device ceases to share data with the first study. Removing tasks for withdrawn studies reduces cluttering the user interface with tasks that correspond to withdrawn studies and improves security of the device by not surfacing tasks for withdrawn studies. Reducing clutter of the user interface enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the detailed view for the first study includes a first option affordance (e.g., 646*a*) that, when selected, causes display of additional options regarding the first study. In some embodiments, the additional information is selected from the group consisting of: a consent document for the first study, a privacy policy for the first study, a set of frequently asked questions about the first study, a set of options for getting help with the first study.

In some embodiments, the detailed view for the first study includes a first communication affordance (e.g., 656*d*) that, when selected, initiates communication (e.g., a telephone call, a messaging session, an email) with an external electronic device (e.g., a device associated with a service center or contact for assisting with the first study).

In some embodiments, the detailed view for the first study includes one or more task indications (e.g., 642*a*; 642*b*) (e.g., indications of all tasks (e.g., tasks that are displayed in the task view; tasks that are active (e.g., that can still be completed) and yet to be completed) that are associated with the first study. Displaying tasks associated with the study in the detailed view for the study provides improved feedback as to what tasks are active for the study. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first user interface includes a data view affordance (e.g., 606*c*). In some embodiments, the electronic device, in response to detecting the first input and in accordance with a determination that the first input corresponds to selection of the data view affordance, displays, via the display device, a data view (e.g., 604*c*) that includes concurrently displaying: an indication of data of a first type (e.g., 662) (e.g., sensor data; demographic (e.g., biological data, historical data, medical data) data; call data; messaging data; activity (e.g., physical/exercise activity)) that is accessible to one or more studies in which the user of the electronic device is enrolled, including the first study; and an indication (e.g., 662*b*) (e.g., a graphical and/or alphanumeric indication; an indication of the number of studies with access) associated with one or more studies in which the user of the electronic device is enrolled that have access to the data of the first type, including the first study. Concurrently displaying an indication of a data type along with an indication of which studies have access to that data, based on selection of a single affordance, reduces the number of inputs required to identify studies that have access to that data type and also provides improved feedback as to study access rights. Reducing the number of inputs needed to perform an operation enhances the operability of the device and providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the indication of the data of the first type is an indication of demographic data (e.g., 662) and wherein the indication of the data of the first type is a selectable object (e.g., an affordance) that, when selected, causes display of demographic data (e.g., 668) (e.g., data relevant to a comparison of the user to a larger population (e.g., data regarding age, gender, race, marital status, occupation, area of residence)) associated with the user of the electronic device. In some embodiments, the indication of the data of the first type, when selected, causes display of medical history data for the user of the electronic device; in some embodiments, the data displayed in response to selection of the indication of data of the first type is organized/ordered based on the type of data.

In some embodiments, the one or more studies in which the user of the electronic device is enrolled that have access to the data of the first type is a selectable object (e.g., 662*b*) (e.g., an affordance) that, when selected, causes display of additional information (e.g., 672) (e.g., a list of the one or more studies with access) associated with the one or more studies that have access to the data of the first type.

In some embodiments, the indication of the data of the first type is an indication of sensor (e.g., heart rate sensor; a heart rhythm sensor); a motion sensor; a gyroscope) and usage data (e.g., 664) (usage of the electronic device (e.g., call data; messaging data; email data)) and wherein the indication of the data of the first type is a selectable object (e.g., an affordance) that, when selected, causes display of a sensor and usage data view (e.g., 676). In some embodiments, the sensor and usage data view includes a listing of types of sensor and usage data that is accessible to one or more studies.

In some embodiments, the sensor and usage data view includes a data collection affordance (e.g., 678) that, when selected, modifies a current state (e.g., disables if active, enables if inactive) of sensor data collection (In some embodiments, the data collection affordance, when selected, modifies the state of sensor data collection for multiple sensors). Modifying the state of sensor collection, based on selection of a single affordance, can reduce the number of inputs required to modify the state of data collection across multiple sensor types. Reducing the number of inputs needed to perform an operation enhances the operability of the device and providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. When modification includes disabling collection of sensor data, battery life can be significantly improved.

In some embodiments, the sensor and usage data view includes an export data affordance (e.g., 682) that, when selected, causes collected sensor and usage data to be exported (e.g., shared; transmitted; provided) to one or more studies that have access to (e.g., that have been granted access to) the sensor and usage data.

In some embodiments, the sensor and usage data view includes a first type (e.g., a first type of sensor or a first type of usage) of sensor and usage data affordance (e.g., 680e) that, when selected, causes display of a first type of sensor and usage data view (e.g., 690) that includes information about the first type of sensor and usage data including: an example of data of the first type of sensor and usage data that this accessible (e.g., that is collected and accessible) to one or more studies (e.g., 692) in which the user of the electronic device is enrolled that have access to the data of the first type of sensor and usage data; and an example of data that is not of the first type of sensor and usage data that this accessible to one or more studies in which the user of the electronic device is enrolled that have access to the data of the first type of sensor and usage data.

In some embodiments, the first type of sensor and usage data view includes one or more affordances (e.g., 692a1 692b) associated with the one or more studies that have access to the data of the first type of sensor and usage data, including a first affordance associated with a fifth study that has access to the data of the first type of sensor and usage data, wherein the first affordance associated with a fifth study, when selected, initiates a process for disabling access of the fifth study to the first type of sensor and usage data (e.g., without disabling access of any other studies that currently have access to the first type of sensor and usage data).

Note that details of the processes described above with respect to method 700 (e.g., FIG. 7) are also applicable in an analogous manner to the methods described below. For example, method 900 optionally includes one or more of the characteristics of the various methods described above with reference to method 700. For example, method 700 can be used to interact with and/or manage tasks generated by a research study that is enrolled in via method 900. For another example, method 700 can be used to interact with and/or manage a hearing test task that is performed according method 1100. For brevity, these details are not repeated below.

FIGS. 8A-8U illustrate exemplary user interfaces for enrolling in a research study (e.g., a study managed via a research study management application) using device 600. The user interfaces in these figures are used to illustrate the processes described below, including the processes in FIG. 9.

In FIG. 8A, device 600 displays study view 604b, which is described in more detail with respect to FIG. 6E. Study view 604b includes available study 632a and available study 632b in available study section 632. Device 600 detects, on touch-sensitive display 602, touch input 802, which is a tap gesture corresponding to available study 632a, the Women's Diet study. In response to touch input 802, device 600 displays study detail interface 804, as seen in FIG. 8B.

Figure 8B:
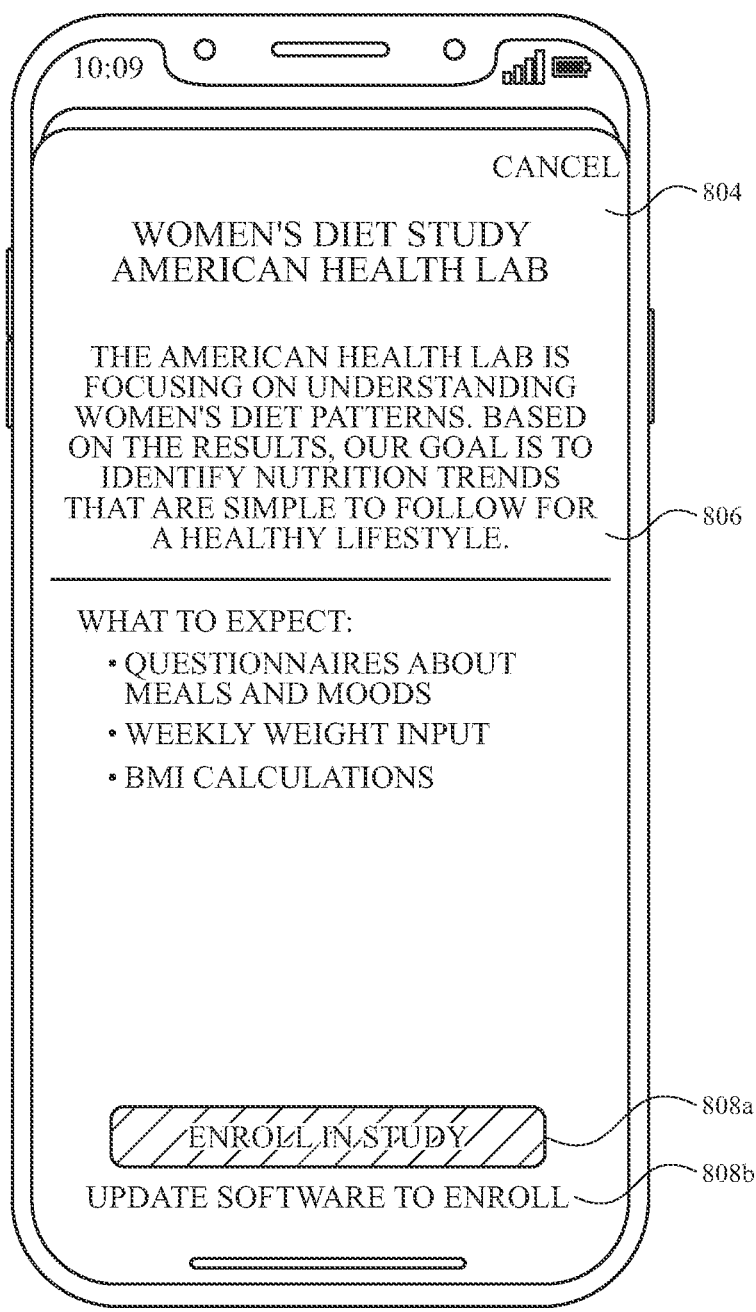

In FIG. 8B, study detail interface 804 for the Women's Diet study includes information section 806 that includes information about the study, including the purpose of the study and expectations of tasks associated with participation in the study. Study detail interface 804 also includes enroll in study affordance 808a, which is greyed out indicating that a requirement of enrollment is not met. Thus, enroll in study affordance 808a, when selected, does not initiate a process for enrolling in the study. In FIG. 8B, device 600 displays indication 808b ("Update Software to Enroll") proximate to affordance 808a that provides an indication of one or more problems that prevent enrollment in the study. As indicated by indication 808b, the Women's Diet study requires that the software of device 600 be updated in order to participate. In some embodiments, an indication of one or more problems that prevent enrollment in the study is displayed in response to selection of enroll in study affordance 808a, rather than being displayed initially. In some embodiments, study interface 804 includes an option (e.g., an affordance) for sharing the research study with an external user. In some embodiments, the option to share the research study is available on device 600, even if device 600 (e.g., the user of device 600) is ineligible to enroll in the study.

Figure 8C:
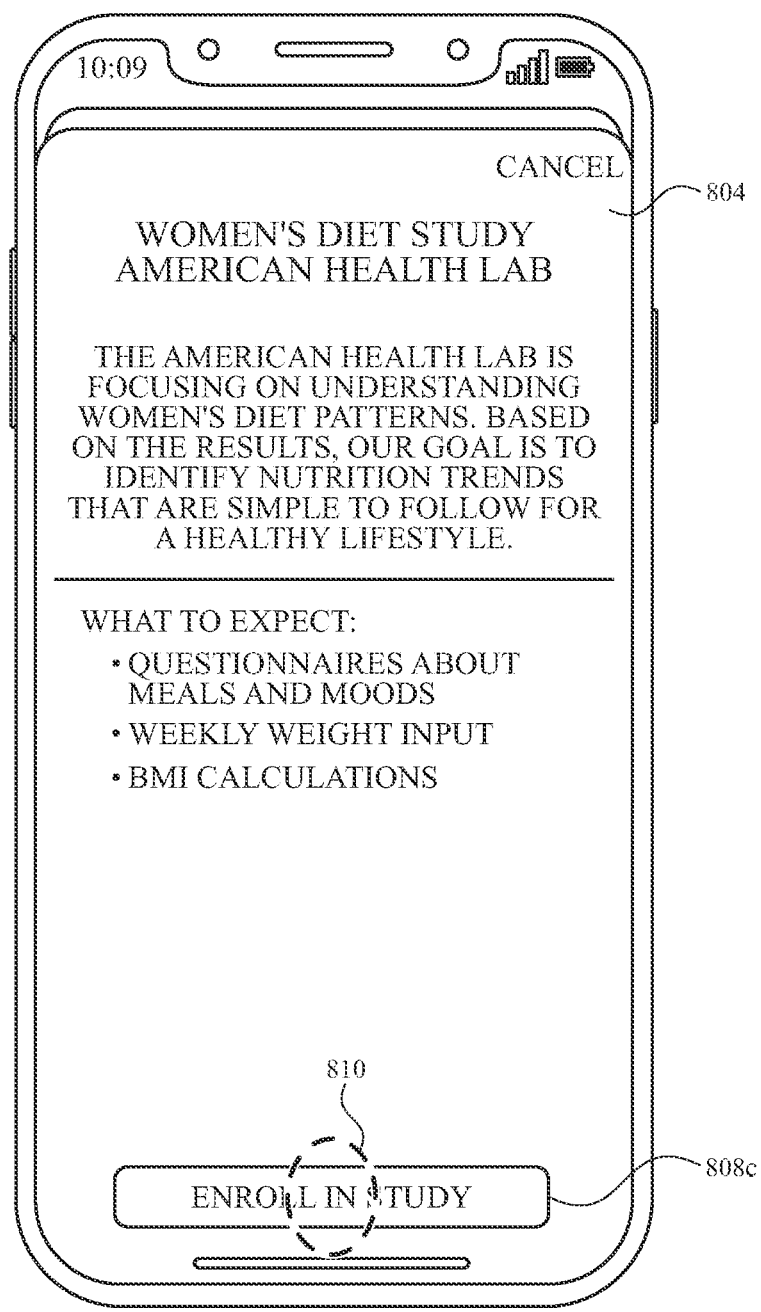

In FIG. 8C, device 600 displays study detail interface 804 after the software (e.g., operating system software) of device 600 has been updated. Study detail interface 804 now includes enroll in study affordance 808c that is not greyed out. Study detail interface 804 does not include indication 808b, as the software updated problem has been resolved.

Figure 8D:
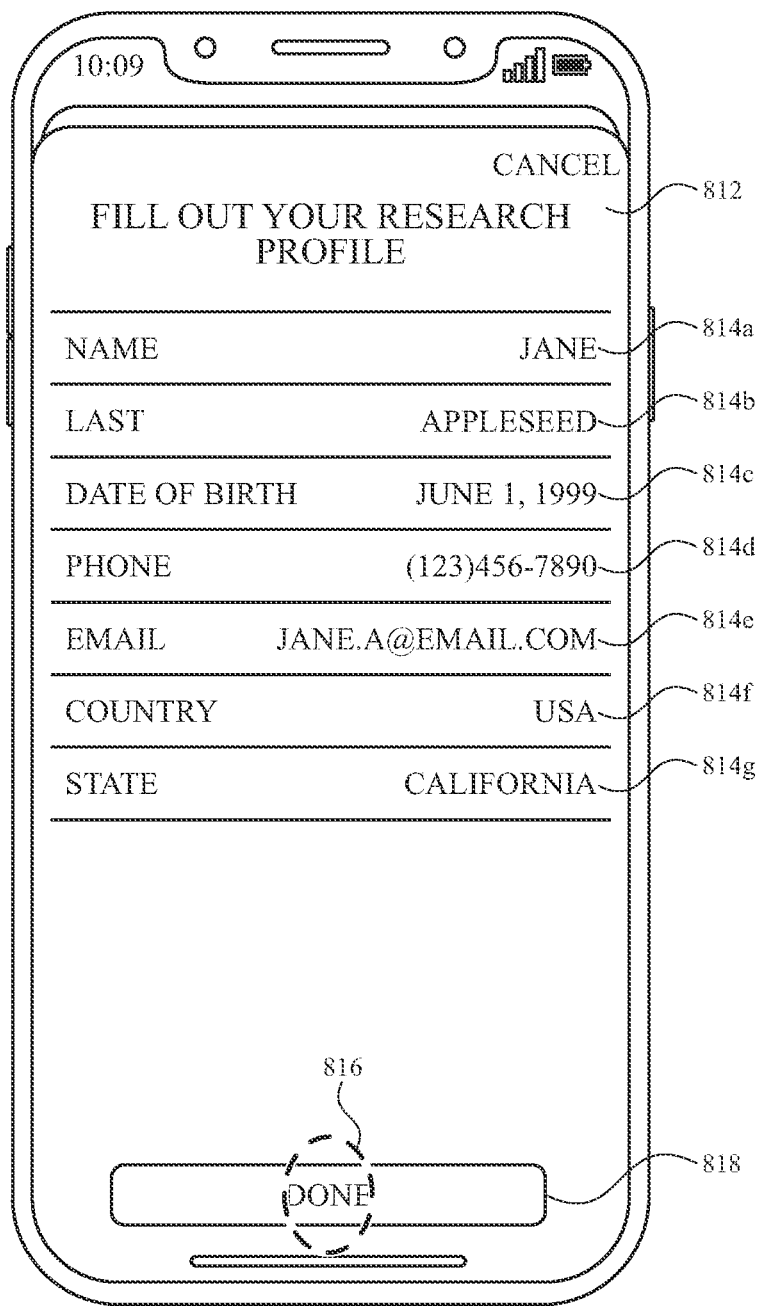

In FIG. 8C, device 600 detects, on touch-sensitive display 602, touch input 810, which is a tap gesture corresponding to enroll in study affordance 808b and, in response, initiates a process for enrolling in the Women's Diet study and displays research profile interface 812, as seen in FIG. 8D.

In FIG. 8D, research profile interface 812 includes fields 814a-814g, pre-populated using information available to (e.g., stored on) device 600 about the user of device 600. In some embodiments, one or more fields are not pre-populated and are to be completed via further user input (e.g., input provided via a soft keyboard). In some embodiments, the information is pre-populated based on information provided to the research study management application via completion of a profile questionnaire task (e.g., task 608a). In some embodiments, the research profile interface 812 is not shown as part of the process for enrollment and information about the user is automatically provided to the study (e.g., automatically provided via previous authorization provided during enrollment in a previous study).

Figure 8E:
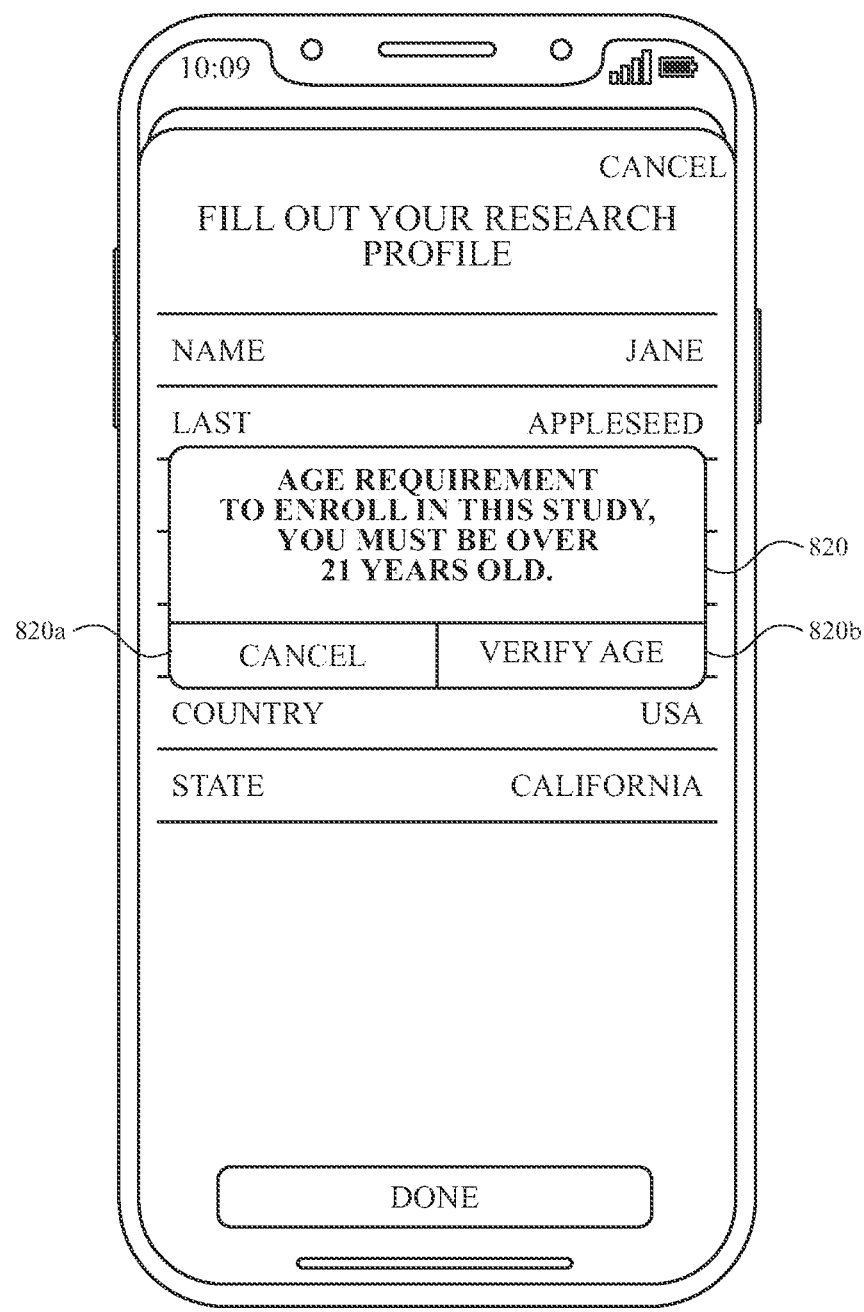

In FIG. 8D, device 600 detects, on touch-sensitive display 602, touch input 816, which is a tap gesture corresponding to done affordance 818 and, in response, displays the interface of FIG. 8E.

In FIG. 8E, device 600 displays notification 820 overlaid on research profile interface 812. Notification 820 provides an indication of one or more problems that prevent enrollment in the study. As indicated by notification 820, the Women's Diet study requires that participates be over 21 years old. Notification 820a includes affordance 820a for dismissing the notification and affordance 820b that, when selected, initiates a process for verifying the user's age. In some embodiments, the enrollment process does not progress beyond research profile interface 812 unless the user's age is verified as being over 21 years old.

Figure 8F:
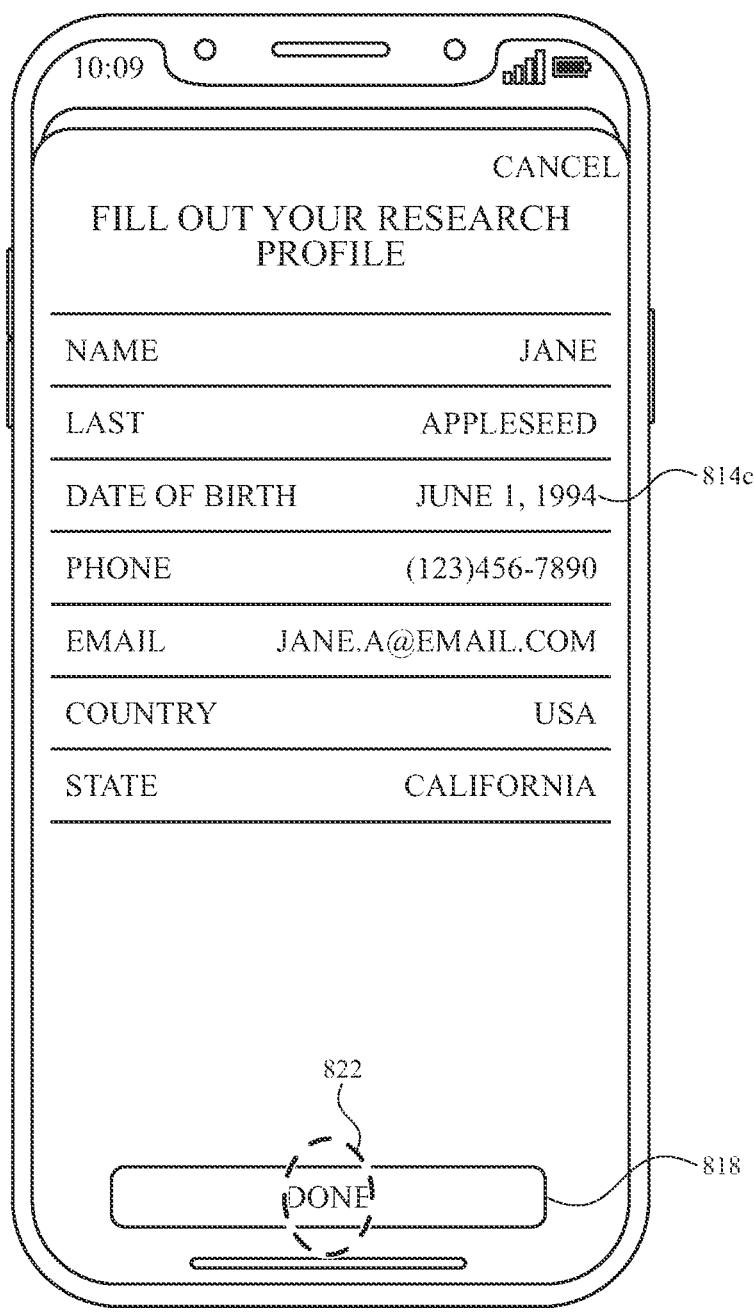

In FIG. 8F, date of birth field 814c has been edited to indicate a birth date of Jun. 1, 1994 (e.g., device 600 received inputs via a soft keyboard revising the birth date), making the user's age over 21 years old. Device 600 detects, on touch-sensitive display 602, touch input 822, which is a second tap gesture corresponding to done affordance 818 and, in response to the input and a determination that the user's entered birth date indicates an age over 21 years, displays requirements interface 824 of FIG. 8G.

Figure 8G:
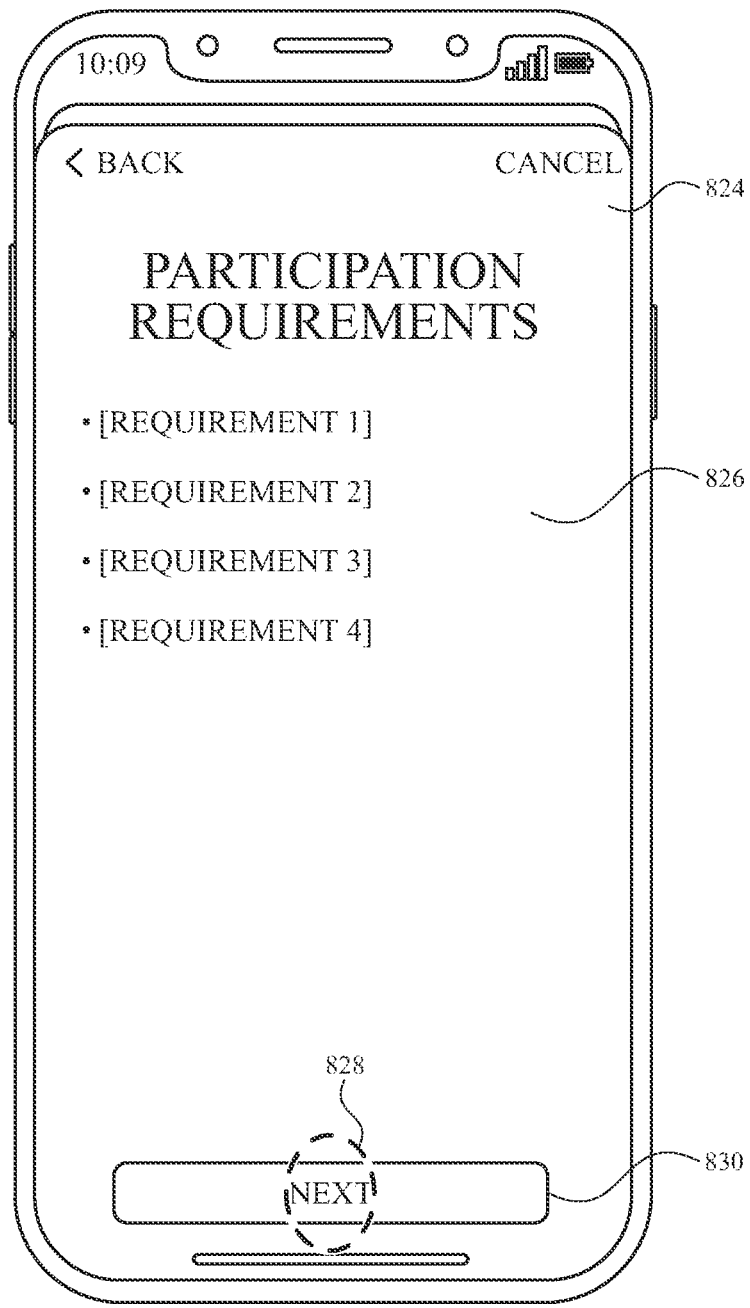

In FIG. 8G, device 600 displays requirements interface 824 that includes indications 826 of the requirements for enrolling in the Women's Diet study. In some embodiments, the requirements can include one or more of software compatibility requirements, hardware compatibility requirements, demographic requirements, health history requirements, data access requirements, and consent requirements. Device 600 detects, on touch-sensitive display 602, touch input 828, which is a tap gesture corresponding to next affordance 830 and, in response displays study partners interface 832.

Figure 8H:
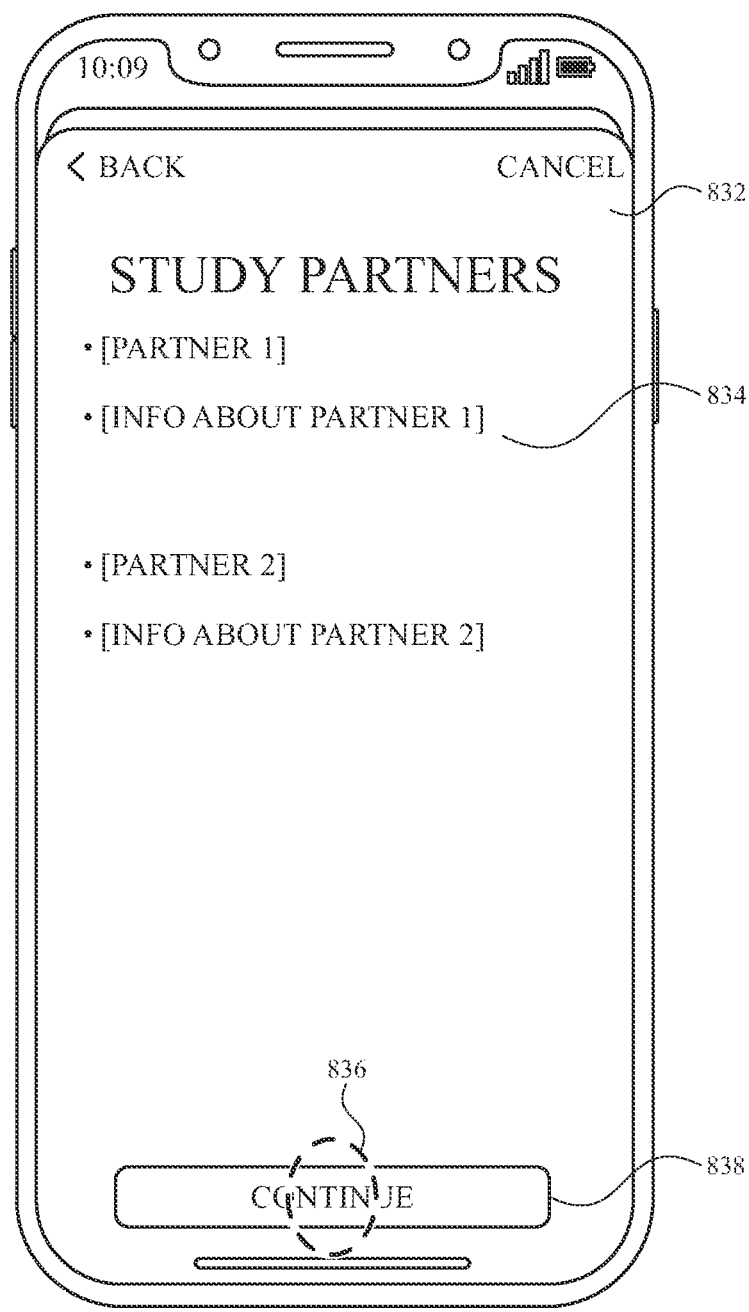

In FIG. 8H, device 600 displays study partners interface 832 that includes section 834 that provides information about one or more study partners associated with the study. In some embodiments, the study partners receive access to data exported by device 600 as part of participation in the research study. Device 600 detects, on touch-sensitive display 602, touch input 836, which is a tap gesture corresponding to continue affordance 838 and, in response displays consent information interface 840 of FIG. 8I.

Figure 8I:
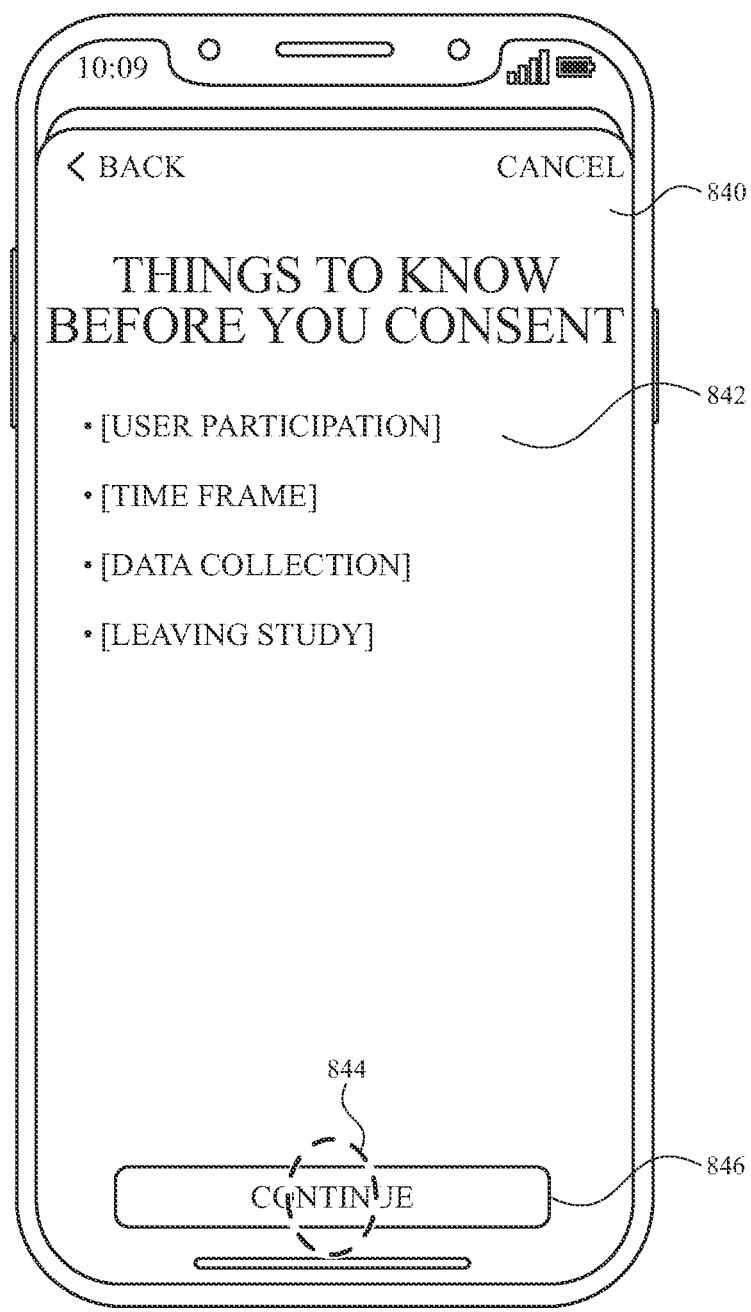
Figure 8J:
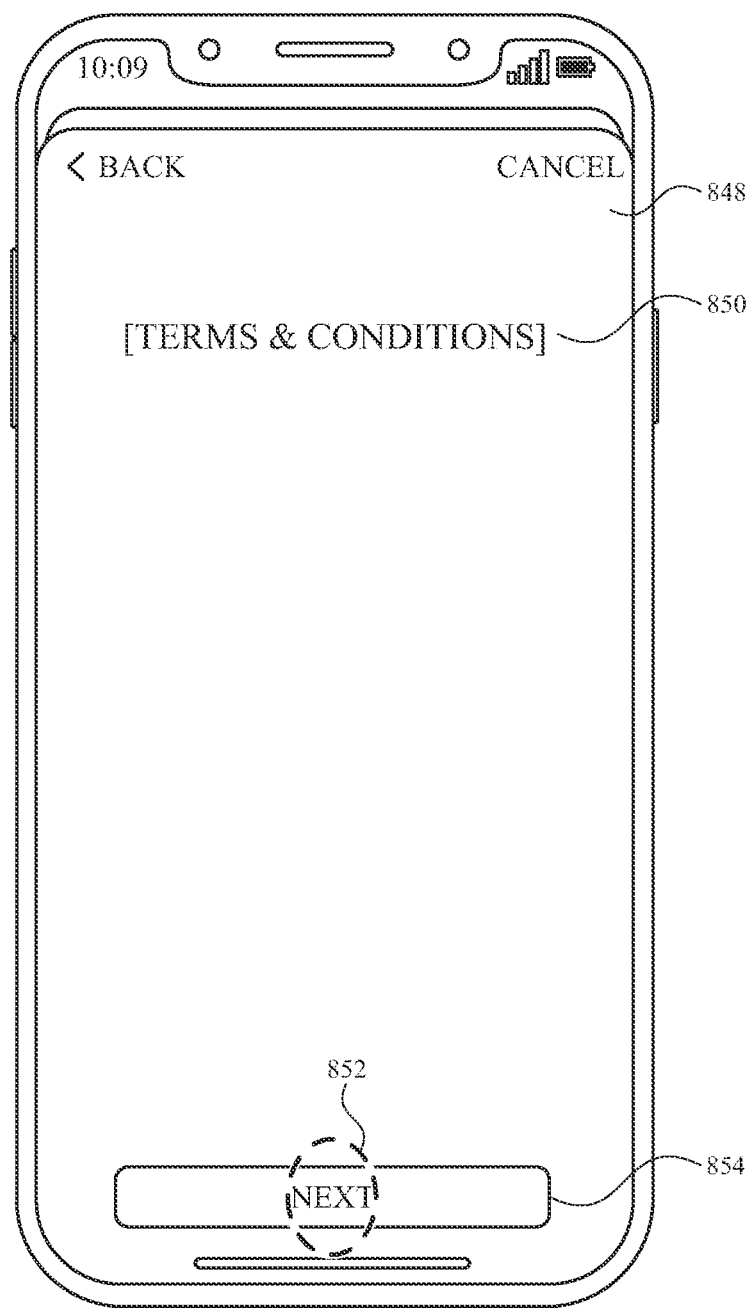
Figure 8K:
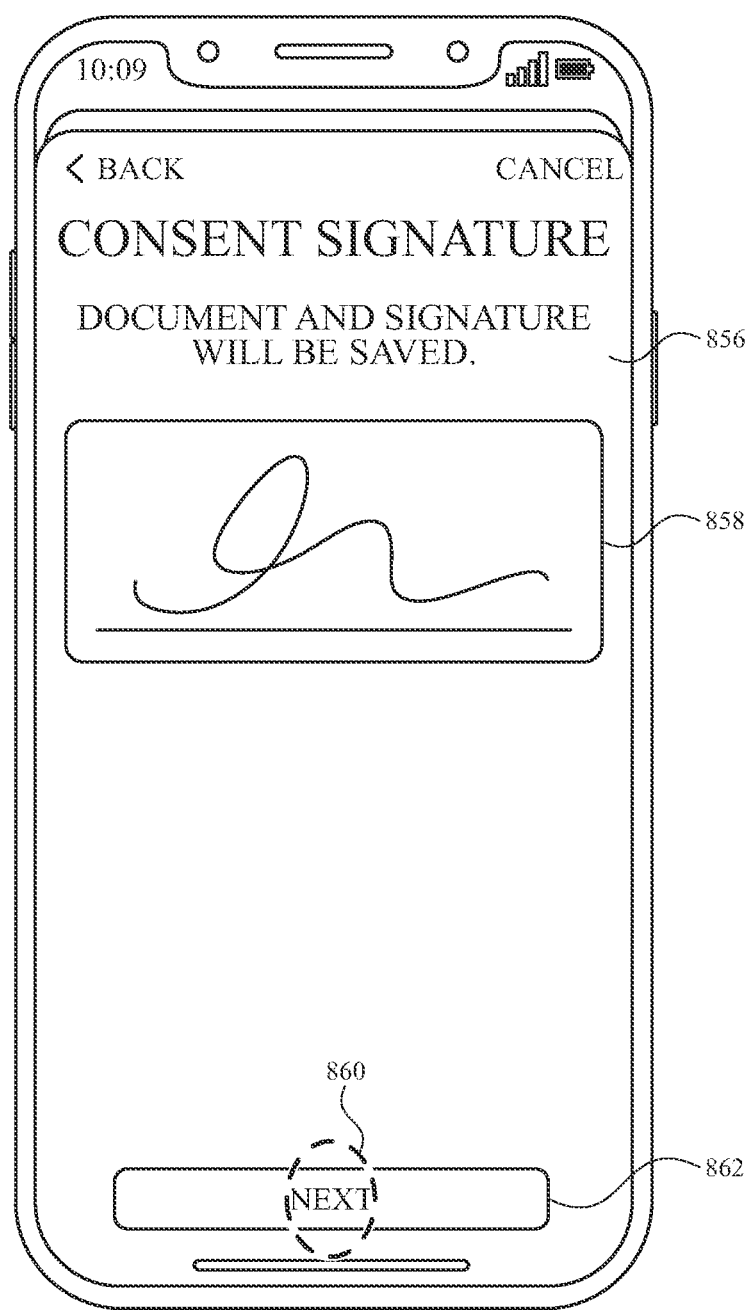

In FIG. 8I, device 600 displays consent information interface 840 that includes section 842 that provides information pertinent to participation in the research study. In some embodiments, such information can include information on tasks associated with the study, the duration of the study, data that is collected as part of the study, and information about how to withdraw from the study. Device 600 detects, on touch-sensitive display 602, touch input 844, which is a tap gesture corresponding to continue affordance 846 and, in response displays terms and conditions interface 848 of FIG. 8J.

In FIG. 8I, device 600 displays terms and conditions interface 848 includes section 850 that provides information regarding terms and conditions of participation in the research study. Device 600 detects, on touch-sensitive display 602, touch input 852, which is a tap gesture corresponding to next affordance 854 and, in response displays consent signature interface 856 of FIG. 8K.

In FIG. 8K, device 600 displays consent signature interface 856 that includes signature field 858. In some embodiments, device 600 detects touch input, on touch-sensitive display 602 that corresponds to a signature. In some embodiments, device 600 accepts a digital signature via a soft keyboard. In some embodiments, device 600 accepts a digital signature in the form of an authenticated token. In some embodiments, device 600 requires biometric authentication (e.g., fingerprint or facial recognition authentication) to accept a signature. In some embodiments, the enrollment process does not progress beyond interface 856 unless a valid signature is provided (e.g., the consent signature is a mandatory requirement for enrollment). Device 600 detects, on touch-sensitive display 602, touch input 860, which is a tap gesture corresponding to next affordance 862 and, in response data request interface 864 of FIG. 8L.

Figure 8L:
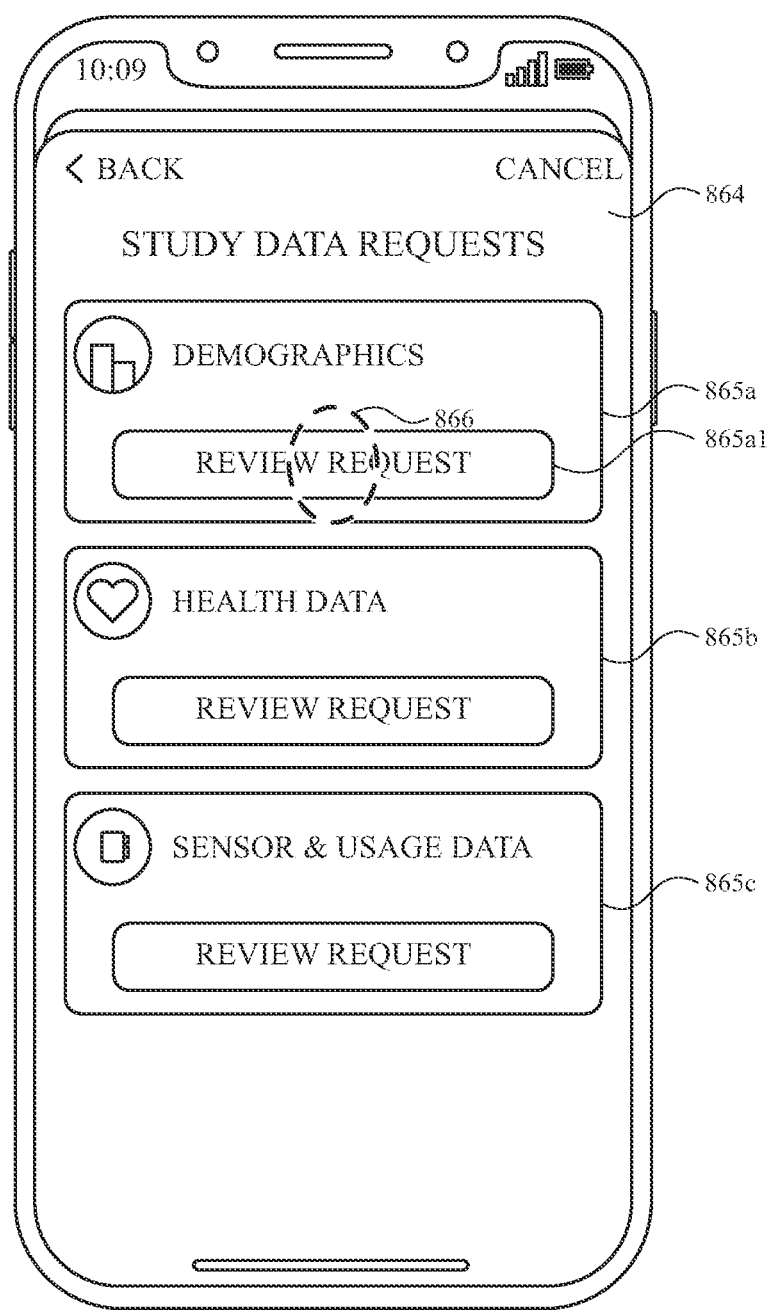

In FIG. 8L, device 600 displays data request interface 864 that presents information about types of data that the study is requesting access to. In some embodiments, one or more of the data requests are mandatory (e.g., enrollment in the study cannot occur without granting access to the mandatory data). As seen in FIG. 8L, the Women's Diet study is requesting access to three types of data: demographic data 865a, health data 865b, and sensor data 865c. In some embodiments, the enrollment process does not proceed until each data request is reviewed and either granted or denied. In FIG. 8L, data request interface 864 includes review affordances 865a1, 865b1, and 865c1 corresponding to demographic data 865a, health data 865b, and sensor and usage data 865c, respectively. Device 600 detects, on touch-sensitive display 602, touch input 866, which is a tap gesture corresponding to review affordance 865a1 of demographics data 865a and, in response displays demographics request interface 867 of FIG. 8M.

Figure 8M:
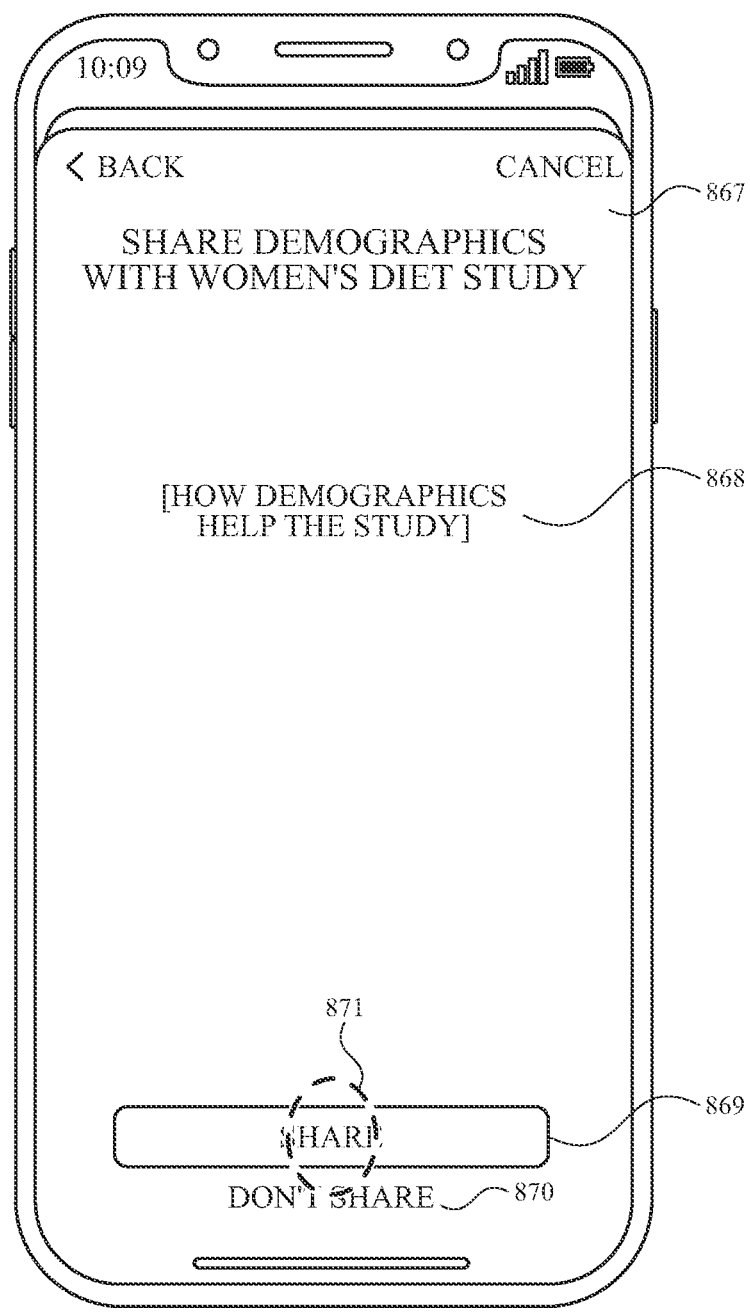

In FIG. 8M, device 600 displays demographics request interface 867 that includes information section 868 that provides information about the demographics data request. In some embodiments, the information section includes information about what particular demographics data is requested by the study and/or information about how the data will be used. Demographics request interface 867 also includes share affordance 869 that, when selected, authorizes the demographics data request and a don't share affordance 870 that, when selected, denies the request for demographics data. In some embodiments, the requested demographics data is mandatory data, required to complete enrollment. In such embodiments, device 600, in response to detecting selection of don't share affordance 870 can provide an indication (e.g., a notification similar to notification 820 of FIG. 8E) that the requested data is mandatory and required for enrollment. In FIG. 8M, device 600 detects, on touch-sensitive display 602, touch input 871, which is a tap gesture corresponding to share affordance 869 and, in response re-displays data request interface 864, as seen in FIG. 8N.

Figure 8N:
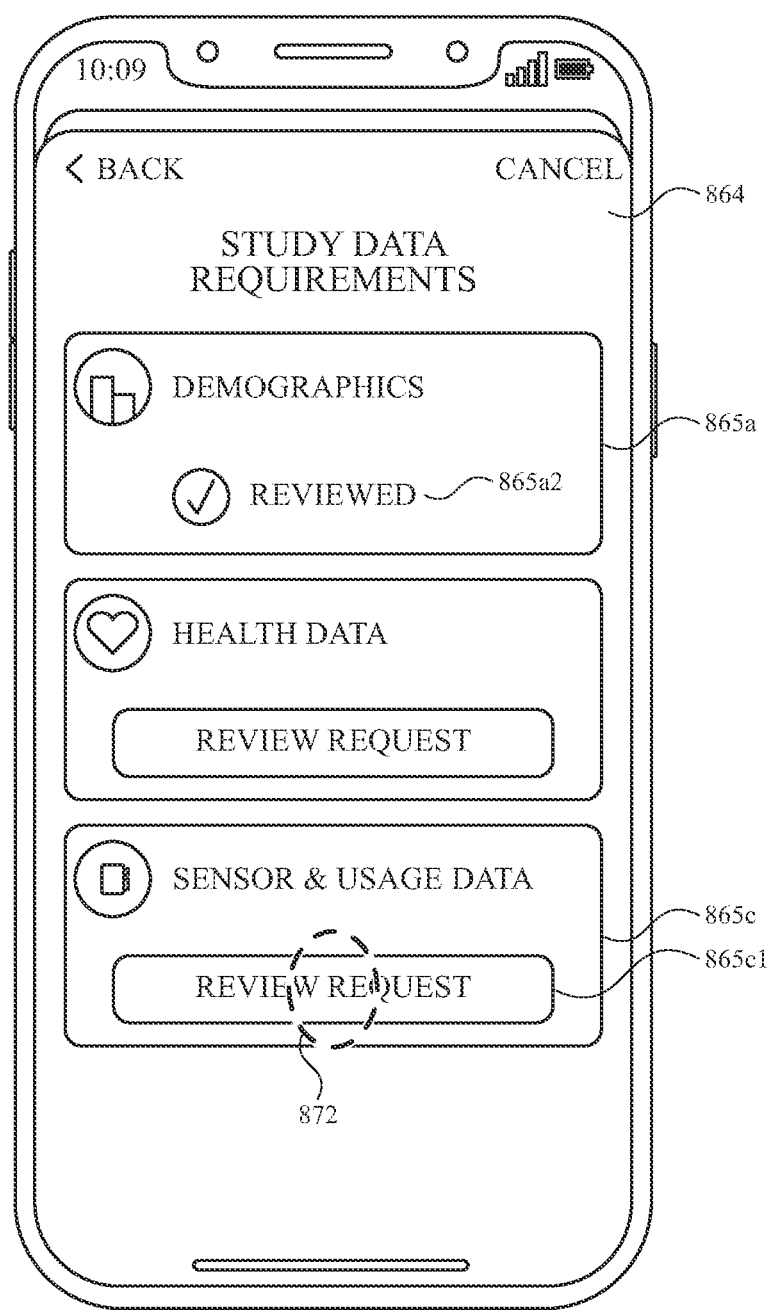
Figure 80:
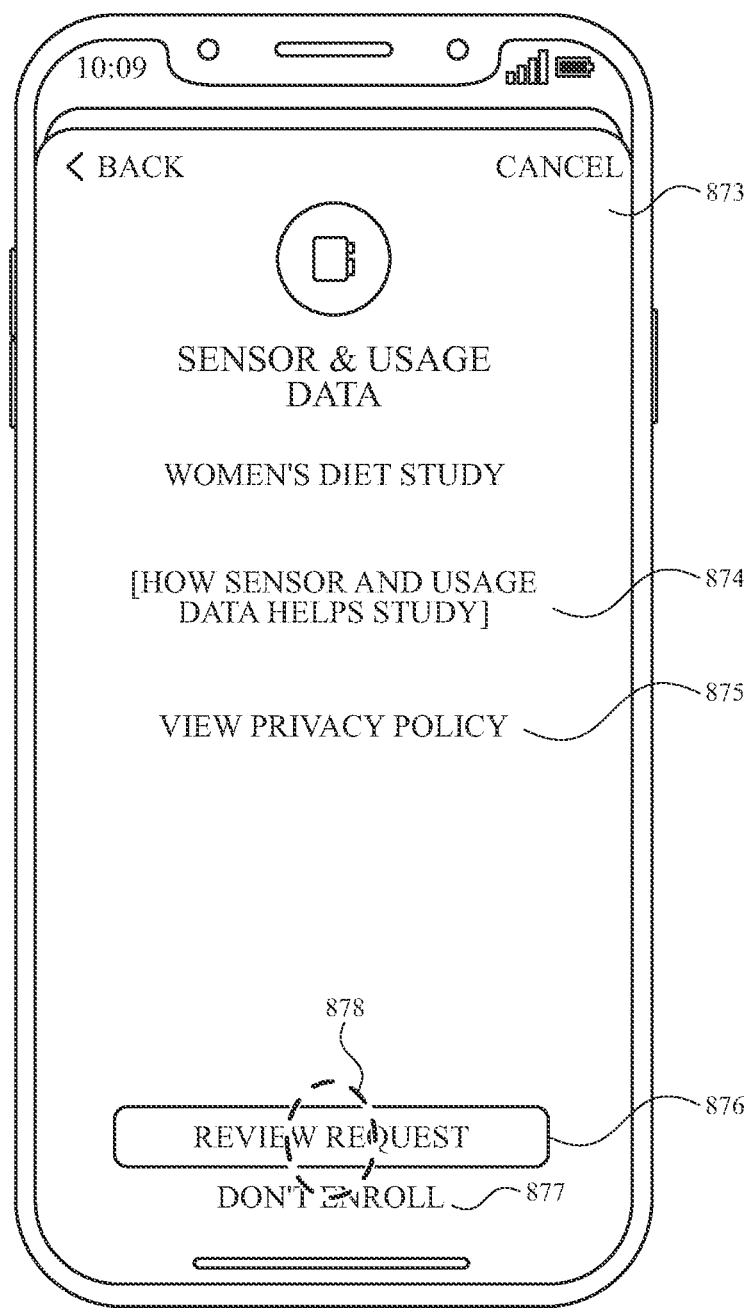

In FIG. 8N, data request interface 864 has been updated to indicate that request for demographics 865a has been reviewed by replacing review affordance 865a1 with reviewed indication 865a2. In some embodiments, indication 865a2 includes an indication of whether the request was approved or denied. Device 600 detects, on touch-sensitive display 602, touch input 872, which is a tap gesture corresponding to review affordance 865c1 of sensor and usage data 865c and, in response displays sensor and usage request interface 873 of FIG. 8O.

In FIG. 8O, device 600 displays sensor and usage request interface 873 which differs in format from data request interface 864. Notably, the sensor and usage data is mandatory data for the Women's Diet study of the present embodiment. While sensor and usage request interface 873 also includes an information section 874 that provides information about the sensor and usage data request, sensor and usage request interface 873 also includes a privacy policy affordance 875 that, when selected, causes device 600 to display detailed information about the studies privacy handling policies. In some embodiments, privacy policy disclosures persist across studies such that the policy is only displayed once during an enrollment process and not re-displayed upon a subsequent enrollment process. Sensor and usage request interface 873 also includes a review affordance 878 for proceeding with review of the sensor and usage data request and a don't enroll affordance 877 that, when selected, denies the sensor and usage data request and exits the enrollment process (e.g., since the requested data is mandatory data). Device 600 detects, on touch-sensitive display 602, touch input 878, which is a tap gesture corresponding to review affordance 878 and, in response displays request detail interface 879a of FIG. 8P.

Figure 8P:
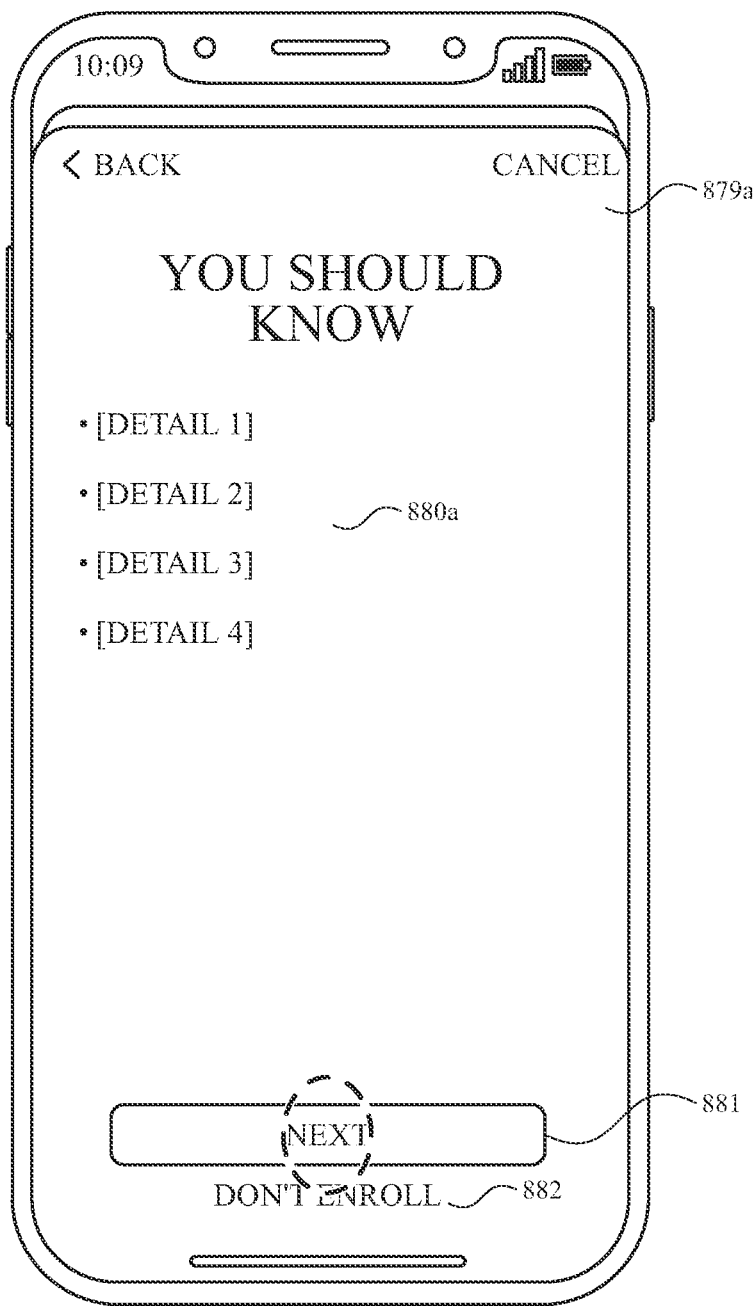

In FIG. 8P, device 600 displays request detail interface 879a that provides additional details 880a about the sensor and usage data request. In some embodiments, the details includes details of which sensors and which usage data is requested. In some embodiments, the details include details on the frequency with which data is requested and the potential impact on the performance (e.g., battery life) of device 600. request detail interface 879a also includes a next affordance 881 and a don't enroll affordance 882 that, when selected, performs a similar function to don't enroll affordance 877. Device 600 detects, on touch-sensitive display 602, touch input 881, which is a tap gesture corresponding to next affordance 881 and, in response displays request detail interface 879b of FIG. 8Q.

Figure 8Q:
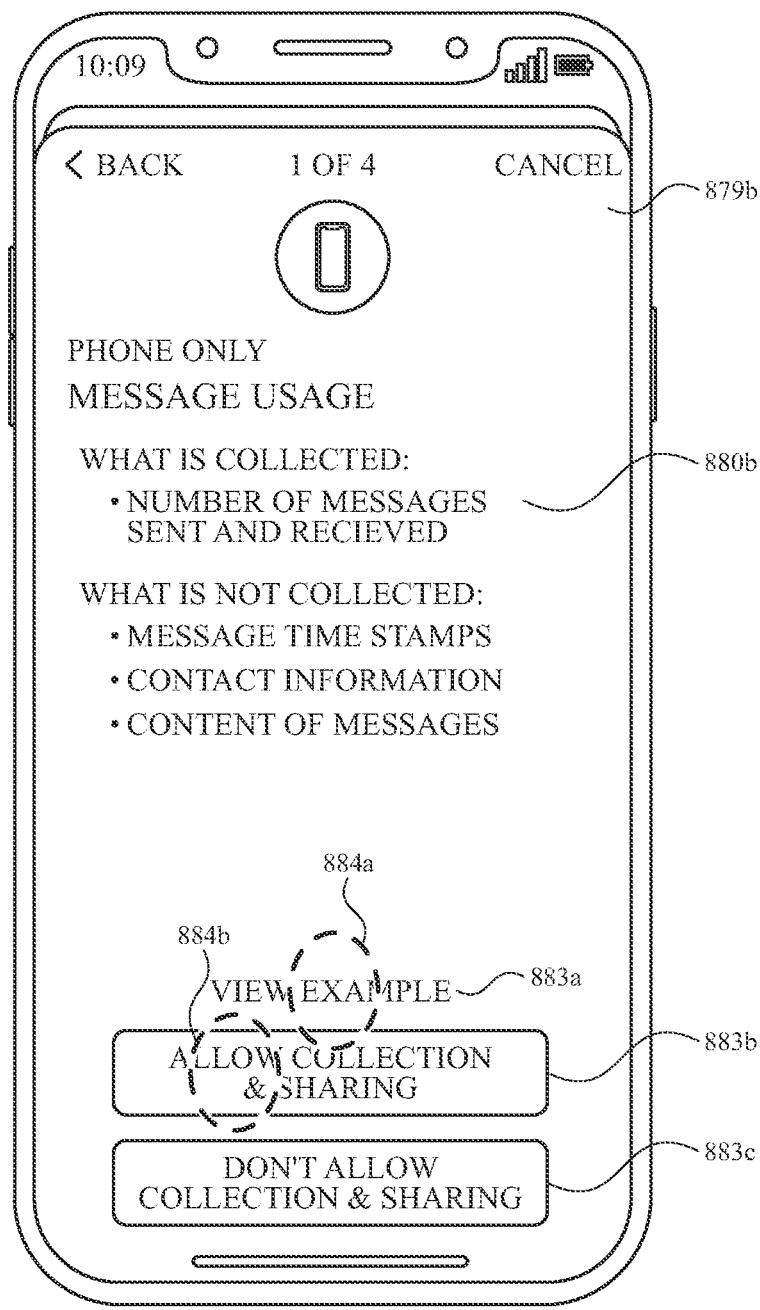

In FIG. 8Q, device 600 displaces request detail interface 879b, which is a $2^{nd}$ interface of details for the sensor and usage request. Request detail interface 879b includes additional details 880b including details of what usage data is requested. In FIG. 8Q, the details indicate that message usage (e.g., text message usage) data is collected from just message usage on device 600 (e.g., is not collected for other devices associated with the user of device 600) and what is collected (e.g., the number of messages) and what is not collected (e.g., the context of messages). Request detail interface 879b includes affordance 883a that, when selected, causes device 600 to display an example of the message usage data that is collected. Request detail interface 879b also includes allow affordance 883b and don't allow affordance 883c. Because the sensor and message data is mandatory for the Women's Diet study, selection of affordance 883c would deny the request and forgo enrollment in the study. In some embodiments, selection of don't allow affordance 883c causes display of a notification similar to notification 820 of FIG. 8E.

In FIG. 8Q, while request detail interface 879b is displayed, device 600 detects, on touch-sensitive display 602, touch inputs 884a and 884b and, in response, performs operations as described below.

Figure 8R:
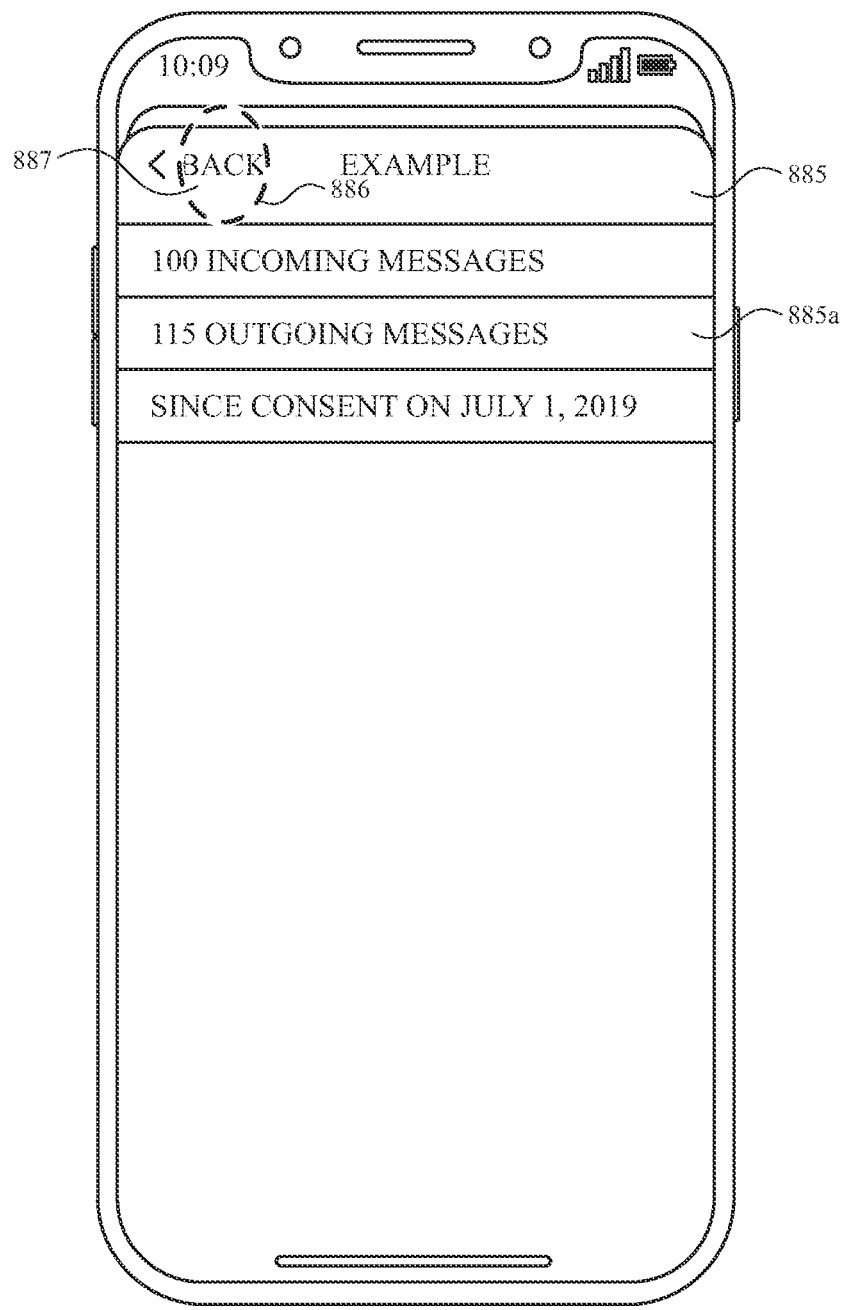

In FIG. 8R, device 600, in response to input 884a on example affordance 883a, displays example interface 885 that includes example data 885a for message usage data that would be collected by the Women's Diet study. Device 600 detects, on touch-sensitive display 602, touch input 886, which is a tap gesture corresponding to back affordance 887 and, in response re-displays request detail interface 879b.

Figure 8S:
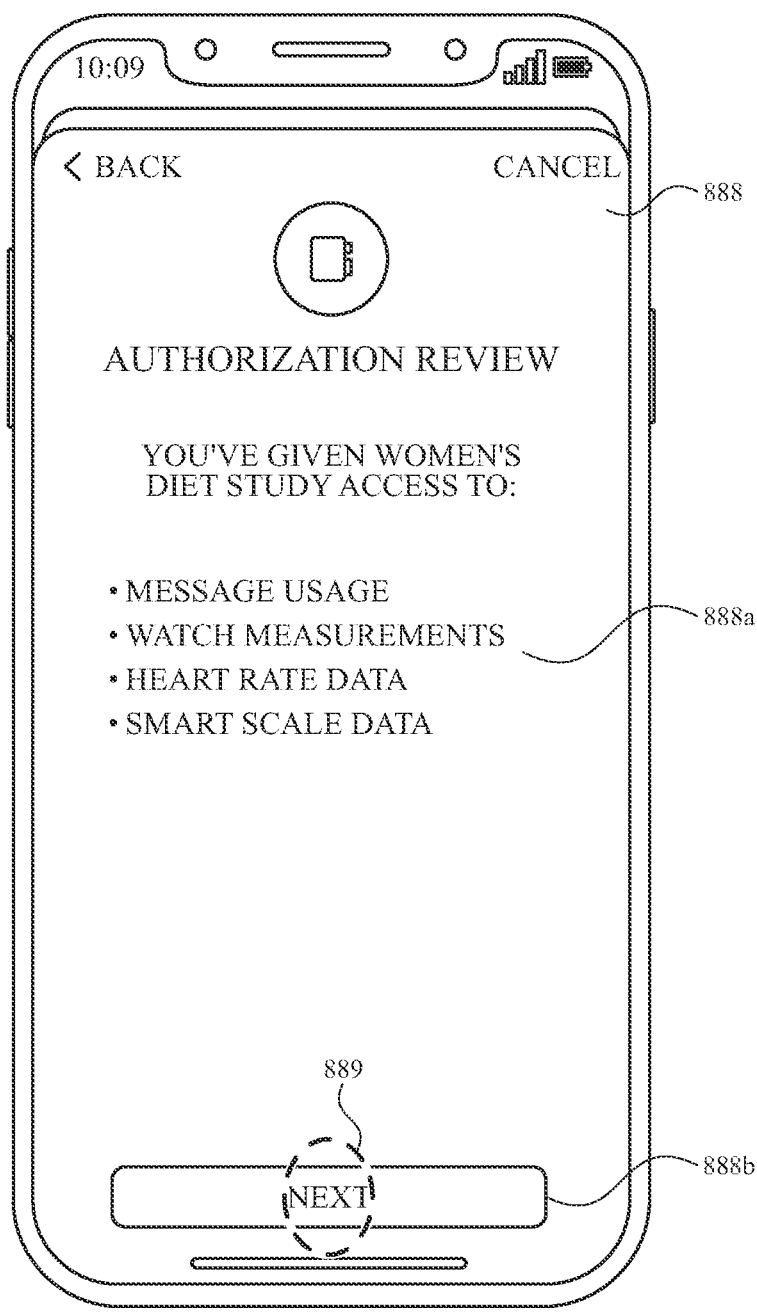

In FIG. 8S, device 600, in response to input 884b on allow affordance 883b of request detail interface 879b, displays final authorization review interface 888 that includes details 888a of what data access authorizations have been provided and a next affordance 888b. In some embodiments, details 888a also include information on what access was requested, but not granted. Device 600 detects, on touch-sensitive display 602, touch input 889, which is a tap gesture corresponding to next affordance 888b and, in response displays enrollment confirmation interface 890, as seen in FIG. 8T.

Figure 8T:
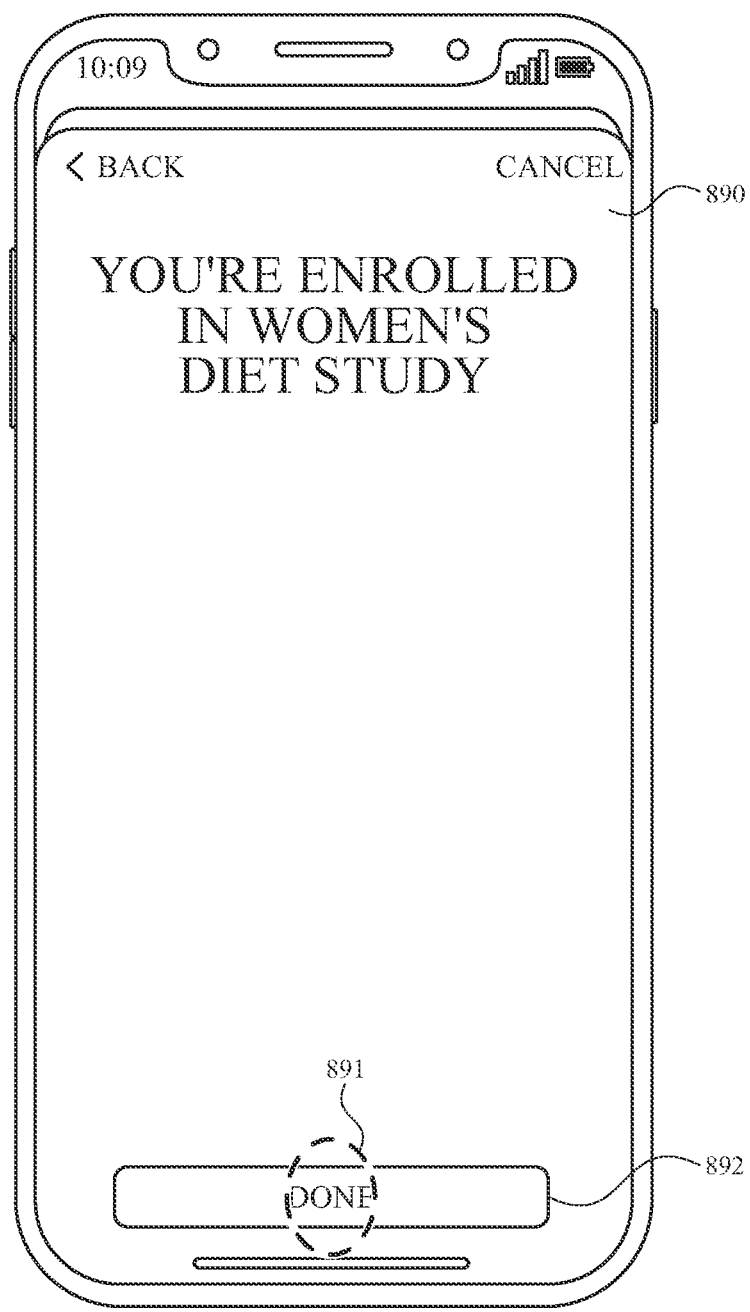

In FIG. 8T, device 600 displays enrollment confirmation interface 890 that indicates successful enrollment in the Women's Diet study. Device 600 detects, on touch-sensitive display 602, touch input 891, which is a tap gesture corresponding to done affordance 892 and, in response re-displays study view 604b, as seen in FIG. 8U.

In FIG. 8U, the Women's Diet study is no longer displayed in the available studies section 632 and is, instead, displayed in the current studies section 630 of study view 604b, indicating that it is now enrolled.

FIG. 9 is a flow diagram illustrating a method for enrolling in research studies using an electronic device in accordance with some embodiments. Method 900 is performed at a device (e.g., 100, 300, 500, 600) with a display device (e.g., 602) and one or more input devices (e.g., 602). Some operations in method 900 are, optionally, combined, the orders of some operations are, optionally, changed, and some operations are, optionally, omitted.

As described below, method 900 provides an intuitive way for enrolling in research studies. The method reduces the cognitive burden on a user for enrolling in research studies, thereby creating a more efficient human-machine interface. For battery-operated computing devices, enabling a user to interact with research studies faster and more efficiently conserves power and increases the time between battery charges.

The electronic device displays (902), via the display device, a research study user interface (e.g., 804) (e.g., an interface generated by a research application; an interface displaying information (e.g., one or more requirements for participation in the first research study) associated with the first research study)) that is associated with a first research study (e.g., an investigation that includes collecting data (e.g., health-related data) from a plurality of users (e.g., the user of the electronic device); an investigation that includes presenting a set of data-collection tasks to a plurality of users (e.g., the user of the electronic device); a heart health study; a reproductive health study; a dietary study; an investigation that has a set of enrollment criteria that must be satisfied to enroll in the first research study).

In some embodiments, displaying the research study user interface includes: displaying, in the research study user interface, first information (e.g., 806) (e.g., details about the purpose of the study, the creator(s) of the study, and/or the requirements of the study) about the research study; and in accordance with a determination that a set of enrollment prevention criteria (e.g., criteria based on requirements of the research study that prohibit enrollment by user having one or more incompatible characteristics (e.g., age, gender)) are not met, displaying in the research study user interface, via the display device, an enrollment affordance (e.g., 808b) (e.g., an affordance that, when selected, initiates a process for enrolling in the research study), wherein the set of one or more inputs includes a first input (e.g., 810) corresponding to the enrollment affordance; and in accordance with a determination the set of enrollment prevention criteria are met, forgoing displaying in the research study user interface the enrollment affordance (e.g., forgo displaying any enrollment affordance; displaying an inactive version (e.g., a non-selectable version; a selectable version that performs a function other than initiating the process for enrolling in the research study)) of the enrollment affordance; forgoing displaying the enrollment affordance until the enrollment prevention criteria are no longer met). Selectively displaying the enrollment affordance based on the set of criteria provides improved visual feedback as to eligibility of the device for enrollment in the study. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the research study user interface includes a share research study affordance that, when selected, initiates a process for sharing the research study with a user of an external device (e.g., notifying the user of the external device about the availability of the research study). In some embodiments, the research study user interface includes the share research study affordance even if the user of the electronic device is not eligible (e.g., currently eligible) to enroll in the research study.

The electronic device, while displaying the research study interface, receives (904), via the one or more input devices, a set of one or more inputs (e.g., 816) that include interaction with the research study user interface that is associated with the first research study (e.g., a request to initiate enrollment; a request to display further information about enrollment requirements).

In some embodiments, the set of one or more inputs includes a first input (e.g., 810) corresponding to a request to initiate a process for enrollment. In some embodiments, in response to receiving the set of one or more inputs and in accordance with a determination that the set of enrollment problem criteria are not met, the electronic device initiates the process for enrollment.

In some embodiments, during the process for enrolling in the research study, the electronic device displays, via the display device, a signature user interface (e.g., 856) configured to receive a consent signature (e.g., 858) (e.g., configured to receive one or more touch gestures corresponding to a signature) of user of the electronic device (e.g., consent to one or more aspects of the research study (e.g., a consent to share data, a consent to grant access to data shared with the research study)).

In some embodiments, during the process for enrolling in the research study and in accordance with a determination that a set of privacy disclosure criteria (In some embodiments, the privacy disclosure criteria are satisfied when the privacy disclosure user interface has not been previously displayed during an enrollment process (e.g., for the current research study; for any research study) are satisfied, the electronic device displays, via the display device, a privacy disclosure user interface (e.g., displayed based on selection of 875) that includes information regarding the degree of privacy maintained for data accessed (e.g., shared with) by the research study. Displaying information regarding the degree of data privacy provides the user with improved visual feedback regarding data privacy policies for the research study and regarding handling of data, should the user enroll in the study. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the set of privacy disclosure criteria are satisfied when the privacy disclosure user interface has not been previously displayed during a process for enrolling in a research study. In some embodiments, during the process for enrolling in the research study and in accordance with a determination that a set of privacy disclosure criteria are not satisfied, the electronic device forgoes displaying the privacy disclosure user interface. In some embodiments, the data privacy disclosure user interface is only shown during enrollment if it has not been previously been shown. Forgoing display of the privacy user interface when the criteria are not met (e.g., when the user interface has previously been shown on the device) reduces cluttering the user interface with already-shown information. Reducing clutter of the user interface enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, during the process for enrolling in the research study, the electronic device displays, via the display device, a data access request user interface (e.g., 864) including: displaying a first request (e.g., 865*a*) (e.g., an affordance associated with the first request) for access to data of a first type (e.g., demographic data, medical information/history data, sensor data (e.g., physiological sensors (e.g., a heart rate sensor; a heart rhythm sensor); a motion sensor; a gyroscope), device usage data (call data; messaging data; activity (e.g., physical/exercise activity)). In some embodiments, while displaying the first request, the electronic device detects, via the one or more input devices, a second input (e.g., a request to scroll the data access request user interface); and in response to detecting the second input, displays (e.g., by scrolling the data access request user interface; by ceasing to display the first request), via the display device, a second request (e.g., 865*b*) for access to data of a second type (e.g., demographic data, medical information/history data, sensor data (e.g., physiological sensors (e.g., a heart rate sensor; a heart rhythm sensor); a motion sensor; a gyroscope), device usage data (call data; messaging data; activity (e.g., physical/exercise activity)) that is different from the first type.

In some embodiments, while displaying the data access request user interface, the electronic device detects, via the one or more inputs devices, a second set of one or more inputs (e.g., 871) (e.g., including an input corresponding to the first request or the second request). In some embodiments, the electronic device, in response to detecting the second set of one or more inputs: in accordance with a determination that the second set of one or more inputs corresponds to approval of the first request for access to data of the first type (e.g., input corresponds to 869), grants the research study access to data of the first type; (In some embodiments, without granting the research study access to data of the second type.) in accordance with a determination that the second set of one or more inputs corresponds to denial of the first request for access to data of the first type (e.g., input corresponds to 870), forgoes granting (e.g., denying) the research study access to data of the first type. In some embodiments, without denying the research study access to data of the second type. In some embodiments, in response to denial of the first request for access to data of the first type and in accordance with a determination that data of the first type is mandatory data (e.g., data to which access must be granted for enrollment), displaying, via the display device, an indication (e.g., an alert) that access to data of the first type is required for enrollment in the research study. In some embodiments, in accordance with a determination that the second set of one or more inputs corresponds to approval of the second request for access to data of the second type, the electronic device grants the research study access to data of the second type; and in accordance with a determination that the second set of one or more inputs corresponds to denial of the second request for access to data of the second type, forgoes granting (e.g., denying) the research study access to data of the second type.

In some embodiments, the data of the first type is sensor data (e.g., data from a heart rate sensor; a heart rhythm sensor; a motion sensor; and/or a gyroscope) or usage data (e.g., 865*c*) (e.g., data from usage of the electronic device (e.g., call data; messaging data; email data)), and data of the first type is mandatory data for enrollment in the research study or non-mandatory data that is not required for enrollment in the research study.

The electronic device, in response to receiving the set of one or more inputs (908): in accordance with a determination that a set of enrollment problem criteria (e.g., criteria that indicates an issue, complication, or problem that prevents (e.g., until the complication is resolved) successful enrollment) (in some embodiments, the set of enrollment complication criteria are based on the set of enrollment criteria that must be satisfied to enroll in the first research study (e.g., the set of enrollment complication criteria are satisfied when a parameter (e.g., an existing parameter associated with the electronic device or a user of the electronic device), a user-entered parameter) does not meet at least one criterion of the set of enrollment criteria) are satisfied, displays (910) an indication (e.g., 808*b*; 820) (e.g., a graphical indication; a textual indication) of a problem (e.g., an issue, complication, or problem) that prevents enrollment in the first research study; and (In some embodiments, the indication is a selectable indication (e.g., an affordance) that, when selected, initiates a process for resolving the complication and/or providing additional information regarding the complication.) in accordance with a determination that the set of enrollment problem criteria are not met, forgoes (912) display of the indication of the complication that prevents enrollment in the first research study. In some embodiments, during the process for enrolling in the research study, in accordance with a determination that the set of enrollment criteria are satisfied, enrolling a user associated with the electronic device in the first research study. Displaying an indication of a problem that prevents enrollment based on a set of enrollment problem criteria being met, without requiring further user input, reduces the steps necessary to identify a problem and provides improved visual feedback as to the problem. Reducing the steps necessary to perform an action and providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the enrollment problem criteria are satisfied when a demographic characteristic (e.g., 814*c*) (e.g., a characteristic relevant to a comparison of the user to a larger population (e.g., data regarding age, gender, race, marital status, occupation, area of residence)) of a user of the electronic device satisfies a demographic incompatibility criteria (e.g., matches an incompatible characteristic value or fails to match a compatible characteristic value).

In some embodiments, the enrollment problem criteria are satisfied when a software characteristic (e.g., a compatible software (e.g., operating system software) version; availability of a required application) of the electronic device satisfies a software incompatibility criteria (e.g., matches an incompatible software characteristic or fails to match a compatible software characteristic).

In some embodiments, the enrollment problem criteria are satisfied when a hardware characteristic (e.g., availability of required hardware (e.g., a required sensor; required processor or circuitry)) of the electronic device satisfies a hardware incompatibility criteria (e.g., matches an incompatible hardware characteristic or fails to match a compatible hardware characteristic).

In some embodiments, the enrollment problem criteria are satisfied when a health information characteristic (e.g., a characteristic relating to the user's current or historical health information (e.g., information indicating a health-related event (e.g., a fall, a heart-related event) within a certain preceding period of time) of a user of the electronic device satisfies a health information incompatibility criteria (e.g., matches an incompatible health information characteristic or fails to match a compatible health information characteristic).

In some embodiments, forgoing displaying in the research study user interface the enrollment affordance includes displaying a first affordance (e.g., 808*a*) (e.g., an ineligibility information affordance; an affordance displayed at a location that corresponds to (e.g., matches) the location that a the enrollment affordance is displayed at when the set of enrollment prevention criteria are not met); and the set of one or more inputs includes a second input corresponding to the first affordance.

In some embodiments, the enrollment problem criteria are satisfied when the electronic device detects an input corresponding to denial of a request for access to data of a third type (e.g., input corresponding to 883*c*) (e.g., demographic data, medical information/history data, sensor data (e.g., physiological sensors (e.g., a heart rate sensor; a heart rhythm sensor); a motion sensor; a gyroscope), device usage data (call data; messaging data; activity (e.g., physical/exercise activity)) that is mandatory for enrollment in the research study.

Note that details of the processes described above with respect to method 900 (e.g., FIG. 9) are also applicable in an analogous manner to the methods described below. For example, method 700 optionally includes one or more of the characteristics of the various methods described above with reference to method 900. For example, method 700 can be used to interact with and/or manage tasks generated by a research study that is enrolled in via method 900. For another example, method 1100 can be used to interact with and/or manage a hearing test task for a study that was enrolled in via method 900. For brevity, these details are not repeated below.

FIGS. 10A-10X illustrate exemplary user interfaces for conducting hearing tests using device 600. In some embodiments, the hearing tests are conducted to gather data for use in research studies being managed by a research management application. The user interfaces in these figures are used to illustrate the processes described below, including the processes in FIG. 11.

In FIG. 10A, device 600 displays task view 604*a*, which is described in more detail with respect to FIG. 6A. Task view 604*a* includes task 608*d* that is a speech and noise test that is associated with an Annual Medical History study. Device 600 detects, on touch-sensitive display 602, touch input 1002*a*, which is a tap gesture corresponding to task 608*d*. In response to touch input 1002*a*, device 600 displays speech and noise test interface 1004*a*, as seen in FIG. 10B.

Figure 10B:
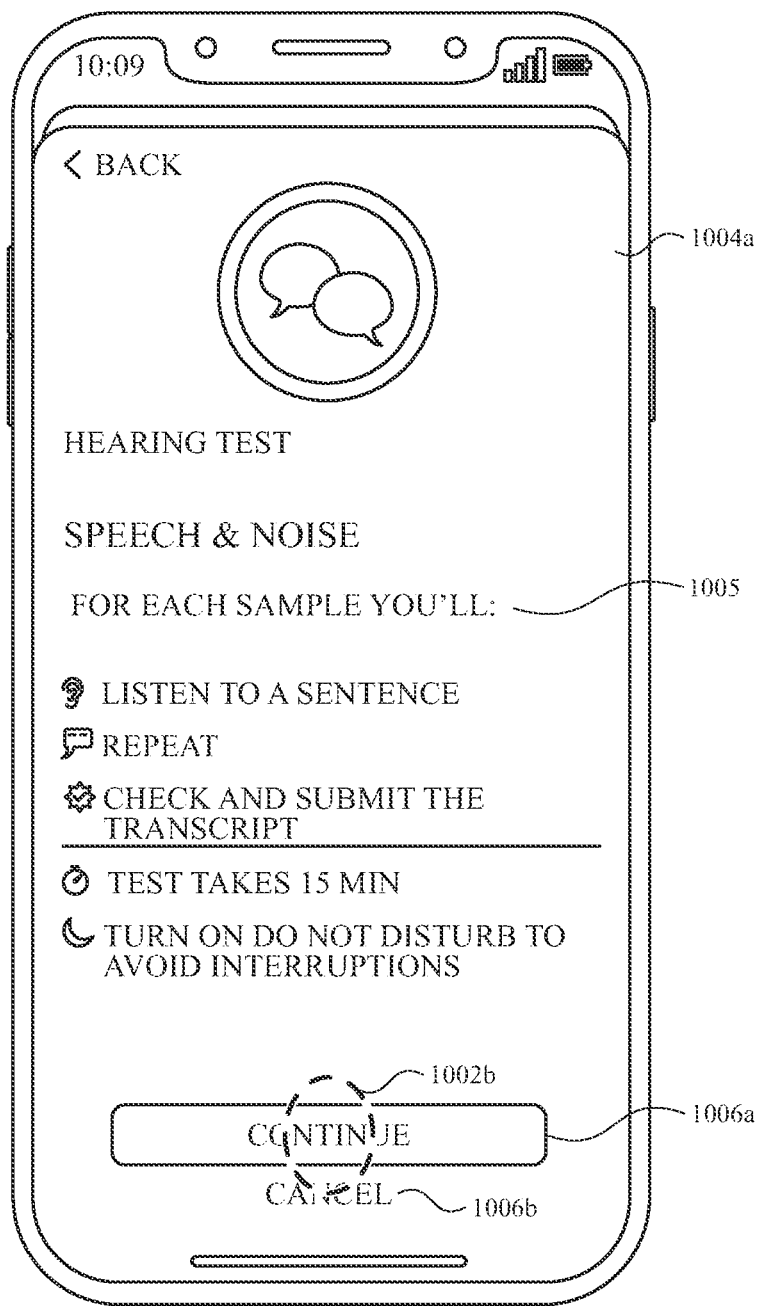

In FIG. 10B, device 600 displays speech and noise test interface 1004*a* that includes information 1005 about the speech and noise test and affordance 1006*a* for continuing with the test and affordance 1006*b* for cancelling the test. Device 600 detects, on touch-sensitive display 602, touch input 1002*b*, which is a tap gesture corresponding to continue affordance 1006*b*. In response to touch input 1002*b*, device 600 displays speech and noise test interface 1004*b*, as seen in FIG. 10C.

Figure 10C:
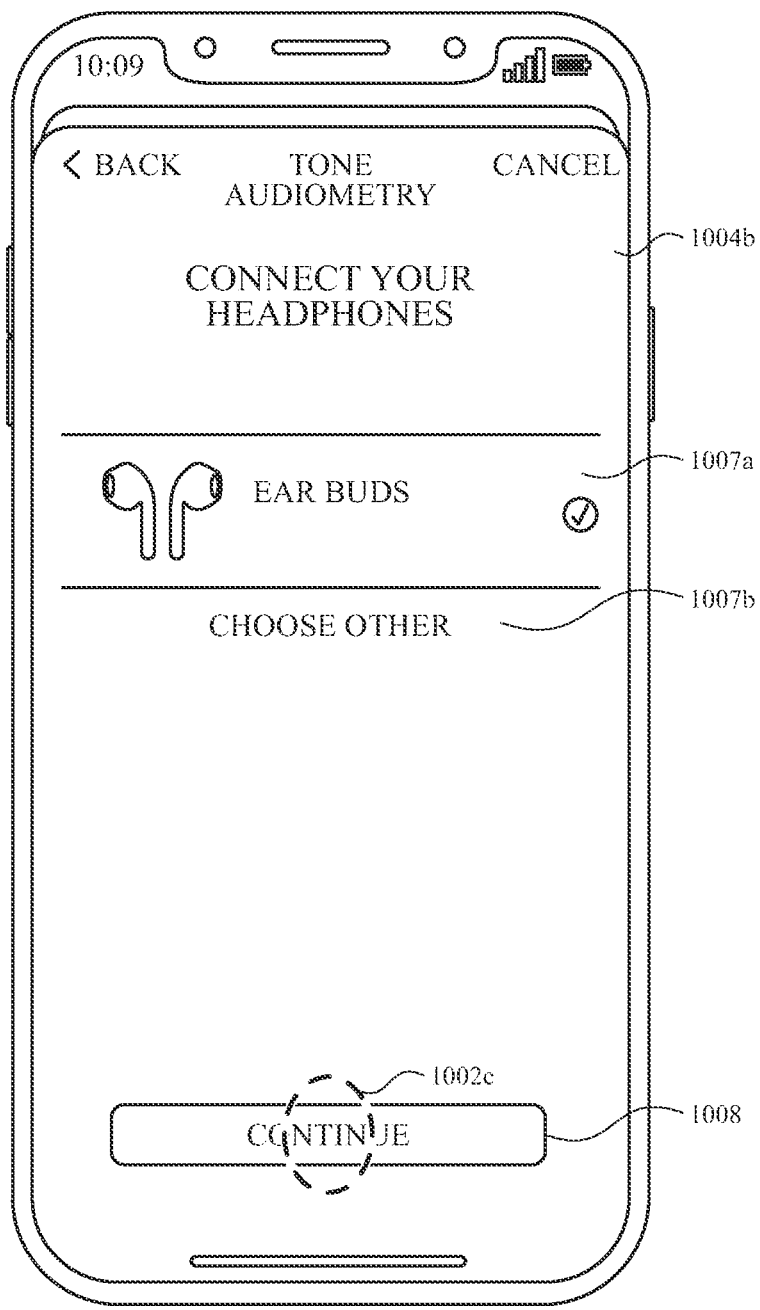

In FIG. 10C, device 600 displays speech and noise test interface 1004*b* that includes section 1007*a* or selecting a set of headphones with which to conduct the test. In some embodiments, when multiple sets of headphones are connected to device 600, section 1007*a* includes multiple options. Interface 1004*b* also includes affordance 1007*b* that, when selected, presents options to choose alternative headphones (e.g., headphones that are not a preferred or recommended headphones; headphones that are not currently connected to device 600 but that have previously been connected to device 600). Device 600 detects, on touch-sensitive display 602, touch input 1002*c*, which is a tap gesture corresponding to continue affordance 1008 and, in response, displays speech and noise test interface 1004*c* in FIG. 10D.

Figure 10D:
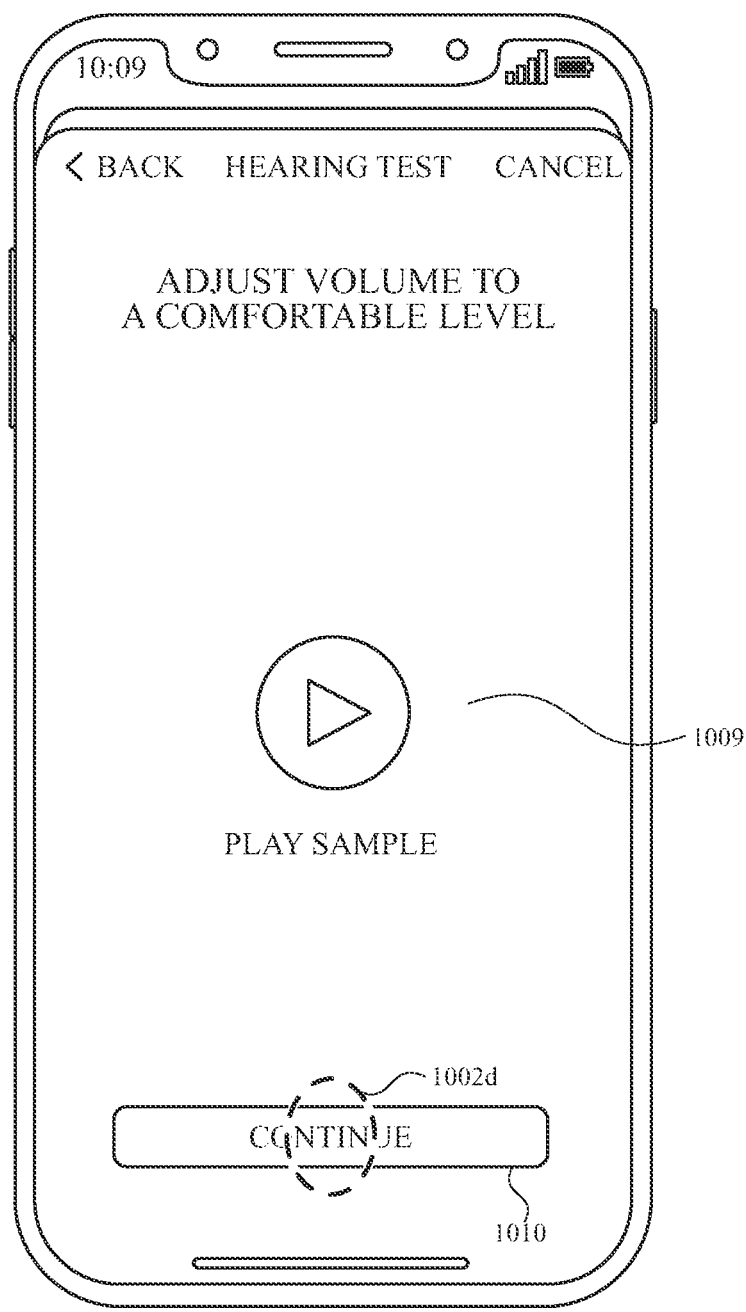

In FIG. 10D, device 600 displays speech and noise test interface 1004*c* that can be used to adjust audio volume for the test. Interface 1004*c* includes affordance 1009 that, when selected, plays an audio sample for calibrating audio output volume for the test. Device 600 detects, on touch-sensitive display 602, touch input 1002*d*, which is a tap gesture corresponding to continue affordance 1010 and, in response, displays speech and noise test interface 1004*d* in FIG. 10E.

Figure 10E:
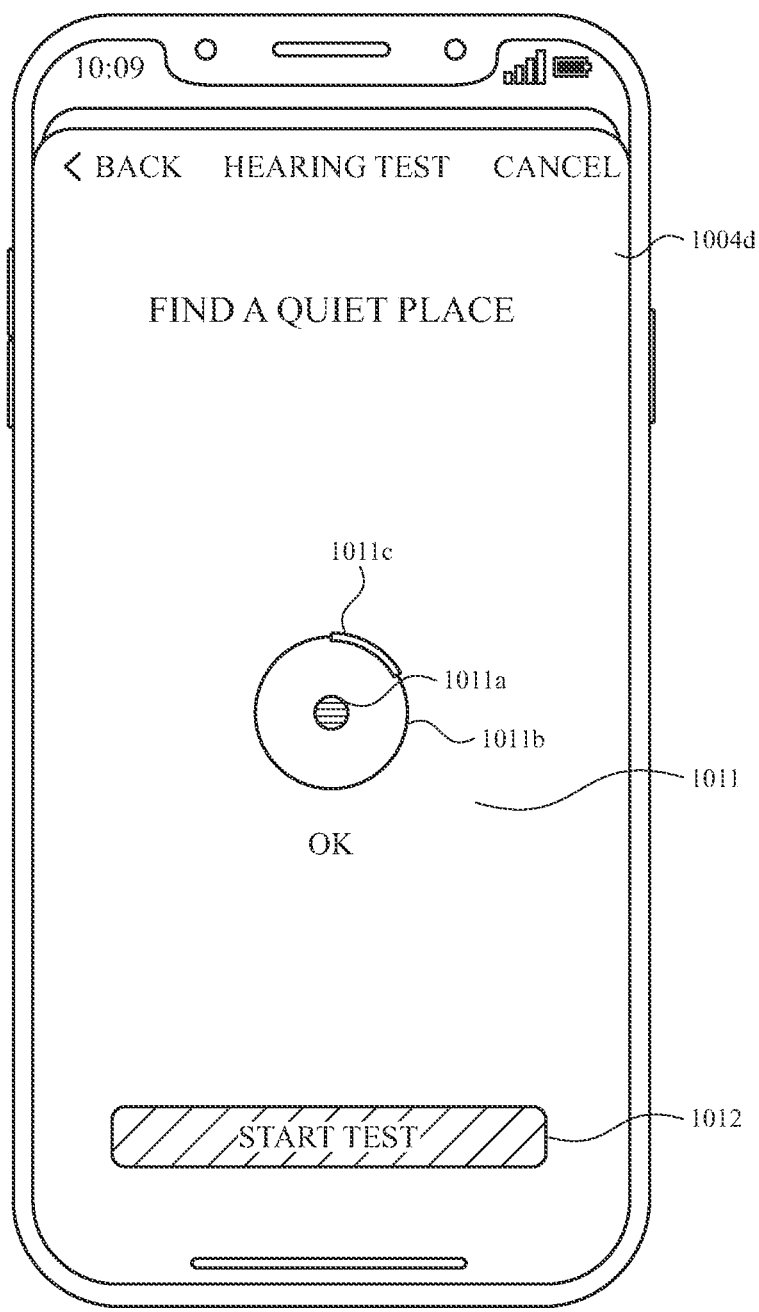

In FIG. 10E, device 600 displays speech and noise test interface 1004*d* which includes an instruction for the user to find a quiet place for the test. Interface 1004*d* includes ambient noise level indication 1011 that visual depicts the current ambient noise level relative to a threshold level that is required to proceed with the test. Indicator 1011 includes a level indicator 1011*a* that grows as the ambient noise level increases. Indicator 1011 also includes a ring portion 1011*b* that depicts the threshold level of noise cannot be exceed (e.g., level indicator 1011*a* cannot grow outside the bounds of the ring portion) if the test is to continue. Indicator 1011 also includes a filled portion 1011*c* that traverses the ring to indicate the time remaining in the ambient noise level check process. The ambient noise level check of interface 1004*d* is complete when the filled portion extends across the entire ring. Interface 1004*d* includes start affordance 1012 that is currently in a disabled state because the ambient noise level check is not complete.

Figure 10F:
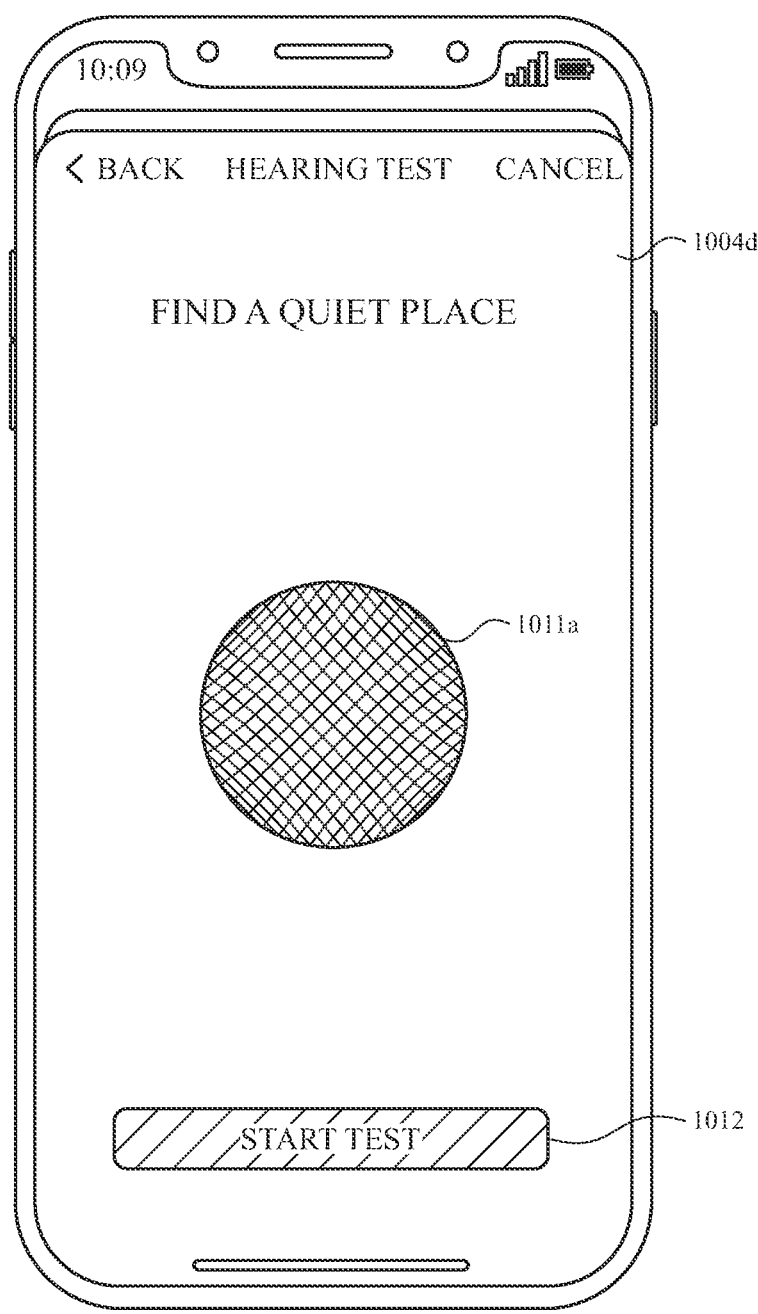

In FIG. 10F, device 600 is displaying interface 1004*d* with noise level indicator 1011*a* reflecting an ambient noise level that exceeds the threshold noise level. In FIG. 10F, noise level indicator 1011*a*, after crossing the threshold level, is displayed with a different color than the color of the indicator in FIG. 10E. In some embodiments, the ambient noise level cannot exceed the threshold level during the entire period of the test (e.g., the test period must be restarted if the threshold is exceeded). In some embodiments, the test pauses if ambient noise level exceeds the threshold, but the check process automatically resumes (e.g., the filled portion continues to fill) once the noise level drops below the threshold. In some embodiments, the ambient noise level must only be below the threshold value by the end of the test period.

Figure 10G:
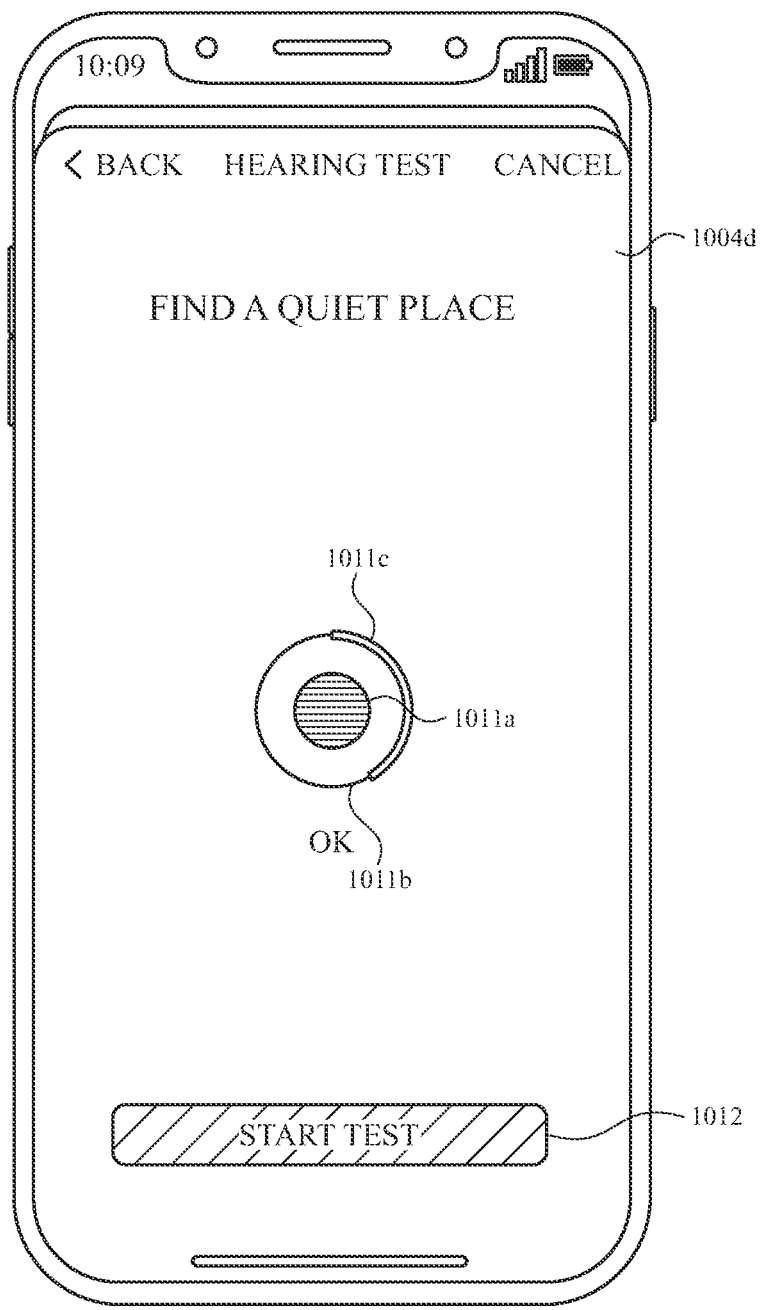

In FIG. 10G, device 600 is displaying interface 1004*d* at a later point in time than shown in FIG. 10F. The ambient noise level has dropped to below the threshold, as indicated by the reduced size of noise level indicator 1011*a*. Filled portion 1011*c* indicates that more than half the time required for the ambient noise level check still remains. Start affordance 1012 remains disabled while the check is ongoing.

Figure 10H:
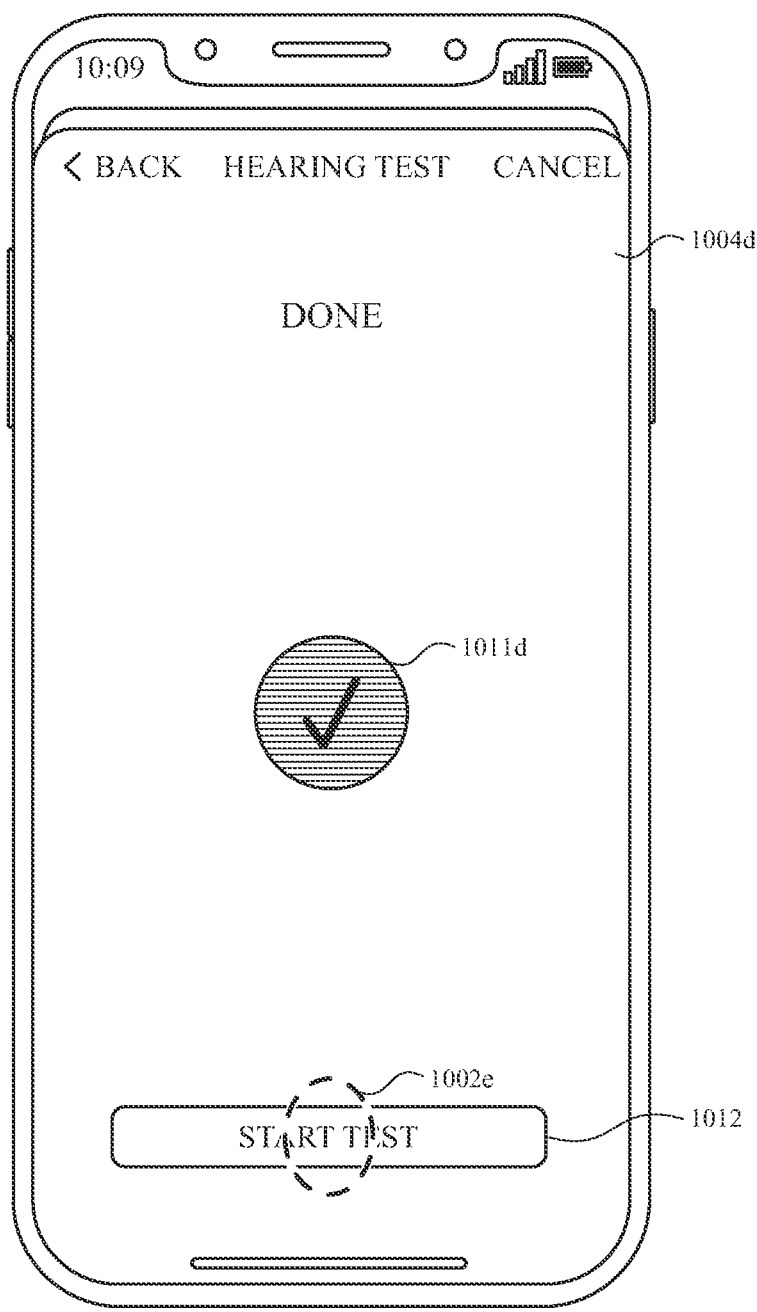

In FIG. 10H, the ambient noise level test has successfully completed, as indicated by indicator 1011 transitioning to state 1011*d*. Start affordance 1012 is now enabled (e.g., as indicated by the no longer being grayed out). Device 600 detects, on touch-sensitive display 602, touch input 1002*e*, which is a tap gesture corresponding to start affordance 1012 and, in response, displays speech and noise test interface 1004*e* in FIG. 10I. In some embodiments, selection of start affordance 1012 initiates a practice test (e.g., a test in which inputs are not used to assess a user's hearing), if device 600 has not previously performed a hearing test.

Figure 10I:
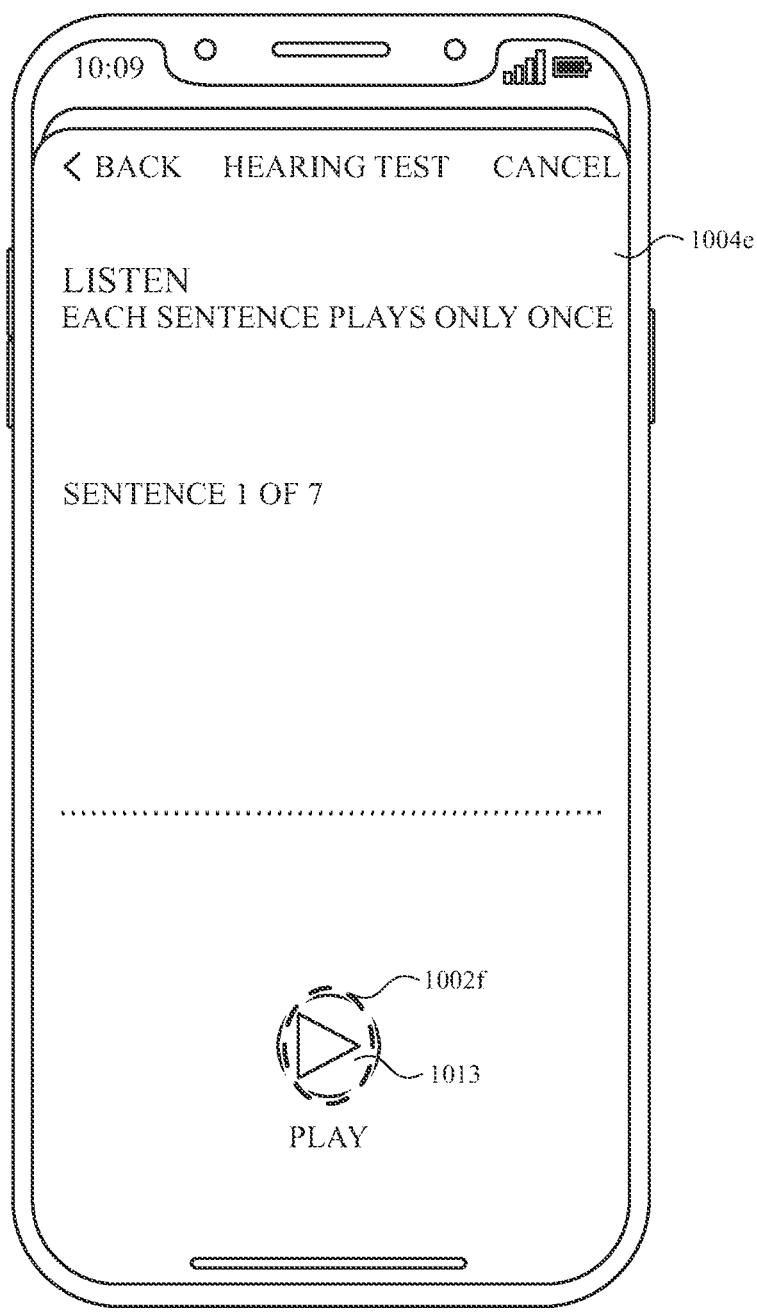

In FIG. 10I, device 600 displays speech and noise test interface 1004*e*. Interface 1004*e* includes instructions for the user to listen to a sentence that will be played once, upon selection of play affordance 1013. Device 600 detects, on touch-sensitive display 602, touch input 1002*f*, which is a tap gesture corresponding to play affordance 1013 and, in response, outputs a spoken sentence (e.g., "this is an example sentence") as shown in FIG. 10J.

Figure 10J:
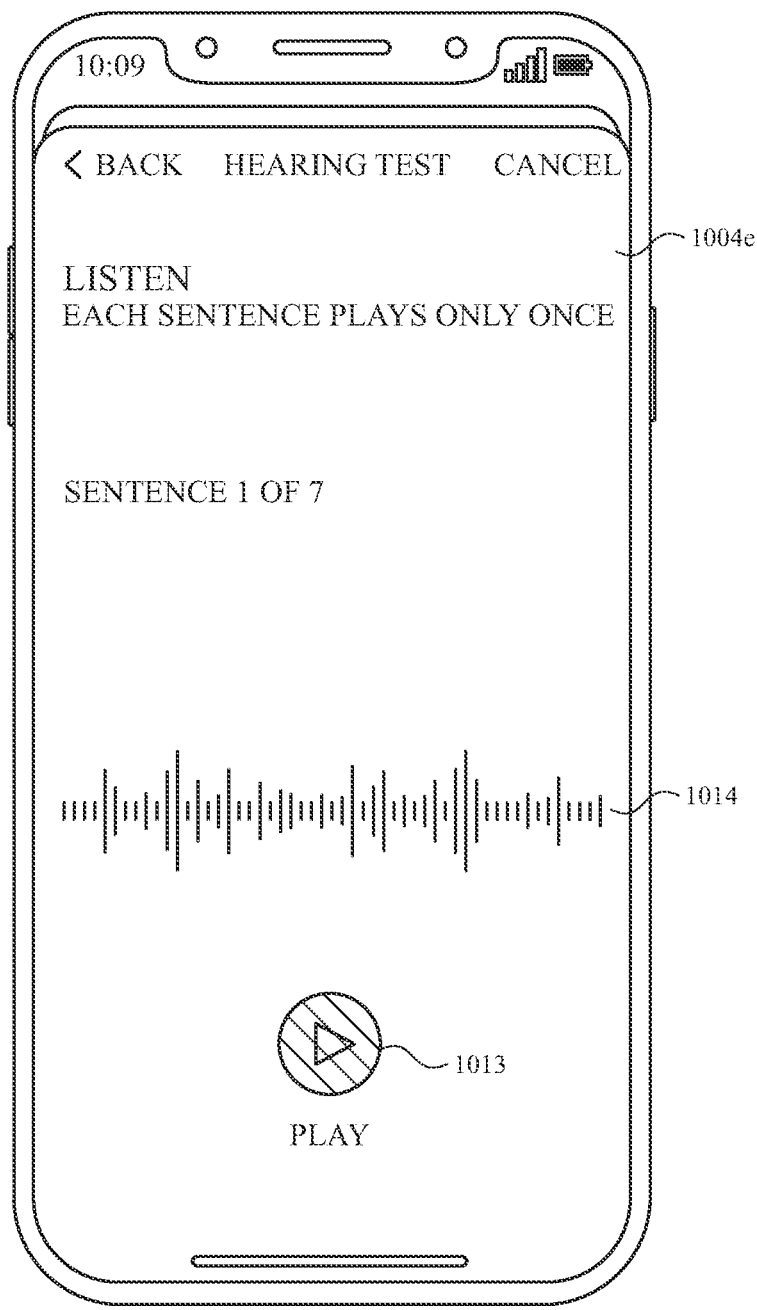

In FIG. 10J, interface 1004*e* displays visual indicator 1014 that provides a graphical representation of the spoken sentence currently being audibly outputted. Play affordance 1013 is disabled during the audio output. Upon completion of playback, device 600 displays speech and noise test interface 1004*f*.

Figure 10K:
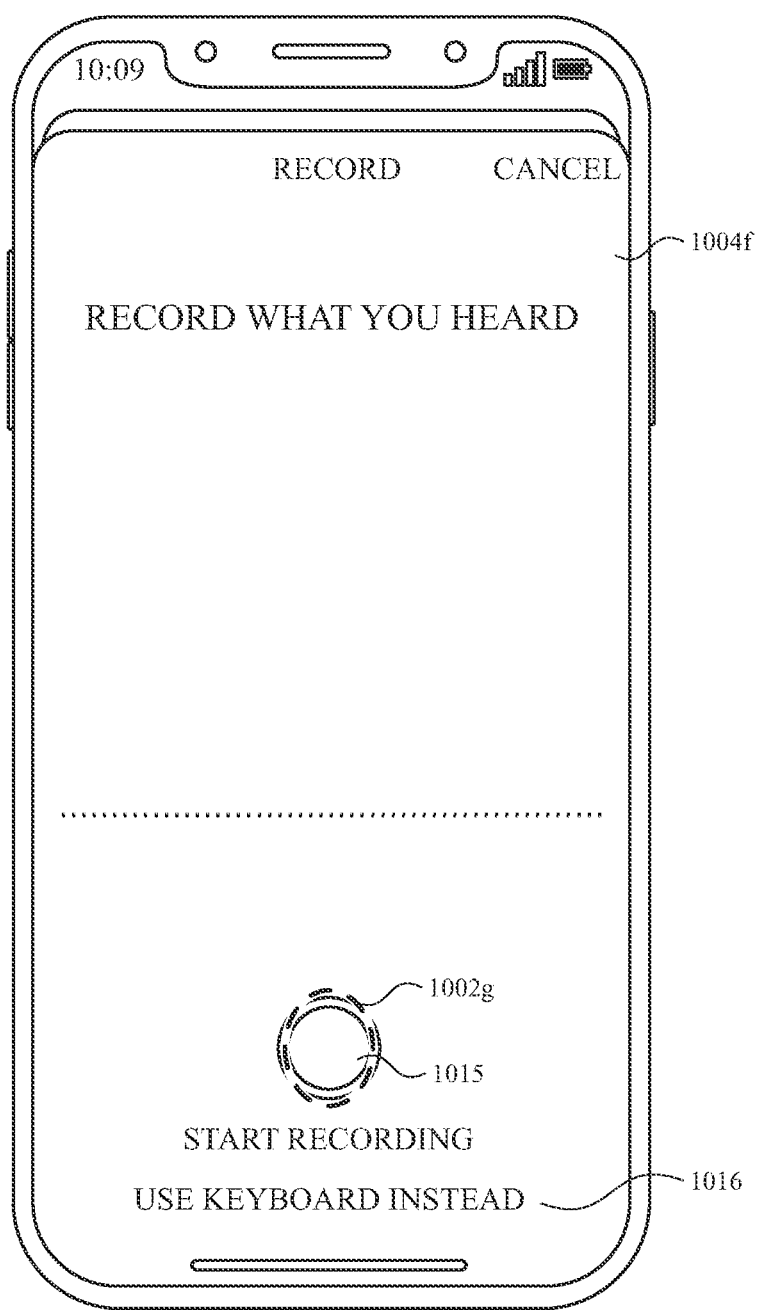

In FIG. 10K, device 600 displays speech and noise test interface 1004*f* that is used to receive an input based on the spoken sentence, as heard by the user of device 600. Interface 1004*f* includes an instruction to record what was heard and a record affordance 1015 for initiating recording via the one or more microphones of device 600. In some embodiments, the one or more microphones is a microphone of an external set of headphones connected to device 600. Interface 1004*f* also includes keyboard affordance 1016 that, when selected causes display of a soft keyboard for inputting text based on the spoken sentence, as heard by the user of device 600. Device 600 detects, on touch-sensitive display 602, touch input 1002*g*, which is a tap gesture corresponding to record affordance 1015 and, in response, starts recording.

Figure 10L:
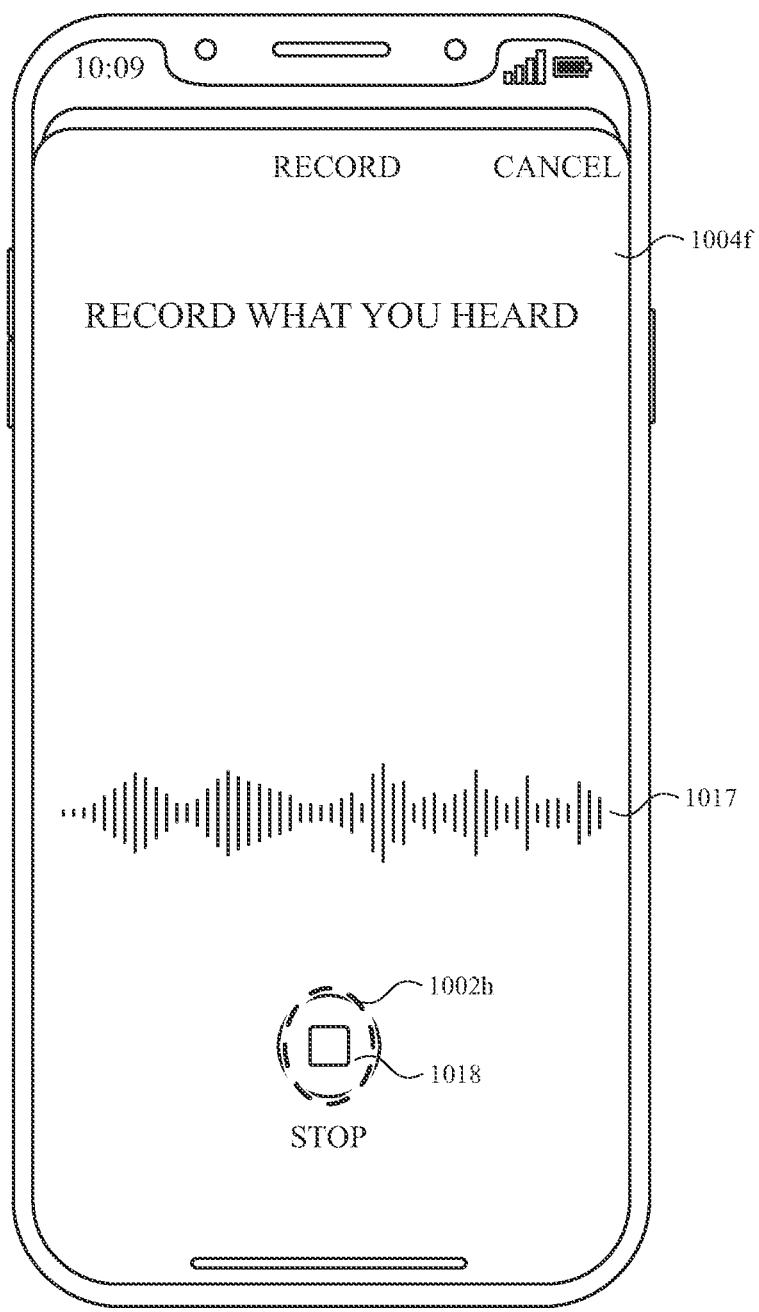

In FIG. 10L, device 600 displays speech and noise test interface 1004*f* with a visual indicator 1017 that provide a graphical indication of the audio input being received via the one or more microphones. In FIG. 10L, interface 1004*f* includes, while recording audio, a stop affordance 1018 for stopping audio recording. Device 600 detects, on touch-sensitive display 602, touch input 1002*h*, which is a tap gesture corresponding to stop affordance 1018 and, in response, stops recording and displays speech and noise test interface 1004*g* of FIG. 10M.

Figure 10M:
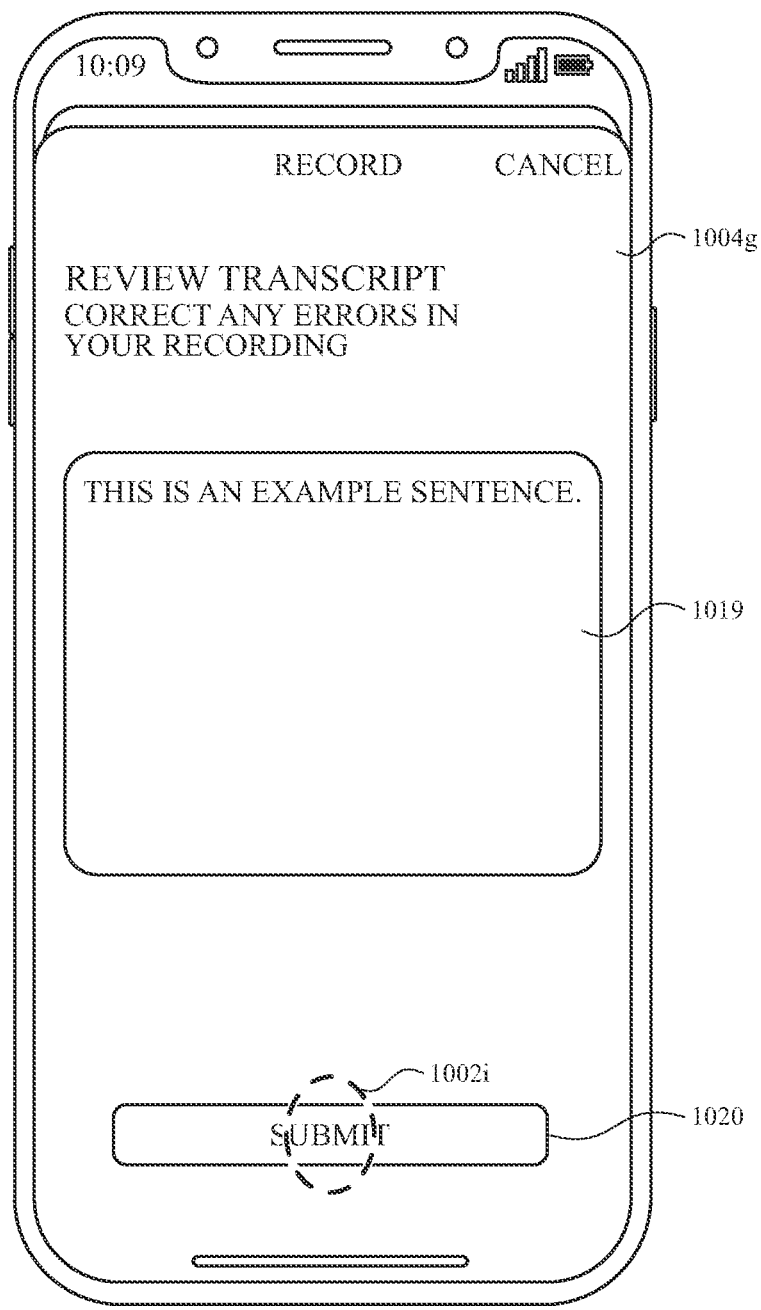

In FIG. 10M, device 600 displays speech and noise test interface 1004*g* that includes section 1019 that displays a speech-to-text indication ("This is an example sentence") of what was recorded. Interface 1004*g* includes instructions to review the text transcript for accuracy. Interface 1004*g* also includes a submit affordance. Device 600 detects, on touch-sensitive display 602, touch input 1002*i*, which is a tap gesture corresponding to submit affordance 1020 and, in response, submits the sentence "This is an example sentence" as an input for use in determining the user's hearing level.

Figure 10N:
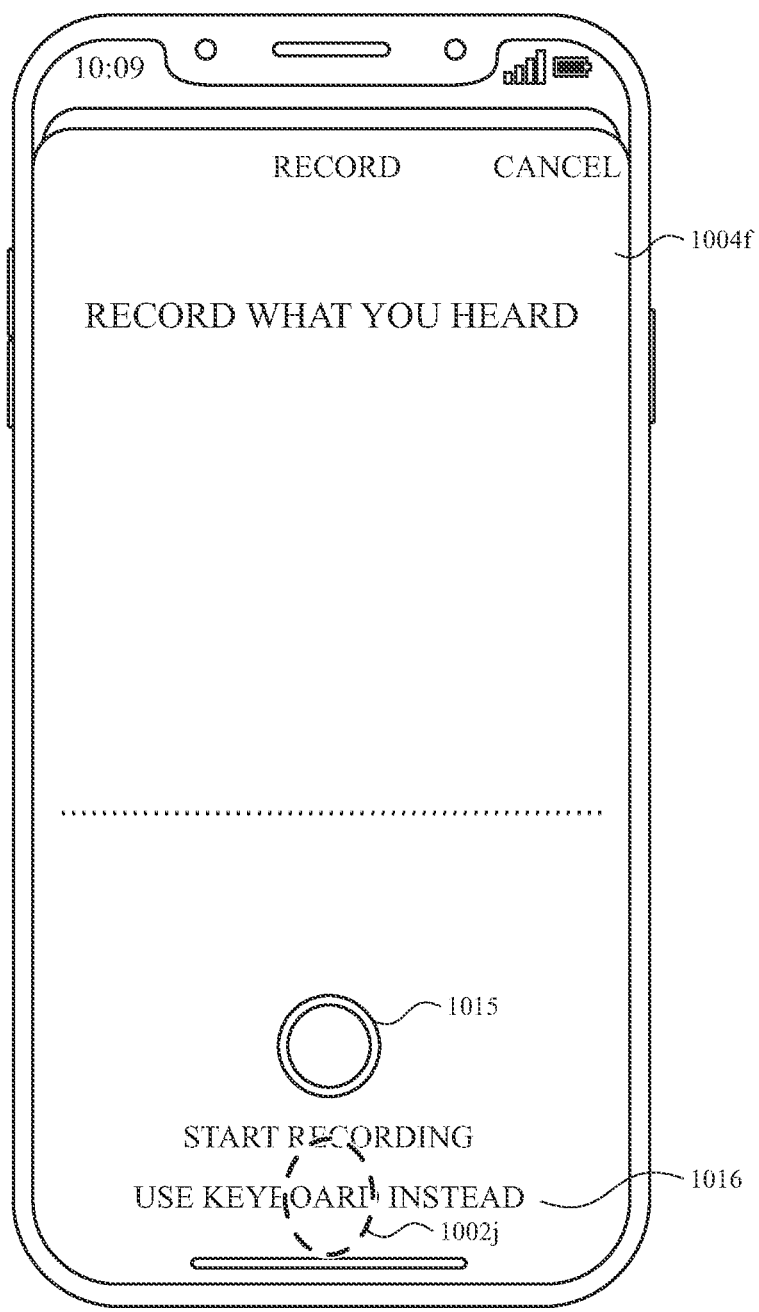

In FIG. 10N, device 600 displays speech and noise test interface 1004f after having audibly outputted a second spoken sentence ("this is another sentence"). Device 600 detects, on touch-sensitive display 602, touch input 1002j, which is a tap gesture corresponding to keyboard affordance 1016 and, in response, causes display of soft keyboard, as seen in FIG. 10O.

Figure 10O:
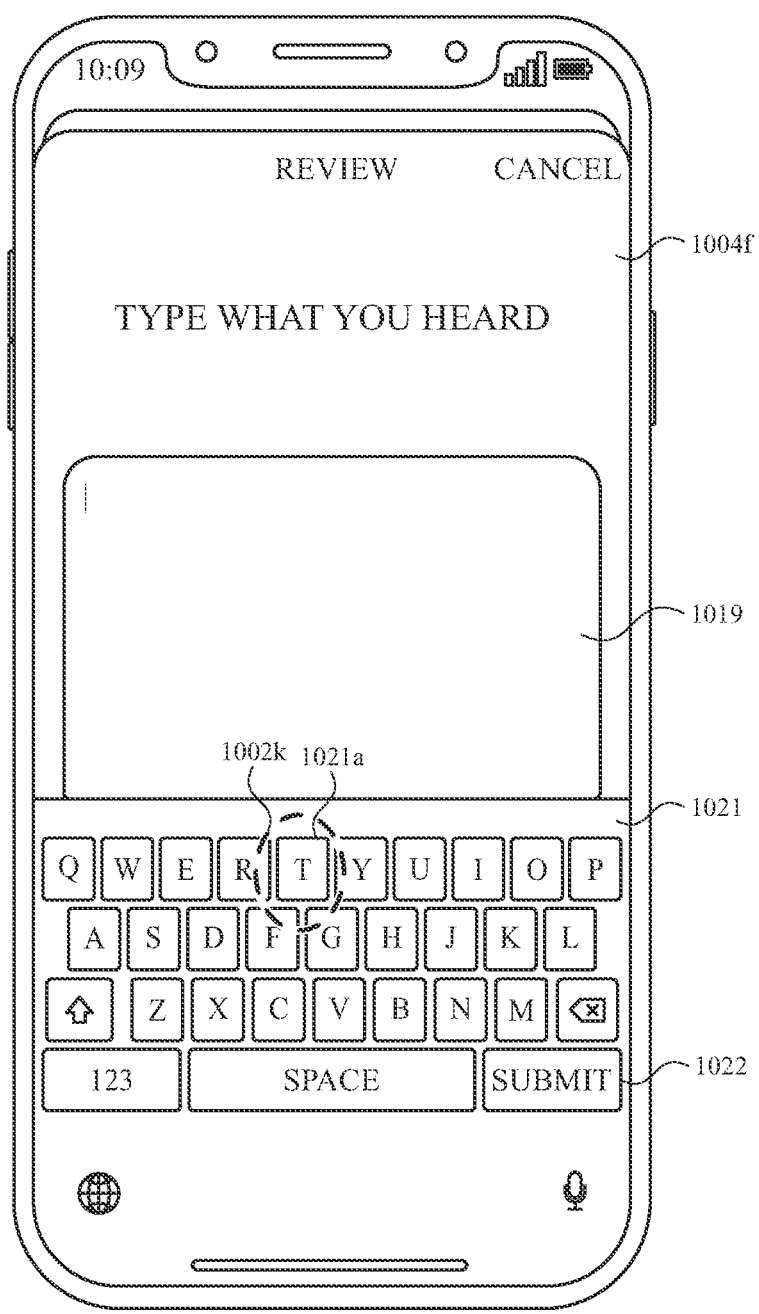

In FIG. 10O, device 600 displays speech and noise test interface 1004f with soft keyboard 1021. Soft keyboard 1021 includes a submit affordance 1022. Device 600 detects, on display 602, touch input 1002i, which is a tap gesture corresponding to "T" key 1021a and, in response begins entering text section 1019.

Figure 10P:
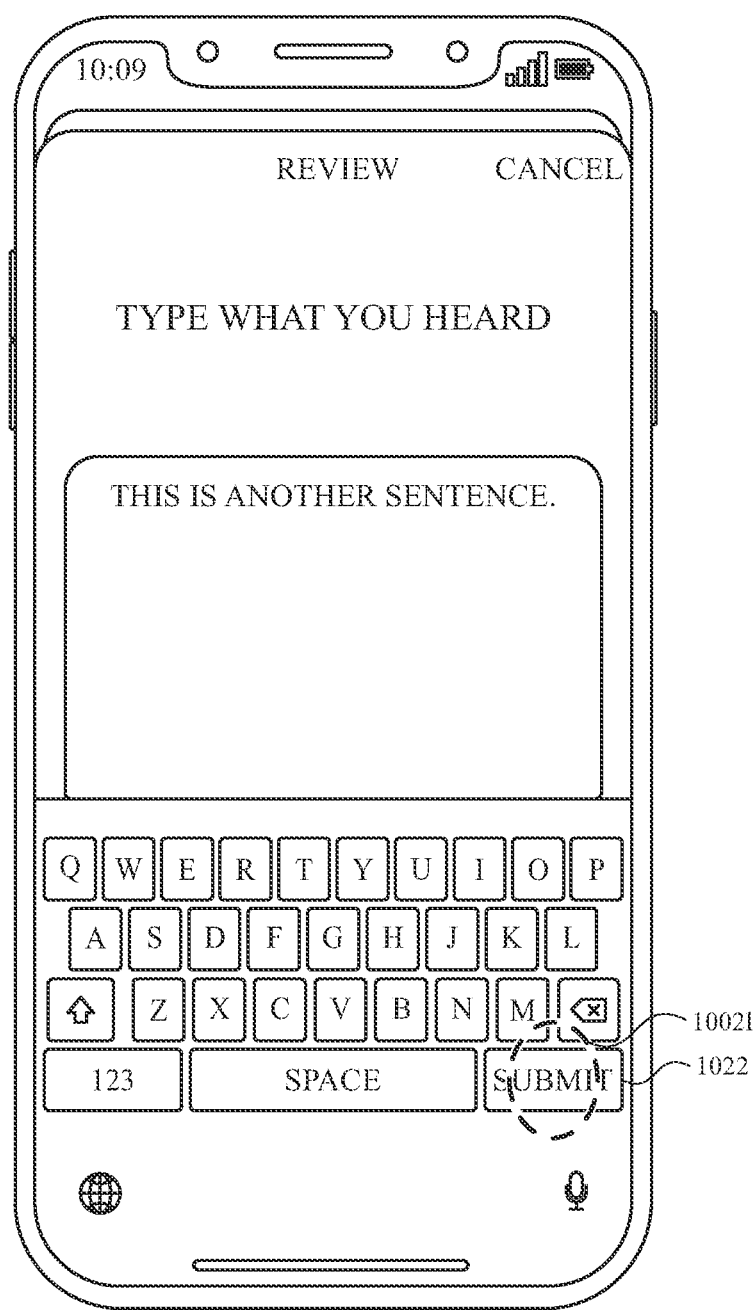

In FIG. 10P, device 600 displays speech and noise test interface 1004g with the typed sentence "This is another sentence" in text section 1019, based on input received via the soft keyboard. Device 600 detects, on touch-sensitive display 602, touch input 1002l, which is a tap gesture corresponding to submit affordance 1022 and, in response, submits the sentence "This is another sentence" as a second input for use in the determining the user's hearing level.

Figure 10Q:
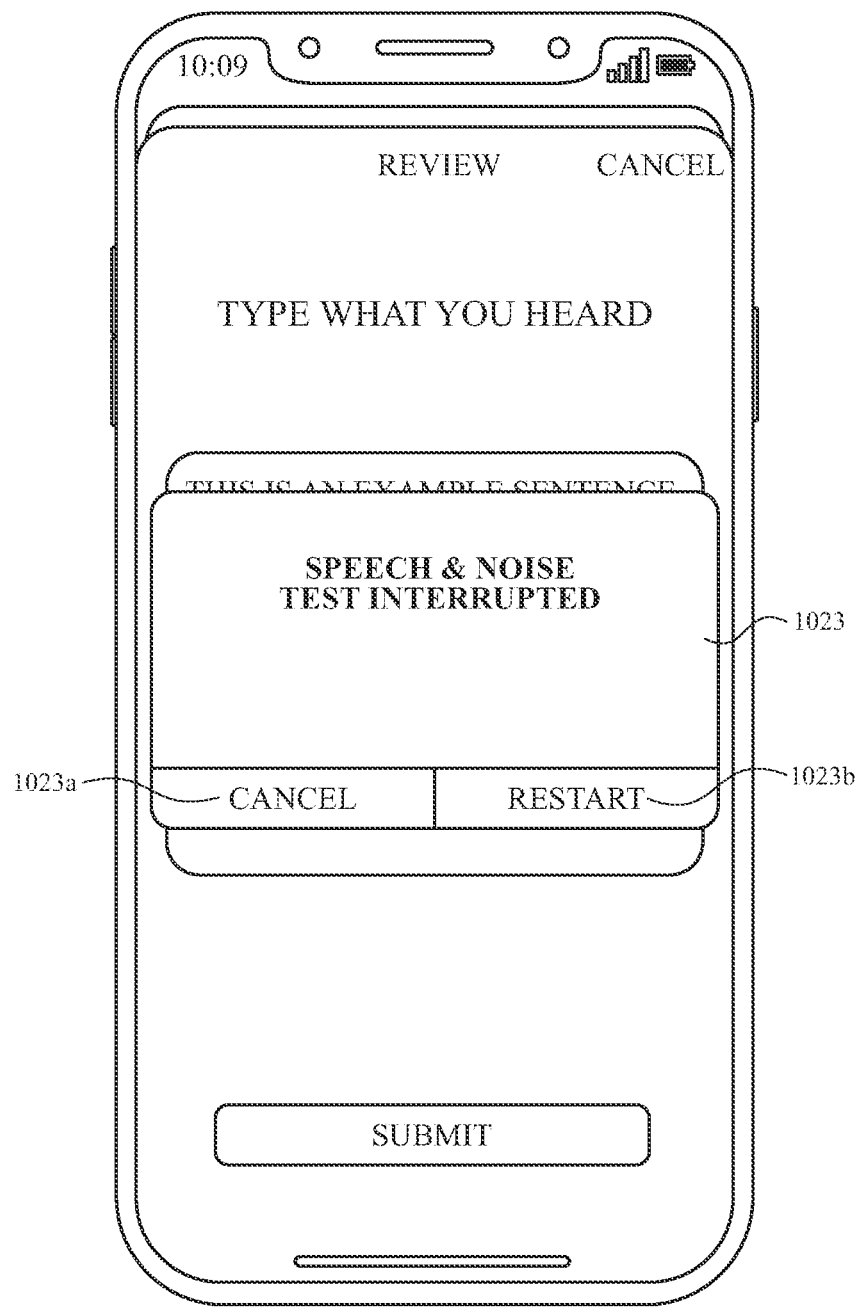

In FIG. 10Q, device 600 detects, while displaying speech and noise test interface 1004g, that the current ambient noise level has risen above a threshold noise level. In some embodiments, device 600 monitors the ambient noise level continuously throughout the performance of the hearing test. In some embodiments, device 600 monitors the ambient noise level periodically during the hearing test (e.g., only during the period during which audio is being outputted or inputted). In response to detecting that the ambient noise level has risen above a threshold noise level, device 600 displays notification 1023 that indicates that the speech and noise hearing test has been interrupted. Notification 1023 includes cancel affordance 1023a that, when selected, cancels the hearing test. Notification 1023 also includes affordance 1023b that, when selected, restarts the hearing test. In some embodiments, the hearing test is restarted from the beginning (e.g., re-initiated). In some embodiments, the hearing test is restarted at the point of interruption (e.g., the test is resumed). In some embodiments, notification 1023 includes an indication of the ambient noise level. In some embodiments, after successfully completing the speech and noise test, device 600 displays results of the test. In some embodiments, notification 1023 is displayed in response to detecting that the headphones being used to administer the test have been disconnected.

Figure 10R:
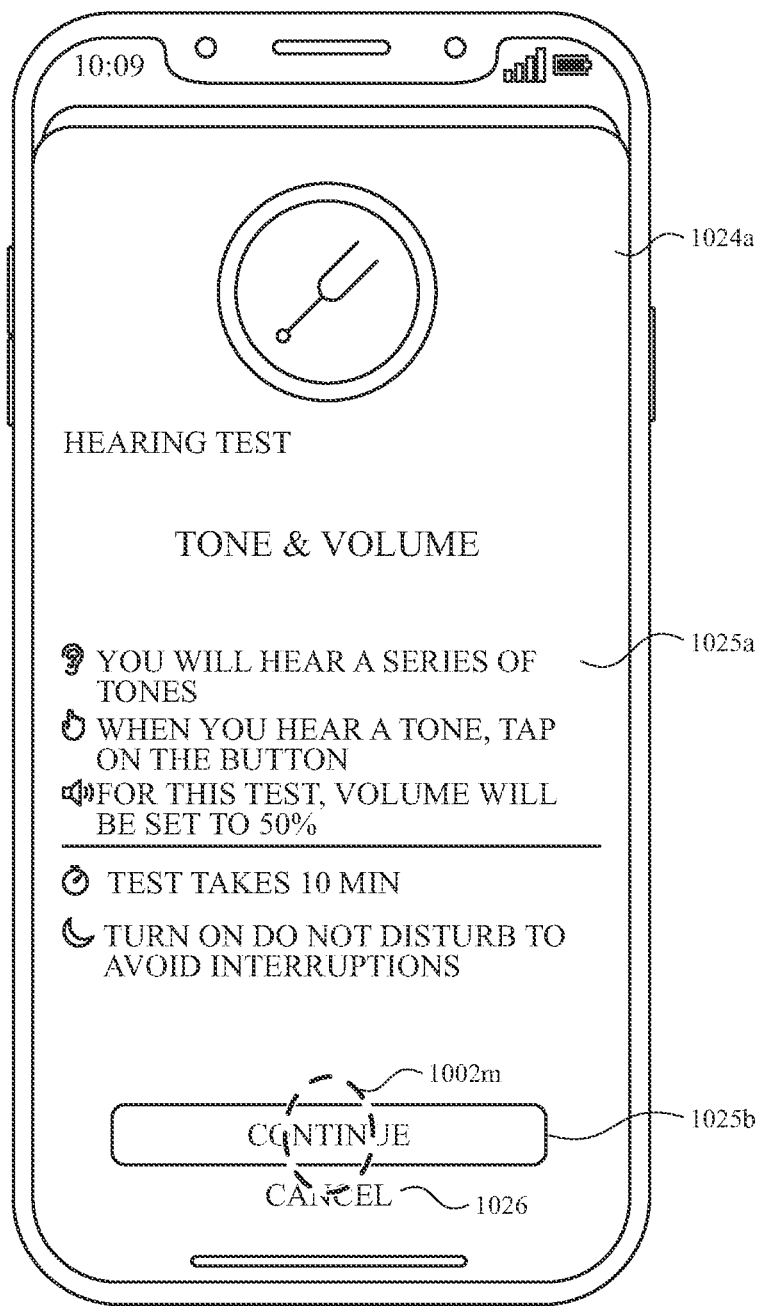

In FIG. 10R, device 600 displays tone and volume test interface 1024a. In some embodiments, the tone and volume test is used to test a different characteristic of a user's hearing than that tested by the speech and noise test. In some embodiments, interface 1024a is displayed in response to selection of task 608e of task view 604a of FIG. 6C. Interface 1024a includes information 1025a about the tone and noise test and affordance 1025b for continuing with the test as well as affordance 1026 for cancelling the test. Device 600 detects, on touch-sensitive display 602, touch input 1002m, which is a tap gesture corresponding to continue affordance 1025 and, in response, displays tone and volume test interface 1024b of FIG. 10S.

Figure 10S:
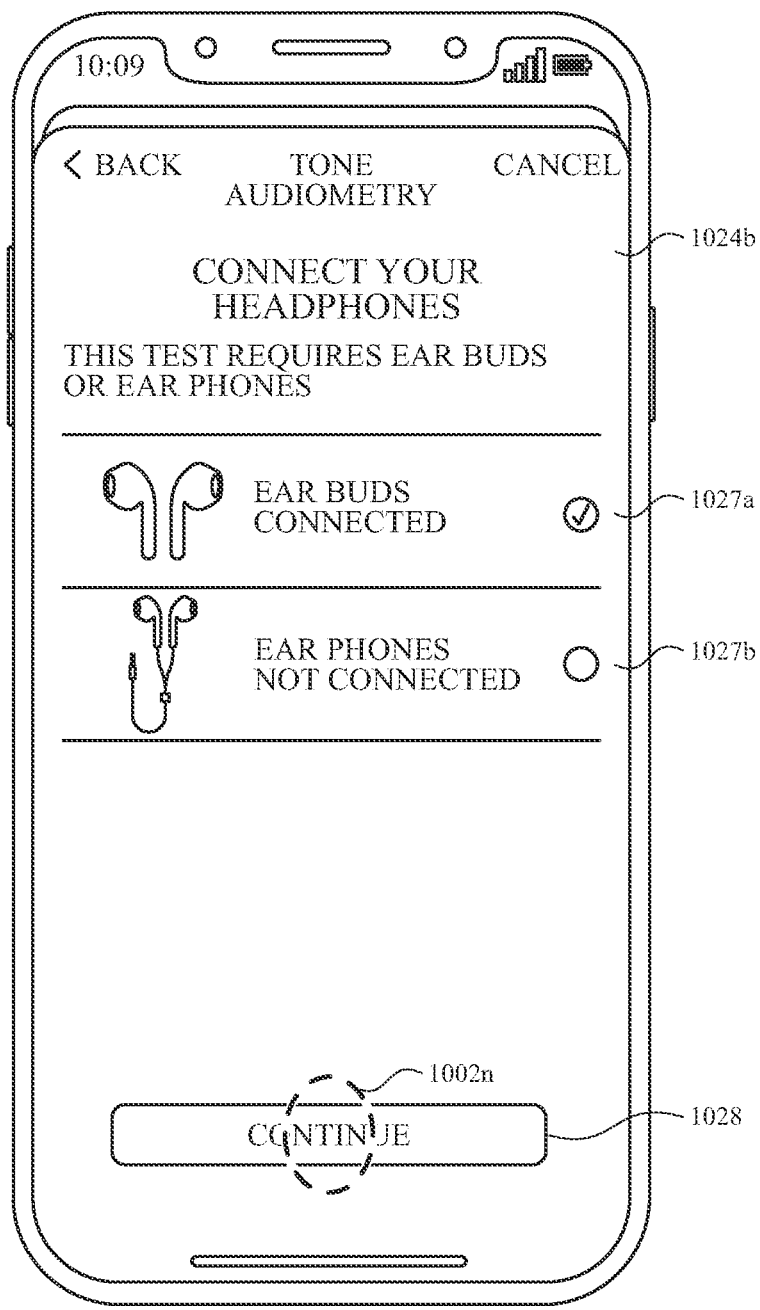

In FIG. 10S, device 600 displays tone and volume test interface 1024b that includes instructions to connect headphones, which are required for the test. Interface 1024b includes first headphone affordance 1027a and second headphone affordance 1027b, for selecting one of two available sets of headphones. Notably, interface 1024b does not a include an affordance for choosing a different set of headphones than those displayed (e.g., an affordance such as affordance 1007b of FIG. 10C) because the tone and volume test of the present embodiment requires headphones of a specific type (e.g., calibrated headphones, headphones from a specific manufacturer that meet certain standards required for testing). Device 600 detects, on touch-sensitive display 602, touch input 1002n, which is a tap gesture corresponding to continue affordance 1028 and, in response, displays tone and volume test interface 1024b of FIG. 10T. In some embodiments, in response to input 1002n, device 600 performs an ambient noise level check, as described above with respect to FIGS. 10E-10H.

Figure 10T:
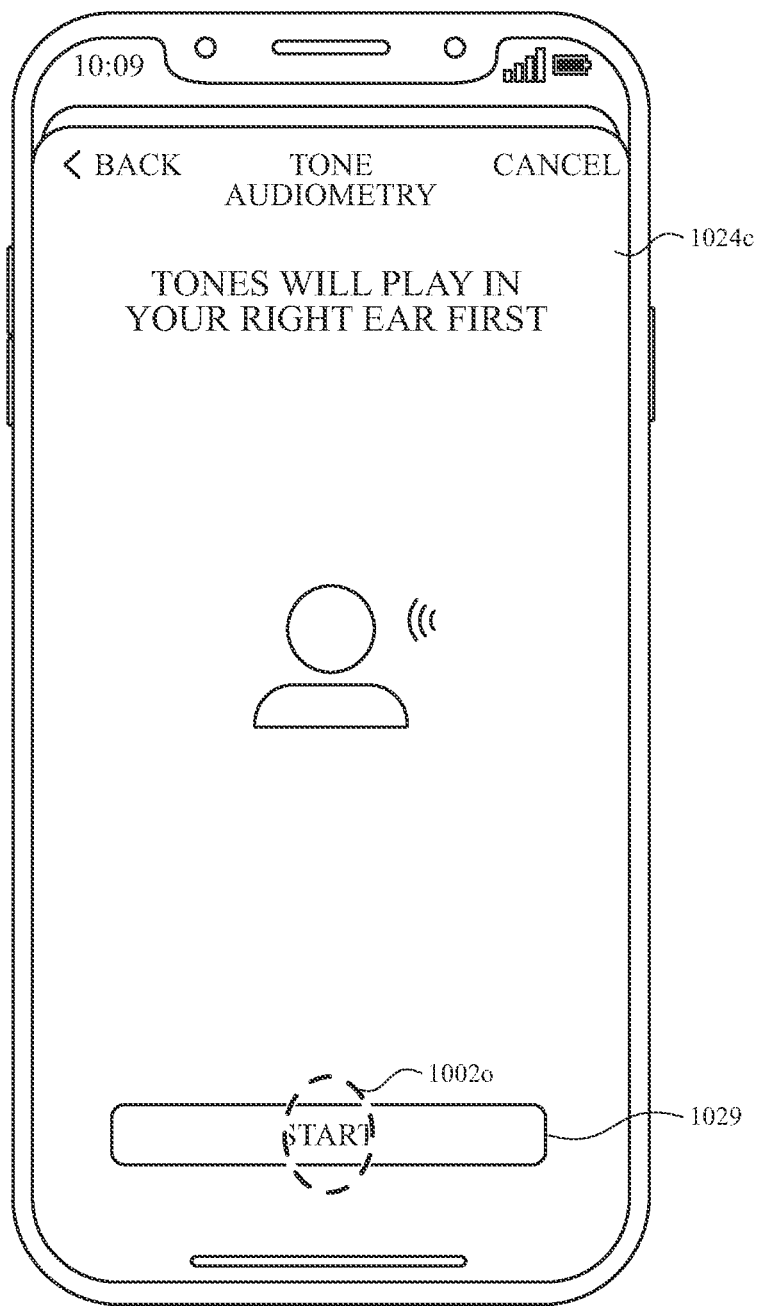

In FIG. 10T, device 600 displays tone and volume test interface 1024c. Interface 1024c includes information about the tone and volume test and includes a start affordance 1029 for initiating the output of tones. Device 600 detects, on touch-sensitive display 602, touch input 1002o, which is a tap gesture corresponding to start affordance 1029 and, in response, initiates a tone playback sequence and displays tone and volume test interface 1024d, as seen in FIG. 10U.

Figure 10U:
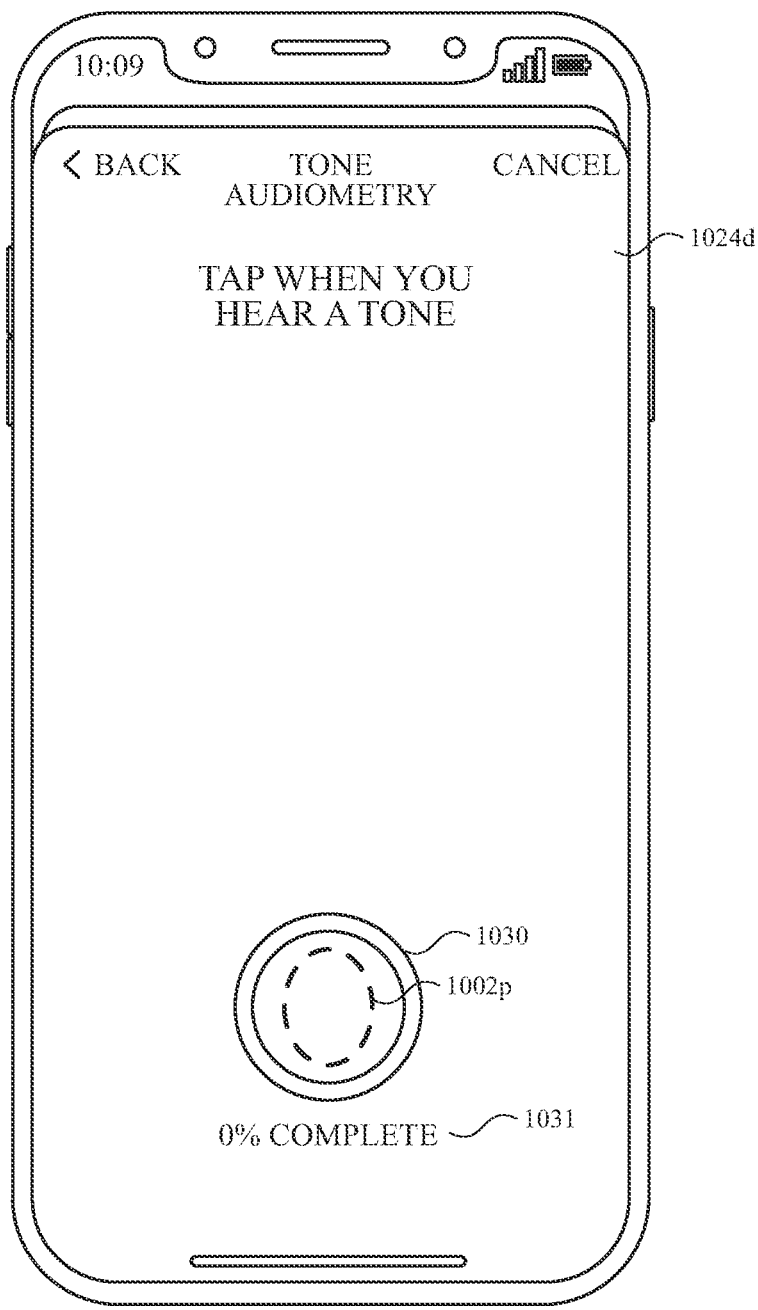

In FIG. 10U, device 600 displays tone and volume test interface 1024d that includes instructions to tap affordance 1030 when a tone is heard. Interface 1024d also includes indication 1031 of the percentage of the tone and volume test that has been completed (e.g., based on the number of tones outputted as a percentage of the total tones to be outputted). While displaying interface 1024d, device 600 outputs and audio tone detects touch input 1002p, which is a tap gesture corresponding to tap affordance 1030. In some embodiments, device 600 assesses the hearing of the user based on whether an input is received within a predetermined period of time after outputting the audio tone and/or based on the timing a received input relative to output of the audio tone.

Figure 10V:
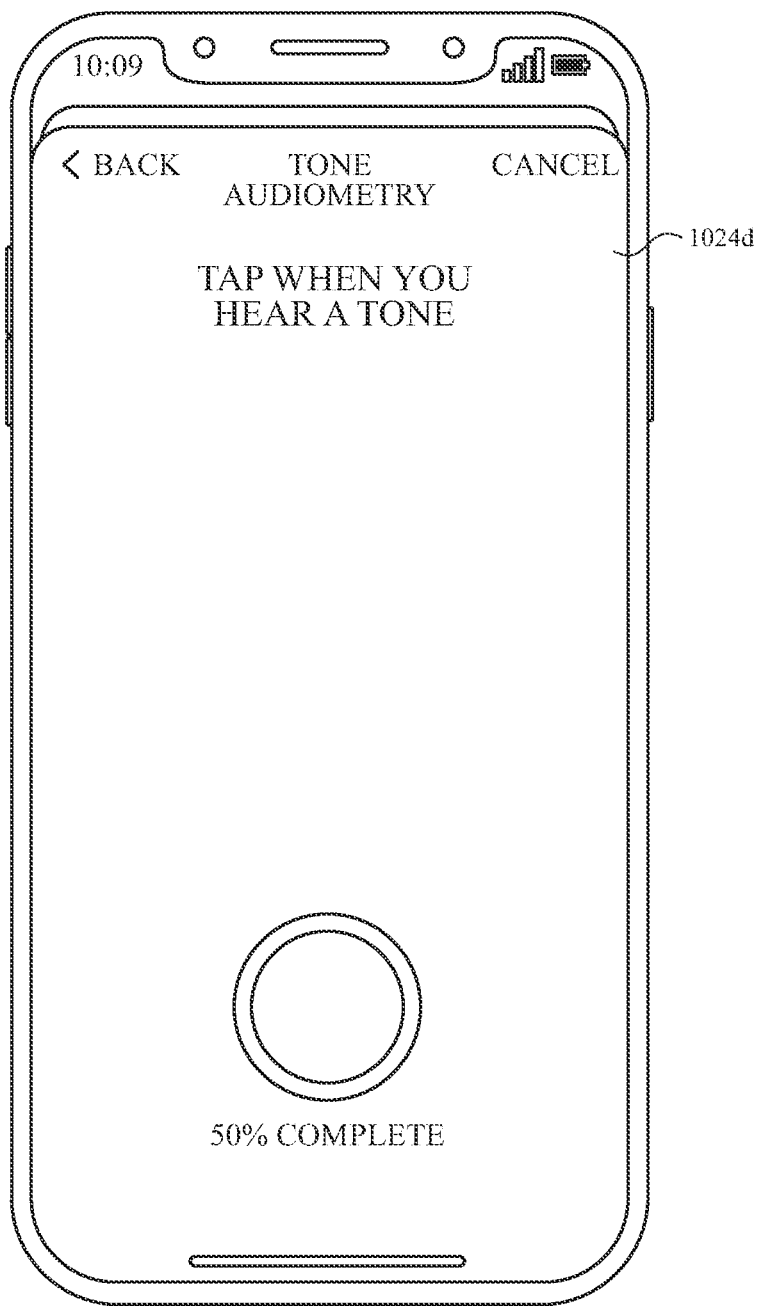

FIG. 10V depicts device 600 displaying tone and volume test interface 1024d at a later point in time, after 50% of the total tones have been outputted, as indicated by indication 1031.

Figure 10W:
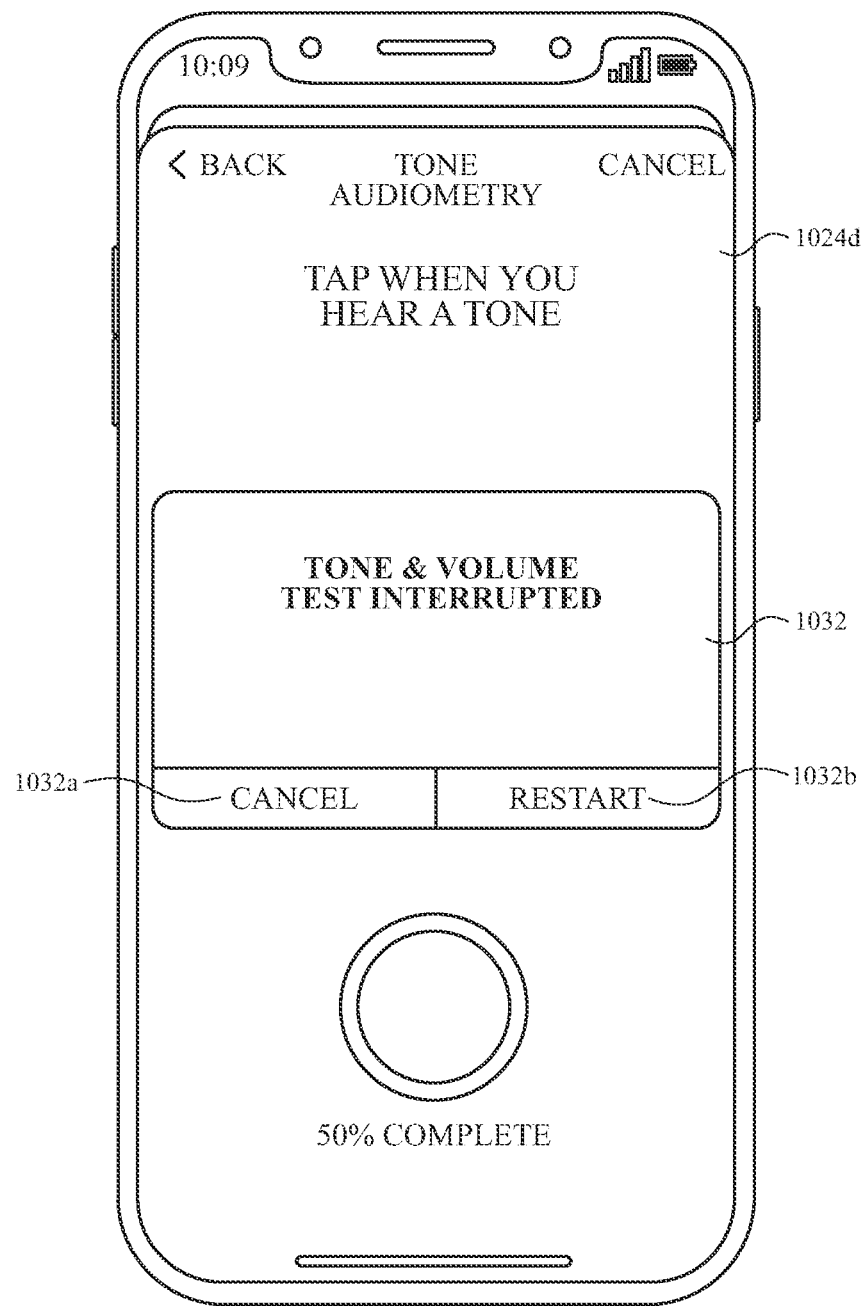

In FIG. 10W, while displaying interface 1024d at the 50% completion mark, device 600 detects that the current ambient noise level has risen above a threshold noise level. In some embodiments, device 600 monitors the ambient noise level continuously throughout the performance of the hearing test. In some embodiments, device 600 monitors the ambient noise level periodically during the hearing test (e.g., only during the period during which audio is being outputted). In response to detecting that the ambient noise level has risen above a threshold noise level, device 600 displays notification 1032 that indicates that the tone and volume hearing test has been interrupted. Notification 1032 includes cancel affordance 1032a that, when selected, cancels the hearing test. Notification 1032 also includes affordance 1032b that, when selected, restarts the hearing test. In some embodiments, the hearing test is restarted from the beginning (e.g., re-initiated). In some embodiments, the hearing test is restarted at the point of interruption (e.g., the test is resumed). In some embodiments, notification 1032 includes an indication of the ambient noise level.

FIG. 10X depicts device 600 displaying tone and volume test interface 1024e that indicates that the tone and volume test has been completed. Interface 1024e includes done affordance 1033 that, when selected, causes re-display of task view 604a.

FIG. 11 is a flow diagram illustrating a method for interacting with hearing tests using an electronic device in accordance with some embodiments. Method 1100 is performed at a device (e.g., 100, 300, 500, 600) with a display device (e.g., 602), one or more input devices (e.g., 602), and one or more microphones. Some operations in method 1100 are, optionally, combined, the orders of some operations are, optionally, changed, and some operations are, optionally, omitted.

As described below, method 1100 provides an intuitive way for interacting with hearing tests. The method reduces the cognitive burden on a user for interacting with hearing tests, thereby creating a more efficient human-machine interface. For battery-operated computing devices, enabling a user to interact with research studies faster and more efficiently conserves power and increases the time between battery charges.

The electronic device (e.g., 600) displays (1102), via the display device, a hearing test user interface (e.g., 1004*d*) (e.g., an interface generated by a research application; an interface displaying information associated with a hearing examination ((e.g., instructions for performing the hearing examination)) that is associated with a hearing test (e.g., a procedure for assessing one or more attributes of hearing of a user of the electronic device; a procedure that includes outputting a set of one or more audio outputs and receiving a set of one or more user inputs and, assessing, based on one or more characteristics (e.g., content, timing) of the set of one or more user inputs, the one or more attributes of the user's hearing).

The electronic device, while displaying the hearing test user interface, receives (1104), via the one or more input devices, a set of one or more inputs (e.g., 1002*e*) corresponding to a request to initiate the hearing test.

The electronic device, in response to receiving the set of one or more inputs, initiates (1106) the hearing test.

In some embodiments, initiating the hearing test includes: causing output of an audio representation (e.g., represented by 1014) of a first set of one or more words (e.g., pre-recorded human speech or synthesized human speech); detecting, via the one or more input devices or via the one or more microphones, input of a second set of one or more words (e.g., represented by 1017) (e.g., detecting speech or detecting text entry (e.g., via one or more keyboards)); and displaying, via the display device, a representation of the second set of one or more words (e.g., 1019) (e.g., a text transcript of the second set of one or more words). In some embodiments, after displaying the representation of the second set of one or more words, detecting input corresponding to confirmation of the second set of one or more words or detecting a second set of one or more inputs that correspond to revision of the second set of one or more words and using the second set of one or more words or the revised second set of one or more words as data for assessing the user's hearing. Displaying a representation of the set of one or more words inputted by the user for the hearing test provides improved visual feedback as to what was detected by the device (e.g., via input devices of the device (e.g., a microphone and/or keyboard). Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first set of one or more words is a sentence (e.g., represented by 1014) (e.g., a plurality of words that includes at least a subject and predicate and conveys a complete concept) (e.g., a sentence outputted as pre-record human speech or a sentence outputted as synthesized speech).

In some embodiments, the input of the second set of one or more is an audio input (e.g., an utterance) detected via the one or microphones (e.g., input represented by 1017) (In some embodiments, the input is processed using one or more speech-to-text algorithms).

In some embodiments, the input of the second set of one or more is text input detected via the one or input devices (e.g., 1002*k*) (e.g., one or more keyboards).

In some embodiments, after displaying the representation of the second set of one or more words, the electronic device detects a third set of one or more inputs (e.g., 1002*i*); in response detecting the third set of one or more inputs: in accordance with the third set of one or more inputs corresponding to a request to submit the second set of one or more words as a valid input for the hearing test (e.g., submit the second set of one or more words as input for assessing the user's hearing), submits the second set of one or more words; and in accordance with the third set of one or more inputs corresponding to a request to revise the second set of one or more words, initiates a process to revise the second set of one or more words (e.g., without submitting the second set of one or more words).

In some embodiments, initiating the hearing test includes: displaying a response affordance (e.g., 1030) that, when selected, logs a response input for use in the hearing test; causing output of a first audio output (e.g., a first audio tone; an output having consistent audio properties for its duration) having a first value of a first audio characteristic (e.g., a first tone played while displaying 1024*d*) (e.g., an intensity (e.g., in decibels) or a frequency (e.g., in hertz) of the ambient noise); and monitoring, for a first period of time after causing output of the first audio output, for input corresponding to selection of the response affordance, including: in accordance with a determination that an input corresponding to selection of the response affordance occurs within the first period of time, logging a response to the first audio output; and in accordance with a determination that an input corresponding to selection of the response affordance does not occur within the first period of time, forgo logging a response to the first audio output; and causing output of a second audio output (e.g., a second audio tone; an output having consistent audio properties for its duration) having a second value of the first audio characteristic that is different from the first value of the first audio characteristic; and monitoring, for a second period of time (e.g., the same as or different from the first period of time) after causing output of the second audio output, for input corresponding to selection of the response affordance, including: in accordance with a determination that an input corresponding to selection of the response affordance occurs within the second period of time, logging a response to the second audio output; and in accordance with a determination that an input corresponding to selection of the response affordance does not occur within the second period of time, forgo logging a response to the second audio output (e.g., forgo logging any response; logging an indication that no response was received in the second period of time). In some embodiments, the absence and/or presence of logged responses to the audio outputs are used to assess the user's hearing.

In some embodiments, during the hearing test, the electronic device displays, via the display device, an indication of progress of the hearing test towards completion (e.g., 1031) (e.g., a percentage value based on the amount of issued tones compared to the total tones of the test). Displaying a graphical indication of progress of the hearing test provides the user with feedback as to the status of the hearing test. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, prior to causing output of a first audio output, the electronic device displays, via the display device, a prompt (1004*d*) to find a location with a low level of ambient noise (e.g., "find a quiet place").

In some embodiments, prior to causing output of a first audio output, the electronic device displays, via the display device, a prompt (e.g., 1024*c*) to provide an input corresponding to the response affordance after hearing the first audio output. In some embodiments, the first audio output is output via external headphones and the prompt to provide an input includes an indication of which ear the first audio output will be outputted at.

In some embodiments, the electronic device, during the hearing test (e.g., after outputting the first audio output but before outputting the second audio output): in accordance with a determination that a first set of test interruption criteria (In some embodiments, the first set of test interruption criteria includes one or more criterion selected from an ambient level of noise that exceeds a threshold value; a communication event (e.g., an incoming phone call), a suspension of the hearing test application, and disconnection of a set of connected speakers (e.g., headphones)) are met, suspends (e.g., pausing; cancelling) the hearing test and displays, via the display device, a re-initiation affordance (e.g., 1023*b*) that, when selected, re-initializes the hearing test (e.g., restarts the hearing test from the beginning and discards any data from the suspended test); in accordance with a determination that the first set of test interruption criteria are not met, forgoes suspending the hearing test and forgoes displaying the re-initiation affordance. Displaying a re-initiation affordance for the hearing test, in conjunction with suspending the hearing test, based a set of criteria being met provides the user with improved feedback as to the state of the device and assists in reducing errors in performance of the hearing test. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The electronic device, during the hearing test (e.g., after outputting at least one audio output as part of administering the hearing examination and receiving at least one user input after outputting the at least one audio output that is identified (e.g., classified) as being responsive to the at least one audio output)), detects (1108), via the one or more microphones, an ambient noise level (e.g., see FIG. 10Q) (e.g., the noise level in the present environment) (In some embodiments, the ambient noise level excludes noise determined to be noise that is generated by a user of the electronic device) (In some embodiments, the ambient noise level is determined based on a single measurement; in some embodiments, the ambient noise level is determined based on a plurality of measurements (e.g., an average of a set of measurements taken over a period of time)) that includes an audio characteristic (e.g., an intensity (e.g., in decibels) or a frequency (e.g., in hertz) of the ambient noise).

In some embodiments, the electronic device, during the hearing test, detects the disconnection of a first set of one or more external speakers (e.g., see FIG. 10Q) (e.g., wired or wireless headphones) connected to the electronic device; and in response to detecting the disconnection of the first set of one or more external speakers, suspends (e.g., pausing; cancelling) the hearing test (and, in some embodiments, displaying, via the display device, a restart affordance).

In response to detecting the ambient noise level (1110), the electronic device, in accordance with a determination that the audio characteristic of the ambient noise level exceeds a first threshold value, suspends (1112) (e.g., pausing; cancelling) the hearing test and displays, via the display device, a restart affordance (e.g., 1023*b*) that, when selected, restarts (e.g., resumes or restarts from the beginning) the hearing test.

In some embodiments, the restart affordance, when selected, re-initializes the hearing test (e.g., restarts the hearing test from the beginning and discards any data from the suspended teste. In some embodiments, in accordance with determination that the audio characteristic of the ambient noise level exceeds a first threshold value, the hearing test cannot be resumed and can only be restarted or cancelled entirely.

In response to detecting the ambient noise level (1110), the electronic device, in accordance with a determination that the audio characteristic of the ambient noise level does not exceed the first threshold value, proceeds (1114) (e.g., forgo suspending of the hearing examination) with the hearing test (e.g., outputting further audio outputs as part of administering the hearing examination) and forgoes display of the restart affordance (e.g., 1023*b*). Displaying a restart affordance for the hearing test, in conjunction with suspending the hearing test, based on an ambient noise level provides the user with improved feedback as to the current ambient noise level and assists in reducing errors in performance of the hearing test. Providing improved feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the electronic device, prior to initiating the hearing test (e.g., prior to receiving data (e.g., inputs) that are used to assess the user's hearing) and in response to the set of one or more inputs, performs an initial ambient noise level assessment (e.g., see FIGS. 10E to 10H) that includes detecting, via the one or more microphones, an initial ambient noise level (In some embodiments, the initial ambient noise level is determined based on a single measurement; in some embodiments, the initial ambient noise level is determined based on a plurality of measurements (e.g., an average of a set of measurements taken over a period of time)) that includes a second audio characteristic (e.g., an intensity (e.g., in decibels) or a frequency (e.g., in hertz) of the ambient noise); and in accordance with a determination that the second audio characteristic of the ambient noise level exceeds a second threshold value (e.g., a threshold value that is the same as the first threshold value; a threshold value that is different than the first threshold value), forgoes initiating the hearing test (e.g., forgo initiating until an initial ambient noise level assessment is completed). In some embodiments, in accordance with a determination that the second audio characteristic of the ambient noise level does not exceed a second threshold value, initiating the hearing test.

In some embodiments, performing the initial ambient noise level assessment includes displaying, via the display device, a graphical indication of a current value of the detected initial ambient noise level (e.g., 1011*a*) (e.g., displaying a ring with a visual indication of the ring being filled by the current ambient noise level with the full ring being filled when the ambient noise level reaching the second threshold value). Displaying a graphical indication of the current ambient noise level provides visual feedback as to noise being detected by the microphones. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, performing the initial ambient noise level assessment includes displaying, via the display device, an indication (e.g., 1011*c*) of the time remaining until completion of the initial ambient noise level assessment (e.g., a graphical or alphanumeric indication). Displaying a graphical indication of the time remaining provides the user with feedback as to when the hearing test will proceed. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, prior to initiating the hearing test (e.g., prior to receiving data (e.g., inputs) that are used to assess the user's hearing) and in response to the set of one or more inputs, the electronic device displays, via the display device, a prompt (e.g., 1004*b*) to connect a second set of one or more external speakers (e.g., wired or wireless headphones). In some embodiments, after displaying the prompt to connect the second set of one or more external speakers and in accordance with a determination that the second set of one or more external speakers are not connected, forgo initiating the hearing test (e.g., forgo initiating until connection of the second set of one or more external speakers is detected).

In some embodiments, after displaying the prompt to connect the second set of one or more external speakers, the electronic device displays: an indication (e.g., an identifier of the third set of one or more external speakers) that the electronic device is configured to output audio signals associated with the hearing test via a third set of one or more external speakers (e.g., wired or wireless headphones; a set that is the same as the second set of one or more external speakers); and a first affordance (1027*b*) that, when selected, initiates a process for configuring the electronic device to output audio signals associated with the hearing test via a fourth set of one or more external speakers (e.g., wired or wireless headphones) that is different from the third set of one or more external speakers.

In some embodiments, prior to initiating the hearing test (e.g., prior to receiving data (e.g., inputs) that are used to assess the user's hearing) and in response to the set of one or more inputs, the electronic device displays, via the display device, a prompt to enable a do-not-disturb mode (e.g., a mode during which at least audio notifications/alerts are suppressed). In some embodiments, the prompt to enable a do-not-disturb mode includes an affordance that, when selected, enables the do-not-disturb mode. Displaying a prompt to enable a do-not-disturb mode provides the user with feedback as to a mode that can assist in reducing hearing test errors (e.g., by reducing disruptive interruptions). Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, prior to initiating the hearing test (e.g., prior to receiving data (e.g., inputs) that are used to assess the user's hearing) and in response to the set of one or more inputs, the electronic device displays, via the display device, a prompt (e.g., 1004*d*) to find a location with a low level of ambient noise (e.g., "find a quiet place").

In some embodiments, concurrently with displaying the prompt to find a location with a low level of ambient noise, the electronic device displays, via the display device, a second graphical indication (e.g., 1011*a*) of a current value of the detected ambient noise level (e.g., displaying a circle that changes in size based on the ambient noise level). Displaying a graphical indication of the current ambient noise level provides visual feedback as to noise being detected by the microphones. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the second graphical indication of the current value of the detected ambient noise level includes an indication (e.g., 1011*c*) of the time remaining until completion of a second initial ambient noise level assessment (e.g., a graphical or alphanumeric indication). Displaying a graphical indication of the time remaining provides the user with feedback as to when the hearing test will proceed. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the second graphical indication: in accordance with a determination that a third audio characteristic (e.g., an intensity (e.g., in decibels) or a frequency (e.g., in hertz) of the ambient noise) of the detected ambient noise level exceeds a third threshold value (e.g., a threshold value that is the same as the first threshold value; a threshold value that is different than the first threshold value), is displayed with a first value for a first visual characteristic (e.g., a first color); and in accordance with a determination that a third audio characteristic of the detected ambient noise level does not exceed the third threshold value, is displayed with a second value for the first visual characteristic (e.g., compare 1011*a* of FIG. 10E to FIG. 10F) (e.g., a second color). Displaying the graphical indication of the current ambient noise level with different visual characteristics based on a relationship to a threshold value (e.g., a threshold at which the hearing test will not proceed) provides improved visual feedback as to the ambient noise level and its relevance to the hearing test. Providing improved visual feedback enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the graphical indication of the current value of the detected ambient noise level, the electronic device detects completion of the second initial ambient noise level assessment; and in response to detecting the completion of the second initial ambient noise level assessment, displays, via the display device, an indication (e.g., 1011d) that the second initial ambient noise level assessment is complete (e.g., a check mark). In some embodiments, ceasing to display the graphical indication of the current value of the detected ambient noise level.

In some embodiments, prior to initiating the hearing test (e.g., prior to receiving data (e.g., inputs) that are used to assess the user's hearing) and in response to the set of one or more inputs, the electronic device initiates a practice hearing test (e.g., a procedure that includes outputting a set of one or more audio outputs and receiving a set of one or more user inputs; a procedure that is similar to the hearing test, but does not include the collection and/or use of data for assessing hearing), wherein data from the practice hearing test is not used to assess the hearing of a user of the electronic device.

In some embodiments, prior to initiating the hearing test (e.g., prior to receiving data (e.g., inputs) that are used to assess the user's hearing) and in response to the set of one or more inputs, the electronic device displays, via the display device, a prompt (e.g., 1004c) to adjust an audio output volume (e.g., a volume of output via wired or wireless headphones). In some embodiments, the prompt to adjust the audio output volume is displayed with an affordance that, when selected, outputs an audio sample of assisting in adjusting volume.

In some embodiments, prior to initiating the hearing test (e.g., prior to receiving data (e.g., inputs) that are used to assess the user's hearing) and in response to the set of one or more inputs, the electronic device displays, via the display device, an indication (e.g., 1027a) (e.g., an identifier of the fifth set of one or more external speakers) that the electronic device is configured to output audio signals associated with the hearing test via a fifth set of one or more external speakers (e.g., wired or wireless headphones; a set that is the same as the second set of one or more external speakers), wherein the fifth set of one or more external speakers satisfy a set of compatibility criteria (e.g., the fifth set of one or more external speakers are manufactured by a specific manufacturer, meet a hardware requirement, meeting a software requirement). In some embodiments, in accordance with a determination that connected external speakers do not satisfy the set of compatibility criteria, forgo initiating the hearing test (e.g., forgo until the speakers that satisfy the compatibility criteria are connected).

Note that details of the processes described above with respect to method 1100 (e.g., FIG. 11) are also applicable in an analogous manner to the methods described above. For example, method 700 optionally includes one or more of the characteristics of the various methods described above with reference to method 1100. For example, method 700 can be used to interact with and/or manage hearing tests performed via method 1100. For brevity, these details are not repeated herein.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve and advance research studies. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to conduct health-related research and/or identify studies of interest. Accordingly, use of such personal information data enables users to identify pertinent health research and pertinent studies. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, research study data requests, the present technology can be configured to allow users to select to "opt in" or "opt out" of participation in the collection of personal information data during registration for services or anytime thereafter. In another example, users can select not to provide requested data to a research study. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, research studies of interest can be identified based on non-personal information data or a bare minimum amount of personal information, such as the content being requested by the device associated with a user, other non-personal information available to the research study organizers, or publicly available information.

What is claimed is:

1. An electronic device, comprising:
a display device;
one or more input devices;
one or more processors; and
memory storing one or more programs configured to be executed by the one or more processors, the one or more programs including instructions for:
displaying, via the display device, a first user interface that includes:
a task view affordance associated with a plurality of different studies including a first study in which a user of the electronic device is enrolled and a second study in which the user of the electronic device is enrolled; and
a data view affordance;
while displaying the first user interface, detecting, via the one or more input devices, a first input; and
in response to detecting the first input:
in accordance with a determination that the first input corresponds to selection of the task view affordance, displaying, via the display device, a task view that includes concurrently displaying:
a first task corresponding to the first study, wherein the first task is a first data-collection task; and
a second task corresponding to the second study, wherein the second task is a second data-collection task; and
in accordance with a determination that the first input corresponds to selection of the data view affordance, displaying, via the display device, a data view that includes concurrently displaying:
an indication of data of a first type that is accessible to one or more studies in which the user of the electronic device is enrolled, including the first study, wherein the indication of the data of the first type is an indication of sensor and usage data and wherein the indication of the data of the first type is a selectable object that, when selected, causes display of a sensor and usage data view; and
an indication associated with one or more studies in which the user of the electronic device is enrolled that have access to the data of the first type, including the first study.

2. The electronic device of claim 1, wherein displaying the task view includes:
in accordance with a determination that a first set of permissions has been granted, displaying, via the display device, a third task; and
in accordance with a determination that a second set of permissions has been granted, forgoing displaying the third task.

3. The electronic device of claim 1, wherein the task view includes an indication of a degree of participation by a user associated with the electronic device in a plurality of research studies that includes at least the first study and the second study.

4. The electronic device of claim 1, wherein the task view affordance includes an indication of available tasks.

5. The electronic device of claim 1, wherein the task view includes a fourth task that does not correspond to a specific study.

6. The electronic device of claim 1, wherein tasks in the task view are displayed in an order and wherein:
in accordance with a determination that a remaining time for completion of the first task is less than a remaining time for completion of the second task, the first task is displayed before the second task in the order; and
in accordance with a determination that the remaining time for completion of the first task is greater than the remaining time for completion of the second task, the first task is displayed after the second task in the order.

7. The electronic device of claim 1, wherein the first task is a selectable object that is displayed in a first manner and the second task is a selectable object that is displayed in a second manner, and wherein the one or more programs further include instructions for:
   detecting, via the one or more input devices, a second input;
   in response to detecting the second input:
      in accordance with a determination that the second input corresponds to the first task, initiating a process for completing the first task, wherein the first task corresponding to the first study ceases to be displayed in the first manner in the task view upon completion of the first task; and
      in accordance with a determination that the second input corresponds to the second task, initiating a process for completing the second task, wherein the second task corresponding to the second study ceases to be displayed in the second manner in the task view upon completion of the second task.

8. The electronic device of claim 1, wherein the task view includes a fifth task and wherein the fifth task is a completed task.

9. The electronic device of claim 1, wherein the electronic device includes one or more sensors, and wherein the one or more programs further include instructions for:
   prior to detecting the first input, detecting, via the one or more sensors, a sensor event; and
   in response to detecting the sensor event and in accordance with a determination that the sensor event satisfies a set of task generation criteria, generating the first task.

10. The electronic device of claim 1, wherein the task view includes a sixth task, and wherein the one or more programs further include instructions for:
   detecting, via the one or more input devices, a third input corresponding to the sixth task; and
   in response to detecting the third input, initiating a process for enrolling the user of the electronic device in a third study.

11. The electronic device of claim 1, wherein the first user interface includes a study view affordance associated with the plurality of different studies, and wherein the one or more programs further include instructions for:
   in response to detecting the first input and in accordance with a determination that the first input corresponds to selection of the study view affordance, displaying, via the display device, a study view that includes concurrently displaying:
   a graphical representation of the first study; and
   a graphical representation of the second study.

12. The electronic device of claim 1, wherein the indication of the data of the first type is an indication of demographic data and wherein the indication of the data of the first type is a selectable object that, when selected, causes display of demographic data associated with the user of the electronic device.

13. The electronic device of claim 1, wherein the of the one or more studies in which the user of the electronic device is enrolled that have access to the data of the first type is a selectable object that, when selected, causes display of additional information associated with the one or more studies that have access to the data of the first type.

14. The electronic device of claim 1, wherein the sensor and usage data view includes a data collection affordance that, when selected, modifies a current state of sensor data collection.

15. The electronic device of claim 1, wherein the sensor and usage data view includes an export data affordance that, when selected, causes collected sensor and usage data to be exported to one or more studies that have access to the sensor and usage data.

16. The electronic device of claim 1, wherein the sensor and usage data view includes a first type of sensor and usage data affordance that, when selected, causes display of a first type of sensor and usage data view that includes information about the first type of sensor and usage data including:
   an example of data of the first type of sensor and usage data that this accessible to one or more studies in which the user of the electronic device is enrolled that have access to the data of the first type of sensor and usage data; and
   an example of data that is not of the first type of sensor and usage data that this accessible to one or more studies in which the user of the electronic device is enrolled that have access to the data of the first type of sensor and usage data.

17. The electronic device of claim 16, wherein the first type of sensor and usage data view includes one or more affordances associated with the one or more studies that have access to the data of the first type of sensor and usage data, including a first affordance associated with a fifth study that has access to the data of the first type of sensor and usage data, wherein the first affordance associated with a fifth study, when selected, initiates a process for disabling access of the fifth study to the first type of sensor and usage data.

18. A non-transitory computer-readable storage medium storing one or more programs configured to be executed by one or more processors of an electronic device with a display device and one or more input devices, the one or more programs including instructions for:
   displaying, via the display device, a first user interface that includes:
      a task view affordance associated with a plurality of different studies including a first study in which a user of the electronic device is enrolled and a second study in which the user of the electronic device is enrolled; and
      a data view affordance;
   while displaying the first user interface, detecting, via the one or more input devices, a first input; and
   in response to detecting the first input:
      in accordance with a determination that the first input corresponds to selection of the task view affordance, displaying, via the display device, a task view that includes concurrently displaying:
         a first task corresponding to the first study, wherein the first task is a first data-collection task; and
         a second task corresponding to the second study, wherein the second task is a second data-collection task; and
      in accordance with a determination that the first input corresponds to selection of the data view affordance, displaying, via the display device, a data view that includes concurrently displaying:
         an indication of data of a first type that is accessible to one or more studies in which the user of the electronic device is enrolled, including the first study, wherein the indication of the data of the first type is an indication of sensor and usage data and wherein the indication of the data of the first type is a selectable object that, when selected, causes display of a sensor and usage data view; and an indication associated with one or more studies in which the user of the electronic device is enrolled that have access to the data of the first type, including the first study.

19. A method comprising:

at an electronic device having a display device and one or more input devices:

displaying, via the display device, a first user interface that includes:

a task view affordance associated with a plurality of different studies including a first study in which a user of the electronic device is enrolled and a second study in which the user of the electronic device is enrolled; and a data view affordance;

while displaying the first user interface, detecting, via the one or more input devices, a first input; and in response to detecting the first input:

in accordance with a determination that the first input corresponds to selection of the task view affordance, displaying, via the display device, a task view that includes concurrently displaying:

a first task corresponding to the first study, wherein the first task is a first data-collection task; and a second task corresponding to the second study, wherein the second task is a second data-collection task; and in accordance with a determination that the first input corresponds to selection of the data view affordance, displaying, via the display device, a data view that includes concurrently displaying:

an indication of data of a first type that is accessible to one or more studies in which the user of the electronic device is enrolled, including the first study, wherein the indication of the data of the first type is an indication of sensor and usage data and wherein the indication of the data of the first type is a selectable object that, when selected, causes display of a sensor and usage data view; and an indication associated with one or more studies in which the user of the electronic device is enrolled that have access to the data of the first type, including the first study.

20. The non-transitory computer-readable storage medium of claim 18, wherein displaying the task view includes:

in accordance with a determination that a first set of permissions has been granted, displaying, via the display device, a third task; and in accordance with a determination that a second set of permissions has been granted, forgoing displaying the third task.

21. The non-transitory computer-readable storage medium of claim 18, wherein the task view includes an indication of a degree of participation by a user associated with the electronic device in a plurality of research studies that includes at least the first study and the second study.

22. The non-transitory computer-readable storage medium of claim 18, wherein the task view affordance includes an indication of available tasks.

23. The non-transitory computer-readable storage medium of claim 18, wherein the task view includes a fourth task that does not correspond to a specific study.

24. The non-transitory computer-readable storage medium of claim 18, wherein tasks in the task view are displayed in an order and wherein:

in accordance with a determination that a remaining time for completion of the first task is less than a remaining time for completion of the second task, the first task is displayed before the second task in the order; and in accordance with a determination that the remaining time for completion of the first task is greater than the remaining time for completion of the second task, the first task is displayed after the second task in the order.

25. The non-transitory computer-readable storage medium of claim 18, wherein the first task is a selectable object that is displayed in a first manner and the second task is a selectable object that is displayed in a second manner, and wherein the one or more programs further include instructions for:

detecting, via the one or more input devices, a second input;

in response to detecting the second input:

in accordance with a determination that the second input corresponds to the first task, initiating a process for completing the first task, wherein the first task corresponding to the first study ceases to be displayed in the first manner in the task view upon completion of the first task; and in accordance with a determination that the second input corresponds to the second task, initiating a process for completing the second task, wherein the second task corresponding to the second study ceases to be displayed in the second manner in the task view upon completion of the second task.

26. The non-transitory computer-readable storage medium of claim 18, wherein the task view includes a fifth task and wherein the fifth task is a completed task.

27. The non-transitory computer-readable storage medium of claim 18, wherein the electronic device includes one or more sensors, and wherein the one or more programs further include instructions for:

prior to detecting the first input, detecting, via the one or more sensors, a sensor event; and in response to detecting the sensor event and in accordance with a determination that the sensor event satisfies a set of task generation criteria, generating the first task.

28. The non-transitory computer-readable storage medium of claim 18, wherein the task view includes a sixth task, and wherein the one or more programs further include instructions for:

detecting, via the one or more input devices, a third input corresponding to the sixth task; and in response to detecting the third input, initiating a process for enrolling the user of the electronic device in a third study.

29. The non-transitory computer-readable storage medium of claim 18, wherein the first user interface includes a study view affordance associated with the plurality of different studies, and wherein the one or more programs further include instructions for:

in response to detecting the first input and in accordance with a determination that the first input corresponds to selection of the study view affordance, displaying, via the display device, a study view that includes concurrently displaying:

a graphical representation of the first study; and
a graphical representation of the second study.

30. The non-transitory computer-readable storage medium of claim 18, wherein the indication of the data of the first type is an indication of demographic data and wherein the indication of the data of the first type is a selectable object that, when selected, causes display of demographic data associated with the user of the electronic device.

31. The non-transitory computer-readable storage medium of claim 18, wherein the of the one or more studies in which the user of the electronic device is enrolled that have access to the data of the first type is a selectable object that, when selected, causes display of additional information associated with the one or more studies that have access to the data of the first type.

32. The non-transitory computer-readable storage medium of claim 18, wherein the sensor and usage data view includes a data collection affordance that, when selected, modifies a current state of sensor data collection.

33. The non-transitory computer-readable storage medium of claim 18, wherein the sensor and usage data view includes an export data affordance that, when selected, causes collected sensor and usage data to be exported to one or more studies that have access to the sensor and usage data.

34. The non-transitory computer-readable storage medium of claim 18, wherein the sensor and usage data view includes a first type of sensor and usage data affordance that, when selected, causes display of a first type of sensor and usage data view that includes information about the first type of sensor and usage data including:
  an example of data of the first type of sensor and usage data that this accessible to one or more studies in which the user of the electronic device is enrolled that have access to the data of the first type of sensor and usage data; and
  an example of data that is not of the first type of sensor and usage data that this accessible to one or more studies in which the user of the electronic device is enrolled that have access to the data of the first type of sensor and usage data.

35. The non-transitory computer-readable storage medium of claim 34, wherein the first type of sensor and usage data view includes one or more affordances associated with the one or more studies that have access to the data of the first type of sensor and usage data, including a first affordance associated with a fifth study that has access to the data of the first type of sensor and usage data, wherein the first affordance associated with a fifth study, when selected, initiates a process for disabling access of the fifth study to the first type of sensor and usage data.

36. The method of claim 19, wherein displaying the task view includes:
  in accordance with a determination that a first set of permissions has been granted, displaying, via the display device, a third task; and
  in accordance with a determination that a second set of permissions has been granted, forgoing displaying the third task.

37. The method of claim 19, wherein the task view includes an indication of a degree of participation by a user associated with the electronic device in a plurality of research studies that includes at least the first study and the second study.

38. The method of claim 19, wherein the task view affordance includes an indication of available tasks.

39. The method of claim 19, wherein the task view includes a fourth task that does not correspond to a specific study.

40. The method of claim 19, wherein tasks in the task view are displayed in an order and wherein:
  in accordance with a determination that a remaining time for completion of the first task is less than a remaining time for completion of the second task, the first task is displayed before the second task in the order; and
  in accordance with a determination that the remaining time for completion of the first task is greater than the remaining time for completion of the second task, the first task is displayed after the second task in the order.

41. The method of claim 19, wherein the first task is a selectable object that is displayed in a first manner and the second task is a selectable object that is displayed in a second manner, the method further comprising:
  detecting, via the one or more input devices, a second input;
  in response to detecting the second input:
    in accordance with a determination that the second input corresponds to the first task, initiating a process for completing the first task, wherein the first task corresponding to the first study ceases to be displayed in the first manner in the task view upon completion of the first task; and
    in accordance with a determination that the second input corresponds to the second task, initiating a process for completing the second task, wherein the second task corresponding to the second study ceases to be displayed in the second manner in the task view upon completion of the second task.

42. The method of claim 19, wherein the task view includes a fifth task and wherein the fifth task is a completed task.

43. The method of claim 19, wherein the electronic device includes one or more sensors, the method further comprising:
  prior to detecting the first input, detecting, via the one or more sensors, a sensor event; and
  in response to detecting the sensor event and in accordance with a determination that the sensor event satisfies a set of task generation criteria, generating the first task.

44. The method of claim 19, wherein the task view includes a sixth task, the method further comprising:
  detecting, via the one or more input devices, a third input corresponding to the sixth task; and
  in response to detecting the third input, initiating a process for enrolling the user of the electronic device in a third study.

45. The method of claim 19, wherein the first user interface includes a study view affordance associated with the plurality of different studies, the method further comprising:
  in response to detecting the first input and in accordance with a determination that the first input corresponds to selection of the study view affordance, displaying, via the display device, a study view that includes concurrently displaying:
    a graphical representation of the first study; and
    a graphical representation of the second study.

46. The method of claim 19, wherein the indication of the data of the first type is an indication of demographic data and wherein the indication of the data of the first type is a selectable object that, when selected, causes display of demographic data associated with the user of the electronic device.

47. The method of claim 19, wherein the of the one or more studies in which the user of the electronic device is enrolled that have access to the data of the first type is a selectable object that, when selected, causes display of additional information associated with the one or more studies that have access to the data of the first type.

48. The method of claim 19, wherein the sensor and usage data view includes a data collection affordance that, when selected, modifies a current state of sensor data collection.

49. The method of claim 19, wherein the sensor and usage data view includes an export data affordance that, when selected, causes collected sensor and usage data to be exported to one or more studies that have access to the sensor and usage data.

50. The method of claim 19, wherein the sensor and usage data view includes a first type of sensor and usage data affordance that, when selected, causes display of a first type of sensor and usage data view that includes information about the first type of sensor and usage data including:

an example of data of the first type of sensor and usage data that this accessible to one or more studies in which the user of the electronic device is enrolled that have access to the data of the first type of sensor and usage data; and an example of data that is not of the first type of sensor and usage data that this accessible to one or more studies in which the user of the electronic device is enrolled that have access to the data of the first type of sensor and usage data.

51. The method of claim 50, wherein the first type of sensor and usage data view includes one or more affordances associated with the one or more studies that have access to the data of the first type of sensor and usage data, including a first affordance associated with a fifth study that has access to the data of the first type of sensor and usage data, wherein the first affordance associated with a fifth study, when selected, initiates a process for disabling access of the fifth study to the first type of sensor and usage data.

* * * * *

UNITED STATES PATENT AND TRADEMARK OFFICE
CERTIFICATE OF CORRECTION

| | | |
|---|---|---|
| PATENT NO. | : 12,127,829 B2 | Page 1 of 1 |
| APPLICATION NO. | : 17/584190 | |
| DATED | : October 29, 2024 | |
| INVENTOR(S) | : Matthew Crowley | |

It is certified that error appears in the above-identified patent and that said Letters Patent is hereby corrected as shown below:

In the Claims

In Column 71, Lines 62-63, Claim 13, delete "wherein the of the one or more studies", and insert --wherein the indication associated with the one or more studies--, therefor.

In Column 75, Line 11, Claim 31, delete "wherein the of the one or more studies", and insert --wherein the indication associated with the one or more studies--, therefor.

In Column 77, Lines 4-5, Claim 47, delete "wherein the of the one or more studies", and insert --wherein the indication associated with the one or more studies--, therefor.

Signed and Sealed this
Eighth Day of April, 2025

Coke Morgan Stewart
*Acting Director of the United States Patent and Trademark Office*